US011512115B2

(12) United States Patent
Kraemer-Kuehl et al.

(10) Patent No.: US 11,512,115 B2
(45) Date of Patent: Nov. 29, 2022

(54) MODIFIED S1 SUBUNIT OF THE CORONAVIRUS SPIKE PROTEIN

(71) Applicant: Boehringer Ingelheim Vetmedica GmbH, Ingelheim am Rhein (DE)

(72) Inventors: Annika Kraemer-Kuehl, Seesen (DE); Thomas Min Stephan, Hannover (DE); Hans-Christian Philipp, Hemmingen (DE)

(*) Notice: Subject to any disclaimer, the term of this patent is extended or adjusted under 35 U.S.C. 154(b) by 99 days.

(21) Appl. No.: 16/867,650

(22) Filed: May 6, 2020

(65) Prior Publication Data

US 2020/0354410 A1 Nov. 12, 2020

(30) Foreign Application Priority Data

May 10, 2019 (EP) .................................. 19173821
Nov. 29, 2019 (EP) .................................. 19212627

(51) Int. Cl.
| | |
|---|---|
| *A61K 39/00* | (2006.01) |
| *A61K 39/215* | (2006.01) |
| *C12N 7/00* | (2006.01) |
| *A61K 39/12* | (2006.01) |
| *C07K 14/165* | (2006.01) |
| *C07K 14/005* | (2006.01) |
| *C12N 15/85* | (2006.01) |
| *A61P 31/14* | (2006.01) |

(52) U.S. Cl.
CPC .......... *C07K 14/005* (2013.01); *A61K 39/215* (2013.01); *A61P 31/14* (2018.01); *C12N 7/00* (2013.01); *C12N 15/85* (2013.01); *C12N 2770/20022* (2013.01); *C12N 2770/20023* (2013.01); *C12N 2800/10* (2013.01)

(58) Field of Classification Search
CPC ........ C07K 14/005; C12N 2770/20022; C12N 2770/20034; C12N 7/00; A61K 2039/5254
See application file for complete search history.

(56) References Cited

U.S. PATENT DOCUMENTS 8,828,407 B2 * 9/2014 Britton .................... A61P 31/16
435/235.1
2006/0257852 A1 11/2006 Rappuoli et al.
2019/0046634 A1 * 2/2019 Van Santen ............ A61K 39/12

FOREIGN PATENT DOCUMENTS

| WO | 86/05806 A1 | 10/1986 |
| WO | 2014/177873 A1 | 11/2014 |
| WO | 2019/046634 A1 | 3/2019 |

OTHER PUBLICATIONS

Casais, Rosa, et al., Recombinant Avian Infectious Bronchitis Virus Expressing a Heterologous Spike Gene Demonstrates that the Spike Protein Is a Determinant of Cell Tropism, J. Virology, Aug. 2003, vol. 77, No. 16, p. 9084-9089.
Bickerton, Erica, et al., The S2 subunit of Infectious Bronchitis Virus Beaudette Is a determinant of Cellular Tropism, J. Virology ASM, Oct. 2018, vol. 92, Issue 19, e01044-18.
Ellis, Samantha et al., Recombinant Infectious Bronchitis Viruses Expressing Chimeric Spike Glycoproteins Induce Partial Protective Immunity against Homologous Challenge despite Limited Replication In Vivo, J. Virology ASM, Dec. 2018, vol. 92, Issue 23, e01473-18.
Fang, Shou Guo, et al., Selection of and recombination between minor variants lead to the adaptation of an avian coronavirus to primate cells, Biochemical and Biophysical Research Communications, 2005, vol. 336, p. 417-423.
Communication/Extended Search Report, PCT/EP2020/062526, dated Oct. 4, 2019.
International Search Report and Written Opinion, PCT/EP2020/062526, dated Jun. 24, 2020.

* cited by examiner

Primary Examiner — Barry A Chestnut
(74) Attorney, Agent, or Firm — Jamie L. Graham

(57) ABSTRACT

The present invention relates i.a. to a recombinant avian coronavirus spike protein or fragment thereof comprising a mutation at amino acid position 267 to Cysteine. Further, the present invention relates to an immunogenic composition comprising an avian coronavirus with such spike protein.

33 Claims, 10 Drawing Sheets

Specification includes a Sequence Listing.

SEQUENCE LISTING

```
<160> NUMBER OF SEQ ID NOS: 84

<210> SEQ ID NO 1
<211> LENGTH: 1162
<212> TYPE: PRT
<213> ORGANISM: Avian infectious bronchitis virus

<400> SEQUENCE: 1

Met Leu Val Thr Pro Leu Leu Leu Val Thr Leu Leu Cys Ala Leu Cys
1               5                   10                  15

Ser Ala Ala Leu Tyr Asp Ser Ser Ser Tyr Val Tyr Tyr Tyr Gln Ser
                20                  25                  30

Ala Phe Arg Pro Pro Asp Gly Trp His Leu His Gly Gly Ala Tyr Ala
            35                  40                  45

Val Val Asn Ile Ser Ser Glu Ser Asn Asn Ala Gly Ser Ser Ser Gly
        50                  55                  60

Cys Thr Val Gly Ile Ile His Gly Gly Arg Val Val Asn Ala Ser Ser
65                  70                  75                  80

Ile Ala Met Thr Ala Pro Ser Ser Gly Met Ala Trp Ser Ser Ser Gln
                85                  90                  95

Phe Cys Thr Ala Tyr Cys Asn Phe Ser Asp Thr Thr Val Phe Val Thr
                100                 105                 110

His Cys Tyr Lys His Gly Gly Cys Pro Ile Thr Gly Met Leu Gln Gln
            115                 120                 125

His Ser Ile Arg Val Ser Ala Met Lys Asn Gly Gln Leu Phe Tyr Asn
        130                 135                 140

Leu Thr Val Ser Val Ala Lys Tyr Pro Thr Phe Lys Ser Phe Gln Cys
145                 150                 155                 160

Val Asn Asn Leu Thr Ser Val Tyr Leu Asn Gly Asp Leu Val Tyr Thr
                165                 170                 175

Ser Asn Glu Thr Thr Asp Val Thr Ser Ala Gly Val Tyr Phe Lys Ala
            180                 185                 190

Gly Gly Pro Ile Thr Tyr Lys Val Met Arg Glu Val Arg Ala Leu Ala
        195                 200                 205

Tyr Phe Val Asn Gly Thr Ala Gln Asp Val Ile Leu Cys Asp Gly Ser
    210                 215                 220

Pro Arg Gly Leu Leu Ala Cys Gln Tyr Asn Thr Gly Asn Phe Ser Asp
225                 230                 235                 240

Gly Phe Tyr Pro Phe Thr Asn Ser Ser Leu Val Lys Gln Lys Phe Ile
                245                 250                 255

Val Tyr Arg Glu Asn Ser Val Asn Thr Thr Phe Thr Leu His Asn Phe
            260                 265                 270
```

```
Thr Phe His Asn Glu Thr Gly Ala Asn Pro Asn Pro Ser Gly Val Gln
            275                 280                 285

Asn Ile Gln Thr Tyr Gln Thr Gln Thr Ala Gln Ser Gly Tyr Tyr Asn
        290                 295                 300

Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
                325                 330                 335

Asn Asn Gly Leu Trp Phe Asn Ser Leu Ser Val Ser Ile Ala Tyr Gly
                340                 345                 350

Pro Leu Gln Gly Gly Cys Lys Gln Ser Val Phe Ser Gly Arg Ala Thr
            355                 360                 365

Cys Cys Tyr Ala Tyr Ser Tyr Gly Gly Pro Leu Leu Cys Lys Gly Val
        370                 375                 380

Tyr Ser Gly Glu Leu Asp His Asn Phe Glu Cys Gly Leu Leu Val Tyr
385                 390                 395                 400

Val Thr Lys Ser Gly Gly Ser Arg Ile Gln Thr Ala Thr Glu Pro Pro
                405                 410                 415

Val Ile Thr Gln His Asn Tyr Asn Ile Thr Leu Asn Thr Cys Val
            420                 425                 430

Asp Tyr Asn Ile Tyr Gly Arg Thr Gly Gln Gly Phe Ile Thr Asn Val
        435                 440                 445

Thr Asp Ser Ala Val Ser Tyr Asn Tyr Leu Ala Asp Ala Gly Leu Ala
    450                 455                 460

Ile Leu Asp Thr Ser Gly Ser Ile Asp Ile Phe Val Val Gln Ser Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
        515                 520                 525

Thr Asn Gly Thr Arg Arg Phe Arg Arg Ser Ile Thr Glu Ser Val Glu
    530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
        595                 600                 605

Asn Cys Leu Gln Tyr Ile Cys Gly Asn Ser Leu Glu Cys Arg Asn Leu
    610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
            660                 665                 670

Gly Glu Phe Asn Ile Thr Leu Phe Leu Thr Thr Pro Ser Ser Pro Arg
        675                 680                 685
```

```
Arg Arg Ser Phe Ile Glu Asp Leu Leu Phe Thr Ser Val Glu Ser Val
690             695                 700

Gly Leu Pro Thr Asp Asp Ala Tyr Lys Asn Cys Thr Ala Gly Pro Leu
705             710                 715                 720

Gly Phe Leu Lys Asp Leu Ala Cys Ala Arg Glu Tyr Asn Gly Leu Leu
                725                 730                 735

Val Leu Pro Pro Ile Ile Thr Ala Glu Met Gln Thr Leu Tyr Thr Ser
                740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
770             775                 780

Thr Gln Ser Leu Leu Leu Lys Asn Gln Glu Lys Ile Ala Ala Ser Phe
785             790                 795                 800

Asn Lys Ala Ile Gly His Met Gln Glu Gly Phe Arg Ser Thr Ser Leu
                805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
835             840                 845

Val Ile Gln Glu Ile Tyr Gln Gln Leu Asp Ala Ile Gln Ala Asn Ala
850             855                 860

Gln Val Asp Arg Leu Ile Thr Gly Arg Leu Ser Ser Leu Ser Val Leu
865             870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
            930                 935                 940

Phe Val Asn Val Thr Ala Ile Val Gly Phe Cys Val Lys Pro Ala Asn
945             950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile Val Thr Leu Thr Ser Cys Gln Ala
                995                 1000                1005

Asn Tyr Val Ser Val Asn Lys Thr Val Ile Thr Thr Phe Val Asp
    1010            1015                1020

Asn Asp Asp Phe Asp Phe Asn Asp Glu Leu Ser Lys Trp Trp Asn
    1025            1030                1035

Asp Thr Lys His Glu Leu Pro Asp Phe Asp Lys Phe Asn Tyr Thr
    1040            1045                1050

Val Pro Ile Leu Asp Ile Asp Ser Glu Ile Asp Arg Ile Gln Gly
    1055            1060                1065

Val Ile Gln Gly Leu Asn Asp Ser Leu Ile Asp Leu Glu Lys Leu
    1070            1075                1080

Ser Ile Leu Lys Thr Tyr Ile Lys Trp Pro Trp Tyr Val Trp Leu
    1085            1090                1095

Ala Ile Ala Phe Ala Thr Ile Ile Phe Ile Leu Ile Leu Gly Trp
```

```
              1100                1105                1110
Val  Phe  Phe  Met  Thr  Gly  Cys  Cys  Gly  Cys  Cys  Gly  Cys  Phe
         1115                1120                1125

Gly  Ile  Met  Pro  Leu  Met  Ser  Lys  Cys  Gly  Lys  Lys  Ser  Ser  Tyr
         1130                1135                1140

Tyr  Thr  Thr  Phe  Asp  Asn  Asp  Val  Val  Thr  Glu  Gln  Tyr  Arg  Pro
         1145                1150                1155

Lys  Lys  Ser  Val
         1160

<210> SEQ ID NO 2
<211> LENGTH: 1162
<212> TYPE: PRT
<213> ORGANISM: Avian infectious bronchitis virus

<400> SEQUENCE: 2

Met  Leu  Val  Thr  Pro  Leu  Leu  Val  Thr  Leu  Leu  Cys  Ala  Leu  Cys
1                   5                   10                  15

Ser  Ala  Ala  Leu  Tyr  Asp  Ser  Ser  Tyr  Val  Tyr  Tyr  Gln  Ser
              20                  25                  30

Ala  Phe  Arg  Pro  Pro  Asp  Gly  Trp  His  Leu  His  Gly  Ala  Tyr  Ala
         35                  40                  45

Val  Val  Asn  Ile  Ser  Ser  Glu  Ser  Asn  Asn  Ala  Gly  Ser  Ser  Gly
    50                  55                  60

Cys  Thr  Val  Gly  Ile  Ile  His  Gly  Gly  Arg  Val  Val  Asn  Ala  Ser  Ser
65                  70                  75                  80

Ile  Ala  Met  Thr  Ala  Pro  Ser  Ser  Gly  Met  Ala  Trp  Ser  Ser  Gln
              85                  90                  95

Phe  Cys  Thr  Ala  Tyr  Cys  Asn  Phe  Ser  Asp  Thr  Thr  Val  Phe  Val  Thr
              100                 105                 110

His  Cys  Tyr  Lys  His  Gly  Gly  Cys  Pro  Ile  Thr  Gly  Met  Leu  Gln  Gln
         115                 120                 125

His  Ser  Ile  Arg  Val  Ser  Ala  Met  Lys  Asn  Gly  Gln  Leu  Phe  Tyr  Asn
    130                 135                 140

Leu  Thr  Val  Ser  Val  Ala  Lys  Tyr  Pro  Thr  Phe  Lys  Ser  Phe  Gln  Cys
145                 150                 155                 160

Val  Asn  Asn  Leu  Thr  Ser  Val  Tyr  Leu  Asn  Gly  Asp  Leu  Val  Tyr  Thr
              165                 170                 175

Ser  Asn  Glu  Thr  Thr  Asp  Val  Thr  Ser  Ala  Gly  Val  Tyr  Phe  Lys  Ala
         180                 185                 190

Gly  Gly  Pro  Ile  Thr  Tyr  Lys  Val  Met  Arg  Glu  Val  Arg  Ala  Leu  Ala
         195                 200                 205

Tyr  Phe  Val  Asn  Gly  Thr  Ala  Gln  Asp  Val  Ile  Leu  Cys  Asp  Gly  Ser
    210                 215                 220

Pro  Arg  Gly  Leu  Leu  Ala  Cys  Gln  Tyr  Asn  Thr  Gly  Asn  Phe  Ser  Asp
225                 230                 235                 240

Gly  Phe  Tyr  Pro  Phe  Thr  Asn  Ser  Ser  Leu  Val  Lys  Gln  Lys  Phe  Ile
              245                 250                 255

Val  Tyr  Arg  Glu  Asn  Ser  Val  Asn  Thr  Thr  Cys  Thr  Leu  His  Asn  Phe
         260                 265                 270

Thr  Phe  His  Asn  Glu  Thr  Gly  Ala  Asn  Pro  Asn  Pro  Ser  Gly  Val  Gln
    275                 280                 285

Asn  Ile  Gln  Thr  Tyr  Gln  Thr  Gln  Thr  Ala  Gln  Ser  Gly  Tyr  Tyr  Asn
290                 295                 300
```

```
Phe Asn Phe Ser Phe Leu Ser Ser Phe Val Tyr Lys Glu Ser Asn Phe
305                 310                 315                 320

Met Tyr Gly Ser Tyr His Pro Ser Cys Asn Phe Arg Leu Glu Thr Ile
            325                 330                 335

Asn Asn Gly Leu Trp Phe Asn Ser Leu Ser Val Ser Ile Ala Tyr Gly
            340                 345                 350

Pro Leu Gln Gly Gly Cys Lys Gln Ser Val Phe Ser Gly Arg Ala Thr
            355                 360                 365

Cys Cys Tyr Ala Tyr Ser Gly Gly Pro Leu Leu Cys Lys Gly Val
370                 375                 380

Tyr Ser Gly Glu Leu Asp His Asn Phe Glu Cys Gly Leu Leu Val Tyr
385                 390                 395                 400

Val Thr Lys Ser Gly Ser Arg Ile Gln Thr Ala Thr Glu Pro Pro
                405                 410                 415

Val Ile Thr Gln His Asn Tyr Asn Asn Ile Thr Leu Asn Thr Cys Val
                420                 425                 430

Asp Tyr Asn Ile Tyr Gly Arg Thr Gly Gln Gly Phe Ile Thr Asn Val
            435                 440                 445

Thr Asp Ser Ala Val Ser Tyr Asn Tyr Leu Ala Asp Ala Gly Leu Ala
450                 455                 460

Ile Leu Asp Thr Ser Gly Ser Ile Asp Ile Phe Val Val Gln Ser Glu
465                 470                 475                 480

Tyr Gly Leu Asn Tyr Tyr Lys Val Asn Pro Cys Glu Asp Val Asn Gln
                485                 490                 495

Gln Phe Val Val Ser Gly Gly Lys Leu Val Gly Ile Leu Thr Ser Arg
            500                 505                 510

Asn Glu Thr Gly Ser Gln Leu Leu Glu Asn Gln Phe Tyr Ile Lys Ile
            515                 520                 525

Thr Asn Gly Thr Arg Arg Phe Arg Arg Ser Ile Thr Glu Ser Val Glu
530                 535                 540

Asn Cys Pro Tyr Val Ser Tyr Gly Lys Phe Cys Ile Lys Pro Asp Gly
545                 550                 555                 560

Ser Ile Ala Thr Ile Val Pro Lys Gln Leu Glu Gln Phe Val Ala Pro
                565                 570                 575

Leu Leu Asn Val Thr Glu Asn Val Leu Ile Pro Asn Ser Phe Asn Leu
            580                 585                 590

Thr Val Thr Asp Glu Tyr Ile Gln Thr Arg Met Asp Lys Val Gln Ile
            595                 600                 605

Asn Cys Leu Gln Tyr Ile Cys Gly Asn Ser Leu Glu Cys Arg Asn Leu
610                 615                 620

Phe Gln Gln Tyr Gly Pro Val Cys Asp Asn Ile Leu Ser Val Val Asn
625                 630                 635                 640

Ser Val Gly Gln Lys Glu Asp Met Glu Leu Leu Asn Phe Tyr Ser Ser
                645                 650                 655

Thr Lys Pro Ala Gly Phe Asn Thr Pro Val Leu Ser Asn Val Ser Thr
            660                 665                 670

Gly Glu Phe Asn Ile Thr Leu Phe Leu Thr Thr Pro Ser Ser Pro Arg
            675                 680                 685

Arg Arg Ser Phe Ile Glu Asp Leu Leu Phe Thr Ser Val Glu Ser Val
            690                 695                 700

Gly Leu Pro Thr Asp Asp Ala Tyr Lys Asn Cys Thr Ala Gly Pro Leu
705                 710                 715                 720

Gly Phe Leu Lys Asp Leu Ala Cys Ala Arg Glu Tyr Asn Gly Leu Leu
```

```
                725                 730                 735
Val Leu Pro Pro Ile Ile Thr Ala Glu Met Gln Thr Leu Tyr Thr Ser
            740                 745                 750

Ser Leu Val Ala Ser Met Ala Phe Gly Gly Ile Thr Ala Ala Gly Ala
            755                 760                 765

Ile Pro Phe Ala Thr Gln Leu Gln Ala Arg Ile Asn His Leu Gly Ile
            770                 775                 780

Thr Gln Ser Leu Leu Leu Lys Asn Gln Glu Lys Ile Ala Ala Ser Phe
785                 790                 795                 800

Asn Lys Ala Ile Gly His Met Gln Glu Gly Phe Arg Ser Thr Ser Leu
                805                 810                 815

Ala Leu Gln Gln Ile Gln Asp Val Val Asn Lys Gln Ser Ala Ile Leu
            820                 825                 830

Thr Glu Thr Met Ala Ser Leu Asn Lys Asn Phe Gly Ala Ile Ser Ser
            835                 840                 845

Val Ile Gln Glu Ile Tyr Gln Gln Leu Asp Ala Ile Gln Ala Asn Ala
            850                 855                 860

Gln Val Asp Arg Leu Ile Thr Gly Arg Leu Ser Ser Leu Ser Val Leu
865                 870                 875                 880

Ala Ser Ala Lys Gln Ala Glu Tyr Ile Arg Val Ser Gln Gln Arg Glu
                885                 890                 895

Leu Ala Thr Gln Lys Ile Asn Glu Cys Val Lys Ser Gln Ser Ile Arg
            900                 905                 910

Tyr Ser Phe Cys Gly Asn Gly Arg His Val Leu Thr Ile Pro Gln Asn
            915                 920                 925

Ala Pro Asn Gly Ile Val Phe Ile His Phe Ser Tyr Thr Pro Asp Ser
930                 935                 940

Phe Val Asn Val Thr Ala Ile Val Gly Phe Cys Val Lys Pro Ala Asn
945                 950                 955                 960

Ala Ser Gln Tyr Ala Ile Val Pro Ala Asn Gly Arg Gly Ile Phe Ile
                965                 970                 975

Gln Val Asn Gly Ser Tyr Tyr Ile Thr Ala Arg Asp Met Tyr Met Pro
            980                 985                 990

Arg Ala Ile Thr Ala Gly Asp Ile  Val Thr Leu Thr Ser  Cys Gln Ala
            995                 1000                1005

Asn Tyr Val Ser Val Asn Lys  Thr Val Ile Thr Thr  Phe Val Asp
       1010                1015                1020

Asn Asp  Asp Phe Asp Phe Asn  Asp Glu Leu Ser Lys  Trp Trp Asn
    1025                1030                1035

Asp Thr Lys His Glu Leu Pro  Asp Phe Asp Lys Phe  Asn Tyr Thr
       1040                1045                1050

Val Pro Ile Leu Asp Ile Asp  Ser Glu Ile Asp Arg  Ile Gln Gly
       1055                1060                1065

Val Ile Gln Gly Leu Asn Asp  Ser Leu Ile Asp Leu  Glu Lys Leu
       1070                1075                1080

Ser Ile Leu Lys Thr Tyr Ile  Lys Trp Pro Trp Tyr  Val Trp Leu
       1085                1090                1095

Ala Ile Ala Phe Ala Thr Ile  Ile Phe Ile Leu Ile  Leu Gly Trp
       1100                1105                1110

Val Phe Phe Met Thr Gly Cys  Cys Gly Cys Cys Cys  Gly Cys Phe
       1115                1120                1125

Gly Ile Met Pro Leu Met Ser  Lys Cys Gly Lys Lys  Ser Ser Tyr
       1130                1135                1140
```

Tyr Thr Thr Phe Asp Asn Asp Val Val Thr Glu Gln Tyr Arg Pro
            1145                1150                1155

Lys Lys Ser Val
    1160

<210> SEQ ID NO 3
<211> LENGTH: 1155
<212> TYPE: PRT
<213> ORGANISM: Avian infectious bronchitis virus

<400> SEQUENCE: 3

Met Leu Asp Lys Pro Leu Leu Leu Val Thr Leu Trp Tyr Ala Leu Cys
1               5                   10                  15

Ser Ala Leu Leu Tyr Asp Asn Asn Thr Tyr Val Tyr Tyr Tyr Gln Ser
                20                  25                  30

Ala Phe Arg Pro Gly Pro Gly Trp His Leu Tyr Gly Gly Ala Tyr Ala
            35                  40                  45

Val Asp Arg Val Phe Asn Glu Thr Asn Asn Ala Gly Ser Ala Ser Asp
    50                  55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
            100                 105                 110

His Cys Phe Lys Asn Gln Leu Gly Ser Cys Pro Leu Thr Gly Met Ile
        115                 120                 125

Pro Gln Asn His Ile Arg Ile Ser Ala Met Arg Asp Gly Val Leu Phe
    130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
            180                 185                 190

Lys Ser Gly Gly Pro Val Thr Tyr Lys Val Met Lys Glu Val Lys Ala
        195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Cys Lys Leu Thr
            260                 265                 270

Asn Phe Ser Phe Thr Asn Val Ser Asn Ala Ser Pro Asn Ser Gly Gly
        275                 280                 285

Val Asp Thr Phe Gln Leu Tyr Gln Thr Ser Thr Ala Gln Asp Gly Tyr
    290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr

```
                340             345             350
Tyr Gly Pro Ile Gln Gly Gly Cys Lys Gln Ser Val Phe Ser Asn Arg
            355             360             365

Ala Thr Cys Cys Tyr Ala Tyr Ser Tyr Gln Gly Pro Ser Arg Cys Lys
        370             375             380

Gly Val Tyr Arg Gly Glu Leu Thr Gln Tyr Phe Glu Cys Gly Leu Leu
385             390             395             400

Val Tyr Val Thr Lys Ser Asp Gly Ser Arg Ile Gln Thr Arg Ser Glu
            405             410             415

Pro Leu Val Leu Thr Gln Tyr Asn Tyr Asn Asn Ile Thr Leu Asn Lys
            420             425             430

Cys Val Glu Tyr Asn Ile Tyr Gly Arg Val Gly Gln Gly Phe Ile Thr
            435             440             445

Asn Val Thr Glu Ala Thr Ala Asn Tyr Ser Tyr Leu Ala Asp Gly Gly
            450             455             460

Leu Ala Ile Leu Asp Thr Ser Gly Ala Ile Asp Ile Phe Val Val Gln
465             470             475             480

Gly Ala Tyr Gly Leu Asn Tyr Tyr Lys Val Asn Pro Cys Glu Asp Val
            485             490             495

Asn Gln Gln Phe Val Val Ser Gly Gly Asn Leu Val Gly Ile Leu Thr
            500             505             510

Ser His Asn Glu Thr Gly Ser Glu Ser Ile Glu Asn Gln Phe Tyr Ile
            515             520             525

Lys Leu Thr Asn Gly Thr Arg Arg Ser Arg Arg Ser Val Thr Gly Asn
            530             535             540

Val Thr Asn Cys Pro Tyr Val Ser Tyr Gly Lys Phe Cys Ile Lys Pro
545             550             555             560

Asp Gly Ser Leu Ser Ile Ile Val Pro Gln Glu Leu Glu Gln Phe Val
            565             570             575

Ala Pro Leu Phe Asn Val Thr Glu His Val Leu Ile Pro Asp Ser Phe
            580             585             590

Asn Leu Thr Val Thr Asp Glu Tyr Ile Gln Thr Arg Met Asp Lys Val
            595             600             605

Gln Ile Ile Cys Leu Gln Tyr Val Cys Gly Asn Ser Ile Glu Cys Arg
            610             615             620

Lys Leu Phe Gln Gln Tyr Gly Pro Val Cys Asp Asn Ile Leu Ser Val
625             630             635             640

Val Asn Gly Val Gly Gln Arg Glu Asp Met Glu Leu Leu Ser Phe Tyr
            645             650             655

Ser Ser Thr Lys Pro Ser Gly Tyr Asn Thr Pro Ile Phe Asn Asn Val
            660             665             670

Ser Thr Gly Asp Phe Asn Ile Ser Leu Leu Leu Thr Pro Pro Asn Ser
            675             680             685

Pro Thr Gly Arg Ser Phe Ile Glu Asp Leu Leu Phe Thr Ser Val Glu
            690             695             700

Ser Val Gly Leu Pro Thr Asp Glu Glu Tyr Lys Lys Cys Thr Ala Gly
705             710             715             720

Pro Leu Gly Phe Val Lys Asp Leu Val Cys Ala Arg Glu Tyr Asn Gly
            725             730             735

Leu Leu Val Leu Pro Pro Ile Ile Thr Ala Glu Met Gln Thr Met Tyr
            740             745             750

Thr Ser Ser Leu Val Ala Ser Met Ala Leu Gly Gly Ile Thr Ala Ala
            755             760             765
```

Gly Ala Ile Pro Phe Ala Thr Gln Leu Gln Ala Arg Ile Asn His Leu
    770             775                 780
Gly Ile Thr Asn Ser Leu Leu Lys Asn Gln Glu Lys Ile Ala Ala
785             790              795                 800
Ser Phe Asn Lys Ala Ile Gly His Met Gln Glu Gly Phe Lys Ser Thr
                805             810                 815
Ser Leu Ala Leu Gln Gln Ile Gln Asp Val Val Asn Lys Gln Ser Ser
                820             825                 830
Ile Leu Thr Glu Thr Met Gln Ser Leu Asn Lys Asn Phe Gly Ala Ile
        835             840             845
Ser Ser Val Ile Gln Asp Ile Tyr Gln Gln Leu Asp Ala Ile Gln Ala
    850             855             860
Asp Ala Gln Val Asp Arg Leu Ile Thr Gly Arg Leu Ser Ser Leu Ser
865             870             875                 880
Val Leu Ala Ser Ala Lys Gln Ala Glu Tyr His Arg Val Ser Gln Gln
                885             890             895
Arg Glu Leu Ala Thr Gln Lys Ile Asn Glu Cys Val Lys Ser Gln Ser
            900             905             910
Asn Arg Tyr Ser Phe Cys Gly Asn Gly Arg His Val Leu Thr Ile Pro
        915             920             925
Gln Asn Ala Pro Asn Gly Ile Val Phe Ile His Phe Thr Tyr Thr Pro
    930             935             940
Glu Ser Phe Val Asn Val Thr Ala Ile Val Gly Phe Cys Val Asn Pro
945             950             955                 960
Ala Asn Ala Ser His Tyr Ala Ile Val Pro Val Asn Gly Arg Gly Val
                965             970             975
Phe Ile Glu Val Asn Gly Ser Tyr Tyr Ile Thr Ala Arg Asp Met Tyr
            980             985             990
Met Pro Arg Asp Ile Thr Ala Gly Asp Ile Val Thr Leu Thr Ser Cys
        995             1000            1005
Gln Ala Asn Tyr Val Asn Val Asn Lys Thr Val Ile Asn Thr Phe
    1010            1015            1020
Val Glu Asp Asp Asp Phe Asp Phe Tyr Asp Glu Leu Ser Lys Trp
    1025            1030            1035
Trp Asn Asp Thr Lys His Glu Leu Pro Asp Phe Asp Glu Phe Asn
    1040            1045            1050
Tyr Thr Val Pro Val Leu Asn Ile Ser Asn Glu Ile Asp Arg Ile
    1055            1060            1065
Gln Gln Val Ile Gln Gly Leu Asn Asp Ser Leu Ile Asp Leu Glu
    1070            1075            1080
Thr Leu Ser Ile Leu Lys Thr Tyr Ile Lys Trp Pro Trp Tyr Val
    1085            1090            1095
Trp Leu Ala Ile Ala Phe Leu Thr Ile Ile Phe Ile Leu Val Leu
    1100            1105            1110
Cys Trp Ile Phe Phe Met Thr Gly Cys Cys Gly Cys Cys Cys Gly
    1115            1120            1125
Cys Phe Gly Ile Ile Pro Leu Met Ser Lys Cys Gly Lys Lys Ser
    1130            1135            1140
Ser Tyr Tyr Thr Thr Phe Asp Asn Asp Val Val Thr
    1145            1150            1155

<210> SEQ ID NO 4
<211> LENGTH: 1156

<212> TYPE: PRT
<213> ORGANISM: Avian infectious bronchitis virus

<400> SEQUENCE: 4

```
Met Leu Val Lys Ser Leu Phe Leu Val Thr Ile Leu Cys Ala Leu Cys
1               5                   10                  15

Ser Ala Asn Leu Phe Asp Ser Asp Asn Tyr Val Tyr Tyr Tyr Gln
            20                  25                  30

Ser Ala Phe Arg Pro Pro Asn Gly Trp His Leu Gln Gly Gly Ala Tyr
            35                  40                  45

Ala Val Val Ser Ser Thr Asn Tyr Thr Asn Asn Ala Gly Ser Ala His
        50                  55                  60

Gly Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110

Thr His Cys Tyr Ser Ser Gly Ser Gly Ser Cys Pro Ile Thr Gly Met
            115                 120                 125

Ile Pro Arg Asp His Ile Arg Ile Ser Ala Met Lys Asn Gly Ser Leu
130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
        195                 200                 205

Val Leu Ala Tyr Phe Val Asn Gly Thr Ala Gln Asp Val Val Leu Cys
210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Cys Ala Leu
            260                 265                 270

Thr Asn Phe Thr Phe Ser Asn Val Ser Asn Ala Gln Pro Asn Ser Gly
        275                 280                 285

Gly Val Asn Thr Phe His Leu Tyr Gln Thr Gln Thr Ala Gln Ser Gly
    290                 295                 300

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
            340                 345                 350

Thr Tyr Gly Pro Leu Gln Gly Gly Cys Lys Gln Ser Val Phe Ser Gly
        355                 360                 365

Lys Ala Thr Cys Cys Tyr Ala Tyr Ser Tyr Arg Gly Pro Met Ala Cys
370                 375                 380

Lys Gly Val Tyr Ser Gly Glu Leu Ser Thr Asn Phe Glu Cys Gly Leu
385                 390                 395                 400
```

```
Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Ile Thr Leu Asp
        420                 425                 430

Lys Cys Val Ala Tyr Asn Ile Tyr Gly Arg Val Gly Gln Gly Phe Ile
            435                 440                 445

Thr Asn Val Thr Asp Ser Ala Ala Asn Phe Ser Tyr Leu Ala Asp Gly
    450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
                485                 490                 495

Val Asn Gln Gln Phe Val Val Ser Gly Gly Asn Ile Val Gly Ile Leu
            500                 505                 510

Thr Ser Arg Asn Glu Thr Gly Ser Glu Gln Val Glu Asn Gln Phe Tyr
        515                 520                 525

Val Lys Leu Thr Asn Ser Ser His Arg Arg Lys Arg Ser Ile Gly Gln
    530                 535                 540

Asn Val Thr Ser Cys Pro Tyr Val Ser Tyr Gly Arg Phe Cys Ile Glu
545                 550                 555                 560

Pro Asp Gly Ser Leu Lys Met Ile Val Pro Glu Glu Leu Lys Gln Phe
                565                 570                 575

Val Ala Pro Leu Leu Asn Ile Thr Glu Ser Val Leu Ile Pro Asn Ser
            580                 585                 590

Phe Asn Leu Thr Val Thr Asp Glu Tyr Ile Gln Thr Arg Met Asp Lys
        595                 600                 605

Val Gln Ile Asn Cys Leu Gln Tyr Val Cys Gly Asn Ser Leu Glu Cys
    610                 615                 620

Arg Lys Leu Phe Gln Gln Tyr Gly Pro Val Cys Asp Asn Ile Leu Ser
625                 630                 635                 640

Val Val Asn Ser Val Ser Gln Lys Glu Asp Met Glu Leu Leu Ser Phe
                645                 650                 655

Tyr Ser Ser Thr Lys Pro Lys Gly Tyr Asp Thr Pro Val Leu Ser Asn
            660                 665                 670

Val Ser Thr Gly Glu Phe Asn Ile Ser Leu Leu Leu Lys Pro Pro Ser
        675                 680                 685

Ser Pro Ser Gly Arg Ser Phe Ile Glu Glu Leu Leu Phe Thr Ser Val
    690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn
                725                 730                 735

Gly Leu Leu Val Leu Pro Pro Ile Ile Thr Ala Asp Met Gln Thr Met
            740                 745                 750

Tyr Thr Ala Ser Leu Val Gly Ala Met Ala Phe Gly Gly Ile Thr Ser
        755                 760                 765

Ala Ala Ala Ile Pro Phe Ala Thr Gln Ile Gln Ala Arg Ile Asn His
    770                 775                 780

Leu Gly Ile Thr Gln Ser Leu Leu Met Lys Asn Gln Glu Lys Ile Ala
785                 790                 795                 800

Ala Ser Phe Asn Lys Ala Ile Gly His Met Gln Glu Gly Phe Arg Ser
                805                 810                 815
```

Thr Ser Leu Ala Leu Gln Gln Ile Gln Asp Val Val Asn Lys Gln Ser
            820                 825                 830

Ala Ile Leu Thr Glu Thr Met Asn Ser Leu Asn Lys Asn Phe Gly Ala
        835                 840                 845

Ile Thr Ser Val Ile Gln Asp Ile Tyr Ala Gln Leu Asp Ala Ile Gln
    850                 855                 860

Ala Asp Ala Gln Val Asp Arg Leu Ile Thr Gly Arg Leu Ser Ser Leu
865                 870                 875                 880

Ser Val Leu Ala Ser Ala Lys Gln Ser Glu Tyr Ile Arg Val Ser Gln
                885                 890                 895

Gln Arg Glu Leu Ala Thr Gln Lys Ile Asn Glu Cys Val Lys Ser Gln
            900                 905                 910

Ser Asn Arg Tyr Gly Phe Cys Gly Ser Gly Arg His Val Leu Ser Ile
        915                 920                 925

Pro Gln Asn Ala Pro Asn Gly Ile Val Phe Ile His Phe Thr Tyr Thr
    930                 935                 940

Pro Glu Ser Phe Val Asn Val Thr Ala Ile Val Gly Phe Cys Val Asn
945                 950                 955                 960

Pro Ala Asn Ala Ser Gln Tyr Ala Ile Val Pro Ala Asn Gly Arg Gly
                965                 970                 975

Ile Phe Ile Gln Val Asn Gly Thr Tyr Tyr Ile Thr Ala Arg Asp Met
            980                 985                 990

Tyr Met Pro Arg Asp Ile Thr Ala Gly Asp Ile Val Thr Leu Thr Ser
        995                 1000                1005

Cys Gln Ala Asn Tyr Val Asn Val Asn Lys Thr Val Ile Thr Thr
    1010                1015                1020

Phe Val Glu Asp Asp Asp Phe Asp Phe Asp Asp Glu Leu Ser Lys
    1025                1030                1035

Trp Trp Asn Asp Thr Lys His Gln Leu Pro Asp Phe Asp Asp Phe
    1040                1045                1050

Asn Tyr Thr Val Pro Ile Leu Asn Ile Ser Gly Glu Ile Asp Tyr
    1055                1060                1065

Ile Gln Gly Val Ile Gln Gly Leu Asn Asp Ser Leu Ile Asp Leu
    1070                1075                1080

Glu Glu Leu Ser Ile Ile Lys Thr Tyr Ile Lys Trp Pro Trp Tyr
    1085                1090                1095

Val Trp Leu Ala Ile Phe Phe Ala Ile Ile Ile Phe Ile Leu Ile
    1100                1105                1110

Leu Gly Trp Val Phe Phe Met Thr Gly Cys Cys Gly Cys Cys Cys
    1115                1120                1125

Gly Cys Phe Gly Ile Ile Pro Leu Met Ser Lys Cys Gly Lys Lys
    1130                1135                1140

Ser Ser Tyr Tyr Thr Thr Phe Asp Asn Asp Val Val Thr
    1145                1150                1155

<210> SEQ ID NO 5
<211> LENGTH: 1156
<212> TYPE: PRT
<213> ORGANISM: Avian infectious bronchitis virus

<400> SEQUENCE: 5

Met Leu Gly Lys Ser Leu Phe Val Val Thr Leu Leu Phe Ala Leu Cys
1               5                   10                  15

Ser Ala Ala Leu Phe Asp Asn Asn Glu Thr Val Tyr Tyr Tyr Gln Ser
            20                  25                  30

```
Ala Phe Arg Pro Ala Asp Gly Trp His Leu His Gly Gly Ala Tyr Ala
            35                  40                  45

Val Val Asn Val Ser Leu Gln Thr Ser Asn Ala Gly Thr Val Ser Glu
 50                  55                  60

Cys Ile Ala Gly Ala Ile Ser Trp Ser Lys Glu Phe Ser Ala Ser Ala
 65                  70                  75                  80

Val Ala Met Thr Ala Pro Gln Leu Gly Met Thr Trp Ser Thr Arg Gln
                 85                  90                  95

Phe Cys Thr Ala His Cys Asn Phe Ser Asp Phe Thr Val Phe Val Thr
                100                 105                 110

His Cys Phe Lys His Gly Thr Gly Leu Cys Pro Leu Thr Gly Phe Ile
            115                 120                 125

Pro Ser Gly Phe Ile Arg Val Ser Ala Met Arg Lys Gly Ser Asn Ser
130                 135                 140

Leu Phe Tyr Asn Leu Thr Val Ser Val Thr Lys Tyr Pro Arg Phe Lys
145                 150                 155                 160

Ser Leu Gln Cys Val Asn Asn Tyr Thr Ser Val Tyr Leu Asn Gly Asp
                165                 170                 175

Leu Val Phe Thr Ser Asn Glu Thr Lys Pro Val Ser Ala Ala Gly Val
            180                 185                 190

Ser Phe Lys Ala Gly Gly Pro Ile Thr Tyr Lys Ile Met Asn Glu Val
        195                 200                 205

Lys Val Leu Ala Tyr Phe Val Asn Gly Thr Ala Gln Thr Val Ile Pro
210                 215                 220

Cys Asp Gly Ser Pro Arg Gly Leu Leu Ala Cys Gln Tyr Asn Thr Gly
225                 230                 235                 240

Asn Phe Ser Asp Gly Phe Tyr Pro Tyr Thr Asn Ser Ser Leu Val Lys
                245                 250                 255

Glu Arg Phe Ile Val Tyr Arg Glu Ser Ser Val Asn Thr Ile Cys Val
            260                 265                 270

Leu Thr Asn Phe Thr Phe Ser Asn Val Ser Asn Ala Leu Pro Asn Thr
        275                 280                 285

Gly Asn Val His Ser Ile Val Leu His Gln Thr Gln Thr Ala Gln Ser
290                 295                 300

Gly Tyr Tyr Asn Leu Asn Phe Ser Phe Leu Ser Gly Phe Arg Tyr Val
305                 310                 315                 320

Glu Ser Asp Phe Met Tyr Gly Ser Tyr His Pro Lys Cys Ser Phe Arg
                325                 330                 335

Pro Glu Thr Ile Asn Asn Gly Leu Trp Phe Asn Ser Leu Ser Val Ser
            340                 345                 350

Leu Gly Tyr Gly Pro Leu Gln Gly Gly Cys Lys Gln Ser Val Phe Asn
        355                 360                 365

Asn Lys Ala Thr Cys Cys Tyr Ala Tyr Ser Tyr Asn Gly Pro Thr Leu
370                 375                 380

Cys Lys Gly Val Tyr Ser Gly Glu Leu Gln Lys Thr Phe Glu Cys Gly
385                 390                 395                 400

Leu Leu Val Phe Val Thr Lys Ser Asp Gly Ser Arg Ile Gln Thr Arg
                405                 410                 415

Asn Glu Pro Leu Val Leu Thr Gln His Asn Tyr Asn Asn Ile Thr Leu
            420                 425                 430

Asn Lys Cys Val Glu Tyr Asn Ile Tyr Gly Arg Val Gly Gln Gly Leu
        435                 440                 445
```

Ile Thr Asn Ile Thr Asp Ser Ala Ala Asn His Gly Tyr Leu Ala Asp
450                 455                 460

Gly Gly Leu Ala Val Leu Asp Thr Ser Gly Ala Ile Asp Val Phe Val
465                 470                 475                 480

Val Gln Gly Val Tyr Gly Leu Asn Tyr Tyr Lys Val Asn Pro Cys Glu
                485                 490                 495

Asp Val Asn Gln Gln Phe Val Val Ser Gly Gln Leu Val Gly Ile
            500                 505                 510

Leu Thr Ser Arg Asn Glu Thr Gly Ser Gln Pro Ile Glu Asn Arg Phe
            515                 520                 525

Tyr Val Lys Phe Ser Asn Ser Arg Arg Arg Thr Gly Arg Ser Thr Ile
530                 535                 540

Ala Asn Val Thr Asn Cys Pro Tyr Val Ser Tyr Gly Lys Phe Cys Ile
545                 550                 555                 560

Lys Pro Asp Gly Ser Leu Glu Ile Val Pro Gln Glu Ile Glu His
                565                 570                 575

Phe Val Ala Pro Leu Leu Asn Val Thr Glu His Val Leu Ile Pro Asn
            580                 585                 590

Ser Phe Asn Leu Thr Val Thr Asp Glu Tyr Ile Gln Thr Arg Met Asp
            595                 600                 605

Lys Ile Gln Ile Asn Cys Leu Gln Tyr Val Cys Gly Asn Ser Ile Glu
610                 615                 620

Cys Arg Lys Leu Phe Gln Gln Tyr Gly Pro Val Cys Asp Asn Ile Leu
625                 630                 635                 640

Ser Val Val Asn Thr Val Gly Gln Arg Glu Asp Met Glu Leu Leu Ser
                645                 650                 655

Phe Tyr Ser Ser Thr Lys Pro Lys Asp Tyr Asn Val Pro Ile Phe Ser
            660                 665                 670

Asn Val Ser Thr Gly Asp Phe Asn Ile Ser Leu Leu Leu Thr Pro Pro
            675                 680                 685

Asn Ser Pro Thr Gly Arg Ser Phe Ile Glu Asp Ile Leu Phe Thr Ser
            690                 695                 700

Val Glu Ser Val Gly Leu Pro Thr Asp Glu Glu Tyr Lys Lys Cys Thr
705                 710                 715                 720

Ala Gly Pro Leu Gly Phe Val Lys Asp Leu Val Cys Ala Arg Glu Tyr
                725                 730                 735

Asn Gly Leu Leu Val Leu Pro Pro Ile Ile Thr Ala Asp Met Gln Thr
            740                 745                 750

Met Tyr Thr Ser Thr Leu Val Ala Ser Met Ala Leu Gly Gly Ile Thr
            755                 760                 765

Ala Ala Gly Ala Ile Pro Phe Ala Thr Gln Leu Gln Ala Arg Ile Asn
770                 775                 780

His Leu Gly Ile Thr Gln Ser Leu Leu Leu Lys Asn Gln Glu Lys Ile
785                 790                 795                 800

Ala Ala Ser Phe Asn Lys Ala Ile Gly His Met Gln Glu Gly Phe Arg
                805                 810                 815

Ser Thr Ser Leu Ala Leu Gln Gln Ile Gln Asp Val Val Asn Lys Gln
            820                 825                 830

Ser Ser Ile Leu Thr Glu Thr Met Ala Ser Leu Asn Lys Asn Phe Gly
            835                 840                 845

Ala Ile Ser Ser Val Leu Gln Asp Ile Tyr Gln Gln Leu Asp Ala Ile
850                 855                 860

Gln Ala Asp Ala Gln Val Asp Arg Ile Ile Thr Gly Arg Leu Ser Ser

-continued

```
                865                 870                 875                 880
Leu Ser Val Leu Ala Ser Ala Lys Gln Ser Glu Tyr Tyr Arg Val Ser
                    885                 890                 895
Gln Gln Arg Glu Leu Ala Thr Gln Lys Ile Asn Glu Cys Val Lys Ser
                900                 905                 910
Gln Ser Thr Arg Tyr Ser Phe Cys Gly Asn Gly Arg His Val Leu Thr
            915                 920                 925
Ile Pro Gln Asn Ala Pro Asn Gly Ile Val Phe Ile His Phe Thr Tyr
        930                 935                 940
Thr Pro Glu Ser Phe Val Asn Val Thr Ala Ile Val Gly Phe Cys Val
945                 950                 955                 960
Asn Pro Pro Asn Ala Ser Gln Tyr Ala Leu Val Pro Ala Asn Gly Arg
                965                 970                 975
Gly Ile Phe Ile Gln Val Asn Gly Ser Tyr Tyr Ile Thr Ala Arg Asp
            980                 985                 990
Met Tyr Met Pro Arg Asp Ile Thr Ala Gly Asp Ile Val Thr Leu Thr
        995                 1000                1005
Ser Cys Gln Ala Asn Tyr Val Ser Val Asn Arg Thr Val Ile Thr
    1010                1015                1020
Thr Phe Val Asp Asn Asp Asp Phe Asp Phe Asp Asp Glu Leu Ser
    1025                1030                1035
Lys Trp Trp Asn Asp Thr Lys His Glu Leu Pro Asp Phe Asp Glu
    1040                1045                1050
Phe Asn Tyr Thr Ile Pro Val Leu Asn Ile Ser Asn Glu Ile Asp
    1055                1060                1065
Ile Ile Gln Glu Val Ile Arg Gly Leu Asn Asp Ser Leu Ile Asp
    1070                1075                1080
Leu Glu Ala Leu Ser Ile Leu Lys Thr Tyr Ile Lys Trp Pro Trp
    1085                1090                1095
Tyr Val Trp Leu Ala Ile Ala Phe Leu Thr Ile Ile Phe Ile Leu
    1100                1105                1110
Val Leu Cys Trp Ile Phe Phe Met Thr Gly Cys Cys Gly Cys Cys
    1115                1120                1125
Cys Gly Cys Phe Gly Ile Met Pro Leu Met Ser Lys Cys Gly Lys
    1130                1135                1140
Lys Ser Ser Tyr Tyr Thr Thr Phe Asp Asn Asp Val Val
    1145                1150                1155
```

<210> SEQ ID NO 6
<211> LENGTH: 1156
<212> TYPE: PRT
<213> ORGANISM: Avian infectious bronchitis virus

<400> SEQUENCE: 6

```
Met Leu Val Lys Ser Leu Phe Ile Val Thr Leu Leu Phe Ala Leu Cys
1               5                   10                  15
Ser Ala Ala Leu Phe Asp Asn Asn Gln Ala Val Tyr Tyr Tyr Gln Ser
                20                  25                  30
Ala Phe Arg Pro Ser Ser Gly Trp His Lys His Gly Gly Ala Tyr Ala
            35                  40                  45
Val Ala Asn Val Ser Leu Glu Tyr Ala Asn Ala Gly Ser Ser Thr His
        50                  55                  60
Cys Thr Ala Gly Ala Ile Tyr Trp Ser Lys Asn Phe Thr Ala Ser Ser
65                  70                  75                  80
```

```
Val Ala Met Thr Ala Pro Gly Thr Gly Met Ser Trp Ser Thr Ala Gln
                85                  90                  95

Phe Cys Thr Ala His Cys Asn Phe Ser Asp Phe Thr Val Phe Val Thr
            100                 105                 110

His Cys Tyr Lys Ser Gly Asp Val Cys Pro Leu Thr Gly Leu Ile Pro
            115                 120                 125

Ser Gly Tyr Ile Arg Ile Ser Ala Met Thr Lys Gly Thr Thr Ser Leu
        130                 135                 140

Phe Tyr Asn Leu Thr Val Pro Val Thr Lys Tyr Pro Lys Phe Lys Ser
145                 150                 155                 160

Leu Gln Cys Val Asp Asn Phe Thr Ser Val Tyr Leu Asn Gly Asp Leu
                165                 170                 175

Val Phe Thr Ser Asn Glu Thr Lys Asp Val Ser Ala Ala Gly Val His
                180                 185                 190

Phe Lys Ala Gly Gly Pro Ile Thr Tyr Lys Val Met Glu Lys Val Asp
            195                 200                 205

Val Leu Ala Tyr Phe Val Asn Gly Thr Ala Gln Asp Val Ile Leu Cys
            210                 215                 220

Asp Asn Ser Pro Arg Gly Leu Leu Ala Cys Gln Tyr Asn Thr Gly Asn
225                 230                 235                 240

Phe Ser Asp Gly Phe Tyr Pro Phe Thr Asn Ile Ser Leu Val Lys Glu
                245                 250                 255

Lys Phe Ile Val Tyr Arg Glu Thr Ser Val Asn Thr Thr Cys Val Leu
                260                 265                 270

Thr Asn Phe Thr Phe Thr Asn Val Ser Asn Ala Leu Pro Asn Thr Gly
            275                 280                 285

Gly Val Asn Thr Ile Asn Ile Tyr Gln Thr Gln Thr Ala Gln Ser Gly
        290                 295                 300

Cys Tyr Asn Phe Asn Phe Ser Phe Leu Ser Ser Phe Val Tyr Lys Gln
305                 310                 315                 320

Ser Asp Phe Met Tyr Gly Ser Tyr His Pro Lys Cys Asp Phe Arg Pro
                325                 330                 335

Glu Thr Ile Asn Asn Gly Leu Trp Phe Asn Ser Leu Ser Val Ser Leu
            340                 345                 350

Ala Tyr Gly Pro Leu Gln Gly Gly Cys Lys Gln Ser Val Phe Ser Asn
        355                 360                 365

Arg Ala Thr Cys Cys Tyr Ala Tyr Ser Tyr Asn Gly Pro Arg Leu Cys
        370                 375                 380

Lys Gly Val Tyr Ile Gly Glu Leu Gln Gln Tyr Phe Glu Cys Gly Leu
385                 390                 395                 400

Leu Val Tyr Val Thr Lys Ser Asp Gly Ser Arg Ile Gln Thr Arg Asn
                405                 410                 415

Glu Pro Leu Val Leu Thr His His Asn Tyr Asn Asn Ile Thr Leu Asp
            420                 425                 430

Arg Cys Val Glu Tyr Asn Ile Tyr Gly Arg Ser Gly Gln Gly Phe Ile
            435                 440                 445

Thr Asn Val Thr Ala Ala Ala Asn Tyr Asn Tyr Leu Ala Asp Gly
        450                 455                 460

Gly Leu Ala Ile Leu Asp Thr Ser Gly Ala Ile Asp Ile Phe Val Val
465                 470                 475                 480

Gln Gly Glu Tyr Gly Pro Asn Tyr Tyr Lys Val Asn Pro Cys Glu Asp
                485                 490                 495

Val Asn Gln Gln Phe Val Val Ser Gly Gly Gly Ile Val Gly Val Leu
```

```
                500                 505                 510
Thr Ser His Asn Glu Thr Gly Ser Gln Gln Leu Glu Asn Leu Phe Tyr
            515                 520                 525
Val Lys Leu Thr Asn Ser Thr Arg Arg Thr Arg Arg Ser Thr Ile Ala
            530                 535                 540
Asn Val Thr Thr Cys Pro Tyr Val Ser Tyr Gly Arg Phe Cys Ile Lys
545                 550                 555                 560
Pro Asp Gly Leu Val Ser Glu Ile Val Pro Gln Glu Leu Asp Tyr Phe
                565                 570                 575
Val Ala Pro Leu Leu Asn Val Thr Glu His Val Leu Ile Pro Asn Ser
            580                 585                 590
Phe Asn Leu Thr Val Thr Asp Glu Tyr Ile Gln Thr Arg Met Glu Lys
            595                 600                 605
Val Gln Ile Asn Cys Leu Gln Tyr Val Cys Gly Asn Ser Ile Glu Cys
            610                 615                 620
Arg Asn Leu Phe Gln Gln Tyr Gly Pro Val Cys Asp Asn Ile Leu Ser
625                 630                 635                 640
Ile Val Asn Ser Val Gly Gln Arg Glu Asp Met Glu Ser Leu Thr Phe
                645                 650                 655
Tyr Ser Ser Thr Lys Pro Lys Gly Tyr Asn Thr Pro Ile Phe Ser Asn
            660                 665                 670
Ile Ser Thr Gly Asp Phe Asn Ile Ser Leu Met Leu Thr Pro Pro Ser
            675                 680                 685
Ser Pro Ser Gly Arg Ser Phe Ile Glu Asp Leu Leu Phe Thr Ser Val
            690                 695                 700
Glu Thr Val Gly Leu Pro Thr Asp Ala Glu Tyr Lys Lys Cys Thr Ala
705                 710                 715                 720
Gly Pro Leu Gly Thr Leu Lys Asp Leu Ile Cys Ala Arg Glu Tyr Asn
                725                 730                 735
Gly Leu Leu Val Leu Pro Pro Ile Ile Thr Ala Asp Met Gln Thr Met
            740                 745                 750
Tyr Thr Ala Ser Leu Val Gly Ala Met Ala Phe Gly Gly Ile Thr Ser
            755                 760                 765
Ala Ala Ala Ile Pro Phe Ala Thr Gln Ile Gln Ala Arg Ile Asn His
            770                 775                 780
Leu Gly Ile Thr Gln Ser Leu Leu Met Lys Asn Gln Glu Lys Ile Ala
785                 790                 795                 800
Ala Ser Phe Asn Lys Ala Ile Gly His Met Gln Glu Gly Phe Arg Ser
                805                 810                 815
Thr Ser Leu Ala Leu Gln Gln Ile Gln Asp Val Val Asn Lys Gln Ser
            820                 825                 830
Ala Ile Leu Thr Glu Thr Met Asn Ser Leu Asn Lys Asn Phe Gly Ala
            835                 840                 845
Ile Thr Ser Val Ile Gln Asp Ile Tyr Ala Gln Leu Asp Ala Ile Gln
            850                 855                 860
Ala Asp Ala Gln Val Asp Arg Leu Ile Thr Gly Arg Leu Ser Ser Leu
865                 870                 875                 880
Ser Val Leu Ala Ser Ala Lys Gln Ser Glu Tyr Ile Arg Val Ser Gln
                885                 890                 895
Gln Arg Glu Leu Ala Thr Gln Lys Ile Asn Glu Cys Val Lys Ser Gln
            900                 905                 910
Ser Asn Arg Tyr Gly Phe Cys Gly Ser Gly Arg His Val Leu Ser Ile
            915                 920                 925
```

```
Pro Gln Asn Ala Pro Asn Gly Ile Val Phe Ile His Phe Thr Tyr Thr
        930                 935                 940

Pro Glu Ser Phe Val Asn Val Thr Ala Ile Val Gly Phe Cys Val Ser
945                 950                 955                 960

Pro Ala Asn Ala Ser Gln Tyr Ala Ile Val Pro Ala Asn Gly Arg Gly
            965                 970                 975

Ile Phe Ile Gln Val Asn Gly Thr Tyr Tyr Ile Thr Ala Arg Asp Met
            980                 985                 990

Tyr Met Pro Arg Asp Ile Thr Ala Gly Asp Ile Val Thr Leu Thr Ser
        995                 1000                1005

Cys Gln Ala Asn Tyr Val Asn Val Asn Lys Thr Val Ile Thr Thr
        1010                1015                1020

Phe Val Glu Asp Asp Phe Asp Phe Asp Asp Glu Leu Ser Lys
        1025                1030                1035

Trp Trp Asn Glu Thr Lys His Glu Ile Pro Asp Phe Asp Glu Phe
        1040                1045                1050

Asn Tyr Thr Val Pro Ile Leu Asn Ile Ser Ser Glu Ile Asp Arg
        1055                1060                1065

Ile Gln Gly Val Ile Gln Gly Leu Asn Asp Ser Leu Ile Asn Leu
        1070                1075                1080

Glu Glu Leu Ser Ile Ile Lys Thr Tyr Ile Lys Trp Pro Trp Tyr
        1085                1090                1095

Val Trp Leu Ala Ile Gly Phe Ala Ile Ile Phe Ile Leu Ile
        1100                1105                1110

Leu Gly Trp Val Phe Phe Met Thr Gly Cys Cys Gly Cys Cys Cys
        1115                1120                1125

Gly Cys Phe Gly Ile Ile Pro Leu Met Ser Lys Cys Gly Lys Lys
        1130                1135                1140

Ser Ser Tyr Tyr Thr Thr Phe Asp Asn Asp Val Val Thr
        1145                1150                1155

<210> SEQ ID NO 7
<211> LENGTH: 1169
<212> TYPE: PRT
<213> ORGANISM: Avian infectious bronchitis virus

<400> SEQUENCE: 7

Met Leu Val Gln Pro Leu Leu Leu Val Thr Leu Leu Cys Ala Leu Cys
1               5                   10                  15

Ser Ala Ser Leu Tyr Asn Asn Asp Ser Tyr Val Tyr Tyr Tyr Gln Ser
            20                  25                  30

Ala Phe Arg Pro Phe Asn Gly Trp His Leu His Gly Gly Ala Tyr Ala
        35                  40                  45

Val Val Asn Val Ser Gln Glu Thr Ala Asn Ala Gly Ser Ser Pro Ser
    50                  55                  60

Cys Thr Ala Gly Ala Ile Tyr Trp Ser Lys Asn Phe Thr Ala Ser Ser
65                  70                  75                  80

Val Ala Met Thr Ala Pro Leu Gln Gly Met Gln Trp Ser Thr Ile Gln
                85                  90                  95

Phe Cys Thr Ala His Cys Asn Phe Thr Asn Ile Val Val Phe Val Thr
            100                 105                 110

His Cys Tyr Lys Ser Gly Ser Thr Val Cys Pro Leu Thr Gly Leu Ile
        115                 120                 125

Pro Gln Asn His Ile Arg Ile Ser Ala Met Lys Gln Gly Asn Asn Gly
```

```
            130                 135                 140
Pro Ser Gly Leu Phe Tyr Asn Leu Thr Val Pro Val Thr Lys Tyr Ser
145                 150                 155                 160

Lys Phe Lys Ser Leu Gln Cys Val Asn Asn Gln Thr Ser Val Tyr Leu
                165                 170                 175

Asn Gly Asp Leu Val Phe Thr Ser Asn Glu Thr Lys Asp Val Ser Gly
            180                 185                 190

Ala Gly Val Tyr Phe Lys Ala Gly Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Gly Ser Pro Arg Gly Leu Leu Ala Cys Gln Tyr
225                 230                 235                 240

Asn Thr Gly Lys Phe Ser Asp Gly Phe Tyr Pro Phe Thr Asn Asp Thr
                245                 250                 255

Leu Val Lys Glu Lys Phe Ile Val Tyr Arg Glu Asn Ser Val Asn Thr
            260                 265                 270

Thr Cys Thr Leu Thr Asn Phe Thr Phe Tyr Asn Glu Ser Asn Ala Leu
        275                 280                 285

Pro Asn Asn Gly Gly Val Asp Thr Ile Gln Leu Tyr Gln Thr His Thr
    290                 295                 300

Ala Gln Ser Gly Tyr Tyr Asn Phe Asn Phe Ser Phe Leu Ser Ser Phe
305                 310                 315                 320

Gln Tyr Val Glu Ser Asn Phe Met Tyr Gly Ser Tyr His Pro Lys Cys
                325                 330                 335

Gly Phe Arg Pro Glu Ser Ile Asn Asn Gly Leu Trp Phe Asn Ser Leu
            340                 345                 350

Ser Val Ser Leu Ala Tyr Gly Pro Leu Gln Gly Gly Cys Lys Gln Ser
        355                 360                 365

Val Phe His Gly Arg Ala Thr Cys Cys Tyr Ala Tyr Ser Tyr Asn Gly
    370                 375                 380

Pro Thr Leu Cys Lys Gly Val Tyr Ser Gly Glu Leu Thr Arg Ser Tyr
385                 390                 395                 400

Gln Cys Gly Leu Leu Val Phe Val Thr Lys Ser Asp Gly Ser Arg Ile
                405                 410                 415

Gln Thr Ser Thr Lys Pro Ile Val Leu Thr Gln His Asn Tyr Asn Asn
            420                 425                 430

Ile Thr Leu Asp Arg Cys Val Glu Tyr Asn Ile Tyr Gly Arg Val Gly
        435                 440                 445

Gln Gly Phe Ile Thr Asn Val Thr Glu Ser Ala Ala Ala Phe Asn Tyr
    450                 455                 460

Leu Glu Asp Gly Gly Leu Ala Ile Leu Asp Thr Ser Gly Ala Ile Asp
465                 470                 475                 480

Ile Phe Val Val Gln Gly Glu Tyr Gly Phe Asn Tyr Tyr Lys Val Asn
                485                 490                 495

Pro Cys Glu Asp Val Asn Gln Gln Phe Val Val Ser Gly Gly Asn Leu
            500                 505                 510

Val Gly Ile Leu Thr Ser Ile Asn Gln Thr Gly Ser Gln Ser Ile Glu
        515                 520                 525

Asn Gln Phe Tyr Val Lys Leu Thr Asn Gly Ser Arg Arg Ser Arg Arg
    530                 535                 540

Ser Val Ser Glu Asn Val Thr Ser Cys Pro Tyr Val Ser Tyr Gly Lys
545                 550                 555                 560
```

```
Phe Cys Ile Lys Pro Asp Gly Ser Leu Ser Thr Ile Val Pro Lys Glu
            565                 570                 575

Leu Glu Gln Phe Val Ala Pro Leu Leu Asn Val Thr Glu His Val Leu
        580                 585                 590

Ile Pro Asp Ser Phe Asn Leu Thr Val Thr Asp Glu Tyr Ile Gln Thr
        595                 600                 605

Arg Met Asp Lys Val Gln Ile Asn Cys Leu Gln Tyr Val Cys Gly Asn
        610                 615                 620

Ser Phe Glu Cys Arg Lys Leu Phe Gln Gln Tyr Gly Pro Val Cys Asp
625                 630                 635                 640

Asn Ile Leu Ser Val Val Asn Ser Val Gly Gln Lys Glu Asp Met Glu
            645                 650                 655

Leu Leu Ser Phe Tyr Ser Ser Thr Lys Pro Ser Gly Ile Ser Gln Pro
            660                 665                 670

Leu Phe Asn Asn Phe Ser Thr Gly Asp Phe Asn Ile Ser Leu Leu Leu
            675                 680                 685

Thr Ser Pro Ser Ser Pro Ser Gly Arg Ser Phe Ile Glu Asp Leu Leu
        690                 695                 700

Phe Thr Ser Val Glu Ser Val Gly Leu Pro Thr Asp Glu Ala Tyr Lys
705                 710                 715                 720

Lys Cys Thr Ser Gly Pro Leu Gly Phe Val Lys Asp Leu Val Cys Ala
                725                 730                 735

Arg Glu Tyr Asn Gly Leu Leu Val Leu Pro Pro Ile Ile Thr Ala Glu
            740                 745                 750

Met Gln Thr Met Tyr Thr Ser Leu Val Ala Ser Met Ala Leu Gly
            755                 760                 765

Gly Ile Thr Ala Ala Gly Ala Ile Pro Phe Ala Thr Gln Leu Gln Ala
770                 775                 780

Arg Ile Asn His Leu Gly Ile Thr Gln Ser Leu Leu Met Lys Asn Gln
785                 790                 795                 800

Glu Lys Ile Ala Ala Ser Phe Asn Arg Ala Ile Gly His Met Gln Glu
                805                 810                 815

Gly Phe Lys Ser Thr Ser Leu Ala Leu Gln Gln Ile Gln Asp Val Val
                820                 825                 830

Asn Lys Gln Ser Ala Ile Leu Thr Glu Thr Met Ala Ser Leu Asn Lys
            835                 840                 845

Asn Phe Gly Ala Ile Ser Ser Val Leu Gln Asp Ile Tyr Gln Gln Leu
            850                 855                 860

Asp Val Ile Gln Ala Asp Ala Gln Val Asp Arg Ile Ile Thr Gly Arg
865                 870                 875                 880

Leu Ser Ser Leu Ser Val Leu Ala Ser Ala Lys Gln Ser Glu Tyr Ile
                885                 890                 895

Ala Val Ser Gln Gln Arg Ala Leu Ala Thr Gln Lys Ile Asn Glu Cys
                900                 905                 910

Val Lys Ser Gln Ser Thr Arg Tyr Ser Phe Cys Gly Asn Gly Arg His
            915                 920                 925

Val Leu Thr Ile Pro Gln Asn Ala Pro Asn Gly Ile Val Phe Ile His
            930                 935                 940

Phe Thr Tyr Thr Pro Glu Ser Phe Val Asn Val Thr Ala Ile Val Gly
945                 950                 955                 960

Phe Cys Val Lys Pro Pro Asn Ala Ser His Tyr Ala Ile Val Pro Val
                965                 970                 975
```

```
Asn Gly Arg Gly Ile Phe Ile Gln Val Asn Gly Thr Tyr Tyr Ile Thr
                980                 985                 990

Ser Arg Asp Met Tyr Met Pro Arg Asn Ile Thr Ala Gly Asp Ile Val
        995                 1000                1005

Thr Leu Thr Ser Cys Gln Ala Asn Tyr Val Ser Val Asn Lys Thr
    1010                1015                1020

Val Ile Ser Thr Phe Val Glu Asp Asp Phe Asp Phe Asp Asp
    1025                1030                1035

Glu Leu Ser Lys Trp Trp Asn Asp Thr Lys His Glu Leu Pro Asp
    1040                1045                1050

Phe Asp Glu Phe Asn Tyr Thr Ile Pro Val Leu Asn Ile Ser Asn
    1055                1060                1065

Glu Ile Asp Arg Ile Gln Gly Val Ile Gln Gly Leu Asn Asp Ser
    1070                1075                1080

Leu Ile Asp Leu Glu Thr Leu Ser Ile Leu Lys Thr Tyr Ile Lys
    1085                1090                1095

Trp Pro Trp Tyr Val Trp Leu Ala Ile Phe Phe Ala Ile Val Ile
    1100                1105                1110

Phe Ile Leu Ile Ile Gly Trp Val Phe Phe Met Thr Gly Cys Cys
    1115                1120                1125

Gly Cys Cys Cys Gly Cys Phe Gly Ile Ile Pro Leu Met Asn Lys
    1130                1135                1140

Cys Gly Lys Lys Ser Ser Tyr Tyr Thr Thr Phe Asp Asn Asp Val
    1145                1150                1155

Val Thr Glu Gln Tyr Arg Pro Lys Lys Ser Val
    1160                1165

<210> SEQ ID NO 8
<211> LENGTH: 1159
<212> TYPE: PRT
<213> ORGANISM: Avian infectious bronchitis virus

<400> SEQUENCE: 8

Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
                20                  25                  30

Ala Phe Arg Pro Gly His Gly Trp His Leu His Gly Gly Ala Tyr Ala
            35                  40                  45

Val Val Asn Val Ser Ser Glu Asn Asn Asn Ala Gly Thr Ala Pro Ser
        50                  55                  60

Cys Thr Ala Gly Ala Ile Gly Tyr Ser Lys Asn Phe Ser Ala Ala Ser
65                  70                  75                  80

Val Ala Met Thr Ala Pro Leu Ser Gly Met Ser Trp Ser Ala Ser Ser
                85                  90                  95

Phe Cys Thr Ala His Cys Asn Phe Thr Ser Tyr Ile Val Phe Val Thr
            100                 105                 110

His Cys Phe Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Arg Thr
    130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn His Thr Ser Val Tyr Leu
                165                 170                 175
```

```
Asn Gly Asp Leu Val Phe Thr Ser Gly Tyr Thr Glu Asp Val Val Ala
            180                 185                 190

Ala Gly Val His Phe Lys Ser Gly Pro Ile Thr Tyr Lys Val Met
        195                 200                 205

Arg Glu Val Lys Ala Leu Ala Tyr Phe Val Asn Gly Thr Ala His Asp
210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
                260                 265                 270

Thr Cys Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
        290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
                340                 345                 350

Val Ser Leu Thr Tyr Gly Pro Ile Gln Gly Gly Cys Lys Gln Ser Val
            355                 360                 365

Phe Asn Gly Lys Ala Thr Cys Cys Tyr Ala Tyr Ser Tyr Gly Gly Pro
370                 375                 380

Arg Ala Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
                405                 410                 415

Thr Ala Thr Gln Pro Pro Val Leu Thr Gln Asn Phe Tyr Asn Asn Ile
            420                 425                 430

Thr Leu Gly Lys Cys Val Asp Tyr Asn Val Tyr Gly Arg Thr Gly Gln
            435                 440                 445

Gly Phe Ile Thr Asn Val Thr Asp Leu Ala Thr Ser His Asn Tyr Leu
450                 455                 460

Ala Asp Gly Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Leu
                485                 490                 495

Cys Glu Asp Val Asn Gln Gln Phe Val Val Ser Gly Gly Lys Leu Val
                500                 505                 510

Gly Ile Leu Thr Ser Arg Asn Glu Thr Gly Ser Gln Pro Leu Glu Asn
            515                 520                 525

Gln Phe Tyr Ile Lys Ile Thr Asn Gly Thr His Arg Ser Arg Arg Ser
            530                 535                 540

Val Asn Glu Asn Val Thr Asn Cys Pro Tyr Val Ser Tyr Gly Lys Phe
545                 550                 555                 560

Cys Ile Lys Pro Asp Gly Ser Val Ser Pro Ile Val Pro Lys Glu Leu
                565                 570                 575

Glu Gln Phe Val Ala Pro Leu Leu Asn Val Thr Glu Asn Val Leu Ile
            580                 585                 590
```

```
Pro Asn Ser Phe Asn Leu Thr Val Thr Asp Glu Tyr Ile Gln Thr His
            595                 600                 605

Met Asp Lys Ile Gln Ile Asn Cys Leu Gln Tyr Val Cys Gly Asn Ser
610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                645                 650                 655

Leu Ser Phe Tyr Ser Ser Thr Lys Pro Ser Gly Phe Asn Thr Pro Val
            660                 665                 670

Phe Ser Asn Leu Ser Thr Gly Glu Phe Asn Ile Ser Leu Leu Leu Thr
            675                 680                 685

Thr Pro Ser Ser Pro Arg Gly Arg Ser Phe Ile Glu Asp Leu Leu Phe
690                 695                 700

Thr Ser Val Glu Ser Val Gly Leu Pro Thr Asp Glu Ala Tyr Lys Lys
705                 710                 715                 720

Cys Thr Ala Gly Pro Leu Gly Phe Leu Lys Asp Leu Ala Cys Ala Arg
                725                 730                 735

Glu Tyr Asn Gly Leu Leu Val Leu Pro Pro Ile Ile Thr Ala Glu Met
            740                 745                 750

Gln Thr Leu Tyr Thr Ser Ser Leu Val Val Ser Met Ala Phe Gly Gly
            755                 760                 765

Ile Thr Ser Ala Gly Ala Ile Pro Phe Ala Thr Gln Leu Gln Ala Arg
770                 775                 780

Ile Asn His Leu Gly Ile Thr Gln Ser Leu Leu Leu Lys Asn Gln Glu
785                 790                 795                 800

Lys Ile Ala Ala Ser Phe Asn Lys Ala Ile Gly His Met Gln Glu Gly
                805                 810                 815

Phe Arg Ser Thr Ser Leu Ala Leu Gln Gln Ile Gln Asp Val Val Asn
            820                 825                 830

Lys Gln Ser Ala Ile Leu Thr Glu Thr Met Ala Ser Leu Asn Lys Asn
            835                 840                 845

Phe Gly Ala Ile Ser Ser Val Ile Gln Glu Ile Tyr Gln Gln Leu Asp
850                 855                 860

Ala Ile Gln Ala Asn Ala Gln Val Asp Arg Leu Ile Thr Gly Arg Leu
865                 870                 875                 880

Ser Ser Leu Ser Val Leu Ala Ser Ala Lys Gln Ala Glu Tyr Ile Arg
                885                 890                 895

Val Ser Gln Gln Arg Glu Leu Ala Thr Gln Lys Ile Asn Glu Cys Val
            900                 905                 910

Lys Ser Gln Ser Ile Arg Tyr Ser Phe Cys Gly Asn Gly Arg His Val
            915                 920                 925

Leu Thr Ile Pro Gln Asn Ala Pro Asn Gly Ile Val Phe Ile His Phe
930                 935                 940

Ser Tyr Thr Pro Asp Ser Phe Val Asn Val Thr Ala Ile Val Gly Phe
945                 950                 955                 960

Cys Val Lys Pro Ala Asn Ala Ser Gln Tyr Ala Ile Val Pro Ala Asn
                965                 970                 975

Gly Arg Gly Ile Phe Ile Gln Val Asn Gly Ser Tyr Tyr Ile Thr Ala
            980                 985                 990

Arg Asp Met Tyr Met Pro Arg Ala  Ile Thr Ala Gly Asp  Ile Val Thr
            995                 1000                1005

Leu Thr  Ser Cys Gln Ala Asn  Tyr Val Ser Val Asn  Lys Thr Val
```

```
                    1010               1015                1020
Ile Thr  Thr Phe Val Asp Asn  Asp Asp Phe Asp  Phe Asn Asp Glu
         1025                 1030                1035

Leu Ser  Lys Trp Trp Asn Asp  Thr Lys His Glu  Leu Pro Asp Phe
         1040                 1045                1050

Asp Lys  Phe Asn Tyr Thr Val  Pro Ile Leu Asp  Ile Asp Ser Glu
         1055                 1060                1065

Ile Asp  Arg Ile Gln Gly Val  Ile Gln Gly Leu  Asn Asp Ser Leu
         1070                 1075                1080

Ile Asp  Leu Glu Lys Leu Ser  Ile Leu Lys Thr  Tyr Ile Lys Trp
         1085                 1090                1095

Pro Trp  Tyr Val Trp Leu Ala  Ile Ala Phe Ala  Thr Ile Ile Phe
         1100                 1105                1110

Ile Leu  Ile Leu Gly Trp Val  Phe Phe Met Thr  Gly Cys Cys Gly
         1115                 1120                1125

Cys Cys  Cys Gly Cys Phe Gly  Ile Met Pro Leu  Met Ser Lys Cys
         1130                 1135                1140

Gly Lys  Lys Ser Ser Tyr Tyr  Thr Thr Phe Asp  Asn Asp Val Val
         1145                 1150                1155

Thr

<210> SEQ ID NO 9
<211> LENGTH: 11398
<212> TYPE: DNA
<213> ORGANISM: Artificial Sequence
<220> FEATURE:
<223> OTHER INFORMATION: Plasmid Sequence

<400> SEQUENCE: 9
tcgcgcgttt cggtgatgac ggtgaaaacc tctgacacat gcagctcccg gagacggtca     60
cagcttgtct gtaagcggat gccgggagca gacaagcccg tcaggcgcgc tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tcggccgccc gggtaatacg actcactata gggacttaag atagatatta    480
atatatatct attgcactag ccttgcgcta gatttcaaac ttaacaaaac ggacttaaat    540
acctacagct ggtccccata ggtgttccat tgcagtgcac tttagtgccc tggatggcac    600
ctggccacct gtcaggtttt tgttgttaaa atatcattgt tgctggtatc actgcttgtt    660
ttgccgtgtc tcactttata catccgttgc ttgggctacc tagtatccag cgtcctacgg    720
gcgccgtggt cggttcgagt gcgaaggacc tctggttcat ctagcggtag gcgggtgtgt    780
ggaagtagcg cttcagacgt actggttctg ttgcgtgaaa cgcggggtca cctcccccca    840
catacctcta agggcttttg agcctagcgt tgggctacgt tctcgcacaa ggtcggctat    900
acgacgtttg taggggtag tgccaaacaa cccctgaggt gacaggttct ggtggtgttt    960
cgaaaacaac aatgtgtgtg ccgcataata tgcgcgttat gcattttgga gcaggtagtg   1020
ataaaggagt ggcgcctggt agtactgttc ttaaacagtg gctccccgaa ggaacactcc   1080
ttgtcgataa tgatattgta gattatgttt ctgacgcaca cgtttctgtg ctttcagatt   1140
```

```
gcaataaata taagacagag cacaagtttg atcttgtgat atctgatatg tatacagaca   1200
atgattcaaa agaaaagcat gaaggcgtga tagccaataa tggcaatgat gacgtcttca   1260
tatacctttc aagttttcta cgcaataatt tggctctggg aggcagtttt gctgtaaaat   1320
taacagagac aagttggcat gagagtttat atgacattgc acaggattgt gcatggtgga   1380
caatgttttg tacagcagtg aatgcatctt cttcagaagc attcctgatt ggtgttaatt   1440
acttgggtgc aagtgcaaag gttaaagtta gtggaaaaac actgcacgca aattatatat   1500
tttggaggaa ttgtaattat ttacaaacct ctgcttatag tatatttgat gttgctaagt   1560
ttgatttgag attgaaagca acgccagttg ttaatcttaa gactgaacaa agcacagact   1620
tagtctttaa tttgataaag tgtggtaagt tactggtaag agatgttggt aacacctctt   1680
ttactagtga ctcttttgtg tgcactatgt agtgctgctt tgtatgactc gagttcttac   1740
gtgtactact accaaagtgc cttcagacca cctgatggtt ggcatttaca tgggggtgcg   1800
tatgcggttg ttaatatttc tagtgaatct aataatgcag gctcttcatc tgggtgtact   1860
gttggtatta ttcatggtgg tcgtgttgtt aatgcttctt ctatagctat gacggcaccg   1920
tcatcaggta tggcttggtc tagcagtcag ttttgtactg catactgtaa cttttcagat   1980
actacagtgt ttgttacaca ttgttataaa catggtgggt gtcctataac tggcatgctt   2040
caacagcatt ctatacgtgt ttctgctatg aaaaatggcc agcttttcta aatttaaca   2100 gttagtgtag ctaagtaccc tacttttaaa tcatttcagt gtgttaataa tttaacatcc   2160
gtatatttaa atggtgatct tgtttacacc tctaatgaga ccacagatgt tacatctgca   2220
ggtgtttatt ttaaagctgg tggacctata acttataaag ttatgagaga agttagagcc   2280
ctggcttatt ttgttaatgg tactgcacaa gatgttattt tgtgtgatgg gtcacctaga   2340
ggcttgttag catgccagta taatactggc aattttttcag atggcttta tccttttact   2400 aatagtagtt tagttaagca gaagtttatt gtctatcgtg aaaatagtgt taatactact   2460
tttacgttac acaatttcac ttttcataat gagactggcg ccaacccaaa tcctagtggt   2520
gtccagaata ttcaaactta ccaaacacaa acagctcaga gtggttatta aattttaat   2580 ttttcctttc tgagtagttt tgtttataag gagtctaatt ttatgtatgg atcttatcac   2640
ccaagttgta atttagact agaaactatt aataatggtt tgtggtttaa ttcactttca   2700
gttagtattg cttacggtcc tcttcaaggt ggttgcaagc aatctgtctt tagtggtaga   2760
gcaacctgtt gttatgctta ctcatatgga ggtcctttgc tgtgtaaagg tgtttattca   2820
ggtgagttag atcataattt tgaatgtgga ctgttagttt atgttactaa gagcggtggc   2880
tctcgtatac aaacagccac tgaaccgcca gttataactc aacacaatta taataatatt   2940
actttaaata cttgtgttga ttataatata tatggcagaa ctggccaggg ttttattact   3000
aatgtaaccg actcagctgt tagttataat tatctagcag acgcaggttt ggctatttta   3060
gatacatctg gttccataga catctttgtc gtacaaagtg aatatggtct taattattat   3120
aaggttaacc cttgcgaaga tgtcaaccag cagtttgtag tttctggtgg taaattagta   3180
ggtattctta cttcacgtaa tgagactggt tcccagcttc ttgagaatca gttttacatc   3240
aaaatcacta atggaacacg tcgttttaga cgttctatta ctgaaagtgt tgaaaattgc   3300
ccttatgtta gttatggtaa gttttgtata aaacctgatg gcagtattgc cacaatagta   3360
ccaaaacagt tagaacagtt tgtggcacct ttacttaatg ttactgaaaa tgtgctcata   3420
cctaacagtt taatttaac tgttacagat gagtacatac aaactcggat ggataaggtc   3480
caaattaatt gcctgcagta tatttgtggc aattctctgg agtgcagaaa tttgtttcaa   3540
```

```
caatatggtc ctgtttgcga caacatattg tctgtagtaa atagtgttgg tcaaaaagaa    3600
gatatggaac ttttgaattt ctattcttct actaagccgg ctggttttaa tacaccagtt    3660
cttagtaatg ttagcactgg tgagtttaat attactcttt ttttaacaac gcctagtagt    3720
cctagaaggc gttcttttat tgaagacctt ctatttacaa gtgttgaatc tgttggatta    3780
ccaacagatg acgcatacaa aaattgcact gcaggtcctt taggctttct gaaagacctt    3840
gcatgtgctc gtgaatataa tggttttgct tgtgttgcctc ctattataac agcagaaatg    3900
caaactttgt atacaagctc tctagtagct tctatggctt ttggtggtat tactgcagct    3960
ggtgctatac cttttgccac acaactgcag gctagaatta tcacttggg tattacccag    4020 tcacttcttt tgaagaatca agaaaaaatt gctgcttcct ttaataaggc catcggtcat    4080
atgcaggaag gttttagaag tacatcttta gcattacaac aaattcaaga tgttgttaat    4140
aagcagagtg ctattcttac tgagactatg gcatcactta ataaaaattt tggtgccatt    4200
tcttctgtga ttcaagaaat ctaccagcaa cttgacgcca tacaagcaaa tgctcaagtg    4260
gatcgtctta taactggtag attgtcatca cttttctgttt tagcatctgc taagcaggcg    4320
gagtatatta gagtgtcaca acagcgtgag ttagctactc agaagattaa tgagtgtgtt    4380
aagtcacagt ccattaggta ctccttttgt ggtaatggac gacatgtttt aaccataccg    4440
caaaatgcac ctaatggtat agtgtttata cacttttctt acactccaga tagttttgtt    4500
aatgttactg caatagtggg ttttttgtgta aagccagcta atgctagtca gtatgcaata    4560
gtacccgcta atggtagggg tatttttata caagttaatg gtagttacta catcactgca    4620
cgagatatgt atatgccaag agctattact gcaggagata tagttacgct tacttcttgt    4680
caagcaaatt atgtaagtgt aaataagacc gtcattacta cattcgtaga caatgatgat    4740 tttgattta atgacgaatt gtcaaaatgg tggaatgata ctaagcatga gctaccagac    4800
tttgacaaat tcaattacac agtacctata cttgacattg atagtgaaat tgatcgtatt    4860
caaggcgtta tacagggtct taatgactct ctaatagacc ttgaaaaact ttcaatactc    4920
aaaacttata ttaagtggcc ttggtatgtg tggctagcca tagcttttgc cactattatc    4980
ttcatcttaa tattaggatg gtttttcttc atgactgggt gttgtggttg ttgttgtgga    5040
tgctttggca ttatgcctct aatgagtaag tgtggtaaga atcttcttta ttacacgact    5100
tttgataacg atgtggtaac tgaacaatac agacctaaaa agtctgttta atgatccaaa    5160
gtcccactag tttcttaata gtattaattt tgctttggtg taaacttgta ctaagttgtt    5220
ttagagagtt tattattgcc cttcaacaac taacacaagt tttactccaa attatcgata    5280
gtaatttaca gtctagactg acccttttggc acagtctaga ctaatgttaa acttagaagc    5340
aattattgaa accggtgatc aagtgattca aaaaatcagt ttcaatttac agcatatttc    5400
aagtgtatta aacacagaag tatttgaccc ctttgactat tgttattaca gaggaggtaa    5460
tttttgggaa atagagtcag ctgaagattg ttcaggtgat gatgaattta ttgaataagt    5520
cgctagagga gaatggaagt tttctaacgg cacttacat atttgtagga tttttagcat    5580
tttatcttct aggtagagca cttcaagcat ttgtacaggc tgctgatgct tgttgtttat    5640
tttggtacac gtggtagta attccaggag ttaagggtac agcctttgta tacaagtata    5700
catatggtag aaaacttaac aattcggaat tagaagcagt tgttgttaac gagtttccta    5760
agaacggttg gaataataaa aatccagcaa attttcaaga tgtccaacga aacaaattgt    5820
actcttgact ttgaacagtc agttgagctt tttaaagagt ataatttatt tataactgca    5880
```

```
ttcttgttgt tcttaaccat aatacttcag tatggttatg caacgcgtag taagtttatt      5940
tatatactta aaatgatagt gttatggtgc ttttggcccc ttaacattgc agtaggtgta      6000
atttcatgta tatacccacc aaacacagga ggtcttgtcg cagcgataat acttactgtg      6060
tttgcgtgtc tttcttttgt aggttattgg atccagagta ttagactctt taagcggtgt      6120
agatcttggt ggtcatttaa cccagaatct aacgccgtag gttcaatact cctaactaat      6180
ggtcaacaat gtaattttgc tatagagagt gtgccgatgg tgctttctcc tattataaag      6240
aatggtgttc tttattgtga gggtcagtgg cttgctaaat gtgaaccaga ccacttgcct      6300
aaagacatat ttgtatgcac accagataga cgtaatatct atcgtatggt gcagaaatac      6360
actggtgacc aaagcggaaa taagaaaagg tttgctacat ttgtctatgc aaagcagtca      6420
gtagacactg gcgagctaga aagtgtagca acaggtggaa gtagcccttta cacataaatg      6480 tgtgtgtgta gagagtattt aaaattattc ttcaatagtg cctctatttt aagagcgcgg      6540
aagagtattt gttttgagga tattaatata atcctctttt gttttgtact ctctttacaa      6600
gagttattat ttaagcaaca gttttccctt tcctttgttt ggaagaaagt tgttgttaat      6660
ggtgtagaat tccaagtaga aaatggaaaa gtccactacg aaggaaaccc catttttccaa      6720 aaaggttgtt gtaggttgtg gtcccattat aagaaggatt aaatggatta aaccacctac      6780
actacttact tgtaataagg gcgtttggac ttacaagcgc ttaacaaata cagacgatga      6840
aatggctgac tagttttgga agagcagtta tttcttgtta taaagcccta ctattaactc      6900
agttaagagt attagatagg ttaattttag atcacggacc aaagcgagtc ttaacgtgtg      6960
gtaggcgagt gcttttatct caattagatt tagtttatag gttggcatat acgcccaccc      7020
aatcgctggt atgaataata gtaaagataa tccttttcgc ggagcaatag caagaaaagc      7080
gcgaatttat ctgagagaag gattagagtg tgtttacttt cttaacaaag caggacaagc      7140
agagccttgt cccgcgtgta cctccctagt atttcagggg aaaacttgtg aggaacacac      7200
agataataat aatctttttgt catggcgagc ggtaagacaa ctgggaagac agacgcccca      7260
gcgccagtca tcaaactagg agggccaaaa ccacctaaag ttggttcttc tggaaatgct      7320
agctggtttc aagcactaaa agccaagaag ttaaattcac ctcctcctaa gtttgaaggt      7380
agcggcgttc ctgataatga aaatcttaaa ttaagccagc aacatgggta ctggagacgt      7440
caagccaggt acaagccagg taaaggcgga agaaaatcag tcccagatgc ttggtacttc      7500
tattacactg gaacaggacc agccgctgac ctgaattggg gtgatagcca agatggtata      7560
gtgtgggttt ctgcaaaggg tgctgatact aaatctagat ctaaccaggg tacaagggat      7620
cctgataagt ttgaccaata cccgctacga ttctcagatg gaggacctga tggtaatttc      7680
cgttgggact tcattccaat aaatcgtggt aggagtggaa gatcaacagc ggcttcatca      7740
gcagcatcta gtagagcacc gtcgcgtgat ggctcgcgtg gacgtagaag cggagctgaa      7800
gatgatctta tagctcgtgc agcaaagatc attcaggatc agcagaagaa gggttctcgc      7860
attactaaag ctaaggccga tgaaatggct catcgccggt attgtaagcg tactatccca      7920
cctggttata aggttgatca agtatttggt ccccgtacta aaggtaagga gggaaattt       7980 ggtgatgaca agatgaatga ggagggtatt aaggatgggc gcgttacagc aatgctcaac      8040
ctagtcccta gcagccatgc ttgtctttttt ggaagtagag tgacgcccaa acttcaacca      8100
gatgggctgc acttgagatt tgaatttact actgtggttt ctaggatgaa tccgcagttt      8160
gataattatg tgaaaatttg tgatcagtgt gtcgatggtt tagggactcg gccaaaagac      8220
gatgaaccga gaccaaagtc acgcccaaat tcaagacctg ctacaagaac aagttctcca      8280
```

```
gcgccaagac aacagcgtca aaagaaggag aagaagtcaa agaagcagga tgatgaagta   8340
gataaggcat tgacctcaga tgaggagagg aacaatgcac agctggaatt tgatgatgaa   8400
ccgaaagtga ttaactgggg ggattcagca cttggagaga atgagttgta aagctagatt   8460
tccaacttaa catcatggac gtgcgtatgc tgttttcccc tactatagac tttttagcat   8520
attattttt gctatttgta tggtttatta caggtgaaga ttgtatgtat tgttgtaca    8580
ctcgtatgtt ctatattatg ttttctgtag ttgttattag tgttgttctt gttcttactc   8640
tactgttctc ttttctttat tttagagtat caataagaat caaggaagat aggcatgtag   8700
tttgattacc tacatgtcta tcgccaggga aatgtctaat ctgtctactt agtagcctgg   8760
aaacgaacgg tagacccctta gattttaatt tagtttaatt tttagtttag tttaagttag   8820
tttagagtag gtataaagaa gccagtgccg gggccacgcg gagtacgatc gagggtacag   8880
cactaggacg cccactaggg gaagagctaa attttagttt aagttaagtt taattggcta   8940
agtatagtta aaatttatag gctagtatag agttagagca aaaaaaaaa aaaaaaaaa   9000
aaaaaaaaa aaaaaaaaa aaaaaaaaa aaaaaaaaa aaaaaaaaa aaaaaaaaa        9060
aaaaaaaaa aaaaaaaaag tttaaactta attaagaatt cccttggctc gagttcgaaa   9120
tcggatgccg ggaccgacga gtgcagaggc gtgcaagcga gcttggcgta atcatggtca   9180
tagctgtttc ctgtgtgaaa ttgttatccg ctcacaattc cacacaacat acgagccgga   9240
agcataaagt gtaaagcctg gggtgcctaa tgagtgagct aactcacatt aattgcgttg   9300
cgctcactgc ccgctttcca gtcgggaaac ctgtcgtgcc agctgcatta atgaatcggc   9360
caacgcgcgg ggagaggcgg tttgcgtatt gggcgctctt ccgcttcctc gctcactgac   9420
tcgctgcgct cggtcgttcg gctgcggcga gcggtatcag ctcactcaaa ggcggtaata   9480
cggttatcca cagaatcagg ggataacgca ggaaagaaca tgtgagcaaa aggccagcaa   9540
aaggccagga accgtaaaaa ggccgcgttg ctggcgtttt tccataggct ccgcccccct   9600
gacgagcatc acaaaaatcg acgctcaagt cagaggtggc gaaacccgac aggactataa   9660
agataccagg cgtttccccc tggaagctcc ctcgtgcgct ctcctgttcc gaccctgccg   9720
cttaccggat acctgtccgc ctttctccct tcgggaagcg tggcgctttc tcatagctca   9780
cgctgtaggt atctcagttc ggtgtaggtc gttcgctcca agctgggctg tgtgcacgaa   9840
ccccccgttc agcccgaccg ctgcgcctta tccggtaact atcgtcttga gtccaacccg   9900
gtaagacacg acttatcgcc actggcagca gccactggta acaggattag cagagcgagg   9960
tatgtaggcg gtgctacaga gttcttgaag tggtggccta actacggcta cactagaaga  10020
acagtatttg gtatctgcgc tctgctgaag ccagttacct tcggaaaaag agttggtagc  10080
tcttgatccg gcaaacaaac caccgctggt agcggtggtt ttttgtttg caagcagcag   10140
attacgcgca gaaaaaaagg atctcaagaa gatcctttga tcttttctac ggggtctgac  10200
gctcagtgga acgaaaactc acgttaaggg attttggtca tgagattatc aaaaaggatc  10260
ttcacctaga tccttttaaa ttaaaaatga agttttaaat caatctaaag tatatatgag  10320
taaacttggt ctgacagtta ccaatgctta atcagtgagg cacctatctc agcgatctgt  10380
ctatttcgtt catccatagt tgcctgactc cccgtcgtgt agataactac gatacggag   10440
ggcttaccat ctggccccag tgctgcaatg ataccgcgag acccacgctc accggctcca  10500
gatttatcag caataaacca gccagccgga agggccgagc gcagaagtgg tcctgcaact  10560
ttatccgcct ccatccagtc tattaattgt tgccgggaag ctagagtaag tagttcgcca  10620
```

| | |
|---|---:|
| gttaatagtt tgcgcaacgt tgttgccatt gctacaggca tcgtggtgtc acgctcgtcg | 10680 |
| tttggtatgg cttcattcag ctccggttcc caacgatcaa ggcgagttac atgatccccc | 10740 |
| atgttgtgca aaaagcggt tagctccttc ggtcctccga tcgttgtcag aagtaagttg | 10800 |
| gccgcagtgt tatcactcat ggttatggca gcactgcata attctcttac tgtcatgcca | 10860 |
| tccgtaagat gcttttctgt gactggtgag tactcaacca agtcattctg agaatagtgt | 10920 |
| atgcggcgac cgagttgctc ttgcccggcg tcaatacggg ataataccgc gccacatagc | 10980 |
| agaactttaa aagtgctcat cattggaaaa cgttcttcgg ggcgaaaact ctcaaggatc | 11040 |
| ttaccgctgt tgagatccag ttcgatgtaa cccactcgtg cacccaactg atcttcagca | 11100 |
| tcttttactt tcaccagcgt ttctgggtga gcaaaaacag gaaggcaaaa tgccgcaaaa | 11160 |
| aagggaataa gggcgacacg gaaatgttga atactcatac tcttcctttt tcaatattat | 11220 |
| tgaagcattt atcagggtta ttgtctcatg agcggataca tatttgaatg tatttagaaa | 11280 |
| aataaacaaa taggggttcc gcgcacattt ccccgaaaag tgccacctga cgtctaagaa | 11340 |
| accattatta tcatgacatt aacctataaa aataggcgta tcacgaggcc ctttcgtc | 11398 |

<210> SEQ ID NO 10
<211> LENGTH: 11398
<212> TYPE: DNA
<213> ORGANISM: Artificial Sequence
<220> FEATURE:
<223> OTHER INFORMATION: Plasmid Sequence

<400> SEQUENCE: 10

| | |
|---|---:|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt ggagatcggt acttcgcgaa | 420 |
| tgcgtcgaga tcggccgccc gggtaatacg actcactata gggacttaag atagatatta | 480 |
| atatatatct attgcactag ccttgcgcta gatttcaaac ttaacaaaac ggacttaaat | 540 |
| acctacagct ggtccccata ggtgttccat tgcagtgcac tttagtgccc tggatggcac | 600 |
| ctggccacct gtcaggtttt tgttgttaaa atatcattgt tgctggtatc actgcttgtt | 660 |
| ttgccgtgtc tcactttata catccgttgc ttgggctacc tagtatccag cgtcctacgg | 720 |
| gcgccgtggt cggttcgagt gcgaaggacc tctggttcat ctagcggtag gcgggtgtgt | 780 |
| ggaagtagcg cttcagacgt actggttctg ttgcgtgaaa cgcggggtca cctccccca | 840 |
| catacctcta agggcttttg agcctagcgt tgggctacgt tctcgcacaa ggtcggctat | 900 |
| acgacgtttg taggggtag tgccaaacaa cccctgaggt gacaggttct ggtggtgttt | 960 |
| cgaaaacaac aatgtgtgtg ccgcataata tgcgcgttat gcattttgga gcaggtagtg | 1020 |
| ataaaggagt ggcgcctggt agtactgttc ttaaacagtg gctccccgaa ggaacactcc | 1080 |
| ttgtcgataa tgatattgta gattatgttt ctgacgcaca cgtttctgtg ctttcagatt | 1140 |
| gcaataaata taagacagag cacaagtttg atcttgtgat atctgatatg tatacagaca | 1200 |
| atgattcaaa aagaaagcat gaaggcgtga tagccaataa tggcaatgat gacgtcttca | 1260 |
| tatacctttc aagttttcta cgcaataatt tggctctggg aggcagtttt gctgtaaaat | 1320 |

```
taacagagac aagttggcat gagagtttat atgacattgc acaggattgt gcatggtgga   1380
caatgttttg tacagcagtg aatgcatctt cttcagaagc attcctgatt ggtgttaatt   1440
acttgggtgc aagtgcaaag gttaaagtta gtggaaaaac actgcacgca aattatatat   1500
tttggaggaa ttgtaattat ttacaaacct ctgcttatag tatatttgat gttgctaagt   1560
ttgatttgag attgaaagca acgccagttg ttaatcttaa gactgaacaa aagacagact   1620
tagtctttaa tttgataaag tgtggtaagt tactggtaag agatgttggt aacacctctt   1680
ttactagtga ctcttttgtg tgcactatgt agtgctgctt tgtatgactc gagttcttac   1740
gtgtactact accaaagtgc cttcagacca cctgatggtt ggcatttaca tgggggtgcg   1800
tatgcggttg ttaatatttc tagtgaatct aataatgcag gctcttcatc tgggtgtact   1860
gttggtatta ttcatggtgg tcgtgttgtt aatgcttctt ctatagctat gacggcaccg   1920
tcatcaggta tggcttggtc tagcagtcag ttttgtactg catactgtaa cttttcagat   1980
actacagtgt tgttacaca ttgttataaa catggtgggt gtcctataac tggcatgctt   2040
caacagcatt ctatacgtgt ttctgctatg aaaaatggcc agcttttcta aatttaaca   2100 gttagtgtag ctaagtaccc tacttttaaa tcatttcagt gtgttaataa tttaacatcc   2160
gtatatttaa atggtgatct tgtttacacc tctaatgaga ccacagatgt tacatctgca   2220
ggtgtttatt ttaaagctgg tggacctata acttataaag ttatgagaga agttagagcc   2280
ctggcttatt ttgttaatgg tactgcacaa gatgttattt tgtgtgatgg gtcacctaga   2340
ggcttgttag catgccagta taatactggc aattttttcag atggctttta tccttttact   2400
aatagtagtt tagttaagca gaagtttatt gtctatcgtg aaaatagtgt taatactact   2460
tgtacgttac acaatttcac ttttcataat gagactggcg ccaacccaaa tcctagtggt   2520
gtccagaata ttcaaactta ccaaacacaa acagctcaga gtggttatta taattttaat   2580
ttttcctttc tgagtagttt tgtttataag gagtctaatt ttatgtatgg atcttatcac   2640
ccaagttgta attttagact agaaactatt aataatggtt tgtggtttaa ttcactttca   2700
gttagtattg cttacggtcc tcttcaaggt ggttgcaagc aatctgtctt tagtggtaga   2760
gcaacctgtt gttatgctta ctcatatgga ggtcctttgc tgtgtaaagg tgtttattca   2820
ggtgagttag atcataattt tgaatgtgga ctgttagttt atgttactaa gagcggtggc   2880
tctcgtatac aaacagccac tgaaccgcca gttataactc aacacaatta taataatatt   2940
actttaaata cttgtgttga ttataatata tatggcagaa ctggccaggg ttttattact   3000
aatgtaaccg actcagctgt tagttataat tatctagcag acgcaggttt ggctatttta   3060
gatacatctg gttccataga catctttgtc gtacaaagtg aatatggtct taattattat   3120
aaggttaacc cttgcgaaga tgtcaaccag cagtttgtag tttctggtgg taaattagta   3180
ggtattctta cttcacgtaa tgagactggt tcccagcttc ttgagaatca gttttacatc   3240
aaaatcacta atggaacacg tcgttttaga cgttctatta ctgaaagtgt tgaaaattgc   3300
ccttatgtta gttatggtaa gttttgtata aaacctgatg gcagtattgc cacaatagta   3360
ccaaaacagt tagaacagtt tgtggcacct ttacttaatg ttactgaaaa tgtgctcata   3420
cctaacagtt ttaatttaac tgttacagat gagtacatac aaactcggat ggataaggtc   3480
caaattaatt gcctgcagta tatttgtggc aattctctgg agtgcagaaa tttgtttcaa   3540
caatatggtc ctgtttgcga caacatattg tctgtagtaa atagtgttgg tcaaaaagaa   3600
gatatggaac ttttgaattt ctattcttct actaagccgg ctggttttaa tacaccagtt   3660
```

```
cttagtaatg ttagcactgg tgagtttaat attactcttt ttttaacaac gcctagtagt    3720
cctagaaggc gttcttttat tgaagacctt ctatttacaa gtgttgaatc tgttggatta    3780
ccaacagatg acgcatacaa aaattgcact gcaggtcctt taggctttct gaaagacctt    3840
gcatgtgctc gtgaatataa tggtttgctt gtgttgcctc ctattataac agcagaaatg    3900
caaactttgt atacaagctc tctagtagct tctatggctt ttggtggtat tactgcagct    3960
ggtgctatac cttttgccac acaactgcag gctagaatta atcacttggg tattacccag    4020
tcacttcttt tgaagaatca agaaaaaatt gctgcttcct ttaataaggc catcggtcat    4080
atgcaggaag gttttagaag tacatcttta gcattacaac aaattcaaga tgttgttaat    4140
aagcagagtg ctattcttac tgagactatg gcatcactta ataaaaattt tggtgccatt    4200
tcttctgtga ttcaagaaat ctaccagcaa cttgacgcca tacaagcaaa tgctcaagtg    4260
gatcgtctta taactggtag attgtcatca ctttctgttt tagcatctgc taagcaggcg    4320
gagtatatta gagtgtcaca acagcgtgag ttagctactc agaagattaa tgagtgtgtt    4380
aagtcacagt ccattaggta ctccttttgt ggtaatggac acatgttttt aaccataccg    4440
caaaatgcac ctaatggtat agtgtttata cactttcctt acactccaga tagttttgtt    4500
aatgttactg caatagtggg ttttttgtgta aagccagcta atgctagtca gtatgcaata    4560
gtacccgcta atggtagggg tattttttata caagttaatg gtagttacta catcactgca    4620
cgagatatgt atatgccaag agctattact gcaggagata tagttacgct tacttcttgt    4680
caagcaaatt atgtaagtgt aaataagacc gtcattacta cattcgtaga caatgatgat    4740
tttgatttta atgacgaatt gtcaaaatgg tggaatgata ctaagcatga gctaccagac    4800
tttgacaaat tcaattacac agtacctata cttgacattg atagtgaaat tgatcgtatt    4860
caaggcgtta tacagggtct taatgactct ctaatagacc ttgaaaaact ttcaatactc    4920
aaaacttata ttaagtggcc ttggtatgtg tggctagcca tagcttttgc cactattatc    4980
ttcatcttaa tattaggatg ggttttcttc atgactgggt gttgtggttg ttgttgtgga    5040
tgctttggca ttatgcctct aatgagtaag tgtggtaaga atcttcttta ttacacgact    5100
tttgataacg atgtggtaac tgaacaatac agacctaaaa agtctgtttat atgatccaaa    5160
gtcccactag tttcttaata gtattaattt tgctttggtg taaacttgta ctaagttgtt    5220
ttagagagtt tattattgcc cttcaacaac taacacaagt tttactccaa attatcgata    5280
gtaatttaca gtctagactg acccttggc acagtctaga ctaatgttaa acttagaagc    5340
aattattgaa accggtgatc aagtgattca aaaaatcagt ttcaatttac agcatatttc    5400
aagtgtatta aacacagaag tatttgaccc cttttgactat tgttattaca gaggaggtaa    5460
tttttgggaa atagagtcag ctgaagattg ttcaggtgat gatgaattta ttgaataagt    5520
cgctagagga gaatggaagt tttctaacgg cactttacat atttgtagga tttttagcat    5580
tttatcttct aggtagagca cttcaagcat ttgtacaggc tgctgatgct tgttgtttat    5640
tttggtacac gtggttagta attccaggag ttaagggtac agcctttgta tacaagtata    5700
catatggtag aaaacttaac aattcggaat tagaagcagt tgttgttaac gagtttcctta    5760
agaacggttg gaataataaa aatccagcaa attttcaaga tgtccaacga acaaattgt    5820
actcttgact ttgaacagtc agttgagctt tttaaagagt ataatttatt tataactgca    5880
ttcttgttgt tcttaaccat aatacttcag tatggttatg caacgcgtag taagtttatt    5940
tatatactta aaatgatagt gttatggtgc ttttggcccc ttaacattgc agtaggtgta    6000
atttcatgta tatacccacc aaaacacagga ggtcttgtcg cagcgataat acttactgtg    6060
```

```
tttgcgtgtc tttcttttgt aggttattgg atccagagta ttagactctt taagcggtgt    6120
agatcttggt ggtcatttaa cccagaatct aacgccgtag gttcaatact cctaactaat    6180
ggtcaacaat gtaattttgc tatagagagt gtgccgatgg tgctttctcc tattataaag    6240
aatggtgttc tttattgtga gggtcagtgg cttgctaaat gtgaaccaga ccacttgcct    6300
aaagacatat ttgtatgcac accagataga cgtaatatct atcgtatggt gcagaaatac    6360
actggtgacc aaagcggaaa taagaaaagg tttgctacat ttgtctatgc aaagcagtca    6420
gtagacactg gcgagctaga aagtgtagca acaggtggaa gtagccttta cacataaatg    6480
tgtgtgtgta gagagtattt aaaattattc ttcaatagtg cctctatttt aagagcgcgg    6540
aagagtattt gttttgagga tattaatata aatcctcttt gttttgtact ctctttacaa    6600
gagttattat ttaagcaaca gttttcctt tcctttgttt ggaagaaagt tgttgttaat    6660
ggtgtagaat tccaagtaga aaatggaaaa gtccactacg aaggaaaccc cattttccaa    6720
aaaggttgtt gtaggttgtg gtcccattat aagaaggatt aaatggatta aaccacctac    6780
actacttact tgtaataagg gcgtttggac ttacaagcgc ttaacaaata cagacgatga    6840
aatggctgac tagttttgga agagcagtta tttcttgtta taaagcccta ctattaactc    6900
agttaagagt attagatagg ttaattttag atcacggacc aaagcgagtc ttaacgtgtg    6960
gtaggcgagt gcttttatct caattagatt tagtttatag gttggcatat acgcccaccc    7020
aatcgctggt atgaataata gtaaagataa tccttttcgc ggagcaatag caagaaaagc    7080
gcgaatttat ctgagagaag gattagagtg tgtttacttt cttaacaaag caggacaagc    7140
agagccttgt cccgcgtgta cctccctagt atttcagggg aaaacttgtg aggaacacac    7200
agataataat aatcttttgt catggcgagc ggtaagacaa ctgggaagac agacgcccca    7260
gcgccagtca tcaaactagg agggccaaaa ccacctaaag ttggttcttc tggaaatgct    7320
agctggtttc aagcactaaa agccaagaag ttaaattcac ctcctcctaa gtttgaaggt    7380
agcggcgttc ctgataatga aaatcttaaa ttaagccagc aacatgggta ctggagacgt    7440
caagccaggt acaagccagg taaaggcgga agaaaatcag tcccagatgc ttggtacttc    7500
tattacactg gaacaggacc agccgctgac ctgaattggg gtgatagcca agatggtata    7560
gtgtgggttt ctgcaaaggg tgctgatact aaatctagat ctaaccaggg tacaagggat    7620
cctgataagt ttgaccaata cccgctacga ttctcagatg gaggacctga tggtaatttc    7680
cgttgggact tcattccaat aaatcgtggt aggagtggaa gatcaacagc ggcttcatca    7740
gcagcatcta gtagagcacc gtcgcgtgat ggctcgcgtg gacgtagaag cggagctgaa    7800
gatgatctta tagctcgtgc agcaaagatc attcaggatc agcagaagaa gggttctcgc    7860
attactaaag ctaaggccga tgaaatggct catcgccggt attgtaagcg tactatccca    7920
cctggttata aggttgatca agtatttggt ccccgtacta aggtaaggga ggaaattttt    7980
ggtgatgaca agatgaatga ggagggtatt aaggatgggc gcgttacagc aatgctcaac    8040
ctagtcccta gcagccatgc ttgtctttt ggaagtagag tgacgcccaa acttcaacca    8100
gatgggctgc acttgagatt tgaatttact actgtggttt ctaggatga tccgcagttt    8160 gataattatg tgaaaatttg tgatcagtgt gtcgatggta tagggactcg gccaaaagac    8220
gatgaaccga gaccaaagtc acgcccaaat tcaagacctg ctacaagaac aagttctcca    8280
gcgccaagac aacagcgtca aaagaaggag aagaagtcaa agaagcagga tgatgaagta    8340
gataaggcat tgacctcaga tgaggagagg aacaatgcac agctggaatt tgatgatgaa    8400
```

```
ccgaaagtga ttaactgggg ggattcagca cttggagaga atgagttgta aagctagatt    8460
tccaacttaa catcatggac gtgcgtatgc tgtttttccc tactatagac ttttagcat    8520 attatttttt gctatttgta tggtttatta caggtgaaga ttgtatgtat ttgttgtaca    8580
ctcgtatgtt ctatattatg ttttctgtag ttgttattag tgttgttctt gttcttactc    8640
tactgttctc ttttctttat tttagagtat caataagaat caaggaagat aggcatgtag    8700
tttgattacc tacatgtcta tcgccaggga aatgtctaat ctgtctactt agtagcctgg    8760
aaacgaacgg tagacccttta gattttaatt tagtttaatt tttagtttag tttaagttag    8820
tttagagtag gtataaagaa gccagtgccg gggccacgcg gagtacgatc gagggtacag    8880
cactaggacg cccactaggg gaagagctaa attttagttt aagttaagtt taattggcta    8940
agtatagtta aaatttatag gctagtatag agttagagca aaaaaaaaaa aaaaaaaaaa    9000
aaaaaaaaaa aaaaaaaaaa aaaaaaaaaa aaaaaaaaaa aaaaaaaaaa aaaaaaaaaa    9060
aaaaaaaaaa aaaaaaaaag tttaaactta attaagaatt cccttggctc gagttcgaaa    9120
tcggatgccg ggaccgacga gtgcagaggc gtgcaagcga gcttggcgta atcatggtca    9180
tagctgtttc ctgtgtgaaa ttgttatccg ctcacaattc cacacaacat acgagccgga    9240
agcataaagt gtaagcctg gggtgcctaa tgagtgagct aactcacatt aattgcgttg    9300
cgctcactgc ccgctttcca gtcgggaaac ctgtcgtgcc agctgcatta atgaatcggc    9360
caacgcgcgg ggagaggcgg tttgcgtatt gggcgctctt ccgcttcctc gctcactgac    9420
tcgctgcgct cggtcgttcg gctgcggcga gcggtatcag ctcactcaaa ggcggtaata    9480
cggttatcca cagaatcagg ggataacgca ggaaagaaca tgtgagcaaa aggccagcaa    9540
aaggccagga accgtaaaaa ggccgcgttg ctggcgtttt tccataggct ccgcccccct    9600
gacgagcatc acaaaaatcg acgctcaagt cagaggtggc gaaacccgac aggactataa    9660
agataccagg cgtttccccc tggaagctcc ctcgtgcgct ctcctgttcc gaccctgccg    9720
cttaccggat acctgtccgc ctttctccct tcgggaagcg tggcgctttc tcatagctca    9780
cgctgtaggt atctcagttc ggtgtaggtc gttcgctcca agctgggctg tgtgcacgaa    9840
ccccccgttc agcccgaccg ctgcgcctta tccggtaact atcgtcttga gtccaacccg    9900
gtaagacacg acttatcgcc actggcagca gccactggta acaggattag cagagcgagg    9960
tatgtaggcg gtgctacaga gttcttgaag tggtggccta actacggcta cactagaaga    10020
acagtatttg gtatctgcgc tctgctgaag ccagttacct tcggaaaaag agttggtagc    10080
tcttgatccg gcaaacaaac caccgctggt agcggtggtt tttttgtttg caagcagcag    10140
attacgcgca gaaaaaaagg atctcaagaa gatcctttga tcttttctac ggggtctgac    10200
gctcagtgga acgaaaactc acgttaaggg attttggtca tgagattatc aaaaaggatc    10260
ttcacctaga tccttttaaa ttaaaaatga agttttaaat caatctaaag tatatatgag    10320
taaacttggt ctgacagtta ccaatgctta atcagtgagg cacctatctc agcgatctgt    10380
ctatttcgtt catccatagt tgcctgactc cccgtcgtgt agataactac gatacggag    10440 ggcttaccat ctggccccag tgctgcaatg ataccgcgag acccacgctc accggctcca    10500
gatttatcag caataaacca gccagccgga agggccgagc gcagaagtgg tcctgcaact    10560
ttatccgcct ccatccagtc tattaattgt tgccgggaag ctagagtaag tagttcgcca    10620
gttaatagtt tgcgcaacgt tgttgccatt gctacaggca tcgtggtgtc acgctcgtcg    10680
tttggtatgg cttcattcag ctccggttcc caacgatcaa ggcgagttac atgatccccc    10740
atgttgtgca aaaaagcggt tagctccttc ggtcctccga tcgttgtcag aagtaagttg    10800
```

```
gccgcagtgt tatcactcat ggttatggca gcactgcata attctcttac tgtcatgcca  10860
tccgtaagat gcttttctgt gactggtgag tactcaacca agtcattctg agaatagtgt  10920
atgcggcgac cgagttgctc ttgcccggcg tcaatacggg ataataccgc gccacatagc  10980
agaactttaa aagtgctcat cattggaaaa cgttcttcgg ggcgaaaact ctcaaggatc  11040
ttaccgctgt tgagatccag ttcgatgtaa cccactcgtg cacccaactg atcttcagca  11100
tcttttactt tcaccagcgt ttctgggtga gcaaaaacag gaaggcaaaa tgccgcaaaa  11160
aagggaataa gggcgacacg gaaatgttga atactcatac tcttcctttt tcaatattat  11220
tgaagcattt atcagggtta ttgtctcatg agcggataca tatttgaatg tatttagaaa  11280
aataaacaaa tagggggttcc gcgcacattt ccccgaaaag tgccacctga cgtctaagaa  11340
accattatta tcatgacatt aacctataaa aataggcgta tcacgaggcc ctttcgtc    11398
```

<210> SEQ ID NO 11
<211> LENGTH: 1155
<212> TYPE: PRT
<213> ORGANISM: Avian infectious bronchitis virus

<400> SEQUENCE: 11

```
Met Leu Asp Lys Pro Leu Leu Leu Val Thr Leu Trp Tyr Ala Leu Cys
1               5                   10                  15

Ser Ala Leu Leu Tyr Asp Asn Asn Thr Tyr Val Tyr Tyr Gln Ser
            20                  25                  30

Ala Phe Arg Pro Gly Pro Gly Trp His Leu Tyr Gly Gly Ala Tyr Ala
            35                  40                  45

Val Asp Arg Val Phe Asn Glu Thr Asn Asn Ala Gly Ser Ala Ser Asp
        50                  55                  60

Cys Thr Ala Gly Thr Phe Tyr Glu Ser His Asn Ile Ser Ala Ser Ser
65                  70                  75                  80

Val Ala Met Thr Val Pro His Asn Gly Met Ser Trp Ser Ala Ser Gln
                85                  90                  95

Phe Cys Thr Ala His Cys Asn Phe Ser Asp Phe Thr Val Phe Val Thr
            100                 105                 110

His Cys Phe Lys Asn Gln Leu Gly Ser Cys Pro Leu Thr Gly Met Ile
        115                 120                 125

Pro Gln Asn His Ile Arg Ile Ser Ala Met Arg Asp Gly Val Leu Phe
    130                 135                 140

Tyr Asn Leu Thr Val Ser Val Ser Lys Tyr Pro Arg Phe Lys Ser Leu
145                 150                 155                 160

Gln Cys Val Ser Asn Ser Thr Ser Val Tyr Val Asn Gly Asp Leu Val
                165                 170                 175

Phe Thr Ser Asn Glu Thr Ser Tyr Val Thr Gly Ala Gly Val Tyr Phe
            180                 185                 190

Lys Ser Gly Gly Pro Val Thr Tyr Lys Val Met Lys Glu Val Lys Ala
        195                 200                 205

Leu Ala Tyr Phe Ile Asn Gly Thr Ala Gln Glu Val Ile Leu Cys Asp
    210                 215                 220

Asn Ser Pro Arg Gly Leu Leu Ala Cys Gln Tyr Asn Thr Gly Asn Phe
225                 230                 235                 240

Ser Asp Gly Phe Tyr Pro Phe Thr Asn His Ser Leu Val Lys Asp Arg
                245                 250                 255

Phe Ile Val Tyr Arg Glu Ser Ser Thr Asn Thr Thr Leu Lys Leu Thr
            260                 265                 270
```

```
Asn Phe Ser Phe Thr Asn Val Ser Asn Ala Ser Pro Asn Ser Gly Gly
        275                 280                 285

Val Asp Thr Phe Gln Leu Tyr Gln Thr Ser Thr Ala Gln Asp Gly Tyr
    290                 295                 300

Tyr Asn Phe Asn Leu Ser Phe Leu Ser Ser Phe Val Tyr Lys Pro Ser
305                 310                 315                 320

Asp Phe Met Tyr Gly Ser Tyr His Pro His Cys Lys Phe Arg Pro Glu
                325                 330                 335

Asn Ile Asn Asn Gly Leu Trp Phe Asn Ser Leu Ser Val Ser Leu Thr
                340                 345                 350

Tyr Gly Pro Ile Gln Gly Gly Cys Lys Gln Ser Val Phe Ser Asn Arg
            355                 360                 365

Ala Thr Cys Cys Tyr Ala Tyr Ser Tyr Gln Gly Pro Ser Arg Cys Lys
        370                 375                 380

Gly Val Tyr Arg Gly Glu Leu Thr Gln Tyr Phe Glu Cys Gly Leu Leu
385                 390                 395                 400

Val Tyr Val Thr Lys Ser Asp Gly Ser Arg Ile Gln Thr Arg Ser Glu
                405                 410                 415

Pro Leu Val Leu Thr Gln Tyr Asn Tyr Asn Asn Ile Thr Leu Asn Lys
            420                 425                 430

Cys Val Glu Tyr Asn Ile Tyr Gly Arg Val Gly Gln Gly Phe Ile Thr
        435                 440                 445

Asn Val Thr Glu Ala Thr Ala Asn Tyr Ser Tyr Leu Ala Asp Gly Gly
        450                 455                 460

Leu Ala Ile Leu Asp Thr Ser Gly Ala Ile Asp Ile Phe Val Val Gln
465                 470                 475                 480

Gly Ala Tyr Gly Leu Asn Tyr Tyr Lys Val Asn Pro Cys Glu Asp Val
                485                 490                 495

Asn Gln Gln Phe Val Val Ser Gly Gly Asn Leu Val Gly Ile Leu Thr
            500                 505                 510

Ser His Asn Glu Thr Gly Ser Glu Ser Ile Glu Asn Gln Phe Tyr Ile
        515                 520                 525

Lys Leu Thr Asn Gly Thr Arg Arg Ser Arg Arg Ser Val Thr Gly Asn
        530                 535                 540

Val Thr Asn Cys Pro Tyr Val Ser Tyr Gly Lys Phe Cys Ile Lys Pro
545                 550                 555                 560

Asp Gly Ser Leu Ser Ile Ile Val Pro Gln Glu Leu Glu Gln Phe Val
                565                 570                 575

Ala Pro Leu Phe Asn Val Thr Glu His Val Leu Ile Pro Asp Ser Phe
            580                 585                 590

Asn Leu Thr Val Thr Asp Glu Tyr Ile Gln Thr Arg Met Asp Lys Val
        595                 600                 605

Gln Ile Ile Cys Leu Gln Tyr Val Cys Gly Asn Ser Ile Glu Cys Arg
        610                 615                 620

Lys Leu Phe Gln Gln Tyr Gly Pro Val Cys Asp Asn Ile Leu Ser Val
625                 630                 635                 640

Val Asn Gly Val Gly Gln Arg Glu Asp Met Glu Leu Leu Ser Phe Tyr
                645                 650                 655

Ser Ser Thr Lys Pro Ser Gly Tyr Asn Thr Pro Ile Phe Asn Asn Val
            660                 665                 670

Ser Thr Gly Asp Phe Asn Ile Ser Leu Leu Leu Thr Pro Pro Asn Ser
        675                 680                 685
```

```
Pro Thr Gly Arg Ser Phe Ile Glu Asp Leu Leu Phe Thr Ser Val Glu
    690             695                 700

Ser Val Gly Leu Pro Thr Asp Glu Glu Tyr Lys Lys Cys Thr Ala Gly
705             710                 715                 720

Pro Leu Gly Phe Val Lys Asp Leu Val Cys Ala Arg Glu Tyr Asn Gly
            725                 730                 735

Leu Leu Val Leu Pro Pro Ile Ile Thr Ala Glu Met Gln Thr Met Tyr
            740                 745                 750

Thr Ser Ser Leu Val Ala Ser Met Ala Leu Gly Gly Ile Thr Ala Ala
        755                 760                 765

Gly Ala Ile Pro Phe Ala Thr Gln Leu Gln Ala Arg Ile Asn His Leu
770                 775                 780

Gly Ile Thr Asn Ser Leu Leu Leu Lys Asn Gln Glu Lys Ile Ala Ala
785                 790                 795                 800

Ser Phe Asn Lys Ala Ile Gly His Met Gln Glu Gly Phe Lys Ser Thr
                805                 810                 815

Ser Leu Ala Leu Gln Gln Ile Gln Asp Val Val Asn Lys Gln Ser Ser
            820                 825                 830

Ile Leu Thr Glu Thr Met Gln Ser Leu Asn Lys Asn Phe Gly Ala Ile
        835                 840                 845

Ser Ser Val Ile Gln Asp Ile Tyr Gln Gln Leu Asp Ala Ile Gln Ala
850                 855                 860

Asp Ala Gln Val Asp Arg Leu Ile Thr Gly Arg Leu Ser Ser Leu Ser
865                 870                 875                 880

Val Leu Ala Ser Ala Lys Gln Ala Glu Tyr His Arg Val Ser Gln Gln
                885                 890                 895

Arg Glu Leu Ala Thr Gln Lys Ile Asn Glu Cys Val Lys Ser Gln Ser
            900                 905                 910

Asn Arg Tyr Ser Phe Cys Gly Asn Gly Arg His Val Leu Thr Ile Pro
        915                 920                 925

Gln Asn Ala Pro Asn Gly Ile Val Phe Ile His Phe Thr Tyr Thr Pro
    930                 935                 940

Glu Ser Phe Val Asn Val Thr Ala Ile Val Gly Phe Cys Val Asn Pro
945                 950                 955                 960

Ala Asn Ala Ser His Tyr Ala Ile Val Pro Val Asn Gly Arg Gly Val
                965                 970                 975

Phe Ile Glu Val Asn Gly Ser Tyr Tyr Ile Thr Ala Arg Asp Met Tyr
            980                 985                 990

Met Pro Arg Asp Ile Thr Ala Gly Asp Ile Val Thr Leu Thr Ser Cys
        995                 1000                1005

Gln Ala Asn Tyr Val Asn Val Asn Lys Thr Val Ile Asn Thr Phe
    1010                1015                1020

Val Glu Asp Asp Asp Phe Asp Phe Tyr Asp Glu Leu Ser Lys Trp
    1025                1030                1035

Trp Asn Asp Thr Lys His Glu Leu Pro Asp Phe Asp Glu Phe Asn
    1040                1045                1050

Tyr Thr Val Pro Val Leu Asn Ile Ser Asn Glu Ile Asp Arg Ile
    1055                1060                1065

Gln Gln Val Ile Gln Gly Leu Asn Asp Ser Leu Ile Asp Leu Glu
    1070                1075                1080

Thr Leu Ser Ile Leu Lys Thr Tyr Ile Lys Trp Pro Trp Tyr Val
    1085                1090                1095

Trp Leu Ala Ile Ala Phe Leu Thr Ile Ile Phe Ile Leu Val Leu
```

```
                    1100                1105                1110
Cys Trp Ile Phe Phe Met Thr Gly Cys Cys Gly Cys Cys Cys Gly
        1115                1120                1125

Cys Phe Gly Ile Ile Pro Leu Met Ser Lys Cys Gly Lys Lys Ser
        1130                1135                1140

Ser Tyr Tyr Thr Thr Phe Asp Asn Asp Val Val Thr
        1145                1150                1155

<210> SEQ ID NO 12
<211> LENGTH: 11860
<212> TYPE: DNA
<213> ORGANISM: Artificial Sequence
<220> FEATURE:
<223> OTHER INFORMATION: Plasmid Sequence

<400> SEQUENCE: 12
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ggagatcggt acttcgcgaa     420
tgcgtcgaga tgagctctaa tacgactcac tataggggact taagtgtgat ataaatatat     480
atcatacata ctagccttgt gctagatttc aacttaaca aaacggactt aaatacctac     540
agttggtccc tataggtgtt ccattgcagt gcactttagt gccctggatg cacctggcc     600 acctgtcagg tttttgttat taaaataata ttgttgctgg tatcactgct tgttttgccg     660
tgtctcactt tatacatccg ttgcttgggc tacctagtat ccagcgtcct actggcgttg     720
tggtcggttc gagtgcgaag aacctctggt tcatctagcg gtacgcgggt gtgtggaagt     780
agcgcttcag acgtaccggt tctgttgcgt gaaatacggg gtcacctccc cccacatacc     840
tctaagggct tttgagccta gcgttgggct acgttctcgc acaaggtcgg ctatacggcg     900
tttgtagggg gtagtgccaa acaacccctg aggtgacagg ttctggtggt gtttcgaaaa     960
caacaatgtg tgtgccgcat aatatgcgag taatgcattt tggagcagga agtgacaaag    1020
gagtggcccc aggtagcgct gttcttaggc agtggcttcc cgaaggtaca ctccttgtcg    1080
ataatgatat tgtagattat gtatctgatg cacatgtctc tgtgctttca gattgcaata    1140
aatgtaaaac agagcacaag tttgatcttg tgatatctga tatgtataca gataatgatt    1200
caaagagaaa gcatgaaggc gttgtagcca ataacggcaa tgatgacgtc ttcatatacc    1260
tttcaaactt tcttcgtaac aatttagctc tgggaggcag ttttgccgta aaagtaacag    1320
agacaagttg gcatgagagt ttatatgaca ttgcacagga ttgtgcatgg tggacaatgt    1380
tttgtacagc agtgaatgct tcttcgtcag aagcattctt gattggtgtt aattatttgg    1440
gtgcaagtga aaaggttaga gttagtggta aaccctgca cgcaaattat atattttgga    1500
ggaattgtaa ttatttacaa acttcagcct atagtatatt tgacgttgct aagttttgatt    1560 tgaaattaaa agcaacgcca gttgtgaatt tgaaaactga acaaaagaca gacttagtct    1620
ttaatttaat taagtgtggt aagttactgg taagagatgt tggacaaacc gcttttacta    1680
gtgactcttt ggtatgcact atgtagtgct ttgctctatg ataataatta tattggtgat    1740
```

```
tttagatgta tccagcttgt gaactcaaac ggtgctaatg ttagtgctcc aagcattagc    1800
actgagaccg ttgaagtttc acaaggcctg gggacatatt atgtgttaga tcgagtttat    1860
ttaaatgcca cattattgct tactggttac tacccggtcg atggttctaa gtttagaaac    1920
ctcgctctta cgggaactaa ctcagttagc ttgtcgtggt ttcaaccacc ctatttaagt    1980
cagtttaatg atggcatatt tgcgaaggtg cagaaccttg agacaagtac gccatcaggt    2040
gcaactgcat attttcctac tatagttata ggtagtttgt ttggctatac ttcctatacc    2100
gttgtaatag agccatataa tggtgttata atggcctcag tgtgccagta taccatttgt    2160
cagttacctt acactgattg taagcctaac actaatggta ataagcttat agggttttgg    2220
cacacggatg taaaacccc  aatttgtgtg ttaaagcgaa atttcacgct taatgttaat    2280
gctgatgcat tttatttca  tttttaccaa catggtggta cttttatgc  gtactatgcg    2340 gataaaccct ccgctactac gttttgttt  agtgtatata ttggcgatat tttaacacag    2400
tattatgtgt tacctttcat ctgcaaccca acagctggta gcacttttgc tccgcgctat    2460
tgggttacac ctttggttaa gcgccaatat ttgtttaatt tcaaccagaa gggtgtcatt    2520
actagtgctg ttgattgtgc tagtagttat accagtgaaa taaatgtaa  gacccagagc    2580 atgttaccta gcactggtgt ctatgagtta tccggttata cggtccaacc agttggagtt    2640
gtataccggc gtgttgctaa cctcccagct tgtaatatag aggagtggct tactgctagg    2700 tcagtccccct ccctctcaa ctgggagcgt aagacttttc agaattgtaa ttttaattta    2760
agcagcctgt tacgttatgt tcaggctgag agtttgtttt gtaataatat cgatgcttcc    2820
aaagtgtatg gcaggtgctt tggtagtatt tcagttgata gtttgctgt  accccgaagt    2880 aggcaagttg atttacagct tggtaactct ggatttctgc agactgctaa ttataagatt    2940
gatacagctg ccacttcgtg tcagctgcat tacaccttgc ctaagaataa tgtcaccata    3000
aacaaccata ccccctcgtc ttggaatagg aggtatggct ttaatgatgc tggcgtcttt    3060
ggcaaaaacc aacatgacgt tgtttacgct cagcaatgtt ttactgtaag atctagttat    3120
tgcccgtgtg ctcaaccgga catagttagc ccttgcacta ctcagactaa gcctaagtct    3180
gcttttgtta atgtgggtga ccattgtgaa ggcttaggtg ttttagaaga taattgtggc    3240
aatgctgatc cacataaggg ttgtatctgt gccaacaatt catttattgg atggtcacat    3300
gatacctgcc ttgttaatga tcgctgccaa attttttgcta atatattgtt aaatggcatt    3360
aatagtggta ccacatgttc cacagatttg cagttgccta atactgaagt ggttactggc    3420
atttgtgtca aatatgacct ctacggtatt actggacaag tgtttttaa  agaggttaag    3480 gctgactatt ataatagctg gcaaaccctt ctgtatgatg ttaatggtaa tttgaatggt    3540
tttcgtgatc ttaccactaa caagacttat acgataagga ctgttatag  tggccgtgtt    3600 tctgctgcat ttcataaaga tgcacccgaa ccggctctgc tctatcgtaa tataaattgt    3660
agctatgttt ttagcaataa tatttcccgt gaggagaacc cacttaatta ctttgatagt    3720
tatttgggtt gtgttgttaa tgctgataac cgcacggatg aggcgcttcc taattgtgat    3780
ctccgtatgg gtgctggctt atgcgttgat tattcaaaat cacgcagggc tcaccgatca    3840
gtttctactg gctatcggtt aactacattt gagccataca ctccgatgtt agttaatgat    3900
agtgtccaat ccgttgatgg attatatgag atgcaaatac caaccaattt tactattggg    3960
caccatgagg agttcattca aactagatct ccaaaggtga ctatagattg tgctgcattt    4020
gtctgtggta taacactgc  atgcaggcag cagtggttga gtatggctc  tttctgtgtt    4080 aatgttaatg ccattcttaa tgaggttaat aacctcttgg ataatatgca actacaagtt    4140
```

```
gctagtgcat taatgcaggg tgttactata agttcgagac tgccagacgg catctcaggc   4200
cctatagatg acattaattt tagtcctcta cttggatgca taggttcaac atgtgctgaa   4260
gacggcaatg gacctagtgc aatccgaggg cgttctgcta tagaggattt gttatttgac   4320
aaggtcaaat tatctgatgt tggctttgtc gaggcttata ataattgcac cggtggtcaa   4380
gaagttcgtg acctcctttg tgtacaatct tttaatggca tcaaagtatt acctcctgtg   4440
ttgtcagaga gtcagatctc tggctacaca accggtgcta ctgcggcagc tatgttccca   4500
ccgtggtcag cagctgccgg tgtgccattt agtttaagtg ttcaatatag aattaatggt   4560
ttaggtgtca ctatgaatgt gcttagtgag aaccaaaaga tgattgctag tgcttttaac   4620
aatgcgctgg gtgctatcca ggatgggttt gatgcaacca attctgcttt aggtaagatc   4680
cagtccgttg ttaatgcaaa tgctgaagca ctcaataact tactaaatca actttctaac   4740
aggtttggtg ctattagtgc ttctttacaa gaaattctaa ctcggcttga ggctgtagaa   4800
gcaaaagccc agatagatcg tcttattaat ggcaggttaa ctgcacttaa tgcgtatata   4860
tccaagcaac ttagtgatag tacgcttatt aaagttagtg ctgctcaggc catagaaaag   4920
gtcaatgagt gcgttaagag ccaaaccacg cgtattaatt tctgtggcaa tggtaatcat   4980
atattatctc ttgtccagaa tgcgccttat ggcttatatt ttatacactt cagctatgtg   5040
ccaatatcct ttacaaccgc aaatgtgagt cctggacttt gcatttctgg tgatagagga   5100
ttagcaccta agctggata ttttgttcaa gatgatggag aatggaagtt cacaggcagt   5160
tcatattact accctgaacc cattacagat aaaaacagtg tcattatgag tagttgcgca   5220
gtaaactaca caaaggcacc tgaagttttc ttgaacactt caatacctaa tccacccgac   5280
tttaaggagg agttagataa atggtttaag aatcagacgt ctattgcgcc tgatttatct   5340
ctcgatttcg agaagttaaa tgttactttg ctggacctga cgtatgagat gaacaggatt   5400
caggatgcaa ttaagaagtt aaatgagagc tacatcaacc tcaaggaagt tggcacatat   5460
gaaatgtatg tgaaatggcc ttggtatgtg tggcttgcca ttgcattcct taccattatt   5520
tttattctgg tacttgttg gatattttc atgaccggtt gttgcggttg ttgttgtgga   5580
tgctttggta tcataccgtt aatgagtaag tgtggtaaga atcttcttta ctacacgact   5640
tttgataatg atgtggtaac ttaacaatac agacctaaaa agtctgttta atgattaaaa   5700
gtcccacatc ttttctaata ttattaattc ttcctttggtg taaacttgca ttaagttgtt   5760
ttaaagagtg tgttataaca ctccagcaac tagtacaaat tttactccaa attattaata   5820
gtaacttaca atctagactt ctgctttggc acagtctaga ctaatgttag attttgaagc   5880
aattattgaa actggtcagc aaataactca acaaattagt ttctatttac agcatatttc   5940
aagggtgcta agtactgaat tatttgaccc ctttgaagtt tgtgtttaca gaggaggtaa   6000
ttgttgggag ttagagtcag ctgacgagtt ttcaggtgat gacgaatata ttgagtagat   6060
cgctcgagga gaacggaagt tttctaacag cggtttacgt gttttttagga tttttagcac   6120 tttatctact aggtagagcg cttcaagctt ttgtacaagc ggctgacgct tgttgtcttt   6180
tttggtatac atgggtagta gttcctggag ccaagggcac agcctttgtt tataatcata   6240
catatggtaa aaaacttaac aaaccggagt tagaaacggt tattgttaac gaatttccaa   6300
aaaacggttg gaaatatgga taataccatc aattgtactc ttggtactga acaagcagtt   6360
cagcttttta aggaatataa tctgtttgta actgcattcc tgttgttttt aaccatacta   6420
cttcagtatg gatacgcaac taggagcaag gttatttaca tactgaaaat gatagtgtta   6480
```

```
tggtgctttt ggcccttaa cattgcagta ggtgtaatct catgtatata cccaccaaac    6540
acaggaggtc ttgtcgcagc gataattctt acagtgtttg cgtgtctttc ttttataggt    6600
tattggatcc agagtattag acttttaag cggtgcaggt catggtggtc atttaacccc    6660
gaatctaatg ccgtaggttc aatactccta actaatggtc aacaatgtaa tttgctata    6720
gagagtgtgc cgatggtgct ttctcctatt ataaagaatg gtgctcttta ttgcgagggt    6780
cagtggcttg ctaaatgtga accagaccac ttgcctagag atatatttgt atgcacaccg    6840
gatagacgta atatctatcg tatggtgcaa aaatatactg gtgaccaaag cggaagtaag    6900
aaaaggtttg ccacatttgt ctatgcaaag cagtcagtag atactggcga gctagaaagt    6960
gtgtcagcag taggaggtag tcttacaca taaatgtgtg tgtgtagaga gtatttaaaa    7020
ttattctttg acagtgcctc cgttttaaga gcgcggaaga gtattatttt tgaggatatt    7080
aatataaatc ctctttgttt catactctcc tttcaggagt tattatttaa aaaacagttt    7140
ttccactctt ttgtgccaaa aacaattgtt gttaatggtg taaccttca ggtagacaat    7200
ggaaaagtct actacgaagg aagaccaatt ttccaaaaag gttgttgtag tttgtggtcc    7260
aattataaga aagattagaa taattaaacc acctacaaca cttatttta caaatggcgt    7320
tttaggttac aaacgcttaa caaatacgga tgatgaaatg gctgactagt tttggaagag    7380
ctttcatctc ctgttataaa tccctattac taactcaatt aagagtatta gataggttaa    7440
ttttagatca cggacccaag cgcacattaa cgtgtgctag gcgagtgctt ttagttcaat    7500
tagatttagt ttataggttg gcttatacgc ccacccaatc gctggtatga ataatagtaa    7560
agataatcct tttcgcggag caatagcaag aaaagcgcga attatctga gaggaggatt    7620
agattgtgtt tactttctta acaaagcagg acaagcagag ccttgtcccg cgtgtacctc    7680
cctagtattc caagggaaaa cttgtgagga acactattat aataacaatc ttttgtcatg    7740
gcaagcggta aggcaactgg aaagacagac gccccagcgc cagtcatcaa actaggagga    7800
ccaaagccac ctaagttgg ttcttctgga aatgcatcat ggtttcaacc gataaaggcc    7860
aagaagctaa attcacctgt gcctaaattt gacggtagtg gtgttcctga aaatgaaaat    7920
ctcaagtcaa gccagcaaca tggatactgg agacgccaac acaggttaa gcctggcaaa    7980
ggtggaagaa aaccagtccc tgatgcttgg tacttttact acactggaac aggaccggcc    8040
gccgacctga ttgggtga aactcaagat ggtatagtgt gggttgctgc aaagggtgct    8100
gatactaaat ctagatcaaa ccagggtaca agggatcctg ataagtttga ccaataccca    8160
ctacgattct cagatggagg accggatggt aatttccgtt gggacttcat accaataaat    8220
cgtggtagga gtgggagatc aacagcagct tcatcagcag catctagtag agcaccatct    8280
cgtgagggt cacgtggacg tagaagcgga gttgaagatg atcttatagc tcgcgcagca    8340
aagattatac aggaccagca aaagaagggt gcgcgcatta ccaaggctaa gctgatgaa    8400
atggctcatc gccgctattg caagcgcact atcccacctg gttataaggt tgagcaagta    8460
tttggtcccc gtactaaagg taaggaagga aattttggtg atgacaagat gaatgaggaa    8520
ggtgttaagg atgggcgtgt tacggcaatg ctcaacctag tccctagcag tcatgcttgt    8580
ctttttggaa gtagggtgac gcccaaactg cagccagatg tcttcacct gagatttgaa    8640
tttactactg tggtgtcacg tgatgatccg cagtttgata attatgtgaa aatttgtgat    8700
cagtgtgtcg atggtgtagg gacgcgtcca aaggacgatg aatcgagacc aaagtcacgc    8760
ccaaattcaa gacctgcaac tagaggaaat tctccagcgc cgagacaaca gcgcccaaag    8820
aaggagaaaa agcccaagaa gcaggatgat gaagtagata aggcattgac ctcagatgag    8880
```

```
gagaggaaca atgcacagct ggaatttgat gatgaaccca aggtgattaa ctgggggggac   8940
tctgcactag gtgaaaatga actttgatta acataatgga cttgctgcat ttgctgtcac   9000
attttgttaa atattatttt tgtgttttac tatcaattat tacaggtatt gattgtgatt   9060
atgttcaata cttaagcttc ttctggttgc tttttgcttg ttgtattgtt gctgtgcttt   9120
ttattattgt gattctcatt agtttgcttt atcgtagaaa ttcaatagta agagttaagg   9180
aagataggca tgtagcttag cacctacatg tctatcgcca gggaaatgtc taatctgtct   9240
acttagtagc ctggaaacga acggtagacc cttagatttt aatttagttt aattttttagt  9300
ttagtttaag ttagtttaga gtaggtataa agatgccagt gccggggcca cgcgtagtac   9360
gaccgagggt acagcactag gacgcccact aggggaagag ctaaattttta gtttaagtta   9420
agtttaattg gctaaatata gttaaaattt ataggctagt atagagttag agcaaaaaaa   9480
aaaaaaaaaa aaaaaaaaaa aaaaaaaaaa aaaaaaaaaa aaaaaaaaaa aaaaaaaaaa   9540
aaaaaaaaaa aaaaaaaaaa aaaaaaaaaa aaagcggccg catcggatgc cgggaccgac   9600
gagtgcagag gcgtgcaagc gagcttggcg taatcatggt catagctgtt tcctgtgtga   9660
aattgttatc cgctcacaat tccacacaac atacgagccg aagcataaa gtgtaaagcc   9720
tggggtgcct aatgagtgag ctaactcaca ttaattgcgt tgcgctcact gcccgctttc   9780
cagtcgggaa acctgtcgtg ccagctgcat taatgaatcg gccaacgcgc ggggagaggc   9840
ggtttgcgta ttgggcgctc ttccgcttcc tcgctcactg actcgctgcg ctcggtcgtt   9900
cggctgcggc gagcggtatc agctcactca aaggcggtaa tacggttatc cacagaatca   9960
ggggataacg caggaaagaa catgtgagca aaaggccagc aaaaggccag gaaccgtaaa  10020
aaggccgcgt tgctggcgtt tttccatagg ctccgccccc ctgacgagca tcacaaaaat  10080
cgacgctcaa gtcagaggtg gcgaaacccg acaggactat aaagatacca ggcgtttccc  10140
cctggaagct ccctcgtgcg ctctcctgtt ccgaccctgc cgcttaccgg atacctgtcc  10200
gcctttctcc cttcgggaag cgtggcgctt tctcatagct cacgctgtag gtatctcagt  10260
tcggtgtagg tcgttcgctc caagctgggc tgtgtgcacg aaccccccgt tcagcccgac  10320
cgctgcgcct tatccggtaa ctatcgtctt gagtccaacc cggtaagaca cgacttatcg  10380
ccactggcag cagccactgg taacaggatt agcagagcga ggtatgtagg cggtgctaca  10440
gagttcttga agtggtggcc taactacggg tacactagaa gaacagtatt tggtatctgc  10500
gctctgctga agccagttac cttcggaaaa agagttggta gctcttgatc cggcaaacaa  10560
accaccgctg gtagcggtgg tttttttgtt tgcaagcagc agattacgcg cagaaaaaaa  10620
ggatctcaag aagatccttt gatcttttct acggggtctg acgctcagtg aacgaaaac   10680
tcacgttaag ggattttggt catgagatta tcaaaaagga tcttcaccta gatccttta   10740
aattaaaaat gaagttttaa atcaatctaa agtatatatg agtaaacttg gtctgacagt  10800
taccaatgct taatcagtga ggcacctatc tcagcgatct gtctatttcg ttcatccata  10860
gttgcctgac tccccgtcgt gtagataact acgatacggg agggcttacc atctggcccc  10920
agtgctgcaa tgataccgcg agacccacgc tcaccggctc cagatttatc agcaataaac  10980
cagccagccg gaagggccga gcgcagaagt ggtcctgcaa ctttatccgc ctccatccag  11040
tctattaatt gttgccggga agctagagta agtagttcgc cagttaatag tttgcgcaac  11100
gttgttgcca ttgctacagg catcgtggtg tcacgctcgt cgtttggtat ggcttcattc  11160
agctccggtt cccaacgatc aaggcgagtt acatgatccc ccatgttgtg caaaaaagcg  11220
```

| | | | | | |
|---|---|---|---|---|---|
| gttagctcct | tcggtcctcc | gatcgttgtc | agaagtaagt | tggccgcagt | gttatcactc | 11280 |
| atggttatgg | cagcactgca | taattctctt | actgtcatgc | catccgtaag | atgctttct | 11340 |
| gtgactggtg | agtactcaac | caagtcattc | tgagaatagt | gtatgcggcg | accgagttgc | 11400 |
| tcttgcccgg | cgtcaatacg | ggataatacc | gcgccacata | gcagaacttt | aaaagtgctc | 11460 |
| atcattggaa | aacgttcttc | ggggcgaaaa | ctctcaagga | tcttaccgct | gttgagatcc | 11520 |
| agttcgatgt | aacccactcg | tgcacccaac | tgatcttcag | catcttttac | tttcaccagc | 11580 |
| gtttctgggt | gagcaaaaac | aggaaggcaa | aatgccgcaa | aaaagggaat | aagggcgaca | 11640 |
| cggaaatgtt | gaatactcat | actcttcctt | tttcaatatt | attgaagcat | ttatcagggt | 11700 |
| tattgtctca | tgagcggata | catatttgaa | tgtatttaga | aaaataaaca | aatagggtt | 11760 |
| ccgcgcacat | ttccccgaaa | agtgccacct | gacgtctaag | aaaccattat | tatcatgaca | 11820 |
| ttaacctata | aaaataggcg | tatcacgagg | ccctttcgtc | | | 11860 |

<210> SEQ ID NO 13
<211> LENGTH: 6905
<212> TYPE: DNA
<213> ORGANISM: Artificial Sequence
<220> FEATURE:
<223> OTHER INFORMATION: Plasmid Sequence

<400> SEQUENCE: 13

| | | | | | |
|---|---|---|---|---|---|
| ttaattaagt | gtggtaagtt | actggtaaga | gatgttggac | aaaccgcttt | tactagtgac | 60 |
| tctttggtat | gcactatgta | gtgctttgct | ctatgataat | aatacttacg | tttactacta | 120 |
| ccaaagtgcc | tttaggcctg | gtccaggttg | gcacctatat | gggggtgctt | atgcagtaga | 180 |
| tagggttttt | aatgaaacca | acaatgcagg | cagtgcatct | gattgcactg | ctggtacttt | 240 |
| ttatgaaagc | cataatattt | ctgcttcttc | tgtagccatg | acagtaccac | ataatggtat | 300 |
| gtcttggtca | gcttcacaat | tttgtacagc | tcattgtaac | ttctcagact | tacagtgtt | 360 |
| cgttacgcat | tgttttaaaa | atcaactcgg | tagttgtccc | ttgacaggta | tgattcctca | 420 |
| gaatcatatt | cgtatttctg | ctatgagaga | tggagttttg | ttttataact | taacagttag | 480 |
| cgtatctaaa | tacctagat | ttaaatcgct | tcaatgtgtt | agcaattcta | catctgtcta | 540 |
| tgtaaatggt | gaccttgttt | tcacttctaa | tgaaacttct | tacgttacgg | gtgcaggcgt | 600 |
| ttattttaaa | agtggtgggc | ctgtaactta | taaagttatg | aaagaagtta | aagccctagc | 660 |
| ctactttatt | aatggtaccg | cacaagaggt | tatttatgt | gataactcac | ctagaggttt | 720 |
| gcttgcatgt | cagtataaca | ctggtaattt | ttcagatgga | ttctacccct | ttactaatca | 780 |
| ttctttagtt | aaggataggt | ttattgtata | tcgagaaagt | agcactaaca | ctactttaaa | 840 |
| gttaactaat | ttcagttttta | ctaatgtaag | taatgcttct | cctaattcag | gtggcgttga | 900 |
| tacttttcaa | ttatatcaaa | caagtactgc | tcaggatggt | tattataatt | ttaatttatc | 960 |
| atttctgagt | agttttgtgt | ataaaccatc | tgattttatg | tatgggtcat | accacccaca | 1020 |
| ttgtaagttt | agaccagaga | atattaataa | tggcttatgg | tttaattcat | tatctgtgtc | 1080 |
| acttacttac | ggacccattc | aaggtggttg | taagcaatct | gttttagta | atagagcaac | 1140 |
| ttgttgctat | gcttattctt | atcaagggcc | tagtagatgt | aagggtgttt | atagagggga | 1200 |
| gctaacgcaa | tactttgaat | gtggacttct | agtttacgta | actaagagtg | atggctctcg | 1260 |
| tatacaaact | agaagtgaac | cactggtgtt | aactcaatat | aattataaca | acattacttt | 1320 |
| aaataagtgt | gttgagtata | atatatatgg | tagggttggt | caaggttta | ttactaatgt | 1380 |
| aactgaagca | actgctaatt | atagttatct | agcagatggt | ggtttagcta | ttttagatac | 1440 |

```
ctcaggagcc atagacatat ttgttgttca aggtgcatat ggtcttaatt attataaggt    1500
taatccctgt gaagatgtta accaacagtt tgtagtgtct ggtggcaact tagttggcat    1560
tcttacatct cataatgaaa caggttctga atctattgag aaccagtttt acatcaaact    1620
cactaacgga acacgtcgct ctagacgttc tgttactggg aatgttacaa attgcccttta   1680 tgttagttat ggcaagtttt gtataaaacc agatggttct ttatctataa tagtaccaca    1740
agaattagaa cagtttgtgg cgcctttatt caatgttact gagcatgtgc tcatacctga    1800
tagttttaat ttaactgtca cagatgagta catacaaact cgtatggata aggttcaaat    1860
tatttgcctt cagtatgttt gtggtaattc tattgaatgc agaaagttgt ttcagcagta    1920
tggacctgtt tgtgataata tattgtctgt tgtaaatggt gtaggtcaaa gagaggatat    1980 ggaacttttta gtttctatt cttctactaa acctagtggt tacaatacac caattttttaa   2040 taatgttagc actggtgact ttaatatttc gctcctacta acaccaccta atagtcctac     2100
tgggcgctct tttattgaag atcttctctt tacaagtgta gaatctgttg gattaccaac    2160
tgatgaagag tataaaaagt gtacagcagg acctttaggt tttgttaaag accttgtttg    2220
tgctagagag tataatggtt tgctcgttct gcctcctatt attactgcgg aaatgcaaac    2280
catgtatact agttctttag tagcctctat ggctttaggt ggcattactg cagctggtgc    2340 tataccttttt gctacacaac tgcaggccag aattaaccat ttgggtatta ctaattctct   2400
tttgttgaaa aaccaagaaa aaattgctgc ttcctttaat aaggccatcg gtcatatgca    2460
ggaagggttt aaaagtactt ctctagcatt acaacagatt caagatgttg ttaataaaca    2520
gagttctatt cttacagaga ctatgcaatc acttaataaa aattttggtg ctatttcctc    2580
tgtaattcaa gacatttacc agcaactaga tgctattcag gcagatgctc aggttgatcg    2640
tcttattaca ggtagactct cttcactatc tgttttagct tctgctaaac aggcagagta    2700
tcatagagtg tcacaacagc gtgagttggc cactcagaaa attaatgagt gtgttaagtc    2760
tcagtctaat aggtattcat tttgtggtaa tggtagacat gttctaacca taccacagaa    2820
tgcacccaat ggcatagtgt ttatacactt tacatacact ccagagagtt ttgttaatgt    2880
tacggcaata gtagggtttt gcgtaaaccc agctaatgct agtcattatg caatagtgcc    2940
tgttaatggc aggggtgttt ttatagaagt taatggtagt tactatatca ctgctcgtga    3000
tatgtatatg ccaagagata ttactgcagg agacatagtc actttgactt cttgtcaagc    3060
aaactatgtt aatgtaaata aaaccgtcat taacacttttt gtggaagatg acgattttga   3120 ttttatgat gaattgtcaa aatggtggaa tgatactaag catgagctac cagatttttga   3180 tgaattcaat tataccgttc cagttttaaa tattagtaat gaaattgaca gaattcaaca    3240
ggttattcag ggattaaatg attccctaat agaccttgaa acactctcaa ttctcaaaac    3300
ttatattaaa tggccttggt atgtgtggct tgccattgca ttccttacca ttatttttat    3360
tctggtactt tgttgatat ttttcatgac cggttgttgc ggttgttgtt gtggatgctt      3420
tggtatcata ccgttaatga gtaagtgtgg taagaaatct tcttactaca cgacttttga    3480
taatgatgtg gtaacttaac aatacagacc taaaaagtct gtttaatgat taaaagtccc    3540
acatcttttc taatattatt aattcttctt tggtgtaaac ttgcattaag ttgttttaaa    3600
gagtgtgtta taacactcca gcaactagta caaattttac tccaaattat taatagtaac    3660
ttacaatcta gacttctgct ttggcacagt ctagactaat gttagatttt gaagcaatta    3720
ttgaaactgg tcagcaaata actcaacaaa ttagtttcta tttacagcat atttcaaggg    3780
```

```
tgctaagtac tgaattattt gaccccttttg aagtttgtgt ttacagagga ggtaattgtt    3840
gggagttaga gtcagctgac gagttttcag gtgatgacga atatattgag tagatcgctc    3900
gagaatcact agtgcggccg cctgcaggtc gaccatatgg gagagctccc aacgcgttgg    3960
atgcatagct tgagtattct atagtgtcac ctaaatagct tggcgtaatc atggtcatag    4020
ctgtttcctg tgtgaaattg ttatccgctc acaattccac acaacatacg agccggaagc    4080
ataaagtgta aagcctgggg tgcctaatga gtgagctaac tcacattaat tgcgttgcgc    4140
tcactgcccg ctttccagtc gggaaacctg tcgtgccagc tgcattaatg aatcggccaa    4200
cgcgcgggga gaggcggttt gcgtattggg cgctcttccg cttcctcgct cactgactcg    4260
ctgcgctcgg tcgttcggct gcggcgagcg gtatcagctc actcaaaggc ggtaatacgg    4320
ttatccacag aatcagggga taacgcagga aagaacatgt gagcaaaagg ccagcaaaag    4380
gccaggaacc gtaaaaaggc cgcgttgctg gcgtttttcc ataggctccg cccccctgac    4440
gagcatcaca aaaatcgacg ctcaagtcag aggtggcgaa acccgacagg actataaaga    4500
taccaggcgt ttccccctgg aagctccctc gtgcgctctc ctgttccgac cctgccgctt    4560
accggatacc tgtccgcctt tctcccttcg ggaagcgtgg cgctttctca tagctcacgc    4620
tgtaggtatc tcagttcggt gtaggtcgtt cgctccaagc tgggctgtgt gcacgaaccc    4680
cccgttcagc ccgaccgctg cgccttatcc ggtaactatc gtcttgagtc caacccggta    4740
agacacgact tatcgccact ggcagcagcc actggtaaca ggattagcag agcgaggtat    4800
gtaggcggtg ctacagagtt cttgaagtgg tggcctaact acggctacac tagaagaaca    4860
gtatttggta tctgcgctct gctgaagcca gttaccttcg gaaaaagagt tggtagctct    4920
tgatccggca aacaaaccac cgctggtagc ggtggttttt ttgtttgcaa gcagcagatt    4980
acgcgcagaa aaaaggatc tcaagaagat cctttgatct tttctacggg gtctgacgct    5040
cagtggaacg aaaactcacg ttaagggatt ttggtcatga gattatcaaa aaggatcttc    5100
acctagatcc ttttaaatta aaaatgaagt tttaaatcaa tctaaagtat atatgagtaa    5160
acttggtctg acagttacca atgcttaatc agtgaggcac ctatctcagc gatctgtcta    5220
tttcgttcat ccatagttgc ctgactcccc gtcgtgtaga taactacgat acgggagggc    5280
ttaccatctg gccccagtgc tgcaatgata ccgcgagacc cacgctcacc ggctccagat    5340
ttatcagcaa taaaccagcc agccggaagg gccgagcgca gaagtggtcc tgcaacttta    5400
tccgcctcca tccagtctat taattgttgc cgggaagcta gagtaagtag ttcgccagtt    5460
aatagtttgc gcaacgttgt tgccattgct acaggcatcg tggtgtcacg ctcgtcgttt    5520
ggtatggctt cattcagctc cggttcccaa cgatcaaggc gagttacatg atcccccatg    5580
ttgtgcaaaa aagcggttag ctccttcggt cctccgatcg ttgtcagaag taagttggcc    5640
gcagtgttat cactcatggt tatggcagca ctgcataatt ctcttactgt catgccatcc    5700
gtaagatgct tttctgtgac tggtgagtac tcaaccaagt cattctgaga atagtgtatg    5760
cggcgaccga gttgctcttg cccggcgtca atacgggata ataccgcgcc acatagcaga    5820
actttaaaag tgctcatcat tggaaaacgt tcttcggggc gaaaactctc aaggatctta    5880
ccgctgttga tccagttcga tgtaaccccac tcgtgcac ccaactgatc ttcagcatct    5940
tttactttca ccagcgtttc tgggtgagca aaaacaggaa ggcaaaatgc cgcaaaaaag    6000
ggaataaggg cgacacggaa atgttgaata ctcatactct tcctttttca atattattga    6060
agcatttatc agggttattg tctcatgagc ggatacatat ttgaatgtat ttagaaaaat    6120
aaacaaatag gggttccgcg cacatttccc cgaaaagtgc cacctgatgc ggtgtgaaat    6180
```

```
accgcacaga tgcgtaagga gaaaataccg catcaggaaa ttgtaagcgt taatattttg    6240
ttaaaattcg cgttaaattt ttgttaaatc agctcatttt ttaaccaata ggccgaaatc    6300
ggcaaaatcc cttataaatc aaaagaatag accgagatag ggttgagtgt tgttccagtt    6360
tggaacaaga gtccactatt aaagaacgtg gactccaacg tcaaagggcg aaaaaccgtc    6420
tatcagggcg atggcccact acgtgaacca tcaccctaat caagtttttt ggggtcgagg    6480
tgccgtaaag cactaaatcg gaaccctaaa gggagccccc gatttagagc ttgacgggga    6540
aagccggcga acgtggcgag aaaggaaggg aagaaagcga aggagcggg cgctagggcg     6600 ctggcaagtg tagcggtcac gctgcgcgta accaccacac ccgccgcgct taatgcgccg    6660
ctacagggcg cgtccattcg ccattcaggc tgcgcaactg ttgggaaggg cgatcggtgc    6720
gggcctcttc gctattacgc cagctggcga aggggggatg tgctgcaagg cgattaagtt    6780
gggtaacgcc agggttttcc cagtcacgac gttgtaaaac gacggccagt gaattgtaat    6840
acgactcact atagggcgaa ttgggcccga cgtcgcatgc tcccggccgc catggccgcg    6900
ggatt                                                                6905

<210> SEQ ID NO 14
<211> LENGTH: 11320
<212> TYPE: DNA
<213> ORGANISM: Artificial Sequence
<220> FEATURE:
<223> OTHER INFORMATION: Plasmid Sequence

<400> SEQUENCE: 14
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc      180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt ggagatcggt acttcgcgaa     420
tgcgtcgaga tgagctctaa tacgactcac tatagggact taagtgtgat ataaatatat     480
atcatacata ctagccttgt gctagatttc aacttaaca aaacggactt aaatacctac      540
agttggtccc tataggtgtt ccattgcagt gcactttagt gccctggatg cacctggcc      600 acctgtcagg ttttttgttat taaaataata ttgttgctgg tatcactgct tgttttgccg    660
tgtctcactt tatacatccg ttgcttgggc tacctagtat ccagcgtcct actggcgttg    720
tggtcggttc gagtgcgaag aacctctggt tcatctagcg gtacgcgggt gtgtggaagt    780
agcgcttcag acgtaccggt tctgttgcgt gaaatacggg gtcacctccc cccacatacc    840
tctaagggct tttgagccta gcgttgggct acgttctcgc acaaggtcgg ctatacggcg    900
tttgtagggg gtagtgccaa acaaccctg aggtgacagg ttctggtggt gtttcgaaaa     960
caacaatgtg tgtgccgcat aatatgcgag taatgcattt tggagcagga agtgacaaag   1020
gagtggcccc aggtagcgct gttcttaggc agtggcttcc cgaaggtaca ctccttgtcg   1080
ataatgatat tgtagattat gtatctgatg cacatgtctc tgtgctttca gattgcaata   1140
aatgtaaaac agagcacaag tttgatcttg tgatatctga tatgtataca gataatgatt   1200
caaagagaaa gcatgaaggc gttgtagcca ataacggcaa tgatgacgtc ttcatatacc   1260
```

```
tttcaaactt tcttcgtaac aatttagctc tgggaggcag ttttgccgta aaagtaacag   1320
agacaagttg gcatgagagt ttatatgaca ttgcacagga ttgtgcatgg tggacaatgt   1380
tttgtacagc agtgaatgct tcttcgtcag aagcattctt gattggtgtt aattatttgg   1440
gtgcaagtga aaaggttaga gttagtggta aaccctgca cgcaaattat atattttgga    1500
ggaattgtaa ttatttacaa acttcagcct atagtatatt tgacgttgct aagtttgatt   1560
tgaaattaaa agcaacgcca gttgtgaatt tgaaaactga acaaaagaca gacttagtct   1620
ttaatttaat taagtgtggt aagttactgg taagagatgt tggacaaacc gcttttacta   1680
gtgactcttt ggtatgcact atgtagtgct ttgctctatg ataataatac ttacgtttac   1740
tactaccaaa gtgcctttag gcctggtcca ggttggcacc tatatggggg tgcttatgca   1800
gtagataggg tttttaatga aaccaacaat gcaggcagtg catctgattg cactgctggt   1860 acttttatg aaagccataa tatttctgct tcttctgtag ccatgacagt accacataat    1920
ggtatgtctt ggtcagcttc acaattttgt acagctcatt gtaacttctc agactttaca   1980
gtgttcgtta cgcattgttt taaaaatcaa ctcggtagtg tcccttgac aggtatgatt    2040 cctcagaatc atattcgtat ttctgctatg agagatggag ttttgtttta aacttaaca    2100 gttagcgtat ctaaataccc tagatttaaa tcgcttcaat gtgttagcaa ttctacatct   2160
gtctatgtaa atggtgacct tgttttcact tctaatgaaa cttcttacgt tacgggtgca   2220
ggcgtttatt ttaaaagtgg tgggcctgta acttataaag ttatgaaaga agttaaagcc   2280
ctagcctact ttattaatgg taccgcacaa gaggttattt tatgtgataa ctcacctaga   2340
ggtttgcttg catgtcagta taacactggt aattttttcag atggattcta cccttttact   2400
aatcattctt tagttaagga taggtttatt gtatatcgag aaagtagcac taacactact   2460
tgtaagttaa ctaatttcag ttttactaat gtaagtaatg cttctcctaa ttcaggtggc   2520
gttgatactt tccaattata tcaaacaagt actgctcagg atggttatta aattttaat    2580 ttatcatttc tgagtagttt tgtgtataaa ccatctgatt ttatgtatgg gtcataccac   2640
ccacattgta agtttagacc agagaatatt aataatggct tatggtttaa ttcattatct   2700
gtgtcactta cttacggacc cattcaaggt ggttgtaagc aatctgtttt tagtaataga   2760
gcaacttgtt gctatgctta ttcttatcaa gggcctagta gatgtaaggg tgtttataga   2820
ggggagctaa cgcaatactt tgaatgtgga cttctagttt acgtaactaa gagtgatggc   2880
tctcgtatac aaactagaag tgaaccactg gtgttaactc aatataatta taacaacatt   2940
actttaaata gtgtgttga gtataatata tatggtaggg ttggtcaagg ttttattact   3000
aatgtaactg aagcaactgc taattatagt tatctagcag atggtggttt agctatttta    3060
gatacctcag gagccataga catatttgtt gttcaaggtg catatggtct taattattat   3120
aaggttaatc cctgtgaaga tgttaaccaa cagtttgtag tgtctggtgg caacttagtt   3180
ggcattctta catctcataa tgaaacaggt tctgaatcta ttgagaacca gttttacatc   3240
aaactcacta acggaacacg tcgctctaga cgttctgtta ctgggaatgt acaaattgc    3300 ccttatgtta gttatggcaa gttttgtata aaaccagatg gttctttatc tataatagta   3360
ccacaagaat tagaacagtt tgtggcgcct ttattcaatg ttactgagca tgtgctcata   3420
cctgatagtt ttaatttaac tgtcacagat gagtacatac aaactcgtat ggataaggtt   3480
caaattattt gccttcagta tgttttgtggt aattctattg aatgcagaaa gttgttcag   3540 cagtatggac ctgtttgtga taatatattg tctgttgtaa atggtgtagg tcaaagagag   3600
gatatggaac ttttaagttt ctattcttct actaaaccta gtggttacaa tacaccaatt   3660
```

```
tttaataatg ttagcactgg tgactttaat atttcgctcc tactaacacc acctaatagt     3720
cctactgggc gctcttttat tgaagatctt ctctttacaa gtgtagaatc tgttggatta     3780
ccaactgatg aagagtataa aaagtgtaca gcaggacctt taggttttgt taaagacctt     3840
gtttgtgcta gagagtataa tggtttgctc gttctgcctc ctattattac tgcggaaatg     3900
caaaccatgt atactagttc tttagtagcc tctatggctt taggtggcat tactgcagct     3960
ggtgctatac cttttgctac acaactgcag gccagaatta accatttggg tattactaat     4020
tctcttttgt tgaaaaacca agaaaaaatt gctgcttcct ttaataaggc catcggtcat     4080
atgcaggaag ggtttaaaag tacttctcta gcattacaac agattcaaga tgttgttaat     4140
aaacagagtt ctattcttac agagactatg caatcactta ataaaatttt tggtgctatt     4200
tcctctgtaa ttcaagacat ttaccagcaa ctagatgcta ttcaggcaga tgctcaggtt     4260
gatcgtctta ttacaggtag actctcttca ctatctgttt tagcttctgc taaacaggca     4320
gagtatcata gagtgtcaca acagcgtgag ttggccactc agaaaattaa tgagtgtgtt     4380
aagtctcagt ctaataggta ttcattttgt ggtaatggta gacatgttct aaccatacca     4440
cagaatgcac ccaatggcat agtgtttata cactttacat acactccaga gagttttgtt     4500
aatgttacgg caatagtagg gttttgcgta aacccagcta atgctagtca ttatgcaata     4560
gtgcctgtta atggcagggg tgttttttata gaagttaatg gtagttacta tatcactgct     4620
cgtgatatgt atatgccaag agatattact gcaggagaca tagtcacttt gacttcttgt     4680
caagcaaact atgttaatgt aaataaaacc gtcattaaca cttttgtgga agatgacgat     4740
tttgattttt atgatgaatt gtcaaaatgg tggaatgata ctaagcatga gctaccagat     4800
tttgatgaat tcaattatac cgttccagtt taaatatta gtaatgaaat tgacagaatt     4860
caacaggtta ttcagggatt aaatgattcc ctaatagacc ttgaaacact ctcaattctc     4920
aaaacttata ttaatggcc ttggtatgtg tggcttgcca ttgcattcct taccattatt     4980
tttattctgg tactttgttg gatattttc atgaccggtt gttgcggttg ttgttgtgga     5040
tgctttggta tcataccgtt aatgagtaag tgtggtaaga atcttcttta ctacacgact     5100
tttgataatg atgtggtaac ttaacaatac agacctaaaa gtctgtttta atgattaaaa     5160
gtcccacatc ttttctaata ttattaattc ttctttggtg taaacttgca ttaagttgtt     5220
ttaaagagtg tgttataaca ctccagcaac tagtacaaat tttactccaa attattaata     5280
gtaacttaca atctagactt ctgctttggc acagtctaga ctaatgttag attttgaagc     5340
aattattgaa actggtcagc aaataactca acaaattagt ttctatttac agcatatttc     5400
aagggtgcta agtactgaat tatttgaccc ctttgaagtt tgtgtttaca gaggaggtaa     5460
ttgttgggag ttagagtcag ctgacgagtt ttcaggtgat gacgaatata ttgagtagat     5520
cgctcgagga gaacggaagt tttctaacag cggtttacgt gttttttagga tttttagcac     5580 tttatctact aggtagagcg cttcaagctt ttgtacaagc ggctgacgct tgttgtcttt     5640
tttggtatac atgggtagta gttcctggag ccaagggcac agcctttgtt tataatcata     5700
catatggtaa aaaacttaac aaaccggagt tagaaacggt tattgttaac gaatttccaa     5760
aaaacggttg gaaatatgga taataccatc aattgtactc ttggtactga caagcagtt     5820 cagcttttta aggaatataa tctgtttgta actgcattcc tgttgttttt aaccatacta     5880
cttcagtatg gatacgcaac taggagcaag gttatttaca tactgaaaat gatagtgtta     5940
tggtgctttt ggccccttaa cattgcagta ggtgtaatct catgtatata cccaccaaac     6000
```

```
acaggaggtc ttgtcgcagc gataattctt acagtgtttg cgtgtctttc ttttataggt    6060
tattggatcc agagtattag acttttaag cggtgcaggt catggtggtc atttaacccc    6120
gaatctaatg ccgtaggttc aatactccta actaatggtc aacaatgtaa ttttgctata    6180
gagagtgtgc cgatggtgct ttctcctatt ataaagaatg gtgctcttta ttgcgagggt    6240
cagtggcttg ctaaatgtga accagaccac ttgcctagag atatatttgt atgcacaccg    6300
gatagacgta atatctatcg tatggtgcaa aaatatactg gtgaccaaag cggaagtaag    6360
aaaaggtttg ccacatttgt ctatgcaaag cagtcagtag atactggcga gctagaaagt    6420
gtgtcagcag taggaggtag tcttacaca taaatgtgtg tgtgtagaga gtatttaaaa    6480
ttattctttg acagtgcctc cgttttaaga gcgcggaaga gtattatttt tgaggatatt    6540
aatataaatc ctctttgttt catactctcc tttcaggagt tattatttaa aaaacagttt    6600
ttccactctt ttgtgccaaa acaattgtt gttaatggtg taacctttca ggtagacaat    6660
ggaaaagtct actacgaagg aagaccaatt ttccaaaaag gttgttgtag tttgtggtcc    6720
aattataaga aagattagaa taattaaacc acctacaaca cttatttta caaatggcgt    6780 tttaggttac aaacgcttaa caaatacgga tgatgaaatg gctgactagt tttggaagag    6840 cttcatctc ctgttataaa tccctattac taactcaatt aagagtatta ataggttaa    6900 ttttagatca cggacccaag cgcacattaa cgtgtgctag gcgagtgctt ttagttcaat    6960
tagatttagt ttataggttg gcttatacgc ccacccaatc gctggtatga ataatagtaa    7020
agataatcct tttcgcggag caatagcaag aaaagcgcga atttatctga gaggaggatt    7080
agattgtgtt tactttctta acaaagcagg acaagcagag ccttgtcccg cgtgtacctc    7140
cctagtattc caagggaaaa cttgtgagga acactattat aataacaatc ttttgtcatg    7200
gcaagcggta aggcaactgg aaagacagac gccccagcgc cagtcatcaa actaggagga    7260
ccaaagccac ctaaagttgg ttcttctgga aatgcatcat ggtttcaacc gataaaggcc    7320
aagaagctaa attcacctgt gcctaaattt gacggtagtg gtgttcctga aaatgaaaat    7380
ctcaagtcaa gccagcaaca tggatactgg agacgccaac acaggtttaa gcctggcaaa    7440
ggtggaagaa aaccagtccc tgatgcttgg tactttact acactggaac aggaccggcc    7500
gccgacctga attggggtga aactcaagat ggtatagtgt gggttgctgc aaagggtgct    7560
gatactaaat ctagatcaaa ccagggtaca agggatcctg ataagtttga ccaatacca    7620 ctacgattct cagatggagg accggatggt aatttccgtt gggacttcat accaataaat    7680
cgtggtagga gtgggagatc aacagcagct tcatcagcag catctagtag agcaccatct    7740 cgtgagggt cacgtggacg tagaagcgga gttgaagatg atcttatagc tcgcgcagca    7800
aagattatac aggaccagca aaagaagggt gcgcgcatta ccaaggctaa gctgatgaa    7860 atggctcatc gccgctattg caagcgcact atcccacctg gttataaggt tgagcaagta    7920
tttggtcccc gtactaaagg taaggaagga aattttggtg atgacaagat gaatgaggaa    7980
ggtgttaagg atgggcgtgt tacggcaatg ctcaacctag tccctagcag tcatgcttgt    8040
ctttttggaa gtagggtgac gcccaaactg cagccagatg gtcttcacct gagatttgaa    8100
tttactactg tggtgtcacg tgatgatccg cagtttgata attatgtgaa atttgtgat    8160 cagtgtgtcg atggtgtagg gacgcgtcca aaggacgatg aatcgagacc aaagtcacgc    8220
ccaaattcaa gacctgcaac tagaggaaat tctccagcgc cgagacaaca gcgcccaaag    8280
aaggagaaaa agcccaagaa gcaggatgat gaagtagata aggcattgac ctcagatgag    8340
gagaggaaca atgcacagct ggaatttgat gatgaaccca aggtgattaa ctgggggac    8400
```

```
tctgcactag gtgaaaatga actttgatta acataatgga cttgctgcat ttgctgtcac    8460
attttgttaa atattatttt tgtgttttac tatcaattat tacaggtatt gattgtgatt    8520
atgttcaata cttaagcttc ttctggttgc tttttgcttg ttgtattgtt gctgtgcttt    8580
ttattattgt gattctcatt agtttgcttt atcgtagaaa ttcaatagta agagttaagg    8640
aagataggca tgtagcttag cacctacatg tctatcgcca gggaaatgtc taatctgtct    8700
acttagtagc ctggaaacga acggtagacc cttagatttt aatttagttt aatttttagt    8760
ttagtttaag ttagtttaga gtaggtataa agatgccagt gccggggcca cgcgtagtac    8820
gaccgagggt acagcactag gacgcccact aggggaagag ctaaattta gtttaagtta    8880 agtttaattg gctaaatata gttaaaattt ataggctagt atagagttag agcaaaaaaa    8940
aaaaaaaaaa aaaaaaaaaa aaaaaaaaaa aaaaaaaaaa aaaaaaaaaa aaaaaaaaaa    9000
aaaaaaaaaa aaaaaaaaaa aaaaaaaaaa aaagcggccg catcggatgc cgggaccgac    9060
gagtgcagag gcgtgcaagc gagcttggcg taatcatggt catagctgtt tcctgtgtga    9120
aattgttatc cgctcacaat tccacacaac atacgagccg aagcataaa gtgtaaagcc    9180 tggggtgcct aatgagtgag ctaactcaca ttaattgcgt tgcgctcact gcccgctttc    9240
cagtcgggaa acctgtcgtg ccagctgcat taatgaatcg gccaacgcgc ggggagaggc    9300
ggtttgcgta ttgggcgctc ttccgcttcc tcgctcactg actcgctgcg ctcggtcgtt    9360
cggctgcggc gagcggtatc agctcactca aaggcggtaa tacggttatc cacagaatca    9420
ggggataacg caggaaagaa catgtgagca aaaggccagc aaaaggccag gaaccgtaaa    9480
aaggccgcgt tgctggcgtt tttccatagg ctccgccccc ctgacgagca tcacaaaaat    9540
cgacgctcaa gtcagaggtg gcgaaacccg acaggactat aaagatacca ggcgtttccc    9600
cctggaagct ccctcgtgcg ctctcctgtt ccgaccctgc cgcttaccgg atacctgtcc    9660
gcctttctcc cttcgggaag cgtggcgctt tctcatagct cacgctgtag gtatctcagt    9720
tcggtgtagg tcgttcgctc caagctgggc tgtgtgcacg aaccccccgt tcagcccgac    9780
cgctgcgcct tatccggtaa ctatcgtctt gagtccaacc cggtaagaca cgacttatcg    9840
ccactggcag cagccactgg taacaggatt agcagagcga ggtatgtagg cggtgctaca    9900
gagttcttga agtggtggcc taactacggc tacactagaa gaacagtatt tggtatctgc    9960
gctctgctga agccagttac cttcggaaaa agagttggta gctcttgatc cggcaaacaa   10020
accaccgctg gtagcggtgg tttttttgtt tgcaagcagc agattacgcg cagaaaaaaa   10080
ggatctcaag aagatccttt gatcttttct acggggtctg acgctcagtg gaacgaaaac   10140
tcacgttaag ggattttggt catgagatta tcaaaaagga tcttcaccta gatccttta   10200 aattaaaaat gaagttttaa atcaatctaa agtatatatg agtaaacttg gtctgacagt   10260
taccaatgct taatcagtga ggcacctatc tcagcgatct gtctatttcg ttcatccata   10320
gttgcctgac tccccgtcgt gtagataact acgatacggg agggcttacc atctggcccc   10380
agtgctgcaa tgataccgcg agacccacgc tcaccggctc cagatttatc agcaataaac   10440
cagccagccg aagggccga gcgcagaagt ggtcctgcaa ctttatccgc ctccatccag   10500
tctattaatt gttgccggga agctagagta agtagttcgc cagttaatag tttgcgcaac   10560
gttgttgcca ttgctacagg catcgtggtg tcacgctcgt cgtttggtat ggcttcattc   10620
agctccggtt cccaacgatc aaggcgagtt acatgatccc ccatgttgtg caaaaaagcg   10680
gttagctcct tcggtcctcc gatcgttgtc agaagtaagt tggccgcagt gttatcactc   10740
```

| | | | | | |
|---|---|---|---|---|---|
| atggttatgg | cagcactgca | taattctctt | actgtcatgc | catccgtaag | atgctttct | 10800 |
| gtgactggtg | agtactcaac | caagtcattc | tgagaatagt | gtatgcggcg | accgagttgc | 10860 |
| tcttgcccgg | cgtcaatacg | ggataatacc | gcgccacata | gcagaacttt | aaaagtgctc | 10920 |
| atcattggaa | aacgttcttc | ggggcgaaaa | ctctcaagga | tcttaccgct | gttgagatcc | 10980 |
| agttcgatgt | aacccactcg | tgcacccaac | tgatcttcag | catcttttac | tttcaccagc | 11040 |
| gtttctgggt | gagcaaaaac | aggaaggcaa | aatgccgcaa | aaagggaat | aagggcgaca | 11100 |
| cggaaatgtt | gaatactcat | actcttcctt | tttcaatatt | attgaagcat | ttatcagggt | 11160 |
| tattgtctca | tgagcggata | catatttgaa | tgtatttaga | aaaataaaca | aatagggggtt | 11220 |
| ccgcgcacat | ttccccgaaa | agtgccacct | gacgtctaag | aaaccattat | tatcatgaca | 11280 |
| ttaacctata | aaaataggcg | tatcacgagg | ccctttcgtc | | | 11320 |

<210> SEQ ID NO 15
<211> LENGTH: 11320
<212> TYPE: DNA
<213> ORGANISM: Artificial Sequence
<220> FEATURE:
<223> OTHER INFORMATION: Plasmid Sequence

<400> SEQUENCE: 15

| | | | | | |
|---|---|---|---|---|---|
| tcgcgcgttt | cggtgatgac | ggtgaaaacc | tctgacacat | gcagctcccg | gagacggtca | 60 |
| cagcttgtct | gtaagcggat | gccgggagca | gacaagcccg | tcaggcgcg | tcagcgggtg | 120 |
| ttggcgggtg | tcggggctgg | cttaactatg | cggcatcaga | gcagattgta | ctgagagtgc | 180 |
| accatatgcg | gtgtgaaata | ccgcacagat | gcgtaaggag | aaaataccgc | atcaggcgcc | 240 |
| attcgccatt | caggctgcgc | aactgttggg | aagggcgatc | ggtgcgggcc | tcttcgctat | 300 |
| tacgccagct | ggcgaaaggg | ggatgtgctg | caaggcgatt | aagttgggta | acgccagggt | 360 |
| tttcccagtc | acgacgttgt | aaaacgacgg | ccagtgaatt | ggagatcggt | acttcgcgaa | 420 |
| tgcgtcgaga | tgagctctaa | tacgactcac | tatagggact | taagtgtgat | ataaatatat | 480 |
| atcatacata | ctagccttgt | gctagatttc | aacttaaca | aaacggactt | aaataccttac | 540 |
| agttggtccc | tataggtgtt | ccattgcagt | gcactttagt | gccctggatg | gcacctggcc | 600 |
| acctgtcagg | ttttttgttat | taaaataata | ttgttgctgg | tatcactgct | tgttttgccg | 660 |
| tgtctcactt | tatacatccg | ttgcttgggc | tacctagtat | ccagcgtcct | actggcgttg | 720 |
| tggtcggttc | gagtgcgaag | aacctctggt | tcatctagcg | gtacgcgggt | gtgtggaagt | 780 |
| agcgcttcag | acgtaccggt | tctgttgcgt | gaaatacggg | gtcacctccc | cccacatacc | 840 |
| tctaagggct | tttgagccta | gcgttgggct | acgttctcgc | acaaggtcgg | ctatacggcg | 900 |
| tttgtagggg | gtagtgccaa | acaaccctg | aggtgacagg | ttctggtggt | gtttcgaaaa | 960 |
| caacaatgtg | tgtgccgcat | aatatgcgag | taatgcattt | tggagcagga | agtgacaaag | 1020 |
| gagtggcccc | aggtagcgct | gttcttaggc | agtggcttcc | cgaaggtaca | ctccttgtcg | 1080 |
| ataatgatat | tgtagattat | gtatctgatg | cacatgtctc | tgtgctttca | gattgcaata | 1140 |
| aatgtaaaac | agagcacaag | tttgatcttg | tgatatctga | tatgtataca | gataatgatt | 1200 |
| caaagagaaa | gcatgaaggc | gttgtagcca | ataacggcaa | tgatgacgtc | ttcatatacc | 1260 |
| tttcaaactt | tcttcgtaac | aatttagctc | tgggaggcag | ttttgccgta | aaagtaacag | 1320 |
| agacaagttg | gcatgagagt | ttatatgaca | ttgcacagga | ttgtgcatgg | tggacaatgt | 1380 |
| tttgtacagc | agtgaatgct | tcttcgtcag | aagcattctt | gattggtgtt | aattatttgg | 1440 |
| gtgcaagtga | aaaggttaga | gttagtggta | aaaccctgca | cgcaaattat | atattttgga | 1500 |

```
ggaattgtaa ttatttacaa acttcagcct atagtatatt tgacgttgct aagtttgatt    1560
tgaaattaaa agcaacgcca gttgtgaatt tgaaaactga acaaaagaca gacttagtct    1620
ttaatttaat taagtgtggt aagttactgg taagagatgt tggacaaacc gcttttacta    1680
gtgactcttt ggtatgcact atgtagtgct ttgctctatg ataataatac ttacgtttac    1740
tactaccaaa gtgcctttag gcctggtcca ggttggcacc tatatggggg tgcttatgca    1800
gtagataggg tttttaatga aaccaacaat gcaggcagtg catctgattg cactgctggt    1860 acttttatg aaagccataa tatttctgct tcttctgtag ccatgacagt accacataat     1920
ggtatgtctt ggtcagcttc acaattttgt acagctcatt gtaacttctc agactttaca    1980
gtgttcgtta cgcattgttt taaaaatcaa ctcggtagtt gtcccttgac aggtatgatt    2040
cctcagaatc atattcgtat ttctgctatg agagatggag ttttgtttta aacttaaca    2100 gttagcgtat ctaaataccc tagatttaaa tcgcttcaat gtgttagcaa ttctacatct    2160
gtctatgtaa atggtgacct tgtttcact tctaatgaaa cttcttacgt tacgggtgca     2220
ggcgtttatt ttaaaagtgg tgggcctgta acttataaag ttatgaaaga agttaaagcc    2280
ctagcctact ttattaatgg taccgcacaa gaggttattt tatgtgataa ctcacctaga    2340
ggtttgcttg catgtcagta taacactggt aattttcag atggattcta ccctttact     2400 aatcattctt tagttaagga taggtttatt gtatatcgag aaagtagcac taacactact    2460
tgtaagttaa ctaatttcag ttttactaat gtaagtaatg cttctcctaa ttcaggtggc    2520
gttgatactt tccaattata tcaaacaagt actgctcagg atggttatta aatttttaat    2580
ttatcatttc tgagtagttt tgtgtataaa ccatctgatt ttatgtatgg gtcataccac    2640
ccacattgta agtttagacc agagaatatt aataatggct tatggtttaa ttcattatct    2700
gtgtcactta cttacggacc cattcaaggt ggttgtaagc aatctgtttt tagtaataga    2760
gcaacttgtt gctatgctta ttcttatcaa gggcctagta gatgtaaggg tgtttataga    2820
ggggagctaa cgcaatactt tgaatgtgga cttctagttt acgtaactaa gagtgatggc    2880
tctcgtatac aaactagaag tgaaccactg gtgttaactc aatataatta taacaacatt    2940
actttaaata gtgtgttga gtataatata tatggtaggg ttggtcaagg ttttattact    3000
aatgtaactg aagcaactgc taattatagt tatctagcag atggtggttt agctatttta    3060
gatacctcag gagccataga catatttgtt gttcaaggtg catatggtct taattattat    3120
aaggttaatc cctgtgaaga tgttaaccaa cagtttgtag tgtctggtgg caacttagtt    3180
ggcattctta catctcataa tgaaacaggt tctgaatcta ttgagaacca gttttacatc    3240
aaactcacta acggaacacg tcgctctaga cgttctgtta ctgggaatgt tacaaattgc    3300
ccttatgtta gttatggcaa gttttgtata aaaccagatg gttctttatc tataatagta    3360
ccacaagaat tagaacagtt tgtggcgcct ttattcaatg ttactgagca tgtgctcata    3420
cctgatagtt ttaatttaac tgtcacagat gagtacatac aaactcgtat ggataaggtt    3480
caaattattt gccttcagta tgtttgtggt aattctattg aatgcagaaa gttgtttcag    3540
cagtatggac ctgtttgtga taatatattg tctgttgtaa atggtgtagg tcaaagagag    3600
gatatggaac ttttaagttt ctattcttct actaaaccta gtggtacaa tacaccaatt    3660 tttaataatg ttagcactgg tgactttaat atttcgctcc tactaacacc acctaatagt    3720
cctactgggc gctcttttat tgaagatctt ctctttacaa gtgtagaatc tgttggatta    3780
ccaactgatg aagagtataa aaagtgtaca gcaggacctt taggttttgt taaagacctt    3840
```

```
gtttgtgcta gagagtataa tggtttgctc gttctgcctc ctattattac tgcggaaatg   3900
caaaccatgt atactagttc tttagtagcc tctatggctt taggtggcat tactgcagct   3960
ggtgctatac cttttgctac acaactgcag gccagaatta accatttggg tattactaat   4020
tctcttttgt tgaaaaacca agaaaaaatt gctgcttcct ttaataaggc catcggtcat   4080
atgcaggaag ggtttaaaag tacttctcta gcattacaac agattcaaga tgttgttaat   4140
aaacagagtt ctattcttac agagactatg caatcactta ataaaaattt tggtgctatt   4200
tcctctgtaa ttcaagacat ttaccagcaa ctagatgcta ttcaggcaga tgctcaggtt   4260
gatcgtctta ttacaggtag actctcttca ctatctgttt tagcttctgc taaacaggca   4320
gagtatcata gagtgtcaca acagcgtgag ttggccactc agaaaattaa tgagtgtgtt   4380
aagtctcagt ctaataggta ttcattttgt ggtaatggta gacatgttct aaccatacca   4440
cagaatgcac ccaatggcat agtgtttata cactttacat acactccaga gagttttgtt   4500
aatgttacgg caatagtagg gttttgcgta aacccagcta atgctagtca ttatgcaata   4560
gtgcctgtta atggcagggg tgtttttata gaagttaatg gtagttacta tatcactgct   4620
cgtgatatgt atatgccaag agatattact gcaggagaca tagtcacttt gacttcttgt   4680
caagcaaact atgttaatgt aaataaaacc gtcattaaca cttttgtgga agatgacgat   4740
tttgattttt atgatgaatt gtcaaaatgg tggaatgata ctaagcatga gctaccagat   4800
tttgatgaat tcaattatac cgttccagtt taaatatta gtaatgaaat tgacagaatt   4860
caacaggtta ttcagggatt aaatgattcc ctaatagacc ttgaaacact ctcaattctc   4920
aaaacttata ttaaatggcc ttggtatgtg tggcttgcca ttgcattcct taccattatt   4980
tttattctgg tactttgttg gatattttc atgaccggtt gttgcggttg ttgttgtgga   5040
tgctttggta tcataccgtt aatgagtaag tgtggtaaga atcttcttta ctacacgact   5100
tttgataatg atgtggtaac ttaacaatac agacctaaaa agtctgttta atgattaaaa   5160
gtcccacatc ttttctaata ttattaattc ttctttggtg taaacttgca ttaagttgtt   5220
ttaaagagtg tgttataaca ctccagcaac tagtacaaat tttactccaa attattaata   5280
gtaacttaca atctagactt ctgctttggc acagtctaga ctaatgttag attttgaagc   5340
aattattgaa actggtcagc aaataactca acaaattagt ttctatttac agcatatttc   5400
aagggtgcta agtactgaat tatttgaccc ctttgaagtt tgtgtttaca gaggaggtaa   5460
ttgttgggag ttagagtcag ctgacgagtt ttcaggtgat gacgaatata ttgagtagat   5520
cgctcgagga gaacggaagt tttctaacag cggtttacgt gtttttagga tttttagcac   5580
tttatctact aggtagagcg cttcaagctt ttgtacaagc ggctgacgct tgttgtcttt   5640
tttggtatac atgggtagta gttcctggag ccaagggcac agcctttgtt tataatcata   5700
catatggtaa aaaacttaac aaaccggagt tagaaacggt tattgttaac gaatttccaa   5760
aaaacggttg gaaatatgga taataccatc aattgtactc ttggtactga acaagcagtt   5820 cagctttta aggaatataa tctgtttgta actgcattcc tgttgttttt aaccatacta   5880
cttcagtatg gatacgcaac taggagcaag gttatttaca tactgaaaat gatagtgtta   5940
tggtgctttt ggccccttaa cattgcagta ggtgtaatct catgtatata cccaccaaac   6000
acaggaggtc ttgtcgcagc gataattctt acagtgtttg cgtgtctttc ttttataggt   6060
tattggatcc agagtattag acttttaag cggtgcaggt catggtggtc atttaacccc   6120
gaatctaatg ccgtaggttc aatactccta actaatggtc aacaatgtaa ttttgctata   6180
gagagtgtgc cgatggtgct ttctcctatt ataaagaatg gtgctcttta ttgcgagggt   6240
```

```
cagtggcttg ctaaatgtga accagaccac ttgcctagag atatatttgt atgcacaccg   6300
gatagacgta atatctatcg tatggtgcaa aaatatactg gtgaccaaag cggaagtaag   6360
aaaaggtttg ccacatttgt ctatgcaaag cagtcagtag atactggcga gctagaaagt   6420
gtgtcagcag taggaggtag tcttacaca taaatgtgtg tgtgtagaga gtatttaaaa    6480
ttattctttg acagtgcctc cgttttaaga gcgcggaaga gtattatttt tgaggatatt   6540
aatataaatc ctctttgttt catactctcc tttcaggagt tattatttaa aaacagttt    6600 ttccactctt ttgtgccaaa acaattgtt gttaatggtg taaccttca ggtagacaat     6660 ggaaaagtct actacgaagg aagaccaatt ttccaaaaag gttgttgtag tttgtggtcc   6720
aattataaga aagattagaa taattaaacc acctacaaca cttatttta caaatggcgt    6780 tttaggttac aaacgcttaa caaatacgga tgatgaaatg gctgactagt tttgaagag    6840 ctttcatctc ctgttataaa tccctattac taactcaatt aagagtatta gataggttaa   6900
ttttagatca cggacccaag cgcacattaa cgtgtgctag gcgagtgctt ttagttcaat   6960
tagatttagt ttataggttg gcttatacgc ccacccaatc gctggtatga ataatagtaa   7020
agataatcct tttcgcggag caatagcaag aaaagcgcga atttatctga gaggaggatt   7080
agattgtgtt tactttctta acaaagcagg acaagcagag ccttgtcccg cgtgtacctc   7140
cctagtattc caagggaaaa cttgtgagga acactattat aataacaatc ttttgtcatg   7200
gcaagcggta aggcaactgg aaagacagac gccccagcgc cagtcatcaa actaggagga   7260
ccaaagccac ctaaagttgg ttcttctgga aatgcatcat ggtttcaacc gataaaggcc   7320
aagaagctaa attcacctgt gcctaaattt gacggtagtg gtgttcctga aaatgaaaat   7380
ctcaagtcaa gccagcaaca tggatactgg agacgccaac acaggtttaa gcctggcaaa   7440
ggtggaagaa aaccagtccc tgatgcttgg tactttact acactggaac aggaccggcc    7500
gccgacctga attggggtga aactcaagat ggtatagtgt gggttgctgc aaagggtgct   7560
gatactaaat ctagatcaaa ccagggtaca agggatcctg ataagtttga ccaataccca   7620
ctacgattct cagatggagg accggatggt aatttccgtt gggacttcat accaataaat   7680
cgtggtagga gtgggagatc aacagcagct tcatcagcag catctagtag agcaccatct   7740 cgtgagggt cacgtggacg tagaagcgga gttgaagatg atcttatagc tcgcgcagca    7800
aagattatac aggaccagca aaagaagggt gcgcgcatta ccaaggctaa ggctgatgaa   7860
atggctcatc gccgctattg caagcgcact atcccacctg gttataaggt tgagcaagta   7920
tttggtcccc gtactaaagg taaggaagga aattttggtg atgacaagat gaatgaggaa   7980
ggtgttaagg atgggcgtgt tacggcaatg ctcaacctag tccctagcag tcatgcttgt   8040
ctttttggaa gtagggtgac gcccaaactg cagccagatg gtcttcacct gagatttgaa   8100
tttactactg tggtgtcacg tgatgatccg cagtttgata attatgtgaa aatttgtgat   8160
cagtgtgtcg atggtgtagg gacgcgtcca aggacgatg aatcgagacc aaagtcacgc    8220
ccaaattcaa gacctgcaac tagaggaaat tctccagcgc cgagacaaca gcgcccaaag   8280
aaggagaaaa agcccaagaa gcaggatgat gaagtagata aggcattgac ctcagatgag   8340
gagaggaaca atgcacagct ggaatttgat gatgaaccca aggtgattaa ctgggggac    8400 tctgcactag gtgaaaatga actttgatta acataatgga cttgctgcat ttgctgtcac   8460
attttgttaa atattatttt tgtgttttac tatcaattat tacaggtatt gattgtgatt   8520
atgttcaata cttaagcttc ttctggttgc ttttgcttg ttgtattgtt gctgtgcttt    8580
```

```
ttattattgt gattctcatt agtttgcttt atcgtagaaa ttcaatagta agagttaagg    8640
aagataggca tgtagcttag cacctacatg tctatcgcca gggaaatgtc taatctgtct    8700
acttagtagc ctggaaacga acggtagacc cttagatttt aatttagttt aatttttagt    8760
ttagtttaag ttagtttaga gtaggtataa agatgccagt gccggggcca cgcgtagtac    8820
gaccgagggt acagcactag gacgcccact aggggaagag ctaaatttta gtttaagtta    8880
agtttaattg ctaaatata gttaaaattt ataggctagt atagagttag agcaaaaaaa    8940
aaaaaaaaaa aaaaaaaaa aaaaaaaaaa aaaaaaaaa aaaaaaaaaa aaaaaaaaaa    9000
aaaaaaaaaa aaaaaaaaa aaaaaaaaaa aaagcggccg catcggatgc cgggaccgac    9060
gagtgcagag gcgtgcaagc gagcttggcg taatcatggt catagctgtt tcctgtgtga    9120
aattgttatc cgctcacaat tccacacaac atacgagccg gaagcataaa gtgtaaagcc    9180
tggggtgcct aatgagtgag ctaactcaca ttaattgcgt tgcgctcact gcccgctttc    9240
cagtcgggaa acctgtcgtg ccagctgcat taatgaatcg gccaacgcgc ggggagaggc    9300
ggtttgcgta ttgggcgctc ttccgcttcc tcgctcactg actcgctgcg ctcggtcgtt    9360
cggctgcggc gagcggtatc agctcactca aaggcggtaa tacggttatc cacagaatca    9420
ggggataacg caggaaagaa catgtgagca aaaggccagc aaaaggccag gaaccgtaaa    9480
aaggccgcgt tgctggcgtt tttccatagg ctccgccccc ctgacgagca tcacaaaaat    9540
cgacgctcaa gtcagaggtg cgaaacccg acaggactat aaagatacca ggcgtttccc    9600
cctggaagct ccctcgtgcg ctctcctgtt ccgaccctgc cgcttaccgg atacctgtcc    9660
gcctttctcc cttcgggaag cgtggcgctt tctcatagct cacgctgtag gtatctcagt    9720
tcggtgtagg tcgttcgctc caagctgggc tgtgtgcacg aacccccgt tcagcccgac    9780
cgctgcgcct tatccggtaa ctatcgtctt gagtccaacc cggtaagaca cgacttatcg    9840
ccactggcag cagccactgg taacaggatt agcagagcga gtatgtagg cggtgctaca    9900
gagttcttga agtggtggcc taactacggc tacactagaa gaacagtatt tggtatctgc    9960
gctctgctga agccagttac cttcggaaaa agagttggta gctcttgatc cggcaaacaa   10020
accaccgctg gtagcggtgg tttttttgtt tgcaagcagc agattacgcg cagaaaaaaa   10080
ggatctcaag aagatccttt gatcttttct acggggtctg acgctcagtg gaacgaaaac   10140
tcacgttaag ggattttggt catgagatta tcaaaaagga tcttcaccta gatcctttta   10200
aattaaaaat gaagttttaa atcaatctaa agtatatatg agtaaacttg gtctgacagt   10260
taccaatgct taatcagtga ggcacctatc tcagcgatct gtctatttcg ttcatccata   10320
gttgcctgac tccccgtcgt gtagataact acgatacggg agggcttacc atctggcccc   10380
agtgctgcaa tgataccgcg agacccacgc tcaccggctc cagatttatc agcaataaac   10440
cagccagccg gaagggccga gcgcagaagt ggtcctgcaa ctttatccgc ctccatccag   10500
tctattaatt gttgccggga agctagagta agtagttcgc cagttaatag tttgcgcaac   10560
gttgttgcca ttgctacagg catcgtggtg tcacgctcgt cgtttggtat ggcttcattc   10620
agctccggtt cccaacgatc aaggcgagtt acatgatccc ccatgttgtg caaaaaagcg   10680
gttagctcct tcggtcctcc gatcgttgtc agaagtaagt tggccgcagt gttatcactc   10740
atggttatgg cagcactgca taattctctt actgtcatgc catccgtaag atgcttttct   10800
gtgactggtg agtactcaac caagtcattc tgagaatagt gtatgcggcg accgagttgc   10860
tcttgcccgg cgtcaatacg ggataatacc gcgccacata gcagaacttt aaaagtgctc   10920
atcattggaa aacgttcttc ggggcgaaaa ctctcaagga tcttaccgct gttgagatcc   10980
```

```
agttcgatgt aacccactcg tgcacccaac tgatcttcag catcttttac tttcaccagc    11040
gtttctgggt gagcaaaaac aggaaggcaa aatgccgcaa aaaagggaat aagggcgaca    11100
cggaaatgtt gaatactcat actcttcctt tttcaatatt attgaagcat ttatcagggt    11160
tattgtctca tgagcggata catatttgaa tgtatttaga aaaataaaca aataggggtt    11220
ccgcgcacat ttccccgaaa agtgccacct gacgtctaag aaaccattat tatcatgaca    11280
ttaacctata aaataggcg tatcacgagg cccctttcgtc                          11320
```

<210> SEQ ID NO 16  
<211> LENGTH: 21  
<212> TYPE: DNA  
<213> ORGANISM: Artificial Sequence  
<220> FEATURE:  
<223> OTHER INFORMATION: Primer Sequence
<400> SEQUENCE: 16

```
cggataacaa tttcacacag g                                              21
```

<210> SEQ ID NO 17  
<211> LENGTH: 21  
<212> TYPE: DNA  
<213> ORGANISM: Artificial Sequence  
<220> FEATURE:  
<223> OTHER INFORMATION: Primer Sequence
<400> SEQUENCE: 17

```
aacactattt tcacgataga c                                              21
```

<210> SEQ ID NO 18  
<211> LENGTH: 27  
<212> TYPE: DNA  
<213> ORGANISM: Artificial Sequence  
<220> FEATURE:  
<223> OTHER INFORMATION: Primer Sequence
<400> SEQUENCE: 18

```
aatactactt gtacgttaca caatttc                                        27
```

<210> SEQ ID NO 19  
<211> LENGTH: 18  
<212> TYPE: DNA  
<213> ORGANISM: Artificial Sequence  
<220> FEATURE:  
<223> OTHER INFORMATION: Primer Sequence
<400> SEQUENCE: 19

```
taaatggtga tcttgttt                                                  18
```

<210> SEQ ID NO 20  
<211> LENGTH: 18  
<212> TYPE: DNA  
<213> ORGANISM: Artificial Sequence  
<220> FEATURE:  
<223> OTHER INFORMATION: Primer Sequence
<400> SEQUENCE: 20

```
gcattcactg ctgtacaa                                                  18
```

<210> SEQ ID NO 21  
<211> LENGTH: 19  
<212> TYPE: DNA  
<213> ORGANISM: Artificial Sequence  
<220> FEATURE:

<223> OTHER INFORMATION: Primer Sequence

<400> SEQUENCE: 21
cgctcttagt aacataaac                                                19

<210> SEQ ID NO 22
<211> LENGTH: 19
<212> TYPE: DNA
<213> ORGANISM: Artificial Sequence
<220> FEATURE:
<223> OTHER INFORMATION: Primer Sequence

<400> SEQUENCE: 22
ctgaggtcaa tgctttatc                                                19

<210> SEQ ID NO 23
<211> LENGTH: 20
<212> TYPE: DNA
<213> ORGANISM: Artificial Sequence
<220> FEATURE:
<223> OTHER INFORMATION: Primer Sequence

<400> SEQUENCE: 23
gacagagcac aagtttgatc                                               20

<210> SEQ ID NO 24
<211> LENGTH: 20
<212> TYPE: DNA
<213> ORGANISM: Artificial Sequence
<220> FEATURE:
<223> OTHER INFORMATION: Primer Sequence

<400> SEQUENCE: 24
acttcaagca tttgtacagg                                               20

<210> SEQ ID NO 25
<211> LENGTH: 21
<212> TYPE: DNA
<213> ORGANISM: Artificial Sequence
<220> FEATURE:
<223> OTHER INFORMATION: Primer Sequence

<400> SEQUENCE: 25
ggtcaacaat gtaattttgc t                                             21

<210> SEQ ID NO 26
<211> LENGTH: 20
<212> TYPE: DNA
<213> ORGANISM: Artificial Sequence
<220> FEATURE:
<223> OTHER INFORMATION: Primer Sequence

<400> SEQUENCE: 26
gcagatgcta aaacagaaag                                               20

<210> SEQ ID NO 27
<211> LENGTH: 20
<212> TYPE: DNA
<213> ORGANISM: Artificial Sequence
<220> FEATURE:
<223> OTHER INFORMATION: Primer Sequence

<400> SEQUENCE: 27
tcacctgaac aatcttcagc                                               20

```
<210> SEQ ID NO 28
<211> LENGTH: 20
<212> TYPE: DNA
<213> ORGANISM: Artificial Sequence
<220> FEATURE:
<223> OTHER INFORMATION: Primer Sequence

<400> SEQUENCE: 28
ggtcaccagt atatttctgc                                              20

<210> SEQ ID NO 29
<211> LENGTH: 20
<212> TYPE: DNA
<213> ORGANISM: Artificial Sequence
<220> FEATURE:
<223> OTHER INFORMATION: Primer Sequence

<400> SEQUENCE: 29
aaagaagcag gatgatgaag                                              20

<210> SEQ ID NO 30
<211> LENGTH: 20
<212> TYPE: DNA
<213> ORGANISM: Artificial Sequence
<220> FEATURE:
<223> OTHER INFORMATION: Primer Sequence

<400> SEQUENCE: 30
aagagatgtt ggtaacacct                                              20

<210> SEQ ID NO 31
<211> LENGTH: 20
<212> TYPE: DNA
<213> ORGANISM: Artificial Sequence
<220> FEATURE:
<223> OTHER INFORMATION: Primer Sequence

<400> SEQUENCE: 31
ctaaaccggc tggttttaat                                              20

<210> SEQ ID NO 32
<211> LENGTH: 20
<212> TYPE: DNA
<213> ORGANISM: Artificial Sequence
<220> FEATURE:
<223> OTHER INFORMATION: Primer Sequence

<400> SEQUENCE: 32
ccatagcttt tgccactatt                                              20

<210> SEQ ID NO 33
<211> LENGTH: 20
<212> TYPE: DNA
<213> ORGANISM: Artificial Sequence
<220> FEATURE:
<223> OTHER INFORMATION: Primer Sequence

<400> SEQUENCE: 33
cgcttgtaaa tagaaggtct                                              20

<210> SEQ ID NO 34
<211> LENGTH: 20
<212> TYPE: DNA
<213> ORGANISM: Artificial Sequence
<220> FEATURE:
<223> OTHER INFORMATION: Primer Sequence
```

<400> SEQUENCE: 34
acataccaag gccacttaat                                              20

<210> SEQ ID NO 35
<211> LENGTH: 20
<212> TYPE: DNA
<213> ORGANISM: Artificial Sequence
<220> FEATURE:
<223> OTHER INFORMATION: Primer Sequence

<400> SEQUENCE: 35
ggtcctgttc cagtatagta                                              20

<210> SEQ ID NO 36
<211> LENGTH: 20
<212> TYPE: DNA
<213> ORGANISM: Artificial Sequence
<220> FEATURE:
<223> OTHER INFORMATION: Primer Sequence

<400> SEQUENCE: 36
cttgtcctgc tttgttaaga                                              20

<210> SEQ ID NO 37
<211> LENGTH: 20
<212> TYPE: DNA
<213> ORGANISM: Artificial Sequence
<220> FEATURE:
<223> OTHER INFORMATION: Primer Sequence

<400> SEQUENCE: 37
gtggatcgtc ttataactgg                                              20

<210> SEQ ID NO 38
<211> LENGTH: 20
<212> TYPE: DNA
<213> ORGANISM: Artificial Sequence
<220> FEATURE:
<223> OTHER INFORMATION: Primer Sequence

<400> SEQUENCE: 38
ctcgcattac aaaggctaag                                              20

<210> SEQ ID NO 39
<211> LENGTH: 20
<212> TYPE: DNA
<213> ORGANISM: Artificial Sequence
<220> FEATURE:
<223> OTHER INFORMATION: Primer Sequence

<400> SEQUENCE: 39
ccagttatag gacacccatc                                              20

<210> SEQ ID NO 40
<211> LENGTH: 20
<212> TYPE: DNA
<213> ORGANISM: Artificial Sequence
<220> FEATURE:
<223> OTHER INFORMATION: Primer Sequence

<400> SEQUENCE: 40
gttggttctt ctggaaatgt                                              20

<210> SEQ ID NO 41
<211> LENGTH: 20

```
<212> TYPE: DNA
<213> ORGANISM: Artificial Sequence
<220> FEATURE:
<223> OTHER INFORMATION: Primer Sequence

<400> SEQUENCE: 41
tcagcatgga cgtgtggtta                                               20

<210> SEQ ID NO 42
<211> LENGTH: 20
<212> TYPE: DNA
<213> ORGANISM: Artificial Sequence
<220> FEATURE:
<223> OTHER INFORMATION: Primer Sequence

<400> SEQUENCE: 42
ccccatgtaa atgccaacca                                               20

<210> SEQ ID NO 43
<211> LENGTH: 61
<212> TYPE: DNA
<213> ORGANISM: Artificial Sequence
<220> FEATURE:
<223> OTHER INFORMATION: Primer Sequence

<400> SEQUENCE: 43
gtatatcgag aaagtagcac taacactact tgtaagttaa ctaatttcag ttttactaat   60
g                                                                   61

<210> SEQ ID NO 44
<211> LENGTH: 20
<212> TYPE: DNA
<213> ORGANISM: Artificial Sequence
<220> FEATURE:
<223> OTHER INFORMATION: Primer Sequence

<400> SEQUENCE: 44
tttgtatacg agagccatca                                               20

<210> SEQ ID NO 45
<211> LENGTH: 20
<212> TYPE: DNA
<213> ORGANISM: Artificial Sequence
<220> FEATURE:
<223> OTHER INFORMATION: Primer Sequence

<400> SEQUENCE: 45
tcagcgtgga catgtggtta                                               20

<210> SEQ ID NO 46
<211> LENGTH: 20
<212> TYPE: DNA
<213> ORGANISM: Artificial Sequence
<220> FEATURE:
<223> OTHER INFORMATION: Primer Sequence

<400> SEQUENCE: 46
ccccatatag gtgccaacct                                               20

<210> SEQ ID NO 47
<211> LENGTH: 33
<212> TYPE: DNA
<213> ORGANISM: Artificial Sequence
<220> FEATURE:
<223> OTHER INFORMATION: Primer Sequence
```

<400> SEQUENCE: 47
cgcggatccg ccaccatgtt ggtgaagtca ctg                                33

<210> SEQ ID NO 48
<211> LENGTH: 33
<212> TYPE: DNA
<213> ORGANISM: Artificial Sequence
<220> FEATURE:
<223> OTHER INFORMATION: Primer Sequence

<400> SEQUENCE: 48
gcggcggccg cttaaacaga cttttaggt ctg                                33

<210> SEQ ID NO 49
<211> LENGTH: 41
<212> TYPE: DNA
<213> ORGANISM: Artificial Sequence
<220> FEATURE:
<223> OTHER INFORMATION: Primer Sequence

<400> SEQUENCE: 49
taatactact tgtgcgttaa ctaattttac ttttagtaat g                      41

<210> SEQ ID NO 50
<211> LENGTH: 18
<212> TYPE: DNA
<213> ORGANISM: Artificial Sequence
<220> FEATURE:
<223> OTHER INFORMATION: Primer Sequence

<400> SEQUENCE: 50 acactactt cacgatag                                                 18

<210> SEQ ID NO 51
<211> LENGTH: 20
<212> TYPE: DNA
<213> ORGANISM: Artificial Sequence
<220> FEATURE:
<223> OTHER INFORMATION: Primer Sequence

<400> SEQUENCE: 51
aatttaacag ttagcgtatc                                              20

<210> SEQ ID NO 52
<211> LENGTH: 43
<212> TYPE: DNA
<213> ORGANISM: Artificial Sequence
<220> FEATURE:
<223> OTHER INFORMATION: Primer Sequence

<400> SEQUENCE: 52
aagtgtggta agttactggt aagagatgtt ggtgaagtca ctg                    43

<210> SEQ ID NO 53
<211> LENGTH: 47
<212> TYPE: DNA
<213> ORGANISM: Artificial Sequence
<220> FEATURE:
<223> OTHER INFORMATION: Primer Sequence

<400> SEQUENCE: 53
agaaaagatg tgggactttt aatcattaaa cagacttttt aggtctg                47

<210> SEQ ID NO 54
<211> LENGTH: 47

```
<212> TYPE: DNA
<213> ORGANISM: Artificial Sequence
<220> FEATURE:
<223> OTHER INFORMATION: Primer Sequence

<400> SEQUENCE: 54
tgattaaaag tcccacatct tttctaatat tattaattct tctttgg          47

<210> SEQ ID NO 55
<211> LENGTH: 46
<212> TYPE: DNA
<213> ORGANISM: Artificial Sequence
<220> FEATURE:
<223> OTHER INFORMATION: Primer Sequence

<400> SEQUENCE: 55
ctcttaccag taacttacca cacttaatta aattaaagac taagtc            46

<210> SEQ ID NO 56
<211> LENGTH: 20
<212> TYPE: DNA
<213> ORGANISM: Artificial Sequence
<220> FEATURE:
<223> OTHER INFORMATION: Primer Sequence

<400> SEQUENCE: 56
caggattgtg catggtggac                                        20

<210> SEQ ID NO 57
<211> LENGTH: 24
<212> TYPE: DNA
<213> ORGANISM: Artificial Sequence
<220> FEATURE:
<223> OTHER INFORMATION: Primer Sequence

<400> SEQUENCE: 57
gaagtgaaya caagatcacc attt                                   24

<210> SEQ ID NO 58
<211> LENGTH: 20
<212> TYPE: DNA
<213> ORGANISM: Artificial Sequence
<220> FEATURE:
<223> OTHER INFORMATION: Primer Sequence

<400> SEQUENCE: 58
tgactgattc tgctgctaaa                                        20

<210> SEQ ID NO 59
<211> LENGTH: 19
<212> TYPE: DNA
<213> ORGANISM: Artificial Sequence
<220> FEATURE:
<223> OTHER INFORMATION: Primer Sequence

<400> SEQUENCE: 59
tcttgaaacc cccaagtag                                         19

<210> SEQ ID NO 60
<211> LENGTH: 20
<212> TYPE: DNA
<213> ORGANISM: Artificial Sequence
<220> FEATURE:
<223> OTHER INFORMATION: Primer Sequence

<400> SEQUENCE: 60
```
tatattcagc atcagttggc                                                 20

<210> SEQ ID NO 61
<211> LENGTH: 20
<212> TYPE: DNA
<213> ORGANISM: Artificial Sequence
<220> FEATURE:
<223> OTHER INFORMATION: Primer Sequence

<400> SEQUENCE: 61
ggattttgtg gtagtggaag                                                 20

<210> SEQ ID NO 62
<211> LENGTH: 23
<212> TYPE: DNA
<213> ORGANISM: Artificial Sequence
<220> FEATURE:
<223> OTHER INFORMATION: Primer Sequence

<400> SEQUENCE: 62
ccactattgc agtaacatta aca                                             23

<210> SEQ ID NO 63
<211> LENGTH: 21
<212> TYPE: DNA
<213> ORGANISM: Artificial Sequence
<220> FEATURE:
<223> OTHER INFORMATION: Primer Sequence

<400> SEQUENCE: 63
ctagactgta agttactatt g                                               21

<210> SEQ ID NO 64
<211> LENGTH: 20
<212> TYPE: DNA
<213> ORGANISM: Artificial Sequence
<220> FEATURE:
<223> OTHER INFORMATION: Primer Sequence

<400> SEQUENCE: 64
ccagggtttt cccagtcacg                                                 20

<210> SEQ ID NO 65
<211> LENGTH: 1156
<212> TYPE: PRT
<213> ORGANISM: Avian infectious bronchitis virus

<400> SEQUENCE: 65

```
Met Leu Val Lys Ser Leu Phe Leu Val Thr Ile Leu Cys Ala Leu Cys
1               5                   10                  15

Ser Ala Asn Leu Phe Asp Ser Asp Asn Asn Tyr Val Tyr Tyr Tyr Gln
            20                  25                  30

Ser Ala Phe Arg Pro Pro Asn Gly Trp His Leu Gln Gly Gly Ala Tyr
        35                  40                  45

Ala Val Val Ser Ser Thr Asn Tyr Thr Asn Asn Ala Gly Ser Ala His
    50                  55                  60

Gly Cys Thr Val Gly Val Ile Lys Asp Val Tyr Asn Gln Ser Val Ala
65                  70                  75                  80

Ser Ile Ala Met Thr Ala Pro Leu Gln Gly Met Ala Trp Ser Lys Ser
                85                  90                  95

Gln Phe Cys Ser Ala His Cys Asn Phe Ser Glu Ile Thr Val Phe Val
            100                 105                 110
```

```
Thr His Cys Tyr Ser Ser Gly Ser Gly Ser Cys Pro Ile Thr Gly Met
            115                 120                 125

Ile Pro Arg Asp His Ile Arg Ile Ser Ala Met Lys Asn Gly Ser Leu
130                 135                 140

Phe Tyr Asn Leu Thr Val Ser Val Ser Lys Tyr Pro Asn Phe Lys Ser
145                 150                 155                 160

Phe Gln Cys Val Asn Asn Phe Thr Ser Val Tyr Leu Asn Gly Asp Leu
                165                 170                 175

Val Phe Thr Ser Asn Lys Thr Thr Asp Val Thr Ser Ala Gly Val Tyr
            180                 185                 190

Phe Lys Ala Gly Gly Pro Val Asn Tyr Ser Ile Met Lys Glu Phe Lys
            195                 200                 205

Val Leu Ala Tyr Phe Val Asn Gly Thr Ala Gln Asp Val Val Leu Cys
            210                 215                 220

Asp Asn Ser Pro Lys Gly Leu Leu Ala Cys Gln Tyr Asn Thr Gly Asn
225                 230                 235                 240

Phe Ser Asp Gly Phe Tyr Pro Phe Thr Asn Ser Thr Leu Val Arg Glu
                245                 250                 255

Lys Phe Ile Val Tyr Arg Glu Ser Ser Val Asn Thr Thr Leu Ala Leu
            260                 265                 270

Thr Asn Phe Thr Phe Ser Asn Val Ser Asn Ala Gln Pro Asn Ser Gly
            275                 280                 285

Gly Val Asn Thr Phe His Leu Tyr Gln Thr Gln Thr Ala Gln Ser Gly
            290                 295                 300

Tyr Tyr Asn Phe Asn Leu Ser Phe Leu Ser Gln Phe Val Tyr Lys Ala
305                 310                 315                 320

Ser Asp Phe Met Tyr Gly Ser Tyr His Pro Ser Cys Ser Phe Arg Pro
                325                 330                 335

Glu Thr Ile Asn Ser Gly Leu Trp Phe Asn Ser Leu Ser Val Ser Leu
            340                 345                 350

Thr Tyr Gly Pro Leu Gln Gly Gly Cys Lys Gln Ser Val Phe Ser Gly
            355                 360                 365

Lys Ala Thr Cys Cys Tyr Ala Tyr Ser Tyr Arg Gly Pro Met Ala Cys
370                 375                 380

Lys Gly Val Tyr Ser Gly Glu Leu Ser Thr Asn Phe Glu Cys Gly Leu
385                 390                 395                 400

Leu Val Tyr Val Thr Lys Ser Asp Gly Ser Arg Ile Gln Thr Arg Thr
                405                 410                 415

Glu Pro Leu Val Leu Thr Gln Tyr Asn Tyr Asn Asn Ile Thr Leu Asp
            420                 425                 430

Lys Cys Val Ala Tyr Asn Ile Tyr Gly Arg Val Gly Gln Gly Phe Ile
            435                 440                 445

Thr Asn Val Thr Asp Ser Ala Ala Asn Phe Ser Tyr Leu Ala Asp Gly
            450                 455                 460

Gly Leu Ala Ile Leu Asp Thr Ser Gly Ala Ile Asp Val Phe Val Val
465                 470                 475                 480

Gln Gly Ile Tyr Gly Leu Asn Tyr Tyr Lys Val Asn Pro Cys Glu Asp
                485                 490                 495

Val Asn Gln Gln Phe Val Val Ser Gly Gly Asn Ile Val Gly Ile Leu
            500                 505                 510

Thr Ser Arg Asn Glu Thr Gly Ser Glu Gln Val Glu Asn Gln Phe Tyr
            515                 520                 525

Val Lys Leu Thr Asn Ser Ser His Arg Arg Lys Arg Ser Ile Gly Gln
```

-continued

```
            530                 535                 540
Asn Val Thr Ser Cys Pro Tyr Val Ser Tyr Gly Arg Phe Cys Ile Glu
545                 550                 555                 560

Pro Asp Gly Ser Leu Lys Met Ile Val Pro Glu Leu Lys Gln Phe
                565                 570                 575

Val Ala Pro Leu Leu Asn Ile Thr Glu Ser Val Leu Ile Pro Asn Ser
                580                 585                 590

Phe Asn Leu Thr Val Thr Asp Glu Tyr Ile Gln Thr Arg Met Asp Lys
                595                 600                 605

Val Gln Ile Asn Cys Leu Gln Tyr Val Cys Gly Asn Ser Leu Glu Cys
                610                 615                 620

Arg Lys Leu Phe Gln Gln Tyr Gly Pro Val Cys Asp Asn Ile Leu Ser
625                 630                 635                 640

Val Val Asn Ser Val Ser Gln Lys Glu Asp Met Glu Leu Leu Ser Phe
                645                 650                 655

Tyr Ser Ser Thr Lys Pro Lys Gly Tyr Asp Thr Pro Val Leu Ser Asn
                660                 665                 670

Val Ser Thr Gly Glu Phe Asn Ile Ser Leu Leu Leu Lys Pro Pro Ser
                675                 680                 685

Ser Pro Ser Gly Arg Ser Phe Ile Glu Glu Leu Leu Phe Thr Ser Val
690                 695                 700

Glu Thr Val Gly Leu Pro Thr Asp Ala Glu Tyr Lys Lys Cys Thr Ala
705                 710                 715                 720

Gly Pro Leu Gly Thr Leu Lys Asp Leu Ile Cys Ala Arg Glu Tyr Asn
                725                 730                 735

Gly Leu Leu Val Leu Pro Pro Ile Ile Thr Ala Asp Met Gln Thr Met
                740                 745                 750

Tyr Thr Ala Ser Leu Val Gly Ala Met Ala Phe Gly Gly Ile Thr Ser
                755                 760                 765

Ala Ala Ala Ile Pro Phe Ala Thr Gln Ile Gln Ala Arg Ile Asn His
                770                 775                 780

Leu Gly Ile Thr Gln Ser Leu Leu Met Lys Asn Gln Glu Lys Ile Ala
785                 790                 795                 800

Ala Ser Phe Asn Lys Ala Ile Gly His Met Gln Glu Gly Phe Arg Ser
                805                 810                 815

Thr Ser Leu Ala Leu Gln Gln Ile Gln Asp Val Val Asn Lys Gln Ser
                820                 825                 830

Ala Ile Leu Thr Glu Thr Met Asn Ser Leu Asn Lys Asn Phe Gly Ala
                835                 840                 845

Ile Thr Ser Val Ile Gln Asp Ile Tyr Ala Gln Leu Asp Ala Ile Gln
                850                 855                 860

Ala Asp Ala Gln Val Asp Arg Leu Ile Thr Gly Arg Leu Ser Ser Leu
865                 870                 875                 880

Ser Val Leu Ala Ser Ala Lys Gln Ser Glu Tyr Ile Arg Val Ser Gln
                885                 890                 895

Gln Arg Glu Leu Ala Thr Gln Lys Ile Asn Glu Cys Val Lys Ser Gln
                900                 905                 910

Ser Asn Arg Tyr Gly Phe Cys Gly Ser Gly Arg His Val Leu Ser Ile
                915                 920                 925

Pro Gln Asn Ala Pro Asn Gly Ile Val Phe Ile His Phe Thr Tyr Thr
                930                 935                 940

Pro Glu Ser Phe Val Asn Val Thr Ala Ile Val Gly Phe Cys Val Asn
945                 950                 955                 960
```

```
Pro Ala Asn Ala Ser Gln Tyr Ala Ile Val Pro Ala Asn Gly Arg Gly
            965                 970                 975

Ile Phe Ile Gln Val Asn Gly Thr Tyr Tyr Ile Thr Ala Arg Asp Met
        980                 985                 990

Tyr Met Pro Arg Asp Ile Thr Ala Gly Asp Ile Val Thr Leu Thr Ser
    995                 1000                1005

Cys Gln Ala Asn Tyr Val Asn Val Asn Lys Thr Val Ile Thr Thr
1010                1015                1020

Phe Val Glu Asp Asp Asp Phe Asp Asp Glu Leu Ser Lys
1025                1030                1035

Trp Trp Asn Asp Thr Lys His Gln Leu Pro Asp Phe Asp Asp Phe
1040                1045                1050

Asn Tyr Thr Val Pro Ile Leu Asn Ile Ser Gly Glu Ile Asp Tyr
1055                1060                1065

Ile Gln Gly Val Ile Gln Gly Leu Asn Asp Ser Leu Ile Asp Leu
1070                1075                1080

Glu Glu Leu Ser Ile Ile Lys Thr Tyr Ile Lys Trp Pro Trp Tyr
1085                1090                1095

Val Trp Leu Ala Ile Phe Phe Ala Ile Ile Ile Phe Ile Leu Ile
1100                1105                1110

Leu Gly Trp Val Phe Phe Met Thr Gly Cys Cys Gly Cys Cys Cys
1115                1120                1125

Gly Cys Phe Gly Ile Ile Pro Leu Met Ser Lys Cys Gly Lys Lys
1130                1135                1140

Ser Ser Tyr Tyr Thr Thr Phe Asp Asn Asp Val Val Thr
1145                1150                1155

<210> SEQ ID NO 66
<211> LENGTH: 6523
<212> TYPE: DNA
<213> ORGANISM: Artificial Sequence
<220> FEATURE:
<223> OTHER INFORMATION: Plasmid Sequence

<400> SEQUENCE: 66
aatcactagt gcggccgcct gcaggtcgac catatgggag agctcccaac gcgttggatg      60
catagcttga gtattctata gtgtcaccta aatagcttgg cgtaatcatg gtcatagctg     120
tttcctgtgt gaaattgtta tccgctcaca attccacaca acatacgagc cggaagcata     180
aagtgtaaag cctggggtgc ctaatgagtg agctaactca cattaattgc gttgcgctca     240
ctgcccgctt tccagtcggg aaacctgtcg tgccagctgc attaatgaat cggccaacgc     300
gcggggagag gcggtttgcg tattgggcgc tcttccgctt cctcgctcac tgactcgctg     360
cgctcggtcg ttcggctgcg gcgagcggta tcagctcact caaaggcggt aatacggtta     420
tccacagaat caggggataa cgcaggaaag aacatgtgag caaaaggcca gcaaaaggcc     480
aggaaccgta aaaaggccgc gttgctggcg tttttccata ggctccgccc ccctgacgag     540
catcacaaaa atcgacgctc aagtcagagg tggcgaaacc cgacaggact ataaagatac     600
caggcgtttc ccctggaagc tccctcgtgc gctctcctgt tccgaccct gccgcttacc      660 ggatacctgt ccgcctttct cccttcggga agcgtggcgc tttctcatag ctcacgctgt     720
aggtatctca gttcggtgta ggtcgttcgc tccaagctgg gctgtgtgca cgaaccccc      780 gttcagcccg accgctgcgc cttatccggt aactatcgtc ttgagtccaa cccggtaaga     840
cacgacttat cgccactggc agcagccact ggtaacagga ttagcagagc gaggtatgta     900
```

```
ggcggtgcta cagagttctt gaagtggtgg cctaactacg gctacactag aagaacagta   960
tttggtatct gcgctctgct gaagccagtt accttcggaa aaagagttgg tagctcttga  1020
tccggcaaac aaaccaccgc tggtagcggt ggttttttg tttgcaagca gcagattacg  1080
cgcagaaaaa aaggatctca agaagatcct ttgatctttt ctacgggtc tgacgctcag  1140 tggaacgaaa actcacgtta agggattttg gtcatgagat tatcaaaaag gatcttcacc  1200
tagatccttt taaattaaaa atgaagtttt aaatcaatct aaagtatata tgagtaaact  1260
tggtctgaca gttaccaatg cttaatcagt gaggcaccta tctcagcgat ctgtctattt  1320
cgttcatcca tagttgcctg actccccgtc gtgtagataa ctacgatacg ggagggctta  1380
ccatctggcc ccagtgctgc aatgataccg cgagacccac gctcaccggc tccagattta  1440
tcagcaataa accagccagc cggaagggcc gagcgcagaa gtggtcctgc aactttatcc  1500
gcctccatcc agtctattaa ttgttgccgg gaagctagag taagtagttc gccagttaat  1560
agtttgcgca acgttgttgc cattgctaca ggcatcgtgg tgtcacgctc gtcgtttggt  1620
atggcttcat tcagctccgg ttcccaacga tcaaggcgag ttacatgatc ccccatgttg  1680
tgcaaaaaag cggttagctc cttcggtcct ccgatcgttg tcagaagtaa gttggccgca  1740
gtgttatcac tcatggttat ggcagcactg cataattctc ttactgtcat gccatccgta  1800
agatgctttt ctgtgactgg tgagtactca accaagtcat tctgagaata gtgtatgcgg  1860
cgaccgagtt gctcttgccc ggcgtcaata cgggataata ccgcgccaca tagcagaact  1920
ttaaaagtgc tcatcattgg aaaacgttct cggggcgaa aactctcaag gatcttaccg  1980
ctgttgagat ccagttcgat gtaacccact cgtgcaccca actgatcttc agcatctttt  2040
actttcacca gcgtttctgg gtgagcaaaa acaggaaggc aaaatgccgc aaaaaaggga  2100
ataagggcga cacggaaatg ttgaatactc atactcttcc ttttcaata ttattgaagc  2160 atttatcagg gttattgtct catgagcgga tacatatttg aatgtattta gaaaaataaa  2220 caaataggg ttccgcgcac atttccccga aaagtgccac ctgatgcggt gtgaaatacc  2280
gcacagatgc gtaaggagaa ataccgcat caggaaattg taagcgttaa tattttgtta  2340
aaattcgcgt taaattttg ttaaatcagc tcatttttta accaataggc cgaaatcggc  2400
aaaatccctt ataaatcaaa agaatagacc gagatagggt tgagtgttgt tccagtttgg  2460
aacaagagtc cactattaaa gaacgtggac tccaacgtca aagggcgaaa aaccgtctat  2520
cagggcgatg gcccactacg tgaaccatca ccctaatcaa gttttttggg gtcgaggtgc  2580
cgtaaagcac taaatcggaa ccctaaaggg agccccgat ttagagcttg acggggaaag  2640
ccggcgaacg tggcgagaaa ggaagggaag aaagcgaaag gagcgggcgc tagggcgctg  2700
gcaagtgtag cggtcacgct gcgcgtaacc accacaccg ccgcgcttaa tgcgccgcta  2760
cagggcgcgt ccattcgcca ttcaggctgc gcaactgttg ggaagggcga tcggtgcggg  2820
cctcttcgct attacgccag ctggcgaaag gggatgtgc tgcaaggcga ttaagttggg  2880
taacgccagg gttttcccag tcacgacgtt gtaaaacgac ggccagtgaa ttgtaatacg  2940
actcactata gggcgaattg ggcccgacgt cgcatgctcc cggccgccat ggccgcggga  3000
ttcgcggatc cgccaatgtt ggtgaagtca ctgttttag tgaccatttt gtgtgcacta  3060
tgtagtgcaa atttgtttga ttctgataat aattatgtgt actactacca aagtgctttt  3120
agaccgccaa atgggtggca cttacaagga ggtgcttatg cagtagtcag ttctactaat  3180
tatactaata atgccggttc tgcacatggg tgcactgttg gtgttattaa ggatgtttat  3240
```

```
aatcaaagtg tggcttccat agctatgaca gcacctcttc agggtatggc ttggtctaag    3300
tcacaattct gtagtgcaca ctgtaatttt tctgaaatta cagtttttgt cacacattgt    3360
tatagtagtg gtagtgggtc gtgtcctata acaggcatga ttccacgtga tcatattcgt    3420
atttctgcaa tgaaaaatgg ttccttattt tataatttaa cagttagcgt atctaaatac    3480
cctaatttta aatcttttca atgtgttaac aacttcacat ctgtttattt aaatggtgat    3540
cttgttttta cttccaacaa aactactgat gttacgtcag caggtgtgta ttttaaagca    3600
ggtggacctg taaattatag tattatgaaa gaatttaagg ttcttgctta ttttgttaat    3660
ggtacagcac aagatgtagt tttgtgcgac aattcccca agggtttgct agcttgtcaa    3720
tataacactg gcaatttttc agatggcttt tatccttta ctaatagtac tttggttagg    3780
gaaaagttca tcgtctatcg tgaaagtagt gttaatacta cttgtgcgtt aactaatttt    3840
acttttagta atgtaagtaa tgcacagcct aatagtggtg gtgttaatac ttttcattta    3900
tatcaaacac aaacagctca gagtggttat tataattta atttgtcatt tctgagtcag    3960
tttgtgtata aggcaagtga ttttatgtat gggtcctacc atcctagttg ttcttttaga    4020
ccagaaacca ttaatagtgg tttatggttt aattccttgt cagtttctct tacctatgga    4080
cccctacagg gagggtgtaa gcaatctgtt tttagtggta aggcaacgtg ttgttacgcc    4140
tactcttata gaggcccaat ggcatgtaaa ggtgtttatt caggtgaatt aagcacgaat    4200
tttgaatgtg gattgctggt ttatgttact aagagtgatg gctctcgtat acagactaga    4260
acagagccct tagtattaac gcaatacaat tataataata ttactttaga taagtgtgtt    4320
gcctataata tatatggcag agtgggccaa ggttttatta ctaatgtgac tgattctgct    4380 gctaattta gttatttagc agatggtggg ttagctattt tagatacgtc gggtgccata    4440
gatgtttttg ttgtacaggg catctatggc cttaattatt acaaggtcaa tccttgtgaa    4500
gatgttaacc aacaatttgt agtgtctggt ggcaatatag ttggcattct tacttctaga    4560
aatgaaacag gttctgaaca ggttgagaac cagttttatg ttaagttaac caatagctca    4620
catcgtcgta agcgttctat tggccaaaac gtaacaagtt gtccttatgt tagctatggc    4680
agattttgta ttgaaccaga tggttcgtta aagatgatag tgccagaaga attgaaacag    4740
tttgtggcac ctttacttaa tattactgaa agtgtactca tacctaacag ttttaatctt    4800
actgttacag atgagtacat acaaacacgt atggataagg tccaaatcaa ttgccttcaa    4860
tatgtttgcg gcaattcttt ggagtgtaga aaattgtttc aacaatatgg tccggtttgt    4920
gataatatat tgtctgttgt aaatagtgtt agtcaaaaag aagatatgga acttttaagc    4980
ttctattcct ctactaaacc aaagggttat gatacaccag ttcttagtaa tgtaagcact    5040
ggtgaattta tatttctct tctcttgaaa cccccaagca gtcctagtgg gcgttctttc    5100
attgaagagc ttttatttac aagtgttgaa acagttggtt tgccaactga tgctgaatat    5160
aaaaaatgca cagcgggacc tttgggtact cttaaagatc ttatctgtgc tagggaatat    5220
aatggtttat tagtgttgcc tccaattatt acggcggata tgcaaacaat gtatactgct    5280
tctttagtgg gtgctatggc ctttggtggt attacatcag ctgcagctat accttttgct    5340
actcagattc aggcaagaat taatcatctt ggtattacac agtctttgtt aatgaaaaat    5400
caagaaaaga ttgctgcttc ctttaataag gccattggtc atatgcagga aggttttaga    5460
agcacttctc tagcattaca acagattcaa gatgttgtta ataagcagag tgctattctt    5520 actgaaaacta tgaattctct taataagaat tttggtgcta ttcatcagt cattcaagat    5580 atttacgcgc aacttgacgc aatccaagca gatgcacaag ttgaccgcct tattactggt    5640
```

```
agactttcat cactctcagt gttagcctct gctaaacagt ctgagtatat tagagttttcc   5700 cagcagcgtg aattagccac tcaaaaaatt aatgagtgtg ttaaatcaca atctaatagg   5760
tacggatttt gtggtagtgg aagacatgtt ctttcgatac cacaaaatgc acctaatggt   5820
atagtgttta tacactttac ttatacacca gagagttttg ttaatgttac tgcaatagtg   5880 ggttttttgtg taaatcctgc taatgctagt cagtatgcta tagtacctgc taatggaagg   5940 ggtatttttta tacaagttaa tggcacgtac tatatcactg cacgtgatat gtatatgcca   6000
cgagacatta ctgcaggaga tatagttact cttacgtctt gtcaagcaaa ttatgttaat   6060
gtaaataaaa ccgtcattac tacatttgta gaagatgacg atttgattt tgatgatgag   6120 ttgtcaaaat ggtggaatga tactaagcat cagctaccag actttgacga cttcaattac   6180
acagtaccca tacttaatat tagcggtgaa attgattata ttcaaggtgt tatacagggt   6240
cttaatgact cccttataga ccttgaagaa cttttcaataa ttaaaactta tattaagtgg   6300
ccttggtatg tttggcttgc catattcttt gccattatta tctttatcct tatattagga   6360
tgggttttct tcatgactgg atgttgtggt tgttgttgtg ggtgctttgg cattattcct   6420
ctaatgagta agtgtggtaa gaaatcttct tactacacta cttttgataa tgatgtggta   6480
acttaacaat acagacctaa aaagtctgtt taacggccgc cgc                     6523

<210> SEQ ID NO 67
<211> LENGTH: 11320
<212> TYPE: DNA
<213> ORGANISM: Artificial Sequence
<220> FEATURE:
<223> OTHER INFORMATION: Plasmid Sequence

<400> SEQUENCE: 67
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tgagctctaa tacgactcac tatagggact taagtgtgat ataaatatat    480
atcatacata ctagccttgt gctagatttc aacttaaca aaacggactt aaatacctac    540
agttggtccc tataggtgtt ccattgcagt gcactttagt gccctggatg gcacctggcc    600
acctgtcagg ttttttgttat taaaataata ttgttgctgg tatcactgct tgttttgccg    660
tgtctcactt tatacatccg ttgcttgggc tacctagtat ccagcgtcct actggcgttg    720
tggtcggttc gagtgcgaag aacctctggt tcatctagcg gtacgcgggt gtgtggaagt    780
agcgcttcag acgtaccggt tctgttgcgt gaaatacggg gtcacctccc cccacatacc    840
tctaagggct tttgagccta gcgttgggct acgttctcgc acaaggtcgg ctatacggcg    900
tttgtagggg gtagtgccaa acaaccctg aggtgacagg ttctggtggt gtttcgaaaa    960
caacaatgtg tgtgccgcat aatatgcgag taatgcattt tggagcagga agtgacaaag   1020
gagtggcccc aggtagcgct gttcttaggc agtggcttcc cgaaggtaca ctccttgtcg   1080
ataatgatat tgtagattat gtatctgatg cacatgtctc tgtgctttca gattgcaata   1140
```

```
aatgtaaaac agagcacaag tttgatcttg tgatatctga tatgtataca gataatgatt    1200
caaagagaaa gcatgaaggc gttgtagcca ataacggcaa tgatgacgtc ttcatatacc    1260
tttcaaactt tcttcgtaac aatttagctc tgggaggcag ttttgccgta aaagtaacag    1320
agacaagttg gcatgagagt ttatatgaca ttgcacagga ttgtgcatgg tggacaatgt    1380
tttgtacagc agtgaatgct tcttcgtcag aagcattctt gattggtgtt aattatttgg    1440
gtgcaagtga aaaggttaga gttagtggta aaacccctgca cgcaaattat atattttgga   1500
ggaattgtaa ttatttacaa acttcagcct atagtatatt tgacgttgct aagtttgatt    1560
tgaaattaaa agcaacgcca gttgtgaatt tgaaaactga acaaaagaca gacttagtct    1620
ttaatttaat taagtgtggt aagttactgg taagagatgt tggacaaacc gcttttacta    1680
gtgactcttt ggtatgcact atgtagtgct ttgctctatg ataataatac ttacgtttac    1740
tactaccaaa gtgcctttag gcctggtcca ggttggcacc tatatggggg tgcttatgca    1800
gtagataggg tttttaatga aaccaacaat gcaggcagtg catctgattg cactgctggt    1860 acttttatg aaagccataa tatttctgct tcttctgtag ccatgacagt accacataat    1920
ggtatgtctt ggtcagcttc acaattttgt acagctcatt gtaacttctc agactttaca    1980
gtgttcgtta cgcattgttt taaaaatcaa ctcggtagtt gtcccttgac aggtatgatt    2040
cctcagaatc atattcgtat ttctgctatg agagatggag ttttgttta acttaaca     2100 gttagcgtat ctaaataccc tagatttaaa tcgcttcaat gtgttagcaa ttctacatct    2160
gtctatgtaa atggtgacct tgttttcact tctaatgaaa cttcttacgt tacgggtgca    2220
ggcgtttatt ttaaaagtgg tgggcctgta acttataaag ttatgaaaga agttaaagcc    2280
ctagcctact ttattaatgg taccgcacaa gaggttattt tatgtgataa ctcacctaga    2340
ggtttgcttg catgtcagta taacactggt aatttttcag atggattcta cccttttact    2400
aatcattctt tagttaagga taggtttatt gtatatcgag aaagtagcac taacactact    2460
ttaaagttaa ctaatttcag ttttactaat gtaagtaatg cttctcctaa ttcaggtggc    2520
gttgatactt tccaattata tcaaacaagt actgctcagg atggttatta aattttaat    2580 ttatcatttc tgagtagttt tgtgtataaa ccatctgatt ttatgtatgg gtcataccac    2640
ccacattgta agtttagacc agagaatatt aataatggct tatggtttaa ttcattatct    2700
gtgtcactta cttacggacc cattcaaggt ggttgtaagc aatctgtttt tagtaataga    2760
gcaacttgtt gctatgctta ttcttatcaa gggcctagta gatgtaaggg tgtttataga    2820
ggggagctaa cgcaatactt tgaatgtgga cttctagttt acgtaactaa gagtgatggc    2880
tctcgtatac aaactagaag tgaaccactg gtgttaactc aatataatta taacaacatt    2940
actttaaata gtgtgttga gtataatata tatggtaggg ttggtcaagg ttttattact    3000
aatgtaactg aagcaactgc taattatagt tatctagcag atggtggttt agctattta    3060 gatacctcag gagccataga catatttgtt gttcaaggtg catatggtct taattattat    3120
aaggttaatc cctgtgaaga tgttaaccaa cagtttgtag tgtctggtgg caacttagtt    3180
ggcattctta catctcataa tgaaacaggt tctgaatcta ttgagaacca gttttacatc    3240
aaactcacta acggaacacg tcgctctaga cgttctgtta ctgggaatgt acaaattgc    3300 ccttatgtta gttatggcaa gttttgtata aaaccagatg gttcttatc tataatagta    3360 ccacaagaat tagaacagtt tgtggcgcct ttattcaatg ttactgagca tgtgctcata    3420
cctgatagtt ttaatttaac tgtcacagat gagtacatac aaactcgtat ggataaggtt    3480
caaattattt gccttcagta tgttgtggt aattctattg aatgcagaaa gttgtttcag    3540
```

```
cagtatggac ctgtttgtga taatatattg tctgttgtaa atggtgtagg tcaaagagag   3600
gatatggaac ttttaagttt ctattcttct actaaaccta gtggttacaa tacaccaatt   3660
tttaataatg ttagcactgg tgactttaat atttcgctcc tactaacacc acctaatagt   3720
cctactgggc gctcttttat tgaagatctt ctctttacaa gtgtagaatc tgttggatta   3780
ccaactgatg aagagtataa aaagtgtaca gcaggacctt aggttttgt taaagacctt    3840 gtttgtgcta gagagtataa tggtttgctc gttctgcctc ctattattac tgcggaaatg   3900
caaaccatgt atactagttc tttagtagcc tctatggctt taggtggcat tactgcagct   3960
ggtgctatac cttttgctac acaactgcag gccagaatta accatttggg tattactaat   4020
tctcttttgt tgaaaaacca agaaaaaatt gctgcttcct taataaggc catcggtcat    4080 atgcaggaag ggtttaaaag tacttctcta gcattacaac agattcaaga tgttgttaat   4140
aaacagagtt ctattcttac agagactatg caatcactta ataaaatttt ggtgctatt    4200 tcctctgtaa ttcaagacat ttaccagcaa ctagatgcta ttcaggcaga tgctcaggtt   4260
gatcgtctta ttacaggtag actctcttca ctatctgttt tagcttctgc taaacaggca   4320
gagtatcata gagtgtcaca acagcgtgag ttggccactc agaaaattaa tgagtgtgtt   4380
aagtctcagt ctaataggta ttcatttttgt ggtaatggta gacatgttct aaccatacca   4440
cagaatgcac ccaatggcat agtgtttata cactttacat acactccaga gagttttgtt   4500
aatgttacgg caatagtagg gttttgcgta aacccagcta atgctagtca ttatgcaata   4560
gtgcctgtta atggcagggg tgtttttata gaagttaatg gtagttacta tatcactgct   4620
cgtgatatgt atatgccaag agatattact gcaggagaca tagtcacttt gacttcttgt   4680
caagcaaact atgttaatgt aaataaaacc gtcattaaca cttttgtgga agatgacgat   4740
tttgattttt atgatgaatt gtcaaaatgg tggaatgata ctaagcatga gctaccagat   4800
tttgatgaat tcaattatac cgttccagtt ttaaatatta gtaatgaaat tgacagaatt   4860
caacaggtta ttcagggatt aaatgattcc ctaatagacc ttgaaacact ctcaattctc   4920
aaaacttata ttaaatggcc ttggtatgtg tggcttgcca ttgcattcct taccattatt   4980
tttattctgg tactttgttg gatatttttc atgaccggtt gttgcggttg ttgttgtgga   5040
tgctttggta tcataccgtt aatgagtaag tgtggtaaga aatcttctta ctacacgact   5100
tttgataatg atgtggtaac ttaacaatac agacctaaaa agtctgttta atgattaaaa   5160
gtcccacatc ttttctaata ttattaattc ttctttggtg taaacttgca ttaagttgtt   5220
ttaaagagtg tgttataaca ctccagcaac tagtacaaat tttactccaa attattaata   5280
gtaacttaca atctagactt ctgctttggc acagtctaga ctaatgttag attttgaagc   5340
aattattgaa actggtcagc aaataactca acaaattagt ttctatttac agcatatttc   5400
aagggtgcta agtactgaat tatttgaccc ctttgaagtt tgtgtttaca gaggaggtaa   5460
ttgttgggag ttagagtcag ctgacgagtt ttcaggtgat gacgaatata ttgagtagat   5520
cgctcgagga gaacggaagt tttctaacag cggtttacgt gttttttagga tttttagcac   5580 tttatctact aggtagagcg cttcaagctt ttgtacaagc ggctgacgct tgttgtcttt   5640
tttggtatac atgggtagta gttcctggag ccaagggcac agcctttgtt tataatcata   5700
catatggtaa aaaacttaac aaaccggagt tagaaacggt tattgttaac gaatttccaa   5760
aaaacggttg gaaatatgga taataccatc aattgtactc ttggtactga acaagcagtt   5820
cagcttttta aggaatataa tctgtttgta actgcattcc tgttgttttt aaccatacta   5880
```

```
cttcagtatg gatacgcaac taggagcaag gttatttaca tactgaaaat gatagtgtta    5940
tggtgctttt ggccccttaa cattgcagta ggtgtaatct catgtatata cccaccaaac    6000
acaggaggtc ttgtcgcagc gataattctt acagtgtttg cgtgtctttc ttttataggt    6060
tattggatcc agagtattag acttttttaag cggtgcaggt catggtggtc atttaacccc    6120
gaatctaatg ccgtaggttc aatactccta actaatggtc aacaatgtaa ttttgctata    6180
gagagtgtgc cgatggtgct ttctcctatt ataaagaatg gtgctcttta ttgcgagggt    6240
cagtggcttg ctaaatgtga accagaccac ttgcctagag atatatttgt atgcacaccg    6300
gatagacgta atatctatcg tatggtgcaa aaatatactg gtgaccaaag cggaagtaag    6360
aaaaggtttg ccacatttgt ctatgcaaag cagtcagtag atactggcga gctagaaagt    6420
gtgtcagcag taggaggtag tcttttacaca taaatgtgtg tgtgtagaga gtatttaaaa    6480
ttattctttg acagtgcctc cgtttttaaga gcgcggaaga gtattatttt tgaggatatt    6540
aatataaatc ctctttgttt catactctcc tttcaggagt tattatttaa aaaacagttt    6600
ttccactctt ttgtgccaaa acaattgtt gttaatggtg taacctttca ggtagacaat    6660
ggaaaagtct actacgaagg aagaccaatt ttccaaaaag gttgttgtag tttgtggtcc    6720
aattataaga aagattagaa taattaaacc acctacaaca cttattttta caaatggcgt    6780
tttaggttac aaacgcttaa caaatacgga tgatgaaatg gctgactagt tttggaagag    6840 cttcatctc ctgttataaa tccctattac taactcaatt aagagtatta gataggttaa    6900
ttttagatca cggacccaag cgcacattaa cgtgtgctag gcgagtgctt ttagttcaat    6960
tagatttagt ttataggttg gcttatacgc ccacccaatc gctggtatga ataatagtaa    7020
agataatcct tttcgcggag caatagcaag aaaagcgcga atttatctga gaggaggatt    7080
agattgtgtt tactttctta acaaagcagg acaagcagag ccttgtcccg cgtgtacctc    7140
cctagtattc caagggaaaa cttgtgagga acactattat aataacaatc ttttgtcatg    7200
gcaagcggta aggcaactgg aaagacagac gccccagcgc cagtcatcaa actaggagga    7260
ccaaagccac ctaaagttgg ttcttctgga aatgcatcat ggtttcaacc gataaaggcc    7320
aagaagctaa attcacctgt gcctaaattt gacggtagtg gtgttcctga aaatgaaaat    7380
ctcaagtcaa gccagcaaca tggatactgg agacgccaac acaggtttaa gcctggcaaa    7440
ggtggaagaa aaccagtccc tgatgcttgg tactttttact acactggaac aggaccggcc    7500
gccgacctga attggggtga aactcaagat ggtatagtgt gggttgctgc aaagggtgct    7560
gatactaaat ctagatcaaa ccagggtaca agggatcctg ataagtttga ccaatacca    7620 ctacgattct cagatggagg accggatggt aatttccgtt gggacttcat accaataaat    7680
cgtggtagga gtgggagatc aacagcagct tcatcagcag catctagtag agcaccatct    7740
cgtgaggggt cacgtggacg tagaagcgga gttgaagatg atcttatagc tcgcgcagca    7800
aagattatac aggaccagca aaagaagggt gcgcgcatta ccaaggctaa ggctgatgaa    7860
atggctcatc gccgctattg caagcgcact atcccacctg gttataaggt tgagcaagta    7920
tttggtcccc gtactaaagg taaggaagga aattttggtg atgacaagat gaatgaggaa    7980
ggtgttaagg atgggcgtgt tacggcaatg ctcaacctag tccctagcag tcatgcttgt    8040 cttttttggaa gtagggtgac gcccaaactg cagccagatg gtcttcacct gagatttgaa    8100
tttactactg tggtgtcacg tgatgatccg cagtttgata attatgtgaa aattgtgat    8160 cagtgtgtcg atggtgtagg gacgcgtcca aggacgatg aatcgagacc aaagtcacgc    8220
ccaaattcaa gacctgcaac tagaggaaat tctccagcgc cgagacaaca gcgcccaaag    8280
```

```
aaggagaaaa agcccaagaa gcaggatgat gaagtagata aggcattgac ctcagatgag   8340
gagaggaaca atgcacagct ggaatttgat gatgaaccca aggtgattaa ctgggggac    8400 tctgcactag gtgaaaatga actttgatta acataatgga cttgctgcat ttgctgtcac   8460
attttgttaa atattatttt tgtgttttac tatcaattat tacaggtatt gattgtgatt   8520
atgttcaata cttaagcttc ttctggttgc tttttgcttg ttgtattgtt gctgtgcttt   8580
ttattattgt gattctcatt agtttgcttt atcgtagaaa ttcaatagta agagttaagg   8640
aagataggca tgtagcttag cacctacatg tctatcgcca gggaaatgtc taatctgtct   8700
acttagtagc ctggaaacga acggtagacc cttagatttt aatttagttt aatttttagt   8760
ttagtttaag ttagtttaga gtaggtataa agatgccagt gccggggcca cgcgtagtac   8820
gaccgagggt acagcactag gacgcccact aggggaagag ctaaatttta gtttaagtta   8880
agtttaattg gctaaatata gttaaaattt ataggctagt atagagttag agcaaaaaaa   8940
aaaaaaaaaa aaaaaaaaaa aaaaaaaaaa aaaaaaaaaa aaaaaaaaaa aaaaaaaaaa   9000
aaaaaaaaaa aaaaaaaaaa aaaaaaaaaa aaagcggccg catcggatgc cgggaccgac   9060
gagtgcagag gcgtgcaagc gagcttggcg taatcatggt catagctgtt tcctgtgtga   9120
aattgttatc cgctcacaat tccacacaac atacgagccg aagcataaa gtgtaaagcc   9180 tggggtgcct aatgagtgag ctaactcaca ttaattgcgt tgcgctcact gcccgctttc   9240
cagtcgggaa acctgtcgtg ccagctgcat taatgaatcg gccaacgcgc ggggagaggc   9300
ggtttgcgta ttgggcgctc ttccgcttcc tcgctcactg actcgctgcg ctcggtcgtt   9360
cggctgcggc gagcggtatc agctcactca aaggcggtaa tacggttatc cacagaatca   9420
ggggataacg caggaaagaa catgtgagca aaaggccagc aaaaggccag gaaccgtaaa   9480
aaggccgcgt tgctggcgtt tttccatagg ctccgccccc ctgacgagca tcacaaaaat   9540
cgacgctcaa gtcagaggtg gcgaaacccg acaggactat aaagatacca ggcgtttccc   9600
cctggaagct ccctcgtgcg ctctcctgtt ccgaccctgc cgcttaccgg atacctgtcc   9660
gcctttctcc cttcgggaag cgtggcgctt tctcatagct cacgctgtag gtatctcagt   9720
tcggtgtagg tcgttcgctc caagctgggc tgtgtgcacg aaccccccgt tcagcccgac   9780
cgctgcgcct tatccggtaa ctatcgtctt gagtccaacc cggtaagaca cgacttatcg   9840
ccactggcag cagccactgg taacaggatt agcagagcga ggtatgtagg cggtgctaca   9900
gagttcttga agtggtggcc taactacggc tacactagaa gaacagtatt tggtatctgc   9960
gctctgctga agccagttac cttcggaaaa agagttggta gctcttgatc cggcaaacaa  10020
accaccgctg gtagcggtgg ttttttgtt tgcaagcagc agattacgcg cagaaaaaaa   10080
ggatctcaag aagatccttt gatcttttct acggggtctg acgctcagtg gaacgaaaac   10140
tcacgttaag ggattttggt catgagatta tcaaaaagga tcttcaccta gatccttta   10200 aattaaaaat gaagttttaa atcaatctaa agtatatatg agtaaacttg gtctgacagt   10260
taccaatgct taatcagtga ggcacctatc tcagcgatct gtctatttcg ttcatccata  10320
gttgcctgac tccccgtcgt gtagataact acgatacggg agggcttacc atctggcccc  10380
agtgctgcaa tgataccgcg agacccacgc tcaccggctc cagatttatc agcaataaac  10440
cagccagccg aagggccga gcgcagaagt ggtcctgcaa ctttatccgc ctccatccag   10500
tctattaatt gttgccggga agctagagta agtagttcgc cagttaatag tttgcgcaac  10560
gttgttgcca ttgctacagg catcgtggtg tcacgctcgt cgtttggtat ggcttcattc  10620
```

| | |
|---|---|
| agctccggtt cccaacgatc aaggcgagtt acatgatccc ccatgttgtg caaaaaagcg | 10680 |
| gttagctcct tcggtcctcc gatcgttgtc agaagtaagt tggccgcagt gttatcactc | 10740 |
| atggttatgg cagcactgca taattctctt actgtcatgc catccgtaag atgcttttct | 10800 |
| gtgactggtg agtactcaac caagtcattc tgagaatagt gtatgcggcg accgagttgc | 10860 |
| tcttgcccgg cgtcaatacg ggataatacc gcgccacata gcagaacttt aaaagtgctc | 10920 |
| atcattggaa aacgttcttc ggggcgaaaa ctctcaagga tcttaccgct gttgagatcc | 10980 |
| agttcgatgt aacccactcg tgcacccaac tgatcttcag catcttttac tttcaccagc | 11040 |
| gtttctgggt gagcaaaaac aggaaggcaa aatgccgcaa aaaagggaat aagggcgaca | 11100 |
| cggaaatgtt gaatactcat actcttcctt tttcaatatt attgaagcat ttatcagggt | 11160 |
| tattgtctca tgagcggata catatttgaa tgtatttaga aaataaaca aatagggggtt | 11220 |
| ccgcgcacat ttccccgaaa agtgccacct gacgtctaag aaaccattat tatcatgaca | 11280 |
| ttaacctata aaaataggcg tatcacgagg ccctttcgtc | 11320 |

<210> SEQ ID NO 68
<211> LENGTH: 11323
<212> TYPE: DNA
<213> ORGANISM: Artificial Sequence
<220> FEATURE:
<223> OTHER INFORMATION: Plasmid Sequence

<400> SEQUENCE: 68

| | |
|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcggggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt ggagatcggt acttcgcgaa | 420 |
| tgcgtcgaga tgagctctaa tacgactcac tatagggact taagtgtgat ataaatatat | 480 |
| atcatacata ctagccttgt gctagatttc aacttaaca aaacggactt aaataccttac | 540 |
| agttggtccc tataggtgtt ccattgcagt gcactttagt gccctggatg gcacctggcc | 600 |
| acctgtcagg tttttgttat taaaataata ttgttgctgg tatcactgct tgttttgccg | 660 |
| tgtctcactt tatacatccg ttgcttgggc tacctagtat ccagcgtcct actggcgttg | 720 |
| tggtcggttc gagtgcgaag aacctctggt tcatctagcg gtacgcgggt gtgtggaagt | 780 |
| agcgcttcag acgtaccggt tctgttgcgt gaaatacggg gtcacctccc ccacatacc | 840 |
| tctaagggct tttgagccta gcgttgggct acgttctcgc acaaggtcgg ctatacggcg | 900 |
| tttgtagggg gtagtgccaa caacccctg aggtgacagg ttctggtggt gtttcgaaaa | 960 |
| caacaatgtg tgtgccgcat aatatgcgag taatgcattt tggagcagga agtgacaaag | 1020 |
| gagtggcccc aggtagcgct gttcttaggc agtggcttcc cgaaggtaca ctccttgtcg | 1080 |
| ataatgatat tgtagattat gtatctgatg cacatgtctc tgtgctttca gattgcaata | 1140 |
| aatgtaaaac agagcacaag tttgatcttg tgatatctga tatgtataca gataatgatt | 1200 |
| caaagagaaa gcatgaaggc gttgtagcca ataacggcaa tgatgacgtc ttcatatacc | 1260 |
| tttcaaactt tcttcgtaac aatttagctc tgggaggcag ttttgccgta aaagtaacag | 1320 |
| agacaagttg gcatgagagt ttatatgaca ttgcacagga ttgtgcatgg tggacaatgt | 1380 |

```
tttgtacagc agtgaatgct tcttcgtcag aagcattctt gattggtgtt aattatttgg    1440
gtgcaagtga aaaggttaga gttagtggta aaccctgca cgcaaattat atattttgga    1500
ggaattgtaa ttatttacaa acttcagcct atagtatatt tgacgttgct aagtttgatt    1560
tgaaattaaa agcaacgcca gttgtgaatt tgaaaactga acaaaagaca gacttagtct    1620
ttaatttaat taagtgtggt aagttactgg taagagatgt tggtgaagtc actgttttta    1680
gtgaccattt tgtgtgcact atgtagtgca aatttgtttg attctgataa taattatgtg    1740
tactactacc aaagtgcttt tagaccgcca aatgggtggc acttacaagg aggtgcttat    1800
gcagtagtca gttctactaa ttatactaat aatgccggtt ctgcacatgg gtgcactgtt    1860
ggtgttatta aggatgttta taatcaaagt gtggcttcca tagctatgac agcacctctt    1920
cagggtatgg cttggtctaa gtcacaattc tgtagtgcac actgtaattt ttctgaaatt    1980 acagttttg tcacacattg ttatagtagt ggtagtgggt cgtgtcctat aacaggcatg    2040
attccacgtg atcatattcg tatttctgca atgaaaaatg gttccttatt ttataattta    2100
acagttagcg tatctaaata ccctaatttt aaatcttttc aatgtgttaa caacttcaca    2160
tctgtttatt taaatggtga tcttgttttt acttccaaca aaactactga tgttacgtca    2220
gcaggtgtgt attttaaagc aggtggacct gtaaattata gtattatgaa agaatttaag    2280
gttcttgctt attttgttaa tggtacagca caagatgtag ttttgtgcga caattccccc    2340
aagggtttgc tagcttgtca atataacact ggcaattttt cagatggctt ttatccttt    2400 actaatagta ctttggttag ggaaaagttc atcgtctatc gtgaaagtag tgttaatact    2460
acttgtgcgt taactaattt tactttagt aatgtaagta atgcacagcc taatagtggt    2520
ggtgttaata ctttcattt atatcaaaca caaacagctc agagtggtta ttataatttt    2580
aatttgtcat ttctgagtca gtttgtgtat aaggcaagtg attttatgta tgggtcctac    2640
catcctagtt gttcttttag accagaaacc attaatagtg gttatggtt taattccttg    2700 tcagtttctc ttacctatgg acccctacag ggagggtgta agcaatctgt ttttagtggt    2760
aaggcaacgt gttgttacgc ctactcttat agaggcccaa tggcatgtaa aggtgtttat    2820
tcaggtgaat taagcacgaa ttttgaatgt ggattgctgg tttatgttac taagagtgat    2880
ggctctcgta tacagactag aacagagccc ttagtattaa cgcaatacaa ttataataat    2940
attactttag ataagtgtgt tgcctataat atatatggca gagtgggcca aggttttatt    3000
actaatgtga ctgattctgc tgctaatttt agttatttag cagatggtgg gttagctatt    3060
ttagatacgt cgggtgccat agatgttttt gttgtacagg gcatctatgg ccttaattat    3120
tacaaggtca atccttgtga agatgttaac caacaatttg tagtgtctgg tggcaatata    3180
gttggcattc ttacttctag aaatgaaaca ggttctgaac aggttgagaa ccagtttat    3240 gttaagttaa ccaatagctc acatcgtcgt aagcgttcta ttggccaaaa cgtaacaagt    3300
tgtccttatg ttagctatgg cagattttgt attgaaccag atggttcgtt aaagatgata    3360
gtgccagaag aattgaaaca gtttgtggca cctttactta atattactga aagtgtactc    3420
atacctaaca gttttaatct tactgttaca gatgagtaca tacaaacacg tatggataag    3480
gtccaaatca attgccttca atatgtttgc ggcaattctt tggagtgtag aaaattgttt    3540
caacaatatg gtccggtttg tgataatata ttgtctgttg taaatagtgt tagtcaaaaa    3600
gaagatatgg aacttttaag cttctattcc tctactaaac caagggtta tgatacacca    3660 gttcttagta atgtaagcac tggtgaattt aatatttctc ttctcttgaa accccaagc    3720
```

```
agtcctagtg ggcgttcttt cattgaagag ctttttattta caagtgttga aacagttggt    3780
ttgccaactg atgctgaata taaaaaatgc acagcgggac cttttgggtac tcttaaagat    3840
cttatctgtg ctagggaata taatggttta ttagtgttgc ctccaattat tacggcggat    3900
atgcaaacaa tgtatactgc ttctttagtg ggtgctatgg cctttggtgg tattacatca    3960
gctgcagcta taccttttgc tactcagatt caggcaagaa ttaatcatct tggtattaca    4020
cagtctttgt taatgaaaaa tcaagaaaag attgctgctt cctttaataa ggccattggt    4080
catatgcagg aaggttttag aagcacttct ctagcattac aacagattca agatgttgtt    4140
aataagcaga gtgctattct tactgaaact atgaattctc ttaataagaa ttttggtgct    4200
attacatcag tcattcaaga tatttacgcg caacttgacg caatccaagc agatgcacaa    4260
gttgaccgcc ttattactgg tagacttttca tcactctcag tgttagcctc tgctaaacag    4320
tctgagtata ttagagtttc ccagcagcgt gaattagcca ctcaaaaaat taatgagtgt    4380
gttaaatcac aatctaatag gtacggattt tgtggtagtg aagacatgt tctttcgata    4440
ccacaaaatg cacctaatgg tatagtgttt atacacttta cttatacacc agagagttttt  4500
gttaatgtta ctgcaatagt gggttttttgt gtaaatcctg ctaatgctag tcagtatgct    4560
atagtacctg ctaatggaag gggtatttttt atacaagtta atggcacgta ctatatcact    4620
gcacgtgata tgtatatgcc acgagacatt actgcaggag atatagttac tcttacgtct    4680
tgtcaagcaa attatgttaa tgtaaataaa accgtcatta ctacatttgt agaagatgac    4740
gatttt gatt tgatgatga gttgtcaaaa tggtggaatg atactaagca tcagctacca    4800
gactttgacg acttcaatta cacagtaccc atacttaata ttagcggtga aattgattat    4860
attcaaggtg ttatacaggg tcttaatgac tcccttatag accttgaaga actttcaata    4920
attaaaactt atattaagtg gccttggtat gtttggcttg ccatattctt tgccattatt    4980
atctttatcc ttatattagg atgggttttc ttcatgactg gatgttgtgg ttgttgttgt    5040
gggtgctttg gcattattcc tctaatgagt aagtgtggta gaaatcttc ttactacact    5100
acttttgata atgatgtggt aacttaacaa tacagaccta aaaagtctgt ttaatgatta    5160
aaagtcccac atcttttcta atattattaa ttccttcttttg gtgtaaactt gcattaagtt    5220
gttttaaaga gtgtgttata acactccagc aactagtaca aattttactc caattatta    5280
atagtaactt acaatctaga cttctgcttt ggcacagtct agactaatgt tagattttga    5340
agcaattatt gaaactggtc agcaaataac tcaacaaatt agtttctatt tacagcatat    5400
ttcaagggtg ctaagtactg aattatttga ccccttttgaa gtttgtgttt acagaggagg    5460
taattgttgg gagttagagt cagctgacga gttttcaggt gatgacgaat atattgagta    5520
gatcgctcga ggagaacgga agttttctaa cagcggttta cgtgttttta ggattttttag    5580
cactttatct actaggtaga gcgcttcaag cttttgtaca agcggctgac gcttgttgtc    5640
ttttttggta tacatgggta gtagttcctg gagccaaggg cacagccttt gtttataatc    5700
atacatatgg taaaaaactt aacaaaccgg agttagaaac ggttattgtt aacgaatttc    5760
caaaaaacgg ttggaaatat ggataatacc atcaattgta ctcttggtac tgaacaagca    5820
gttcagcttt ttaaggaata taatctgttt gtaactgcat tcctgttgtt tttaaccata    5880
ctacttcagt atggatacgc aactaggagc aaggttattt acatactgaa atgatagtg     5940
ttatggtgct tttggcccct taacattgca gtaggtgtaa tctcatgtat atacccacca    6000
aacacaggag gtcttgtcgc agcgataatt cttacagtgt ttgcgtgtct ttctttttata  6060
ggttattgga tccagagtat tagacttttt aagcggtgca ggtcatggtg gtcatttaac    6120
```

```
cccgaatcta atgccgtagg ttcaatactc ctaactaatg gtcaacaatg taattttgct    6180
atagagagtg tgccgatggt gctttctcct attataaaga atggtgctct ttattgcgag    6240
ggtcagtggc ttgctaaatg tgaaccagac cacttgccta gagatatatt tgtatgcaca    6300
ccggatagac gtaatatcta tcgtatggtg caaaaatata ctggtgacca aagcggaagt    6360
aagaaaaggt ttgccacatt tgtctatgca aagcagtcag tagatactgg cgagctagaa    6420
agtgtgtcag cagtaggagg tagtctttac acataaatgt gtgtgtgtag agagtatttA    6480
aaattattct ttgacagtgc ctccgtttta agagcgcgga agagtattat ttttgaggat    6540
attaatataa atcctctttg tttcatactc tcctttcagg agttattatt taaaaaacag    6600
tttttccact cttttgtgcc aaaaacaatt gttgttaatg gtgtaacctt tcaggtagac    6660
aatggaaaag tctactacga aggaagacca attttccaaa aaggttgttg tagtttgtgg    6720
tccaattata agaaagatta gaataattaa accacctaca acacttatttt ttacaaatgg    6780 cgttttaggt tacaaacgct taacaaatac ggatgatgaa atggctgact agttttggaa    6840
gagctttcat ctcctgttat aaatccctat tactaactca attaagagta ttagataggt    6900
taattttaga tcacggaccc aagcgcacat taacgtgtgc taggcgagtg cttttagttc    6960
aattagattt agtttatagg ttggcttata cgcccaccca atcgctggta tgaataatag    7020
taaagataat ccttttcgcg gagcaatagc aagaaaagcg cgaatttatc tgagaggagg    7080
attagattgt gtttactttc ttaacaaagc aggacaagca gagccttgtc ccgcgtgtac    7140
ctccctagta ttccaaggga aaacttgtga ggaacactat tataataaca atcttttgtc    7200
atggcaagcg gtaaggcaac tggaaagaca gacgccccag cgccagtcat caaactagga    7260
ggaccaaagc cacctaaagt tggttcttct ggaaatgcat catggtttca accgataaag    7320
gccaagaagc taaattcacc tgtgcctaaa tttgacggta gtggtgttcc tgaaaatgaa    7380
aatctcaagt caagccagca acatggatac tggagacgcc aacacaggtt taagcctggc    7440
aaaggtggaa gaaaaccagt ccctgatgct tggtactttt actacactgg aacaggaccg    7500
gccgccgacc tgaattgggg tgaaactcaa gatggtatag tgtgggttgc tgcaaagggt    7560
gctgatacta aatctagatc aaaccagggt acaagggatc ctgataagtt tgaccaatac    7620
ccactacgat tctcagatgg aggaccggat ggtaatttcc gttgggactt cataccaata    7680
aatcgtggta ggagtgggag atcaacagca gcttcatcag cagcatctag tagagcacca    7740
tctcgtgagg ggtcacgtgg acgtagaagc ggagttgaag atgatcttat agctcgcgca    7800
gcaaagatta tacaggacca gcaaagaag ggtgcgcgca ttaccaaggc taaggctgat    7860
gaaatggctc atcgccgcta ttgcaagcgc actatcccac ctggttataa ggttgagcaa    7920
gtatttggtc cccgtactaa aggtaaggaa ggaaattttg gtgatgacaa gatgaatgag    7980
gaaggtgtta aggatgggcg tgttacggca atgctcaacc tagtccctag cagtcatgct    8040
tgtctttttg gaagtagggt gacgcccaaa ctgcagccag atggtcttca cctgagattt    8100
gaatttacta ctgtggtgtc acgtgatgat ccgcagtttg ataattatgt gaaaatttgt    8160
gatcagtgtg tcgatggtgt agggacgcgt ccaaaggacg atgaatcgag accaaagtca    8220
cgcccaaatt caagacctgc aactagagga aattctccag cgccgagaca acagcgccca    8280
aagaaggaga aaaagcccaa gaagcaggat gatgaagtag ataaggcatt gacctcagat    8340
gaggagagga acaatgcaca gctggaattt gatgatgaac ccaaggtgat taactggggg    8400
gactctgcac taggtgaaaa tgaactttga ttaacataat ggacttgctg catttgctgt    8460
```

```
cacattttgt taaatattat ttttgtgttt tactatcaat tattacaggt attgattgtg   8520
attatgttca atacttaagc ttcttctggt tgcttttgc ttgttgtatt gttgctgtgc    8580
tttttattat tgtgattctc attagtttgc tttatcgtag aaattcaata gtaagagtta   8640
aggaagatag gcatgtagct tagcacctac atgtctatcg ccagggaaat gtctaatctg   8700
tctacttagt agcctggaaa cgaacggtag acccttagat tttaatttag tttaattttt   8760
agtttagttt aagttagttt agagtaggta taaagatgcc agtgccgggg ccacgcgtag   8820
tacgaccgag ggtacagcac taggacgccc actagggaa gagctaaatt ttagtttaag    8880
ttaagtttaa ttggctaaat atagttaaaa tttataggct agtatagagt tagagcaaaa   8940
aaaaaaaaaa aaaaaaaaaa aaaaaaaaaa aaaaaaaaaa aaaaaaaaaa aaaaaaaaaa   9000
aaaaaaaaaa aaaaaaaaaa aaaaaaaaaa aaaaagcgg ccgcatcgga tgccgggacc    9060
gacgagtgca gaggcgtgca agcgagcttg gcgtaatcat ggtcatagct gtttcctgtg   9120
tgaaattgtt atccgctcac aattccacac aacatacgag ccggaagcat aaagtgtaaa   9180
gcctggggtg cctaatgagt gagctaactc acattaattg cgttgcgctc actgcccgct   9240
ttccagtcgg gaaacctgtc gtgccagctg cattaatgaa tcggccaacg cgcggggaga   9300
ggcggtttgc gtattgggcg ctcttccgct tcctcgctca ctgactcgct gcgctcggtc   9360
gttcggctgc ggcgagcggt atcagctcac tcaaaggcgg taatacggtt atccacagaa   9420
tcaggggata acgcaggaaa gaacatgtga gcaaaaggcc agcaaaaggc caggaaccgt   9480
aaaaaggccg cgttgctggc gtttttccat aggctccgcc cccctgacga gcatcacaaa   9540
aatcgacgct caagtcagag gtggcgaaac ccgacaggac tataaagata ccaggcgttt   9600
ccccctggaa gctccctcgt gcgctctcct gttccgaccc tgccgcttac cggatacctg   9660
tccgcctttc tcccttcggg aagcgtggcg ctttctcata gctcacgctg taggtatctc   9720
agttcggtgt aggtcgttcg ctccaagctg ggctgtgtgc acgaaccccc cgttcagccc   9780
gaccgctgcg ccttatccgg taactatcgt cttgagtcca acccggtaag acacgactta   9840
tcgccactgg cagcagccac tggtaacagg attagcagag cgaggtatgt aggcggtgct   9900
acagagttct tgaagtggtg gcctaactac ggctacacta agaacagt atttggtatc     9960
tgcgctctgc tgaagccagt taccttcgga aaaagagttg gtagctcttg atccggcaaa  10020
caaaccaccg ctggtagcgg tggtttttt gtttgcaagc agcagattac gcgcagaaaa   10080
aaaggatctc aagaagatcc tttgatcttt tctacggggt ctgacgctca gtggaacgaa  10140
aactcacgtt aagggatttt ggtcatgaga ttatcaaaaa ggatcttcac ctagatcctt  10200
ttaaattaaa aatgaagttt taaatcaatc taaagtatat atgagtaaac ttggtctgac  10260
agttaccaat gcttaatcag tgaggcacct atctcagcga tctgtctatt tcgttcatcc  10320
atagttgcct gactccccgt cgtgtagata actacgatac gggagggctt accatctggc  10380
cccagtgctg caatgatacc gcgagaccca cgctcaccgg ctccagattt atcagcaata  10440
aaccagccag ccggaagggc cgagcgcaga agtggtcctg caactttatc cgcctccatc  10500
cagtctatta attgttgccg ggaagctaga gtaagtagtt cgccagttaa tagtttgcgc  10560
aacgttgttg ccattgctac aggcatcgtg gtgtcacgct cgtcgtttgg tatggcttca  10620
ttcagctccg gttcccaacg atcaaggcga gttacatgat cccccatgtt gtgcaaaaaa  10680
gcggttagct ccttcggtcc tccgatcgtt gtcagaagta agttggccgc agtgttatca  10740
ctcatggtta tggcagcact gcataattct cttactgtca tgccatccgt aagatgcttt  10800
tctgtgactg gtgagtactc aaccaagtca ttctgagaat agtgtatgcg gcgaccgagt  10860
```
tgctcttgcc cggcgtcaat acgggataat accgcgccac atagcagaac tttaaaagtg    10920
ctcatcattg gaaaacgttc ttcggggcga aaactctcaa ggatcttacc gctgttgaga    10980
tccagttcga tgtaacccac tcgtgcaccc aactgatctt cagcatcttt tactttcacc    11040
agcgtttctg ggtgagcaaa aacaggaagg caaaatgccg caaaaagggg aataagggcg    11100
acacggaaat gttgaatact catactcttc cttttcaat attattgaag catttatcag     11160
ggttattgtc tcatgagcgg atacatattt gaatgtattt agaaaaataa acaaataggg    11220
gttccgcgca catttccccg aaaagtgcca cctgacgtct aagaaaccat tattatcatg    11280
acattaacct ataaaaatag gcgtatcacg aggccctttc gtc                      11323

<210> SEQ ID NO 69
<211> LENGTH: 11407
<212> TYPE: DNA
<213> ORGANISM: Artificial Sequence
<220> FEATURE:
<223> OTHER INFORMATION: Vector sequence

<400> SEQUENCE: 69
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tcggccgccc gggtaatacg actcactata gggacttaag atagatatta    480
atatatatct attgcactag ccttgcgcta gatttcaaac ttaacaaaac ggacttaaat    540
acctacagct ggtccccata ggtgttccat tgcagtgcac tttagtgccc tggatggcac    600
ctggccacct gtcaggtttt tgttgttaaa atatcattgt tgctggtatc actgcttgtt    660
ttgccgtgtc tcactttata catccgttgc ttgggctacc tagtatccag cgtcctacgg    720
gcgccgtggt cggttcgagt gcgaaggacc tctggttcat ctagcggtag gcgggtgtgt    780
ggaagtagcg cttcagacgt actggttctg ttgcgtgaaa cgcggggtca cctcccccca    840
catacctcta agggcttttg agcctagcgt tgggctacgt tctcgcacaa ggtcggctat    900
acgacgtttg taggggggtag tgccaaacaa cccctgaggt gacaggttct ggtggtgttt    960
cgaaaacaac aatgtgtgtg ccgcataata tgcgcgttat gcattttgga gcaggtagtg   1020
ataaaggagt ggcgcctggt agtactgttc ttaaacagtg gctccccgaa ggaacactcc   1080
ttgtcgataa tgatattgta gattatgttt ctgacgcaca cgtttctgtg ctttcagatt   1140
gcaataaata taagacagag cacaagtttg atcttgtgat atctgatatg tatacagaca   1200
atgattcaaa aagaaagcat gaaggcgtga tagccaataa tggcaatgat gacgtcttca   1260
tatacctttc aagttttcta cgcaataatt tggctctggg aggcagtttt gctgtaaaat   1320
taacagagac aagttggcat gagagtttat atgacattgc acaggattgt gcatggtgga   1380
caatgttttg tacagcagtg aatgcatctt cttcagaagc attcctgatt ggtgttaatt   1440
acttgggtgc aagtgcaaag gttaaagtta gtggaaaaac actgcacgca aattatatat   1500
tttggaggaa ttgtaattat ttacaaacct ctgcttatag tatatttgat gttgctaagt   1560

```
ttgatttgag attgaaagca acgccagttg ttaatcttaa gactgaacaa aagacagact    1620
tagtctttaa tttgataaag tgtggtaagt tactggtaag agatgttggt gaagtcactg    1680
tttttagtga ccattttgtg tgcactatgt agtgcaaatt tgtttgattc tgataataat    1740
tatgtgtact actaccaaag tgcttttaga ccgccaaatg ggtggcactt acaaggaggt    1800
gcttatgcag tagtcagttc tactaattat actaataatg ccggttctgc acatgggtgc    1860
actgttggtg ttattaagga tgtttataat caaagtgtgg cttccatagc tatgacagca    1920
cctcttcagg gtatggcttg gtctaagtca caattctgta gtgcacactg taattttct     1980 gaaattacag ttttttgtcac acattgttat agtagtggta gtgggtcgtg tcctataaca    2040
ggcatgattc cacgtgatca tattcgtatt tctgcaatga aaaatggttc cttattttat    2100
aatttaacag ttagcgtatc taaatacct aattttaaat cttttcaatg tgttaacaac     2160
ttcacatctg tttatttaaa tggtgatctt gttttactt ccaacaaaac tactgatgtt     2220
acgtcagcag gtgtgtattt taaagcaggt ggacctgtaa attatagtat tatgaaagaa    2280
tttaaggttc ttgcttattt tgttaatggt acagcacaag atgtagtttt gtgcgacaat    2340
tcccccaagg gtttgctagc ttgtcaatat aacactggca attttcaga tggcttttat     2400 cctttactat atagtacttt ggttaggaa agttcatcg tctatcgtga aagtagtgtt      2460
aatactactt gtgcgttaac taattttact tttagtaatg taagtaatgc acagcctaat    2520
agtggtggtg ttaatacttt tcatttatat caaacacaaa cagctcagag tggttattat    2580
aattttaatt tgtcatttct gagtcagttt gtgtataagg caagtgattt tatgtatggg    2640
tcctaccatc ctagttgttc ttttagacca gaaaccatta atagtggttt atggtttaat    2700
tccttgtcag tttctcttac ctatggaccc ctacagggag ggtgtaagca atctgttttt    2760
agtggtaagg caacgtgttg ttacgcctac tcttatagag gcccaatggc atgtaaaggt    2820
gtttattcag gtgaattaag cacgaatttt gaatgtggat tgctggttta tgttactaag    2880
agtgatggct ctcgtataca gactagaaca gagcccttag tattaacgca atacaattat    2940
aataatatta ctttagataa gtgtgttgcc tataatatat atggcagagt gggccaaggt    3000
tttattacta atgtgactga ttctgctgct aattttagtt atttagcaga tggtgggtta    3060 gctatttag atacgtcggg tgccatagat gttttttgttg tacagggcat ctatggcctt    3120
aattattaca aggtcaatcc ttgtgaagat gttaaccaac aatttgtagt gtctggtggc    3180
aatatagttg gcattcttac ttctagaaat gaaacaggtt ctgaacaggt tgagaaccag    3240
ttttatgtta agttaaccaa tagctcacat cgtcgtaagc gttctattgg ccaaaacgta    3300
acaagttgtc cttatgttag ctatggcaga ttttgtattg aaccagatgg ttcgttaaag    3360
atgatagtgc cagaagaatt gaaacagttt gtggcacctt tacttaatat tactgaaagt    3420
gtactcatac ctaacagttt taatcttact gttacagatg agtacataca aacacgtatg    3480
gataaggtcc aaatcaattg ccttcaatat gtttgcggca attctttgga gtgtagaaaa    3540
ttgtttcaac aatatggtcc ggtttgtgat aatatattgt ctgttgtaaa tagtgttagt    3600
caaaaagaag atatggaact tttaagcttc tattcctcta ctaaaccaaa gggttatgat    3660
acaccagttc ttagtaatgt aagcactggt gaatttaata tttctcttct cttgaaaccc    3720
ccaagcagtc ctagtgggcg ttctttcatt gaagagcttt tatttacaag tgttgaaaca    3780
gttggtttgc caactgatgc tgaatataaa aaatgcacag cgggaccttt gggtactctt    3840
aaagatctta tctgtgctag ggaatataat ggttttattag tgttgcctcc aattattacg    3900
gcggatatgc aaacaatgta tactgcttct ttagtgggtg ctatggcctt tggtggtatt    3960
```

```
acatcagctg cagctatacc ttttgctact cagattcagg caagaattaa tcatcttggt   4020
attacacagt ctttgttaat gaaaaatcaa gaaaagattg ctgcttcctt taataaggcc   4080
attggtcata tgcaggaagg ttttagaagc acttctctag cattacaaca gattcaagat   4140
gttgttaata agcagagtgc tattcttact gaaactatga attctcttaa taagaatttt   4200
ggtgctatta catcagtcat tcaagatatt tacgcgcaac ttgacgcaat ccaagcagat   4260
gcacaagttg accgccttat tactggtaga ctttcatcac tctcagtgtt agcctctgct   4320
aaacagtctg agtatattag agtttcccag cagcgtgaat tagccactca aaaaattaat   4380
gagtgtgtta aatcacaatc taataggtac ggattttgtg gtagtggaag acatgttctt   4440
tcgataccac aaaatgcacc taatggtata gtgtttatac actttactta tacaccagag   4500
agttttgtta atgttactgc aatagtgggt ttttgtgtaa atcctgctaa tgctagtcag   4560
tatgctatag tacctgctaa tggaaggggt atttttatac aagttaatgg cacgtactat   4620
atcactgcac gtgatatgta tatgccacga gacattactg caggagatat agttactctt   4680
acgtcttgtc aagcaaatta tgttaatgta aataaaaccg tcattactac atttgtagaa   4740
gatgacgatt ttgattttga tgatgagttg tcaaaatggt ggaatgatac taagcatcag   4800
ctaccagact ttgacgactt caattacaca gtacccatac ttaatattag cggtgaaatt   4860
gattatattc aaggtgttat acagggtctt aatgactccc ttatagacct tgaagaactt   4920
tcaataatta aaacttatat taagtggcct tggtatgttt ggcttgccat attctttgcc   4980
attattatct ttatccttat attaggatgg gtttcttca tgactggatg ttgtggttgt   5040
tgttgtgggt gctttggcat tattcctcta atgagtaagt gtggtaagaa atcttcttac   5100
tacactactt ttgataatga tgtggtaact aacaataca gacctaaaaa gtctgtttaa   5160
tgatccaaag tcccactagt ttcttaatag tattaatttt gctttggtgt aaacttgtac   5220
taagttgttt tagagagttt attattgccc ttcaacaact aacacaagtt ttactccaaa   5280
ttatcgatag taatttacag tctagactga ccctttggca cagtctagac taatgttaaa   5340
cttagaagca attattgaaa ccggtgatca agtgattcaa aaaatcagtt tcaatttaca   5400
gcatatttca agtgtattaa acacagaagt atttgacccc tttgactatt gttattacag   5460
aggaggtaat ttttgggaaa tagagtcagc tgaagattgt tcaggtgatg atgaatttat   5520
tgaataagtc gctagaggag aatggaagtt ttctaacggc actttacata tttgtaggat   5580
ttttagcatt ttatcttcta ggtagagcac ttcaagcatt tgtacaggct gctgatgctt   5640
gttgttattt ttggtacacg tggttagtaa ttccaggagt taagggtaca gcctttgtat   5700
acaagtatac atatggtaga aaacttaaca ttcggaatt agaagcagtt gttgttaacg   5760
agtttcctaa gaacggttgg aataataaaa atccagcaaa ttttcaagat gtccaacgaa   5820
acaaattgta ctcttgactt tgaacagtca gttgagcttt taaagagta atttattt    5880 ataactgcat tcttgttgtt cttaaccata atacttcagt atggttatgc aacgcgtagt   5940
aagtttattt atatacttaa aatgatagtg ttatggtgct tttggcccct taacattgca   6000
gtaggtgtaa tttcatgtat atacccacca aacacaggag tcttgtcgc agcgataata   6060 cttactgtgt ttgcgtgtct ttcttttgta ggttattgga tccagagtat tagactcttt   6120
aagcggtgta gatcttggtg gtcatttaac ccagaatcta acgccgtagg ttcaatactc   6180
ctaactaatg gtcaacaatg taattttgct atagagagtg tgccgatggt gctttctcct   6240
attataaaga atggtgttct ttattgtgag ggtcagtggc ttgctaaatg tgaaccagac   6300
```

```
cacttgccta aagacatatt tgtatgcaca ccagatagac gtaatatcta tcgtatggtg   6360
cagaaataca ctggtgacca aagcggaaat aagaaaaggt ttgctacatt tgtctatgca   6420
aagcagtcag tagacactgg cgagctagaa agtgtagcaa caggtggaag tagcctttac   6480
acataaatgt gtgtgtgtag agagtattta aaattattct tcaatagtgc ctctatttta   6540
agagcgcgga agagtatttg ttttgaggat attaatataa atcctctttg ttttgtactc   6600
tctttacaag agttattatt taagcaacag ttttccttt cctttgtttg gaagaaagtt    6660
gttgttaatg gtgtagaatt ccaagtagaa aatggaaaag tccactacga aggaaacccc   6720
attttccaaa aaggttgttg taggttgtgg tcccattata agaaggatta aatggattaa   6780
accacctaca ctacttactt gtaataaggg cgtttggact tacaagcgct taacaaatac   6840
agacgatgaa atggctgact agttttggaa gagcagttat ttcttgttat aaagccctac   6900
tattaactca gttaagagta ttagataggt taatttaga tcacggacca aagcgagtct    6960
taacgtgtgg taggcgagtg ctttttatctc aattagattt agtttatagg ttggcatata   7020
cgcccaccca atcgctggta tgaataatag taaagataat ccttttcgcg gagcaatagc   7080
aagaaaagcg cgaatttatc tgagagaagg attagagtgt gtttactttc ttaacaaagc   7140
aggacaagca gagccttgtc ccgcgtgtac ctccctagta tttcagggga aaacttgtga   7200
ggaacacaca gataataata atcttttgtc atggcgagcg gtaagacaac tgggaagaca   7260
gacgccccag cgccagtcat caaactagga gggccaaaac cacctaaagt tggttcttct   7320
ggaaatgcta gctggtttca agcactaaaa gccaagaagt taaattcacc tcctcctaag   7380
tttgaaggta gcggcgttcc tgataatgaa aatcttaaat taagccagca acatgggtac   7440
tggagacgtc aagccaggta caagccaggt aaaggcggaa gaaaatcagt cccagatgct   7500
tggtacttct attacactgg aacaggacca gccgctgacc tgaattgggg tgatagccaa   7560
gatggtatag tgtgggtttc tgcaaagggt gctgatacta aatctagatc taaccagggt   7620
acaagggatc ctgataagtt tgaccaatac ccgctacgat tctcagatgg aggacctgat   7680
ggtaatttcc gttgggactt cattccaata aatcgtggta ggagtggaag atcaacagcg   7740
gcttcatcag cagcatctag tagagcaccg tcgcgtgatg gctcgcgtgg acgtagaagc   7800
ggagctgaag atgatcttat agctcgtgca gcaaagatca ttcaggatca gcagaagaag   7860
ggttctcgca ttactaaagc taaggccgat gaaatggctc atcgccggta ttgtaagcgt   7920
actatcccac ctggttataa ggttgatcaa gtatttggtc cccgtactaa aggtaaggag   7980
ggaaattttg gtgatgacaa gatgaatgag gagggtatta aggatgggcg cgttacagca   8040
atgctcaacc tagtccctag cagccatgct tgtctttttg gaagtagagt gacgcccaaa   8100
cttcaaccag atgggctgca cttgagattt gaatttacta ctgtggtttc tagggatgat   8160
ccgcagtttg ataattatgt gaaaatttgt gatcagtgtg tcgatggtgt agggactcgg   8220
ccaaaagacg atgaaccgag accaaagtca cgcccaaatt caagacctgc tacaagaaca   8280
agttctccag cgccaagaca acagcgtcaa aagaaggaga agaagtcaaa gaagcaggat   8340
gatgaagtag ataaggcatt gacctcagat gaggagagga acaatgcaca gctggaattt   8400
gatgatgaac cgaaagtgat taactggggg gattcagcac ttggagagaa tgagttgtaa   8460
agctagattt ccaacttaac atcatggacg tgcgtatgct gttttttccct actatagact   8520
ttttagcata ttatttttg ctatttgtat ggtttattac aggtgaagat tgtatgtatt    8580
tgttgtacac tcgtatgttc tatattatgt tttctgtagt tgttattagt gttgttcttg   8640
ttcttactct actgttctct tttctttatt ttagagtatc aataagaatc aaggaagata   8700
```

```
ggcatgtagt ttgattacct acatgtctat cgccagggaa atgtctaatc tgtctactta    8760
gtagcctgga aacgaacggt agaccettag attttaattt agtttaattt ttagtttagt    8820
ttaagttagt ttagagtagg tataaagaag ccagtgccgg ggccacgcgg agtacgatcg    8880
agggtacagc actaggacgc ccactagggg aagagctaaa ttttagttta agttaagttt    8940
aattggctaa gtatagttaa aatttatagg ctagtataga gttagagcaa aaaaaaaaa     9000 aaaaaaaaaa aaaaaaaaaa aaaaaaaaaa aaaaaaaaaa aaaaaaaaaa aaaaaaaaaa    9060
aaaaaaaaaa aaaaaaaaaa aaaaaaaagt ttaaacttaa ttaagaattc ccttggctcg    9120
agttcgaaat cggatgccgg gaccgacgag tgcagaggcg tgcaagcgag cttggcgtaa    9180
tcatggtcat agctgtttcc tgtgtgaaat tgttatccgc tcacaattcc acacaacata    9240
cgagccggaa gcataaagtg taaagcctgg ggtgcctaat gagtgagcta actcacatta    9300
attgcgttgc gctcactgcc cgctttccag tcgggaaacc tgtcgtgcca gctgcattaa    9360
tgaatcggcc aacgcgcggg gagaggcggt ttgcgtattg ggcgctcttc cgcttcctcg    9420
ctcactgact cgctgcgctc ggtcgttcgg ctgcggcgag cggtatcagc tcactcaaag    9480
gcggtaatac ggttatccac agaatcaggg gataacgcag gaaagaacat gtgagcaaaa    9540
ggccagcaaa aggccaggaa ccgtaaaaag gccgcgttgc tggcgttttt ccataggctc    9600
cgcccccctg acgagcatca caaaaatcga cgctcaagtc agaggtggcg aaacccgaca    9660
ggactataaa gataccaggc gtttccccct ggaagctccc tcgtgcgctc tcctgttccg    9720
accctgccgc ttaccggata cctgtccgcc tttctccctt cgggaagcgt ggcgctttct    9780
catagctcac gctgtaggta tctcagttcg gtgtaggtcg ttcgctccaa gctgggctgt    9840
gtgcacgaac cccccgttca gcccgaccgc tgcgccttat ccggtaacta tcgtcttgag    9900
tccaacccgg taagacacga cttatcgcca ctggcagcag ccactggtaa caggattagc    9960
agagcgaggt atgtaggcgg tgctacagag ttcttgaagt ggtggcctaa ctacggctac   10020
actagaagaa cagtatttgg tatctgcgct ctgctgaagc cagttacctt cggaaaaaga   10080
gttggtagct cttgatccgg caaacaaacc accgctggta gcggtggttt ttttgtttgc   10140
aagcagcaga ttacgcgcag aaaaaaagga tctcaagaag atcctttgat cttttctacg   10200
gggtctgacg ctcagtggaa cgaaaactca cgttaaggga ttttggtcat gagattatca   10260
aaaaggatct tcacctagat ccttttaaat taaaaatgaa gttttaaatc aatctaaagt   10320
atatatgagt aaacttggtc tgacagttac caatgcttaa tcagtgaggc acctatctca   10380
gcgatctgtc tatttcgttc atccatagtt gcctgactcc ccgtcgtgta gataactacg   10440
atacgggagg gcttaccatc tggccccagt gctgcaatga taccgcgaga cccacgctca   10500
ccggctccag atttatcagc aataaaccag ccagccggaa gggccgagcg cagaagtggt   10560
cctgcaactt tatccgcctc catccagtct attaattgtt gccgggaagc tagagtaagt   10620
agttcgccag ttaatagttt gcgcaacgtt gttgccattg ctacaggcat cgtggtgtca   10680
cgctcgtcgt ttggtatggc ttcattcagc tccggttccc aacgatcaag gcgagttaca   10740
tgatccccca tgttgtgcaa aaaagcggtt agctccttcg gtcctccgat cgttgtcaga   10800
agtaagttgg ccgcagtgtt atcactcatg gttatggcag cactgcataa ttctcttact   10860
gtcatgccat ccgtaagatg cttttctgtg actggtgagt actcaaccaa gtcattctga   10920
gaatagtgta tgcggcgacc gagttgctct tgcccggcgt caatacggga taataccgcg   10980
ccacatagca gaactttaaa agtgctcatc attggaaaac gttcttcggg gcgaaaactc   11040
```

-continued

```
tcaaggatct taccgctgtt gagatccagt tcgatgtaac ccactcgtgc acccaactga    11100
tcttcagcat cttttacttt caccagcgtt tctgggtgag caaaaacagg aaggcaaaat    11160
gccgcaaaaa agggaataag ggcgacacgg aaatgttgaa tactcatact cttccttttt    11220
caatattatt gaagcattta tcagggttat tgtctcatga gcggatacat atttgaatgt    11280
atttagaaaa ataaacaaat aggggttccg cgcacatttc cccgaaaagt gccacctgac    11340
gtctaagaaa ccattattat catgacatta acctataaaa ataggcgtat cacgaggccc    11400
tttcgtc                                                              11407
```

```
<210> SEQ ID NO 70
<211> LENGTH: 52
<212> TYPE: DNA
<213> ORGANISM: Artificial Sequence
<220> FEATURE:
<223> OTHER INFORMATION: Primer

<400> SEQUENCE: 70
cagagcacaa gtttgatctt gtgatatctg atatgtatac agacaatgat tc            52

<210> SEQ ID NO 71
<211> LENGTH: 32
<212> TYPE: DNA
<213> ORGANISM: Artificial Sequence
<220> FEATURE:
<223> OTHER INFORMATION: Primer

<400> SEQUENCE: 71
acttcaccaa catctcttac cagtaactta cc                                  32

<210> SEQ ID NO 72
<211> LENGTH: 31
<212> TYPE: DNA
<213> ORGANISM: Artificial Sequence
<220> FEATURE:
<223> OTHER INFORMATION: Primer

<400> SEQUENCE: 72
ttactggtaa gagatgttgg tgaagtcact g                                   31

<210> SEQ ID NO 73
<211> LENGTH: 35
<212> TYPE: DNA
<213> ORGANISM: Artificial Sequence
<220> FEATURE:
<223> OTHER INFORMATION: Primer

<400> SEQUENCE: 73
ggactttgga tcattaaaca gactttttag gtctg                               35

<210> SEQ ID NO 74
<211> LENGTH: 32
<212> TYPE: DNA
<213> ORGANISM: Artificial Sequence
<220> FEATURE:
<223> OTHER INFORMATION: Primer

<400> SEQUENCE: 74
aaagtctgtt taatgatcca agtcccact ag                                   32

<210> SEQ ID NO 75
<211> LENGTH: 48
<212> TYPE: DNA
<213> ORGANISM: Artificial Sequence
```

```
<220> FEATURE:
<223> OTHER INFORMATION: Primer

<400> SEQUENCE: 75
cttaactcct ggaattacta accacgtgta ccaaaataaa caacaagc         48

<210> SEQ ID NO 76
<211> LENGTH: 1168
<212> TYPE: PRT
<213> ORGANISM: Avian infectious bronchitis virus

<400> SEQUENCE: 76
```

| | | | | | | | | | | | | | | | |
|---|---|---|---|---|---|---|---|---|---|---|---|---|---|---|---|
| Met | Leu | Val | Lys | Ser | Leu | Phe | Leu | Val | Thr | Ile | Leu | Phe | Ala | Leu | Cys |
| 1 | | | | 5 | | | | | 10 | | | | | 15 | |
| Ser | Ala | Asn | Leu | Tyr | Asp | Asn | Glu | Ser | Phe | Val | Tyr | Tyr | Gln | Ser | |
| | | | 20 | | | | | 25 | | | | | 30 | | |
| Ala | Phe | Arg | Pro | Gly | His | Gly | Trp | His | Leu | His | Gly | Gly | Ala | Tyr | Ala |
| | | 35 | | | | | 40 | | | | | 45 | | | |
| Val | Val | Asn | Val | Ser | Ser | Glu | Asn | Asn | Asn | Ala | Gly | Thr | Ala | Pro | Ser |
| | 50 | | | | | 55 | | | | | 60 | | | | |
| Cys | Thr | Ala | Gly | Ala | Ile | Gly | Tyr | Ser | Lys | Asn | Leu | Ser | Ala | Ala | Ser |
| 65 | | | | | 70 | | | | | 75 | | | | | 80 |
| Val | Ala | Met | Thr | Ala | Pro | Leu | Ser | Gly | Met | Ser | Trp | Ser | Ala | Asn | Ser |
| | | | | 85 | | | | | 90 | | | | | 95 | |
| Phe | Cys | Thr | Ala | His | Cys | Asn | Phe | Thr | Ser | Tyr | Ile | Val | Phe | Val | Thr |
| | | | 100 | | | | | 105 | | | | | 110 | | |
| His | Cys | Tyr | Lys | Ser | Gly | Ser | Asn | Ser | Cys | Pro | Leu | Thr | Gly | Leu | Ile |
| | | 115 | | | | | 120 | | | | | 125 | | | |
| Pro | Ser | Gly | Tyr | Ile | Arg | Ile | Ala | Ala | Met | Lys | His | Gly | Ser | Ala | Met |
| | 130 | | | | | 135 | | | | | 140 | | | | |
| Pro | Gly | His | Leu | Phe | Tyr | Asn | Leu | Thr | Val | Ser | Val | Thr | Lys | Tyr | Pro |
| 145 | | | | | 150 | | | | | 155 | | | | | 160 |
| Lys | Phe | Arg | Ser | Leu | Gln | Cys | Val | Asn | Asn | Tyr | Thr | Ser | Val | Tyr | Leu |
| | | | | 165 | | | | | 170 | | | | | 175 | |
| Asn | Gly | Asp | Leu | Val | Phe | Thr | Ser | Asn | Tyr | Thr | Glu | Asp | Val | Val | Ala |
| | | | 180 | | | | | 185 | | | | | 190 | | |
| Ala | Gly | Val | His | Phe | Lys | Ser | Gly | Gly | Pro | Ile | Thr | Tyr | Lys | Val | Met |
| | | 195 | | | | | 200 | | | | | 205 | | | |
| Arg | Glu | Val | Lys | Ala | Leu | Ala | Tyr | Phe | Val | Asn | Gly | Thr | Ala | His | Asp |
| | 210 | | | | | 215 | | | | | 220 | | | | |
| Val | Ile | Leu | Cys | Asp | Asp | Thr | Pro | Arg | Gly | Leu | Leu | Ala | Cys | Gln | Tyr |
| 225 | | | | | 230 | | | | | 235 | | | | | 240 |
| Asn | Thr | Gly | Asn | Phe | Ser | Asp | Gly | Phe | Tyr | Pro | Phe | Thr | Asn | Thr | Ser |
| | | | | 245 | | | | | 250 | | | | | 255 | |
| Ile | Val | Lys | Asp | Lys | Phe | Ile | Val | Tyr | Arg | Glu | Ser | Ser | Val | Asn | Thr |
| | | | 260 | | | | | 265 | | | | | 270 | | |
| Thr | Leu | Thr | Leu | Thr | Asn | Phe | Thr | Phe | Ser | Asn | Glu | Ser | Gly | Ala | Pro |
| | | 275 | | | | | 280 | | | | | 285 | | | |
| Pro | Asn | Thr | Gly | Gly | Val | Asp | Ser | Phe | Ile | Leu | Tyr | Gln | Thr | Gln | Thr |
| | 290 | | | | | 295 | | | | | 300 | | | | |
| Ala | Gln | Ser | Gly | Tyr | Tyr | Asn | Phe | Asn | Phe | Ser | Phe | Leu | Ser | Ser | Phe |
| 305 | | | | | 310 | | | | | 315 | | | | | 320 |
| Val | Tyr | Arg | Glu | Ser | Asn | Tyr | Met | Tyr | Gly | Ser | Tyr | His | Pro | Arg | Cys |
| | | | | 325 | | | | | 330 | | | | | 335 | |
| Ser | Phe | Arg | Pro | Glu | Thr | Leu | Asn | Gly | Leu | Trp | Phe | Asn | Ser | Leu | Ser |

-continued

```
            340                 345                 350
Val Ser Leu Thr Tyr Gly Pro Ile Gln Gly Gly Cys Lys Gln Ser Val
        355                 360                 365
Phe Asn Gly Lys Ala Thr Cys Cys Tyr Ala Tyr Ser Tyr Gly Gly Pro
        370                 375                 380
Arg Gly Cys Lys Gly Val Tyr Arg Gly Glu Leu Thr Gln His Phe Glu
385                 390                 395                 400
Cys Gly Leu Leu Val Tyr Val Thr Lys Ser Asp Gly Ser Arg Ile Gln
                405                 410                 415
Thr Ala Thr Gln Pro Pro Val Leu Thr Gln Asn Phe Tyr Asn Asn Ile
                420                 425                 430
Asn Leu Gly Lys Cys Val Asp Tyr Asn Ile Tyr Gly Arg Ile Gly Gln
                435                 440                 445
Gly Leu Ile Thr Asn Val Thr Asp Leu Ala Val Ser Tyr Asn Tyr Leu
        450                 455                 460
Ser Asp Ala Gly Leu Ala Ile Leu Asp Thr Ser Gly Ala Ile Asp Ile
465                 470                 475                 480
Phe Val Val Gln Gly Glu Tyr Gly Pro Asn Tyr Tyr Lys Val Asn Pro
                485                 490                 495
Cys Glu Asp Val Asn Gln Gln Phe Val Val Ser Gly Gly Lys Leu Val
                500                 505                 510
Gly Ile Leu Thr Ser Arg Asn Glu Thr Gly Ser Gln Leu Leu Glu Asn
                515                 520                 525
Gln Phe Tyr Ile Lys Ile Thr Asn Gly Thr Arg Arg Ser Arg Arg Ser
        530                 535                 540
Val Thr Glu Asn Val Thr Asn Cys Pro Tyr Val Ser Tyr Gly Lys Phe
545                 550                 555                 560
Cys Ile Lys Pro Asp Gly Ser Ile Ser Val Ile Val Pro Lys Glu Leu
                565                 570                 575
Asp Gln Phe Val Ala Pro Leu Leu Asn Val Thr Glu Tyr Val Leu Ile
                580                 585                 590
Pro Asn Ser Phe Asn Leu Thr Val Thr Asp Glu Tyr Ile Gln Thr Arg
                595                 600                 605
Met Asp Lys Ile Gln Ile Asn Cys Leu Gln Tyr Val Cys Gly Asn Ser
        610                 615                 620
Leu Ala Cys Arg Lys Leu Phe Gln Gln Tyr Gly Pro Val Cys Asp Asn
625                 630                 635                 640
Ile Leu Ser Val Val Asn Ser Val Gly Gln Lys Glu Asp Met Glu Leu
                645                 650                 655
Leu Asn Phe Tyr Ser Ser Thr Lys Pro Ala Arg Phe Asn Thr Pro Val
                660                 665                 670
Phe Ser Asn Leu Ser Thr Gly Glu Phe Asn Ile Ser Leu Leu Leu Thr
        675                 680                 685
Ser Pro Ser Ser Pro Arg Arg Arg Ser Phe Ile Glu Asp Leu Leu Phe
        690                 695                 700
Thr Ser Val Glu Ser Val Gly Leu Pro Thr Asp Asp Ala Tyr Lys Lys
705                 710                 715                 720
Cys Thr Ala Gly Pro Leu Gly Phe Phe Lys Asp Leu Ala Cys Ala Arg
                725                 730                 735
Glu Tyr Asn Gly Leu Leu Val Leu Pro Pro Ile Ile Thr Ala Glu Met
                740                 745                 750
Gln Thr Leu Tyr Thr Ser Ser Leu Val Ala Ser Met Ala Phe Gly Gly
        755                 760                 765
```

```
Ile Thr Ala Ala Gly Ala Ile Pro Phe Ala Thr Gln Leu Gln Ala Arg
    770                 775                 780
Ile Asn His Leu Gly Ile Thr Gln Ser Leu Leu Lys Asn Gln Glu
785                 790                 795                 800
Lys Ile Ala Ala Ser Phe Asn Lys Ala Ile Gly His Met Gln Glu Gly
                805                 810                 815
Phe Arg Ser Thr Ser Leu Ala Leu Gln Gln Ile Gln Asp Val Val Asn
                820                 825                 830
Lys Gln Ser Ala Ile Leu Thr Glu Thr Met Ala Ala Leu Asn Lys Asn
                835                 840                 845
Phe Gly Ala Ile Ser Ser Val Ile Gln Asp Ile Tyr Gln Gln Leu Asp
    850                 855                 860
Ser Ile Gln Ala Asp Ala Gln Val Asp Arg Leu Ile Thr Gly Arg Leu
865                 870                 875                 880
Ser Ser Leu Ser Val Leu Ala Ser Ala Lys Gln Ser Glu Tyr Ile Arg
                885                 890                 895
Val Ser Gln Gln Arg Glu Leu Ala Thr Gln Lys Ile Asn Glu Cys Val
                900                 905                 910
Lys Ser Gln Ser Ile Arg Tyr Ser Phe Cys Gly Asn Gly Arg His Val
                915                 920                 925
Leu Thr Ile Pro Gln Asn Ala Pro Asn Gly Ile Val Phe Ile His Phe
    930                 935                 940
Thr Tyr Thr Pro Glu Ser Phe Ile Asn Val Thr Ala Ile Val Gly Phe
945                 950                 955                 960
Cys Val Ser Pro Ala Asn Ala Ser Gln Tyr Ala Ile Val Pro Ala Asn
                965                 970                 975
Gly Arg Gly Ile Phe Ile Gln Val Asn Gly Ser Tyr Tyr Ile Thr Ala
                980                 985                 990
Arg Asp Met Tyr Met Pro Arg Asp  Ile Thr Ala Gly Asp  Ile Val Thr
                995                1000                1005
Leu Thr  Ser Cys Gln Ala Asn  Tyr Val Ser Val Asn  Lys Thr Val
    1010                1015                1020
Ile Thr  Thr Phe Val Asp Asn  Asp Asp Phe Asp Phe  Asp Asp Glu
    1025                1030                1035
Leu Ser  Lys Trp Trp Asn Asp  Thr Lys His Glu Leu  Pro Asp Phe
    1040                1045                1050
Asp Lys  Phe Asn Tyr Thr Val  Pro Ile Leu Asp Ile  Asp Ser Glu
    1055                1060                1065
Ile Asp  Arg Ile Gln Gly Val  Ile Gln Gly Leu Asn  Asp Ser Leu
    1070                1075                1080
Ile Asp  Leu Glu Thr Leu Ser  Ile Leu Lys Thr Tyr  Ile Lys Trp
    1085                1090                1095
Pro Trp  Tyr Val Trp Leu Ala  Ile Ala Phe Ala Thr  Ile Ile Phe
    1100                1105                1110
Ile Leu  Ile Leu Gly Trp Leu  Phe Phe Met Thr Gly  Cys Cys Gly
    1115                1120                1125
Cys Cys  Cys Gly Cys Phe Gly  Ile Ile Pro Leu Met  Ser Lys Cys
    1130                1135                1140
Gly Lys  Lys Ser Ser Tyr Tyr  Thr Thr Phe Asp Asn  Asp Val Val
    1145                1150                1155
Thr Glu  Gln Tyr Arg Pro Lys  Lys Ser Val
    1160                1165
```

<210> SEQ ID NO 77
<211> LENGTH: 1168
<212> TYPE: PRT
<213> ORGANISM: Avian infectious bronchitis virus

<400> SEQUENCE: 77

```
Met Leu Val Lys Ser Leu Phe Leu Val Thr Ile Leu Phe Ala Leu Cys
1               5                   10                  15

Ser Ala Asn Leu Tyr Asp Asn Glu Ser Phe Val Tyr Tyr Tyr Gln Ser
            20                  25                  30

Ala Phe Arg Pro Gly His Gly Trp His Leu His Gly Gly Ala Tyr Ala
        35                  40                  45

Val Val Asn Val Ser Ser Glu Asn Asn Asn Ala Gly Thr Ala Pro Ser
    50                  55                  60

Cys Thr Ala Gly Ala Ile Gly Tyr Ser Lys Asn Leu Ser Ala Ala Ser
65                  70                  75                  80

Val Ala Met Thr Ala Pro Leu Ser Gly Met Ser Trp Ser Ala Asn Ser
                85                  90                  95

Phe Cys Thr Ala His Cys Asn Phe Thr Ser Tyr Ile Val Phe Val Thr
            100                 105                 110

His Cys Tyr Lys Ser Gly Ser Asn Ser Cys Pro Leu Thr Gly Leu Ile
        115                 120                 125

Pro Ser Gly Tyr Ile Arg Ile Ala Ala Met Lys His Gly Ser Ala Met
    130                 135                 140

Pro Gly His Leu Phe Tyr Asn Leu Thr Val Ser Val Thr Lys Tyr Pro
145                 150                 155                 160

Lys Phe Arg Ser Leu Gln Cys Val Asn Asn Tyr Thr Ser Val Tyr Leu
                165                 170                 175

Asn Gly Asp Leu Val Phe Thr Ser Asn Tyr Thr Glu Asp Val Val Ala
            180                 185                 190

Ala Gly Val His Phe Lys Ser Gly Gly Pro Ile Thr Tyr Lys Val Met
        195                 200                 205

Arg Glu Val Lys Ala Leu Ala Tyr Phe Val Asn Gly Thr Ala His Asp
    210                 215                 220

Val Ile Leu Cys Asp Asp Thr Pro Arg Gly Leu Leu Ala Cys Gln Tyr
225                 230                 235                 240

Asn Thr Gly Asn Phe Ser Asp Gly Phe Tyr Pro Phe Thr Asn Thr Ser
                245                 250                 255

Ile Val Lys Asp Lys Phe Ile Val Tyr Arg Glu Ser Ser Val Asn Thr
            260                 265                 270

Thr Cys Thr Leu Thr Asn Phe Thr Phe Ser Asn Glu Ser Gly Ala Pro
        275                 280                 285

Pro Asn Thr Gly Gly Val Asp Ser Phe Ile Leu Tyr Gln Thr Gln Thr
    290                 295                 300

Ala Gln Ser Gly Tyr Tyr Asn Phe Asn Phe Ser Phe Leu Ser Ser Phe
305                 310                 315                 320

Val Tyr Arg Glu Ser Asn Tyr Met Tyr Gly Ser Tyr His Pro Arg Cys
                325                 330                 335

Ser Phe Arg Pro Glu Thr Leu Asn Gly Leu Trp Phe Asn Ser Leu Ser
            340                 345                 350

Val Ser Leu Thr Tyr Gly Pro Ile Gln Gly Gly Cys Lys Gln Ser Val
        355                 360                 365

Phe Asn Gly Lys Ala Thr Cys Cys Tyr Ala Tyr Ser Tyr Gly Gly Pro
    370                 375                 380
```

```
Arg Gly Cys Lys Gly Val Tyr Arg Gly Glu Leu Thr Gln His Phe Glu
385                 390                 395                 400

Cys Gly Leu Leu Val Tyr Val Thr Lys Ser Asp Gly Ser Arg Ile Gln
            405                 410                 415

Thr Ala Thr Gln Pro Pro Val Leu Thr Gln Asn Phe Tyr Asn Asn Ile
        420                 425                 430

Asn Leu Gly Lys Cys Val Asp Tyr Asn Ile Tyr Gly Arg Ile Gly Gln
            435                 440                 445

Gly Leu Ile Thr Asn Val Thr Asp Leu Ala Val Ser Tyr Asn Tyr Leu
    450                 455                 460

Ser Asp Ala Gly Leu Ala Ile Leu Asp Thr Ser Gly Ala Ile Asp Ile
465                 470                 475                 480

Phe Val Val Gln Gly Glu Tyr Gly Pro Asn Tyr Tyr Lys Val Asn Pro
                485                 490                 495

Cys Glu Asp Val Asn Gln Gln Phe Val Val Ser Gly Gly Lys Leu Val
            500                 505                 510

Gly Ile Leu Thr Ser Arg Asn Glu Thr Gly Ser Gln Leu Leu Glu Asn
        515                 520                 525

Gln Phe Tyr Ile Lys Ile Thr Asn Gly Thr Arg Arg Ser Arg Arg Ser
    530                 535                 540

Val Thr Glu Asn Val Thr Asn Cys Pro Tyr Val Ser Tyr Gly Lys Phe
545                 550                 555                 560

Cys Ile Lys Pro Asp Gly Ser Ile Ser Val Ile Val Pro Lys Glu Leu
                565                 570                 575

Asp Gln Phe Val Ala Pro Leu Leu Asn Val Thr Glu Tyr Val Leu Ile
            580                 585                 590

Pro Asn Ser Phe Asn Leu Thr Val Thr Asp Glu Tyr Ile Gln Thr Arg
        595                 600                 605

Met Asp Lys Ile Gln Ile Asn Cys Leu Gln Tyr Val Cys Gly Asn Ser
    610                 615                 620

Leu Ala Cys Arg Lys Leu Phe Gln Gln Tyr Gly Pro Val Cys Asp Asn
625                 630                 635                 640

Ile Leu Ser Val Val Asn Ser Val Gly Gln Lys Glu Asp Met Glu Leu
                645                 650                 655

Leu Asn Phe Tyr Ser Ser Thr Lys Pro Ala Arg Phe Asn Thr Pro Val
            660                 665                 670

Phe Ser Asn Leu Ser Thr Gly Glu Phe Asn Ile Ser Leu Leu Leu Thr
        675                 680                 685

Ser Pro Ser Ser Pro Arg Arg Arg Ser Phe Ile Glu Asp Leu Leu Phe
    690                 695                 700

Thr Ser Val Glu Ser Val Gly Leu Pro Thr Asp Asp Ala Tyr Lys Lys
705                 710                 715                 720

Cys Thr Ala Gly Pro Leu Gly Phe Phe Lys Asp Leu Ala Cys Ala Arg
                725                 730                 735

Glu Tyr Asn Gly Leu Leu Val Leu Pro Pro Ile Ile Thr Ala Glu Met
            740                 745                 750

Gln Thr Leu Tyr Thr Ser Ser Leu Val Ala Ser Met Ala Phe Gly Gly
        755                 760                 765

Ile Thr Ala Ala Gly Ala Ile Pro Phe Ala Thr Gln Leu Gln Ala Arg
    770                 775                 780

Ile Asn His Leu Gly Ile Thr Gln Ser Leu Leu Leu Lys Asn Gln Glu
785                 790                 795                 800
```

Lys Ile Ala Ala Ser Phe Asn Lys Ala Ile Gly His Met Gln Glu Gly
            805                 810                 815

Phe Arg Ser Thr Ser Leu Ala Leu Gln Gln Ile Gln Asp Val Val Asn
            820                 825                 830

Lys Gln Ser Ala Ile Leu Thr Glu Thr Met Ala Ala Leu Asn Lys Asn
            835                 840                 845

Phe Gly Ala Ile Ser Ser Val Ile Gln Asp Ile Tyr Gln Gln Leu Asp
            850                 855                 860

Ser Ile Gln Ala Asp Ala Gln Val Asp Arg Leu Ile Thr Gly Arg Leu
865                 870                 875                 880

Ser Ser Leu Ser Val Leu Ala Ser Ala Lys Gln Ser Glu Tyr Ile Arg
            885                 890                 895

Val Ser Gln Gln Arg Glu Leu Ala Thr Gln Lys Ile Asn Glu Cys Val
            900                 905                 910

Lys Ser Gln Ser Ile Arg Tyr Ser Phe Cys Gly Asn Gly Arg His Val
            915                 920                 925

Leu Thr Ile Pro Gln Asn Ala Pro Asn Gly Ile Val Phe Ile His Phe
            930                 935                 940

Thr Tyr Thr Pro Glu Ser Phe Ile Asn Val Thr Ala Ile Val Gly Phe
945                 950                 955                 960

Cys Val Ser Pro Ala Asn Ala Ser Gln Tyr Ala Ile Val Pro Ala Asn
            965                 970                 975

Gly Arg Gly Ile Phe Ile Gln Val Asn Gly Ser Tyr Tyr Ile Thr Ala
            980                 985                 990

Arg Asp Met Tyr Met Pro Arg Asp Ile Thr Ala Gly Asp Ile Val Thr
            995                 1000                1005

Leu Thr Ser Cys Gln Ala Asn Tyr Val Ser Val Asn Lys Thr Val
            1010                1015                1020

Ile Thr Thr Phe Val Asp Asn Asp Asp Phe Asp Phe Asp Asp Glu
            1025                1030                1035

Leu Ser Lys Trp Trp Asn Asp Thr Lys His Glu Leu Pro Asp Phe
            1040                1045                1050

Asp Lys Phe Asn Tyr Thr Val Pro Ile Leu Asp Ile Asp Ser Glu
            1055                1060                1065

Ile Asp Arg Ile Gln Gly Val Ile Gln Gly Leu Asn Asp Ser Leu
            1070                1075                1080

Ile Asp Leu Glu Thr Leu Ser Ile Leu Lys Thr Tyr Ile Lys Trp
            1085                1090                1095

Pro Trp Tyr Val Trp Leu Ala Ile Ala Phe Ala Thr Ile Ile Phe
            1100                1105                1110

Ile Leu Ile Leu Gly Trp Leu Phe Phe Met Thr Gly Cys Cys Gly
            1115                1120                1125

Cys Cys Cys Gly Cys Phe Gly Ile Ile Pro Leu Met Ser Lys Cys
            1130                1135                1140

Gly Lys Lys Ser Ser Tyr Tyr Thr Thr Phe Asp Asn Asp Val Val
            1145                1150                1155

Thr Glu Gln Tyr Arg Pro Lys Lys Ser Val
            1160                1165

<210> SEQ ID NO 78
<211> LENGTH: 6217
<212> TYPE: DNA
<213> ORGANISM: Artificial Sequence
<220> FEATURE:
<223> OTHER INFORMATION: Plasmid

<400> SEQUENCE: 78

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta cgccagggt     360
tttcccagtc acgacgttgt aaaacgacgg ccagtgaatt cgagctcggt acctcgcgaa     420
tgcatctaga tatgttggtg aagtcactgt ttctagtgac cattttgttt gcactatgta     480
gtgctaattt atatgacaac gaatcttttg tgtattacta ccagagtgct tttaggccag     540
gacatggttg gcatttacat ggaggtgctt atgcagtagt taatgtgtct agtgaaaata     600
ataatgcagg tactgcccca agttgcactg ctggtgctat tggctacagt aagaatctca     660
gtgcggcctc agtagccatg actgcaccac taagtggtat gtcatggtct gccaactctt     720
tttgtacagc ccactgtaat tttacttctt atatagtgtt tgttacacat tgttataaga     780
gcggatctaa tagttgtcct ttgacaggtc ttattccaag cggttatatt cgtattgctg     840
ctatgaaaca tggaagtgct atgcctggtc acttatttta taatttaaca gtttctgtga     900
ctaaatatcc taagtttaga tcgctacaat gtgttaataa ttatacttct gtatatttaa     960
atggtgacct tgttttcaca tctaactata ctgaagatgt tgtagctgca ggtgtccatt    1020
ttaaaagtgg tggacctata acttataaag ttatgagaga ggttaaagcc ttggcttatt    1080
ttgtcaatgg tactgcacat gatgtcattc tatgtgatga cacacctaga ggtttgttag    1140
catgccaata taatactggc aattttttcag atggcttcta tcctttact aatactagta    1200
ttgttaagga taagtttatt gtttatcgtg aaagtagtgt caatactact tgtacattaa    1260
ctaatttcac gtttagtaat gaaagtggtg cccctcctaa tacaggtggt gttgacagtt    1320
ttattttata ccagacacaa acagctcaga gtgttatta aattttaac ttttcatttc    1380
tgagtagttt tgtttatagg gaaagtaatt atatgtatgg atcttaccat ccacgttgta    1440
gttttagacc tgaaacctt aatggttgt ggtttaattc cctttctgtt tcattaacat    1500
acggtcccat tcaaggtggt tgtaagcaat ctgtatttaa tggtaaagca acttgttgtt    1560
atgcttattc atacggagga cctcgtggtt gtaaaggtgt ctatagaggt gagctaacac    1620
agcattttga atgtggtttg ttagtttatg ttactaagag cgatggctcc cgtatacaaa    1680
ctgcaacaca accacctgta ttaacccaaa atttttataa taacatcaat ttaggtaagt    1740
gtgttgatta taatatatat ggcagaattg gccaaggtct tattactaat gtaaccgact    1800
tagctgttag ttataattat ttatcagacg caggtttggc tattttagat acatctggtg    1860
ccatagacat cttcgttgta caaggtgaat atggtcctaa ctattataag gttaatccat    1920
gtgaagatgt caaccaacag tttgtagttt ctggtggtaa attagtaggt attctcactt    1980
cacgtaatga aacaggttct cagcttcttg agaaccagtt ttatattaaa atcactaatg    2040
gaactcgtcg ttctagacgt tctgttactg aaaatgttac aaattgccct tatgttagtt    2100
atggcaagtt ttgtataaaa cctgatggtt caatttctgt aatagtacca aaagaactgg    2160
atcagtttgt ggcaccttta cttaatgtta ctgaatatgt gctcatacct aacagtttta    2220
atttaactgt tacagatgag tacatacaaa cgcgtatgga taagatccaa attaattgcc    2280
```

```
tgcagtatgt tgtgtggcaat tctttggcct gtagaaagct gtttcaacaa tatgggcctg    2340
tttgtgacaa catattgtct gtagtaaata gtgttggtca aaaagaagat atggaacttt    2400
taaatttcta ttcttctact aaaccagctc gttttaatac accagttttt agtaatctta    2460
gcactggtga gtttaatatt tctcttttgt taacatcccc tagtagtcct aggaggcgtt    2520
cttttattga agatctttta tttacaagtg ttgaatctgt aggattacca acagatgacg    2580
catacaaaaa gtgcactgca ggacctttag gcttttttaa agaccttgca tgtgctcgtg    2640
aatataatgg tttgcttgtg ttgcctccta ttataacagc agaaatgcaa actttgtata    2700
ctagttcttt agtagcttct atggcttttg gtggtattac tgcagctggt gccatacctt    2760
ttgccacaca actgcaggct agaattaatc acttgggtat tacccagtca cttttgttga    2820
agaatcaaga aaaaattgct gcttccttta ataaggccat tggtcatatg caggaaggtt    2880
ttaggagtac atctctagca ttacaacaaa ttcaagatgt tgttaataag cagagtgcta    2940
ttcttactga gactatggca gcacttaata aaaattttgg tgctatttct tctgtgattc    3000
aagacattta ccagcaactt gattccatac aagcagatgc tcaagtggat cggctcataa    3060
ctggtagatt gtcatcactt tctgtcttag catctgctaa gcagtcggag tacattagag    3120
tgtcacaaca gcgtgagtta gctactcaga aaattaatga gtgtgttaaa tcacagtcta    3180
ttaggtattc cttttgtggt aatggacgac atgttttaac cataccacaa aatgccccta    3240
atggtatagt gtttatacac tttacttata caccagagag ctttattaat gttactgcaa    3300
tagtgggttt tgtgtaagt cctgctaatg ctagtcagta tgcaatagtg cccgctaatg    3360
gtaggggtat tttatacaa gttaatggta gttactacat cactgcacga gatatgtata    3420
tgccaagaga tattactgca ggagatatag ttacgcttac ttcttgtcaa gcaaattatg    3480
taagtgtaaa taagaccgtc attactacat ttgtagacaa tgatgatttt gattttgatg    3540
atgaattgtc aaaatggtgg aatgatacta agcatgagct accagacttt gacaaattca    3600
attacacagt acctatactt gacattgata gtgaaattga tcgtattcaa ggcgttatac    3660
agggtcttaa cgactctcta atagaccttg aaacactatc aatactcaaa acttatatta    3720
agtggccttg gtatgtgtgg ttagccatag cttttgccac tattatcttc atcttaatac    3780
taggatggtt gttttcatg actggttgtt gtggttgttg ttgtggatgc tttggcatta    3840
ttcctttaat gagtaagtgt ggtaagaaat cttcttatta cacgactttt gataatgatg    3900
tggtaactga acaatacaga cctaaaaagt ctgtttaaat cggatcccgg gcccgtcgac    3960
tgcagaggcc tgcatgcaag cttggcgtaa tcatggtcat agctgtttcc tgtgtgaaat    4020
tgttatccgc tcacaattcc acacaacata cgagccggaa gcataaagtg taaagcctgg    4080
ggtgcctaat gagtgagcta actcacatta attgcgttgc gctcactgcc cgctttccag    4140
tcgggaaacc tgtcgtgcca gctgcattaa tgaatcggcc aacgcgcggg gagaggcggt    4200
ttgcgtattg ggcgctcttc cgcttcctcg ctcactgact cgctgcgctc ggtcgttcgg    4260
ctgcggcgag cggtatcagc tcactcaaag gcggtaatac ggttatccac agaatcaggg    4320
gataacgcag gaaagaacat gtgagcaaaa ggccagcaaa aggccaggaa ccgtaaaaag    4380
gccgcgttgc tggcgttttt ccataggctc cgcccccctg acgagcatca caaaaatcga    4440
cgctcaagtc agaggtggcg aaacccgaca ggactataaa gataccaggc gtttccccct    4500
ggaagctccc tcgtgcgctc tcctgttccg accctgccgc ttaccggata cctgtccgcc    4560
tttctccctt cggaagcgt ggcgctttct catagctcac gctgtaggta tctcagttcg    4620
gtgtaggtcg ttcgctccaa gctgggctgt gtgcacgaac cccccgttca gcccgaccgc    4680
```

```
tgcgccttat ccggtaacta tcgtcttgag tccaacccgg taagacacga cttatcgcca    4740
ctggcagcag ccactggtaa caggattagc agagcgaggt atgtaggcgg tgctacagag    4800
ttcttgaagt ggtggcctaa ctacggctac actagaagaa cagtatttgg tatctgcgct    4860
ctgctgaagc cagttacctt cggaaaaaga gttggtagct cttgatccgg caaacaaacc    4920
accgctggta gcggtggttt ttttgtttgc aagcagcaga ttacgcgcag aaaaaaagga    4980
tctcaagaag atcctttgat cttttctacg ggtctgacg ctcagtggaa cgaaaactca    5040
cgttaaggga ttttggtcat gagattatca aaaaggatct tcacctagat ccttttaaat    5100
taaaaatgaa gttttaaatc aatctaaagt atatatgagt aaacttggtc tgacagttac    5160
caatgcttaa tcagtgaggc acctatctca gcgatctgtc tatttcgttc atccatagtt    5220
gcctgactcc ccgtcgtgta gataactacg atacgggagg gcttaccatc tggccccagt    5280
gctgcaatga taccgcgaga cccacgctca ccggctccag atttatcagc aataaaccag    5340
ccagccggaa gggccgagcg cagaagtggt cctgcaactt tatccgcctc catccagtct    5400
attaattgtt gccgggaagc tagagtaagt agttcgccag ttaatagttt gcgcaacgtt    5460
gttgccattg ctacaggcat cgtggtgtca cgctcgtcgt ttggtatggc ttcattcagc    5520
tccggttccc aacgatcaag gcgagttaca tgatccccca tgttgtgcaa aaaagcggtt    5580
agctccttcg gtcctccgat cgttgtcaga agtaagttgg ccgcagtgtt atcactcatg    5640
gttatggcag cactgcataa ttctcttact gtcatgccat ccgtaagatg cttttctgtg    5700
actggtgagt actcaaccaa gtcattctga gaatagtgta tgcggcgacc gagttgctct    5760
tgcccggcgt caatacggga taataccgcg ccacatagca gaactttaaa agtgctcatc    5820
attggaaaac gttcttcggg gcgaaaactc tcaaggatct taccgctgtt gagatccagt    5880
tcgatgtaac ccactcgtgc acccaactga tcttcagcat cttttacttt caccagcgtt    5940
tctgggtgag caaaaacagg aaggcaaaat gccgcaaaaa agggaataag ggcgacacgg    6000
aaatgttgaa tactcatact cttcctttt caatattatt gaagcattta tcagggttat    6060
tgtctcatga gcggatacat atttgaatgt atttagaaaa ataaacaaat aggggttccg    6120
cgcacatttc cccgaaaagt gccacctgac gtctaagaaa ccattattat catgacatta    6180
acctataaaa ataggcgtat cacgaggccc tttcgtc                             6217
```

<210> SEQ ID NO 79
<211> LENGTH: 11416
<212> TYPE: DNA
<213> ORGANISM: Artificial Sequence
<220> FEATURE:
<223> OTHER INFORMATION: Plasmid

<400> SEQUENCE: 79

```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgaatt ggagatcggt acttcgcgaa    420
tgcgtcgaga tcggccgccc gggtaatacg actcactata gggacttaag atagatatta    480
```

```
atatatatct attgcactag ccttgcgcta gatttcaaac ttaacaaaac ggacttaaat    540
acctacagct ggtccccata ggtgttccat tgcagtgcac tttagtgccc tggatggcac    600
ctggccacct gtcaggtttt tgttgttaaa atatcattgt tgctggtatc actgcttgtt    660
ttgccgtgtc tcactttata catccgttgc ttgggctacc tagtatccag cgtcctacgg    720
gcgccgtggt cggttcgagt gcgaaggacc tctggttcat ctagcggtag gcgggtgtgt    780
ggaagtagcg cttcagacgt actggttctg ttgcgtgaaa cgcggggtca cctccccca    840 catacctcta agggcttttg agcctagcgt tgggctacgt tctcgcacaa ggtcggctat    900
acgacgtttg tagggggtag tgccaaacaa cccctgaggt gacaggttct ggtggtgttt    960
cgaaaacaac aatgtgtgtg ccgcataata tgcgcgttat gcattttgga gcaggtagtg   1020
ataaaggagt ggcgcctggt agtactgttc ttaaacagtg gctccccgaa ggaacactcc   1080
ttgtcgataa tgatattgta gattatgttt ctgacgcaca cgtttctgtg ctttcagatt   1140
gcaataaata taagacagag cacaagtttg atcttgtgat atctgatatg tatacagaca   1200
atgattcaaa aagaaagcat gaaggcgtga tagccaataa tggcaatgat gacgtcttca   1260
tatacctttc aagttttcta cgcaataatt tggctctggg aggcagtttt gctgtaaaat   1320
taacagagac aagttggcat gagagtttat atgacattgc acaggattgt gcatggtgga   1380
caatgttttg tacagcagtg aatgcatctt cttcagaagc attcctgatt ggtgttaatt   1440
acttgggtgc aagtgcaaag gttaaagtta gtggaaaaac actgcacgca aattatatat   1500
tttggaggaa ttgtaattat ttacaaacct ctgcttatag tatatttgat gttgctaagt   1560
ttgatttgag attgaaagca acgccagttg ttaatcttaa gactgaacaa agacagact   1620 tagtctttaa tttgataaag tgtggtaagt tactggtaag agatgttggt aacacctctt   1680
ttactagtga ctcttttgtg tgcactatgt agtgctaatt tatatgacaa cgaatctttt   1740
gtgtattact accagagtgc ttttaggcca ggacatggtt ggcatttaca tggaggtgct   1800
tatgcagtag ttaatgtgtc tagtgaaaat aataatgcag gtactgcccc aagttgcact   1860
gctggtgcta ttggctacag taagaatctc agtgcggcct cagtagccat gactgcacca   1920
ctaagtggta tgtcatggtc tgccaactct ttttgtacag cccactgtaa ttttacttct   1980
tatatagtgt ttgttacaca ttgttataag agcggatcta atagttgtcc tttgacaggt   2040
cttattccaa gcggttatat tcgtattgct gctatgaaac atggaagtgc tatgcctggt   2100
cacttatttt ataatttaac agtttctgtg actaaatatc ctaagtttag atcgctacaa   2160
tgtgttaata attatacttc tgtatattta aatggtgacc ttgttttcac atctaactat   2220
actgaagatg ttgtagctgc aggtgtccat tttaaaagtg gtggacctat aacttataaa   2280
gttatgagag aggttaaagc cttggcttat tttgtcaatg gtactgcaca tgatgtcatt   2340
ctatgtgatg acacacctag aggtttgtta gcatgccaat ataatactgg caattttca   2400 gatggcttct atccttttac taatactagt attgttaagg ataagtttat tgtttatcgt   2460
gaaagtagtg tcaatactac ttgtacatta actaatttca cgtttagtaa tgaaagtggt   2520
gcccctccta atacaggtgg tgttgacagt tttatttat accagacaca aacagctcag   2580
agtggttatt ataatttaa cttttcattt ctgagtagtt tgtttatag ggaaagtaat    2640 tatatgtatg gatcttacca tccacgttgt agttttagac ctgaaaccct taatggtttg   2700
tggtttaatt ccctttctgt ttcattaaca tacggtccca ttcaaggtgg ttgtaagcaa   2760
tctgtattta atggtaaagc aacttgttgt tatgcttatt catacggagg acctcgtggt   2820
tgtaaaggtg tctatagagg tgagctaaca cagcattttg aatgtggttt gttagtttat   2880
```

```
gttactaaga gcgatggctc ccgtatacaa actgcaacac aaccacctgt attaacccaa    2940 aattttata ataacatcaa tttaggtaag tgtgttgatt ataatatata tggcagaatt     3000
ggccaaggtc ttattactaa tgtaaccgac ttagctgtta gttataatta tttatcagac    3060
gcaggtttgg ctattttaga tacatctggt gccatagaca tcttcgttgt acaaggtgaa    3120
tatggtccta actattataa ggttaatcca tgtgaagatg tcaaccaaca gtttgtagtt    3180
tctggtggta aattagtagg tattctcact tcacgtaatg aaacaggttc tcagcttctt    3240
gagaaccagt tttatattaa aatcactaat ggaactcgtc gttctagacg ttctgttact    3300
gaaaatgtta caaattgccc ttatgttagt tatggcaagt tttgtataaa acctgatggt    3360
tcaatttctg taatagtacc aaaagaactg gatcagtttg tggcaccttt acttaatgtt    3420
actgaatatg tgctcatacc taacagtttt aatttaactg ttacagatga gtacatacaa    3480
acgcgtatgg ataagatcca aattaattgc ctgcagtatg tttgtggcaa ttctttggcc    3540
tgtagaaagc tgtttcaaca atatgggcct gtttgtgaca acatattgtc tgtagtaaat    3600
agtgttggtc aaaaagaaga tatggaactt ttaaatttct attcttctac taaaccagct    3660
cgttttaata caccagtttt tagtaatctt agcactggtg agtttaatat ttctcttttg    3720
ttaacatccc ctagtagtcc taggaggcgt tcttttattg aagatctttt atttacaagt    3780
gttgaatctg taggattacc aacagatgac gcatacaaaa agtgcactgc aggacccttta    3840 ggcttttta aagaccttgc atgtgctcgt gaatataatg gtttgcttgt gttgcctcct    3900
attataacag cagaaatgca aactttgtat actagttctt tagtagcttc tatggcttt     3960 ggtggtatta ctgcagctgg tgccatacct tttgccacac aactgcaggc tagaattaat    4020
cacttgggta ttacccagtc acttttgttg aagaatcaag aaaaaattgc tgcttccttt    4080
aataaggcca ttgctcatat gcaggaaggt tttaggagta catctctagc attacaacaa    4140
attcaagatg ttgttaataa gcagagtgct attcttactg agactatggc agcacttaat    4200
aaaaattttg gtgctatttc ttctgtgatt caagacattt accagcaact tgattccata    4260
caagcagatg ctcaagtgga tcggctcata actggtagat tgtcatcact ttctgtctta    4320
gcatctgcta agcagtcgga gtacattaga gtgtcacaac agcgtgagtt agctactcag    4380
aaaattaatg agtgtgttaa atcacagtct attaggtatt ccttttgtgg taatggacga    4440
catgttttaa ccataccaca aaatgcccct aatggtatag tgtttataca ctttactat     4500 acaccagaga gctttattaa tgttactgca atagtgggtt tttgtgtaag tcctgctaat    4560
gctagtcagt atgcaatagt gcccgctaat ggtaggggta ttttatataca gttaatggt    4620 agttactaca tcactgcacg agatatgtat atgccaagag atattactgc aggagatata    4680
gttacgctta cttcttgtca agcaaattat gtaagtgtaa ataagaccgt cattactaca    4740
tttgtagaca atgatgattt tgatttgat gatgaattgt caaaatggtg gaatgatact    4800
aagcatgagc taccagactt tgacaaattc aattacacag tacctatact tgacattgat    4860
agtgaaattg atcgtattca aggcgttata cagggtctta cgactctct aatagacctt    4920 gaaacactat caatactcaa aacttatatt aagtggcctt ggtatgtgtg gctagccata    4980
gcttttgcca ctattatctt catcttaata ttaggatggg ttttcttcat gactgggtgt    5040
tgtggttgtt gttgtggatg ctttggcatt atgcctctaa tgagtaagtg tggtaagaaa    5100
tcttcttatt acacgacttt tgataacgat gtggtaactg aacaatacag acctaaaaag    5160
tctgtttaat gatccaaagt cccactagtt tcttaatagt attaatttg ctttggtgta    5220
```

```
aacttgtact aagttgtttt agagagttta ttattgccct tcaacaacta acacaagttt    5280
tactccaaat tatcgatagt aatttacagt ctagactgac cctttggcac agtctagact    5340
aatgttaaac ttagaagcaa ttattgaaac cggtgatcaa gtgattcaaa aaatcagttt    5400
caatttacag catatttcaa gtgtattaaa cacagaagta tttgacccct ttgactattg    5460
ttattacaga ggaggtaatt tttgggaaat agagtcagct gaagattgtt caggtgatga    5520
tgaatttatt gaataagtcg ctagaggaga atggaagttt tctaacggca ctttacatat    5580
ttgtaggatt tttagcattt tatcttctag gtagagcact tcaagcattt gtacaggctg    5640
ctgatgcttg ttgtttattt tggtacacgt ggttagtaat tccaggagtt aagggtacag    5700
cctttgtata caagtataca tatggtagaa aacttaacaa ttcggaatta gaagcagttg    5760
ttgttaacga gtttcctaag aacggttgga ataataaaaa tccagcaaat tttcaagatg    5820
tccaacgaaa caaattgtac tcttgacttt gaacagtcag ttgagctttt taaagagtat    5880
aatttattta taactgcatt cttgttgttc ttaaccataa tacttcagta tggttatgca    5940
acgcgtagta agtttattta tatacttaaa atgatagtgt tatggtgctt ttggcccctt    6000
aacattgcag taggtgtaat ttcatgtata tacccaccaa acacaggagg tcttgtcgca    6060
gcgataatac ttactgtgtt tgcgtgtctt tcttttgtag gttattggat ccagagtatt    6120
agactcttta agcggtgtag atcttggtgg tcatttaacc cagaatctaa cgccgtaggt    6180
tcaatactcc taactaatgg tcaacaatgt aattttgcta tagagagtgt gccgatggtg    6240
cttttctccta ttataaagaa tggtgttctt tattgtgagg gtcagtggct gctaaatgt     6300
gaaccagacc acttgcctaa agacatattt gtatgcacac cagatagacg taatatctat    6360
cgtatggtgc agaaatacac tggtgaccaa agcggaaata gaaaaggtt tgctacattt     6420
gtctatgcaa agcagtcagt agacactggc gagctagaaa gtgtagcaac aggtggaagt    6480
agcctttaca cataaatgtg tgtgtgtaga gagtatttaa aattattctt caatagtgcc    6540
tctattttaa gagcgcggaa gagtatttgt tttgaggata ttaatataaa tcctctttgt    6600
tttgtactct ctttacaaga gttattattt aagcaacagt ttttcctttc ctttgtttgg    6660
aagaaagttg ttgttaatgg tgtagaattc caagtagaaa atggaaaagt ccactacgaa    6720
ggaaacccca ttttccaaaa aggttgttgt aggttgtggt cccattataa gaaggattaa    6780
atggattaaa ccacctacac tacttacttg taataagggc gtttggactt acaagcgctt    6840
aacaaataca gacgatgaaa tggctgacta gttttggaag agcagttatt tcttgttata    6900
aagccctact attaactcag ttaagagtat tagataggtt aattttagat cacgaccaa     6960
agcgagtctt aacgtgtggt aggcgagtgc ttttatctca attagattta gtttataggt    7020
tggcatatac gcccacccaa tcgctggtat gaataatagt aaagataatc ctttcgcgg     7080
agcaatagca agaaaagcgc gaatttatct gagagaagga ttagagtgtg tttactttct    7140
taacaaagca ggacaagcag agccttgtcc cgcgtgtacc tccctagtat ttcaggggaa    7200
aacttgtgag gaacacacag ataataataa tcttttgtca tggcgagcgg taagacaact    7260
gggaagacag acgccccagc gccagtcatc aaactaggag ggccaaaacc acctaaagtt    7320
ggttcttctg gaaatgctag ctggtttcaa gcactaaaag ccaagaagtt aaattcacct    7380
cctcctaagt ttgaaggtag cggcgttcct gataatgaaa atcttaaatt aagccagcaa    7440
catgggtact ggagacgtca agccaggtac aagccaggta aaggcggaag aaaatcagtc    7500
ccagatgctt ggtacttcta ttacactgga acaggaccag ccgctgacct gaattggggt    7560
gatagccaag atggtatagt gtgggtttct gcaaagggtg ctgatactaa atctagatct    7620
```

```
aaccagggta caagggatcc tgataagttt gaccaatacc cgctacgatt ctcagatgga   7680
ggacctgatg gtaatttccg ttgggacttc attccaataa atcgtggtag gagtggaaga   7740
tcaacagcgg cttcatcagc agcatctagt agagcaccgt cgcgtgatgg ctcgcgtgga   7800
cgtagaagcg gagctgaaga tgatcttata gctcgtgcag caaagatcat tcaggatcag   7860
cagaagaagg gttctcgcat tactaaagct aaggccgatg aaatggctca tcgccggtat   7920
tgtaagcgta ctatcccacc tggttataag gttgatcaag tatttggtcc ccgtactaaa   7980
ggtaaggagg gaaattttgg tgatgacaag atgaatgagg agggtattaa ggatgggcgc   8040
gttacagcaa tgctcaacct agtccctagc agccatgctt gtcttttgg aagtagagtg    8100
acgcccaaac ttcaaccaga tgggctgcac ttgagatttg aatttactac tgtggtttct   8160
agggatgatc cgcagtttga taattatgtg aaaatttgtg atcagtgtgt cgatggtgta   8220
gggactcggc caaaagacga tgaaccgaga ccaaagtcac gcccaaattc aagacctgct   8280
acaagaacaa gttctccagc gccaagacaa cagcgtcaaa agaaggagaa gaagtcaaag   8340
aagcaggatg atgaagtaga taaggcattg acctcagatg aggagaggaa caatgcacag   8400
ctggaatttg atgatgaacc gaaagtgatt aactgggggg attcagcact tggagagaat   8460
gagttgtaaa gctagatttc caacttaaca tcatggacgt gcgtatgctg ttttcccta    8520
ctatagactt tttagcatat tatttttgc tatttgtatg gttattaca ggtgaagatt      8580
gtatgtattt gttgtacact cgtatgttct atattatgtt ttctgtagtt gttattagtg   8640
ttgttcttgt tcttactcta ctgttctctt ttctttattt tagagtatca ataagaatca   8700
aggaagatag gcatgtagtt tgattaccta catgtctatc gccagggaaa tgtctaatct   8760
gtctacttag tagcctggaa acgaacggta gaccccttaga ttttaattta gtttaatttt 8820
tagtttagtt taagttagtt tagagtaggt ataaagaagc cagtgccggg gccacgcgga   8880
gtacgatcga gggtacagca ctaggacgcc cactagggga agagctaaat tttagttta    8940
gttaagttta attggctaag tatagttaaa atttataggc tagtatagag ttagagcaaa   9000
aaaaaaaaaa aaaaaaaaa aaaaaaaaa aaaaaaaaa aaaaaaaaaa aaaaaaaaaa      9060
aaaaaaaaaa aaaaaaaaaa aaaaaaaaaa aaaaaagtt taaacttaat taagaattcc    9120
cttggctcga gttcgaaatc ggatgccggg accgacgagt gcagaggcgt gcaagcgagc   9180
ttggcgtaat catggtcata gctgtttcct gtgtgaaatt gttatccgct cacaattcca   9240
cacaacatac gagccggaag cataaagtgt aaagcctggg gtgcctaatg agtgagctaa   9300
ctcacattaa ttgcgttgcg ctcactgccc gctttccagt cgggaaacct gtcgtgccag   9360
ctgcattaat gaatcggcca acgcgcgggg agaggcggtt tgcgtattgg gcgctcttcc   9420
gcttcctcgc tcactgactc gctgcgctcg tcgttcggc tgcggcgagc ggtatcagct    9480
cactcaaagg cggtaatacg gttatccaca gaatcagggg ataacgcagg aaagaacatg   9540
tgagcaaaag gccagcaaaa ggccaggaac cgtaaaaagg ccgcgttgct ggcgtttttc   9600
cataggctcc gcccccctga cgagcatcac aaaaatcgac gctcaagtca gaggtggcga   9660
aacccgacag gactataaag ataccaggcg tttccccctg gaagctccct cgtgcgctct   9720
cctgttccga ccctgccgct taccggatac ctgtccgcct ttctcccttc gggaagcgtg   9780
gcgctttctc atagctcacg ctgtaggtat ctcagttcgg tgtaggtcgt tcgctccaag   9840
ctgggctgtg tgcacgaacc ccccgttcag cccgaccgct gcgccttatc cggtaactat   9900
cgtcttgagt ccaacccggt aagacacgac ttatcgccac tggcagcagc cactggtaac   9960
```

```
aggattagca gagcgaggta tgtaggcggt gctacagagt tcttgaagtg gtggcctaac    10020
tacggctaca ctagaagaac agtatttggt atctgcgctc tgctgaagcc agttaccttc    10080
ggaaaaagag ttggtagctc ttgatccggc aaacaaacca ccgctggtag cggtggtttt    10140 tttgttttgca agcagcagat tacgcgcaga aaaaaggat ctcaagaaga tcctttgatc    10200
ttttctacgg ggtctgacgc tcagtggaac gaaaactcac gttaagggat tttggtcatg    10260
agattatcaa aaaggatctt cacctagatc cttttaaatt aaaaatgaag ttttaaatca    10320
atctaaagta tatatgagta aacttggtct gacagttacc aatgcttaat cagtgaggca    10380
cctatctcag cgatctgtct atttcgttca tccatagttg cctgactccc cgtcgtgtag    10440
ataactacga tacgggaggg cttaccatct ggccccagtg ctgcaatgat accgcgagac    10500
ccacgctcac cggctccaga tttatcagca ataaaccagc cagccggaag ggccgagcgc    10560
agaagtggtc ctgcaacttt atccgcctcc atccagtcta ttaattgttg ccgggaagct    10620
agagtaagta gttcgccagt taatagtttg cgcaacgttg ttgccattgc tacaggcatc    10680
gtggtgtcac gctcgtcgtt tggtatggct tcattcagct ccggttccca acgatcaagg    10740
cgagttacat gatcccccat gttgtgcaaa aaagcggtta gctccttcgg tcctccgatc    10800
gttgtcagaa gtaagttggc cgcagtgtta tcactcatgg ttatggcagc actgcataat    10860
tctcttactg tcatgccatc cgtaagatgc ttttctgtga ctggtgagta ctcaaccaag    10920
tcattctgag aatagtgtat gcggcgaccg agttgctctt gcccggcgtc aatacgggat    10980
aataccgcgc cacatagcag aactttaaaa gtgctcatca ttggaaaacg ttcttcgggg    11040
cgaaaactct caaggatctt accgctgttg agatccagtt cgatgtaacc cactcgtgca    11100
cccaactgat cttcagcatc ttttactttc accagcgttt ctgggtgagc aaaaacagga    11160
aggcaaaatg ccgcaaaaaa gggaataagg gcgacacgga aatgttgaat actcatactc    11220
ttcctttttc aatattattg aagcatttat cagggttatt gtctcatgag cggatacata    11280
tttgaatgta tttagaaaaa taaacaaata ggggttccgc gcacatttcc ccgaaaagtg    11340
ccacctgacg tctaagaaac cattattatc atgacattaa cctataaaaa taggcgtatc    11400
acgaggccct ttcgtc                                                    11416
```

<210> SEQ ID NO 80
<211> LENGTH: 29
<212> TYPE: DNA
<213> ORGANISM: Artificial Sequence
<220> FEATURE:
<223> OTHER INFORMATION: Primer

<400> SEQUENCE: 80
catataaatt agcactacat agtgcacac                                       29

<210> SEQ ID NO 81
<211> LENGTH: 35
<212> TYPE: DNA
<213> ORGANISM: Artificial Sequence
<220> FEATURE:
<223> OTHER INFORMATION: Primer

<400> SEQUENCE: 81
atgtagtgct aatttatatg acaacgaatc ttttg                                35

<210> SEQ ID NO 82
<211> LENGTH: 32
<212> TYPE: DNA
<213> ORGANISM: Artificial Sequence

```
<220> FEATURE:
<223> OTHER INFORMATION: Primer

<400> SEQUENCE: 82
acacatacca aggccactta atataagttt tg                                  32

<210> SEQ ID NO 83
<211> LENGTH: 28
<212> TYPE: DNA
<213> ORGANISM: Artificial Sequence
<220> FEATURE:
<223> OTHER INFORMATION: Primer

<400> SEQUENCE: 83
taagtggcct tggtatgtgt ggctagcc                                       28

<210> SEQ ID NO 84
<211> LENGTH: 21
<212> TYPE: DNA
<213> ORGANISM: Artificial Sequence
<220> FEATURE:
<223> OTHER INFORMATION: Primer

<400> SEQUENCE: 84
taatactggy aatttttcag a                                              21
```

MODIFIED S1 SUBUNIT OF THE CORONAVIRUS SPIKE PROTEIN

SEQUENCE LISTING

This application contains a sequence listing in accordance with 37 C.F.R. 1.821-1.825. The sequence listing accompanying this application is hereby incorporated by reference in its entirety.

BACKGROUND OF THE INVENTION

Avian coronavirus infectious bronchitis virus (IBV) is the prototype gammacoronavirus of the family Coronaviridae, order Nidovirales. Infectious bronchitis virus principally infects the upper respiratory epithelium of chickens, causing a respiratory disease, commonly complicated by secondary bacterial pathogens (Cook et al. 2012. Avian Pathol. 41:239-250). Some IBV strains additionally affect the renal tubuli, oviduct and parts of the gastrointestinal tract, leading to pathological lesions and clinical symptoms in these organ systems. The virus has a worldwide presence in both commercial and backyard chicken. Due to its high genomic variability IBV is discriminated in a wide variety of geno-, sero- and protectotypes. IBV is currently regarded as one of the economically most relevant viral pathogens in the poultry industry.

Infectious bronchitis virus is an enveloped virus with a positive sense single-stranded RNA genome of 27.6 kb (Cavanagh 2007. Vet. Res. 38:281-297). The first two-thirds of the viral genome comprise a large coding region (also designated as gene 1), divided into two open reading frames 1a and 1b, which encode for at least 15 nonstructural proteins involved in RNA replication, editing, and transcription. The last one-third of the viral genome codes for structural proteins: the spike protein (S, encoded by gene 2), the envelope protein (E, encoded by gene 3c), the membrane protein (M, encoded by gene 4), and the nucleocapsid protein (N, encoded by gene 6). Proteins S, E and M are part of the viral envelope while protein N forms the ribonucleoprotein core along with the viral RNA. The coronavirus spike protein determines the host species tropism (Kuo et al. 2000. J. Virol. 74:1393-1406). It is a dimeric or trimeric transmembrane protein, which is proteolytically cleaved into two subunits, S1 and S2. The glycosylated S1 domain forms the 'head' of the spike protein and contains the receptor binding domain that interacts with 2,3-linked sialic acids on the host cell surface (Promkuntod et al. 2014. Virology. 448:26-32). The S2 domain contains the remaining part of the ectodomain (the 'stalk'), the transmembrane domain and the endodomain located in the cytoplasm.

The to date widely used live-attenuated IBV vaccine strains H52 and H120 were developed in the 1960s in the Netherlands, by serial passaging of a Massachusetts IBV strain in embryonated chicken eggs (Bijlenga et al. 2004; Avian Pathol. 33:550-557). Said vaccine strains also have to be cultivated in embroynated chicken eggs for production. Today, IBV vaccines (both inactivated and live vaccines) are still propagated in emryonated chicken eggs which is cumbersome and expensive.

The only cell-line adapted IBV described so far is the IBV strain Beaudette, which efficiently replicates in Vero and BHK cells. Casais et al 2003 (J. Virol. 77; 9084-9089) show that the S protein of Beaudette is the determinant of cell line tropism by generating recombinant IBVs using ectodomain sequences of the Beaudette spike, which were able to transfer the extended cell line tropism to another IBV (M41).

WO 2011/004146 discloses that the S2 subunit from Beaudette is responsible for the extended tissue tropism. A sequence within the S2 subunit, a heparan-sulphate binding site from Beaudette, has been identified to be responsible for the extended cell line tropism. Furthermore, Bickerton et al 2018 (Journal of Virology 92 (19)) disclose a Beaudette specific motif of eight amino acids. However, recombinant IBVs with a Beaudette spike S2 subunit are not suitable as vaccines. Ellis et al 2018 (J. Virol. 92(23)) describe that recombinant Beaudette with chimeric spikes with heterologous 51 subunits from M41 or QX in combination with Beaudette spike S2 subunit do not confer sufficient protection against 51 homologous challenges. Also, Beaudette wild type does not provide procection against homologous challenge like other licensed vaccines belonging to the Massachusetts serotype (Hodgson et al 2004: J Virol 78:13804-13811 or Geilhausen et al 1973: Archiv für die gesamte Virusforschung 40: 285-290).

Fang et al 2005 (Biochemical and Biophysical Reaearch Communication 336; pages 417 to 423) disclose that the adaption of Beaudette for propagation in Vero cells resulted in 49 amino acid modifications, 26 located within the spike protein.

Taken together, providing IBV vaccines having an extended cell or tissue tropism by exchanging the spike protein to a heterologous Beaudette Spike protein would not result in IBV vaccines providing sufficient efficacy and with the Beaudette Spike sequence would be limited to protection against a Massachusetts serotype strain challenge and missing cross protection against further genotypes. Furthermore, the prior art motifs or sites identified in Beaudette have not been transferred into IBV vaccines showing both an extended cell culture or tissue tropism and efficacy in protection (no interference between extended tropism and vaccine efficacy has been shown).

Consequently, there is a need for single amino acids or short motifs that can be transferred into IBVs or IBV vaccines without influencing vaccine efficacy but enabling an extended cell or tissue tropism for production.

DETAILED DESCRIPTION OF THE INVENTION

Before the aspects of the present invention are described, it must be noted that as used herein and in the appended claims, the singular forms "a", "an", and "the" include plural reference unless the context clearly dictates otherwise. Thus, for example, reference to "an antigen" includes a plurality of antigens, reference to the "virus" is a reference to one or more viruses and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which might be used in connection with the invention. Nothing herein is to be construed as an admission that the invention is not entitled to antedate such disclosure by virtue of prior invention.

Composition of Matter

The present invention solves the problems inherent in the prior art and provides a distinct advance in the state of the art.

Generally, the present invention provides an avian coronavirus Spike Protein or fragment thereof, wherein at least a part of the 51 subunit is from an avian coronavirus with a restricted cell or tissue tropism, and wherein at amino acid position 267 is a Cysteine.

Further, the present invention provides a recombinant avian coronavirus spike protein or fragment thereof comprising a mutation at amino acid position 267 to Cysteine.

Generally, the present invention also provides an IBV spike protein or fragment thereof, wherein at least a part of the 51 subunit is from an IBV with a restricted cell or tissue tropism, and wherein at amino acid position 267 is a Cysteine.

Further, the present invention provides a recombinant IBV spike protein or fragment thereof comprising a mutation at amino acid position 267 to Cysteine.

Advantageously, the experimental data show that coronavirus strains (strains such as exemplarily H52, QX SP2013-01478 and CR88 IBV strains) have an extended cell or tissue tropism after modifying a single position, position 267, into a Cystein within the spike protein.

The term "coronavirus" is well known to the person skilled in the art. In general coronaviruses are viruses of the subfamily Coronavirinae in the family Coronaviridae, in the order Nidovirales. Coronaviruses are enveloped viruses and have a positive-sense single-stranded RNA genome with a nucleocapsid of helical symmetry. The term "coronavirus" encompasses all strains, genotypes, protectotypes, and serotypes of infectious bronchitis virus. Examples of avian coronaviruses are infectious bronchitis virus (IBV); guinea fowl coronavirus (GfCoV) and turkey coronavirus (TCoV; turkey enteritis virus and bluecomb disease virus).

The term "IBV" refers to the infectious bronchitis virus which is well known to the person skilled in the art. The term "IBV" encompasses all strains, genotypes, protectotypes, and serotypes of infectious bronchitis virus.

The term "mutation" comprises modifications in the viral RNA encoding proteins leading to an alteration of said encoded protein. Further, the term "mutation" comprises genetically engineered mutations. The term mutation relates to, but is not limited to, substitutions (replacement of one or several nucleotides/base pairs), deletions (removal of one, several or all nucleotides/base pairs), and/or insertions (addition of one or several nucleotides/base pairs). As used herein, a mutation may be a single mutation or several mutations, therefore, often the term "mutation(s)" used and relates to both a single mutation and several mutations. However, the term mutation is well known to the person skilled in the art and the person skilled in the art can generate mutations without further ado.

The term "spike" refers to a specific protein of the avian coronavirus or IBV that is well known by the person skilled in the art. The spike protein is the major inducer of antibodies and a protective immune response. Further, the spike (S) protein facilitates cell entry of the avian coronavirus or IBV by binding cellular receptors on the host cell and also by mediating virus-cell membrane fusion with the host cell membranes. In addition, it determines the tissue and cell tropism of the virus strain.

The term "protein", "amino acid" and "polypeptide" are used interchangeably. The term "protein" refers to a sequence of amino acids composed of the naturally occurring amino acids as well as derivatives thereof. The naturally occurring amino acids are well known in the art and are described in standard text books of biochemistry. Within the amino acid sequence the amino acids are connected by peptide bonds. Further, the two ends of the amino acid sequence are referred to as the carboxyl terminus (C-terminus) and the amino terminus (N-terminus). The term "protein" encompasses essentially purified proteins or protein preparations comprising other proteins in addition. Further, the term also relates to protein fragments. Moreover, it includes chemically modified proteins. Such modifications may be artificial modifications or naturally occurring modifications such as phosphorylation, glycosylation, myristylation and the like.

Mutation 267

In one aspect of the avian coronavirus or IBV spike protein or fragment thereof according to the present invention the Cysteine at amino acid position 267 is introduced by a mutation. The wording "introduced" means that the mutation has been introduced by genetic engineering (artificially, e.g., by human intervention).

In another specific aspect of the avian coronavirus or IBV spike protein or fragment thereof according to the present invention the mutation is an amino acid substitution, deletion or insertion.

In another specific aspect of the avian coronavirus or IBV spike protein or fragment thereof according to the present invention a hydrophobic amino acid at amino acid position 267 is mutated into a Cysteine; or a Phenylalanine or Leucine at amino acid position 267 is mutated into a Cysteine.

Extended Cell or Tissue Tropism

In another specific aspect of the avian coronavirus or IBV spike protein or fragment thereof according to the present invention the Cysteine at amino acid position 267 or said mutation at amino acid position 267 to Cysteine leads to an extended cell or tissue tropism of the avian coronavirus or IBV.

The term "cell or tissue" is known by the person skilled in the art. The term cell encompasses cell lines such as the cell lines listed elsewhere herein as well as primary cells. The term tissue encompasses cells from tissues such as the ones listed elsewhere herein, exemplarily such as primary chicken embryo cells from lung or liver or primary chicken fibroblasts. The term encompasses the propagation of cells or tissue (cells) in culture outside the organism. The term "culture" relates to the propagation of cells (such as cell line cells or primary cells or tissue cells) outside the organism under defined culture conditions known by the person skilled in the art.

The term "extended tropism" means that the avian coronavirus or IBV of the invention can be propagated in cells (such as cell lines) or tissue cells (in addition to primary chicken embryo cells from kidney). In contrast, coronavirus vaccines (such as IBV vaccines) or non-cell culture adapted wildtype coronaviruses or IBV's (cell line adapted IBV Beaudette strains are described) can only be propagated in embryonated chicken eggs or primary chicken embryo cells from kidney (after adaption). Accordingly, a coronavirus (such as IBV) of the invention with extended cell or tissue tropism has the capacity to infect and/or replicate in one or more cell lines or tissue cells other than primary chicken embryo cells from kidney. Preferably, the coronavirus (such as IBV) of the invention with extended cell or tissue tropism has the capacity to infect and/or replicate in one or more cell lines as listed herein. Accordingly, a coronavirus or IBV with extended cell or tissue tropism may, for example, have the capacity to infect and/or replicate in PBS-12SF, EB66 or HEK 293T cells.

The term "restricted tropism" means that the avian coronavirus or IBV can be grown if at all only on primary chicken embryo cells from kidney. Accordingly, a coronavirus or IBV with restricted cell or tissue tropism does not have the capacity to infect and/or replicate in e.g. PBS-12SF, EB66 or HEK 293T cells.

Advantageously, the experimental data show that IBV strains such as exemplarily H52 and CR88 have an extended cell or tissue tropism after modifying a single position, position 267, into a Cystein within the spike protein. Further, it has been shown that the modification to a Cystein at Position 267 is genetically stable.

In another specific aspect of the avian coronavirus or IBV spike protein or fragment thereof according to the present invention the avian coronavirus or IBV is infecting and/or replicating in at least one cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an african green monkey kidney cell line, a rabbit kidney cell line, a canine kidney cell line, a chicken liver cell line, a bovine kidney cell line, a porcine kidney cell line and an insect cell line.

In another specific aspect of the avian coronavirus or IBV spike protein or fragment thereof according to the present invention the avian coronavirus is infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+ (*Spodoptera frugiperda*).

In another specific aspect of the avian coronavirus or IBV spike protein or fragment thereof according to the present invention the avian coronavirus or IBV is infecting and/or replicating in at least one cell line selected from the list consisting of: DF-1, EB66, PBS-12, PBS-12SF, BHK, HEK 293T, Vero, MA104 and RK13.

Preferably, the IBV is infecting and/or replicating in the EB66, PBS-12SF or HEK 293T cell line.

All mentioned cell lines are well known to the person skilled in the art and are commercially and/or publicly available. MDCK cells are exemplarily deposited at the American Tissue Culture Collection under accession number ATCC CCL-34 or ATCC CRL-2285. DF-1 cells are exemplarily deposited at the American Tissue Culture Collection under accession number ATCC CRL-12203). PBS-12SF cells are exemplarily deposited at the American Tissue Culture Collection under accession number ATCC PTA-8565 or deposited at RRID under CVCL_1K17. BHK-21 cells are exemplarily deposited at the American Tissue Culture Collection under accession number ATCC CCL-10. HEK 293T cells are exemplarily deposited at the American Tissue Culture Collection under accession number ATCC CRL-3216. Vero cells are exemplarily deposited at the American Tissue Culture Collection under accession number ATCC CCL-81. MA104 and cells are exemplarily deposited at the American Tissue Culture Collection under accession number ATCC CRL-2378. RK13 cells are exemplarily deposited at the American Tissue Culture Collection under accession number ATCC CCL-37.

Numbering of Amino Acid Position 267

In another specific aspect of the avian coronavirus or IBV spike protein or fragment thereof according to the present invention the numbering of amino acid position 267 refers to the amino acid position 267 in the spike protein of an IBV H52, an IBV H120 or an M41.

In another specific aspect of the avian coronavirus or IBV spike protein or fragment thereof according to the present invention the numbering of amino acid position 267 refers to the amino acid position 267 in the spike protein of an IBV H52.

In another specific aspect of the avian coronavirus or IBV spike protein or fragment thereof according to the present invention the numbering of amino acid position 267 refers to the amino acid position 267 in the spike protein as exemplarily given in SEQ ID NO:1.

In another specific aspect of the avian coronavirus or IBV spike protein or fragment thereof according to the present invention the amino acid sequence of SEQ ID NO:1 is used for determining the position numbering in the spike protein.

In another specific aspect of the avian coronavirus or IBV spike protein or fragment thereof according to the present invention for determining the amino position 267 in a spike protein the amino acid sequence is aligned to the amino acid sequence of SEQ ID NO:1.

In another specific aspect of the avian coronavirus or IBV spike protein or fragment thereof according to the present invention the amino acid position 267 is within the S1 subunit of the spike protein.

In another specific aspect of the avian coronavirus or IBV spike protein or fragment thereof according to the present invention the amino acid position 267 corresponds to amino acid position 269 of the spike sequence of IBV CR88.

In another specific aspect of the avian coronavirus or IBV spike protein or fragment thereof according to the present invention the amino acid position 267 corresponds to amino acid position 270 of the spike sequence of IBV QX.

In another specific aspect of the avian coronavirus or IBV spike protein or fragment thereof according to the present invention the amino acid position 267 corresponds to amino acid position 271 of the spike sequence of IBV Q1.

In another specific aspect of the avian coronavirus or IBV spike protein or fragment thereof according to the present invention the amino acid position 267 corresponds to amino acid position 270 of the spike sequence of IBV Var2.

In another specific aspect of the avian coronavirus or IBV spike protein or fragment thereof according to the present invention the amino acid position 267 corresponds to amino acid position 274 of the spike sequence of IBV Brazil.

In another specific aspect of the avian coronavirus or IBV spike protein or fragment thereof according to the present invention the amino acid position 267 corresponds to amino acid position 274 of the spike sequence of IBV Ark99.

In another specific aspect of the avian coronavirus or IBV spike protein or fragment thereof according to the present invention the spike protein has one or more of the following amino acids selected from the group consisting of:

264 is an asparagine, and/or
265 is a threonine, and/or
269 is a leucine, and/or
271 is an asparagine, and/or
272 is a phenylalanine.

The numbering of said amino acid positions refer to the amino acid positions within the spike protein as exemplarily given in SEQ ID NO:1.

Spike

The present invention also provides a spike protein or fragment thereof as described above, wherein the spike protein or fragment thereof is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine haemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV). Thus, the present invention also provides a coronavirus spike protein or fragment thereof, wherein at least a part of the S1 subunit is from a coronavirus with a restricted cell or tissue tropism, and wherein at amino acid position 267 is a Cysteine and wherein the spike protein is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine haemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV). Further, the present invention also provides a recombinant coronavirus spike protein or fragment thereof comprising a mutation at amino acid position 267 to Cysteine, wherein the spike protein is selected from the group consisting of: infectious bronchitis virus (IBV); guinea fowl coronavirus (GfCoV), turkey coronavirus (TCoV; turkey enteritis virus and bluecomb disease virus), feline infectious peritonitis virus (FIPV), feline enteric coronavirus (FECV); Transmissible gastro-enteritis virus (TGEV), porcine respiratory coronavirus (PRCoV), porcine epidemic diarrhea virus (PEDV), porcine haemagglutinating encephalomyelitis virus (PHEV); Severe acute respiratory syndrome coronavirus (SARS-CoV), Middle east respiratory syndrome coronavirus (MERS-CoV) Human Coronavirus 229E (HCoV-229E), human coronavirus NL63 (HCoV-NL63), human coronavirus HKU1 (HCoV-HKU1), human coronavirus OC43 (HCoV-OC43); canine coronavirus (CCoV), canine respiratory coronavirus (CRCoV), Mouse Hepatitis Virus (MHV), Bovine coronavirus (BCV).

In another specific aspect of the avian coronavirus spike protein or fragment thereof according to the present invention the avian coronavirus spike protein or fragment thereof is selected from the group consisting of: infectious bronchitis virus (IBV); guinea fowl coronavirus (GfCoV) and turkey coronavirus (TCoV; turkey enteritis virus and bluecomb disease virus).

In another specific aspect of the avian coronavirus spike protein or fragment thereof according to the present invention the avian coronavirus is IBV (infectious bronchitis virus).

IBV strains can be classified by serotype and genotype. Serotype classification involves treatment of the virus with neutralizing antibodies, whereas genotype classification generally involves examining the sequence of the S1 (spike) protein. However, the different IBV strains are well known to the person skilled in the art. Infectious bronchitis virus was first discovered in the United States in the 1930s.

The first IBV serotype identified was Massachusetts and remained the only serotype until the discovery of a different IBV seroptpye in 1956. Nowadays, several additional serotypes, including Arkansas and Delaware have been identified in the United States of America in addition to the originally identified Massachusetts type. Today, IBV Mass viruses can be identified in many countries of the world.

The IBV strain Beaudette is of Massachusetts type and was derived following at least 150 passages in chick embryos. The IBV strain Beaudette was originally isolated by Beaudette and Hudson (J. Am. Vet. Med. A. 90, 51-60, 1937) and passaged in chicken embryos. Other Massachusetts type IBV strains besides Beaudette are H120, H52, and M41. The H120 strain was passaged 120 times in embryonated chickens eggs.

IBV QX is described as virulent field isolate of IBV which was originally isolated in China. However, the virus has spread towards Europe and has been identified in parts of Western Europe, predominantly in the Netherlands, but also in Germany, France, Belgium, Denmark and in the UK. In addition, the QX genotype or serotype has been described in several countires in Asia and Africa.

The strains designated "Italien-02" or "Italy-02" was isolated in the late 1990's in Italy. The sequence analysis of one of these isolates was published in 2002 (NCBI-BLAST, number AJ457137). However, studies have shown that this Italian-02 strain is widespread in Europe and that, apart from IBV variant strain 4/91 it has become one of the most predominant genotypes in the UK, Spain, France and The Netherlands.

Since 1996 a new Infectious Bronchitis virus (IBV) genotype, referred to as Q1, has circulated in China and was reported for the first time in Italy in 2011. Q1 is associated with an increase of mortality, kidney lesions and proventriculitis.

Furthermore, strains D274, B1648/D8880, D1466, V1397 and Arkansas have been identified in Europe as well.

It is in the general knowledge of a person skilled in the art where to obtain any IBV strains. IBV strains can be commercially purchased, obtained from scientific Institutes or the genomes can be synthetical synthesized as complementary DNA as IBV strains have been sequenced and the sequences have been published and are, thus, available. Furthermore, IBV strains can be isolated from the field. The methods to isolate IBV strains and to characterize the IBV strains are well known to the person skilled in the art. Valter Leonardo de Quadros 2011 (Dissertation, Das Infektiöse Bronchitis Virus (IBV): Molekularbiologische Untersuchungen zur Diagnostik und zum Vorkommen sowie zur Pathogenität des Genotyps IBV QX in spezifisch pathogenfreien (SPF) Broilern, Freie Universität Berlin), Worthington et al. 2009 (Avian Pathology 37(3), 247-257), Liu et al. 2009 (Virus Genes 38: 56-65), Dolz et al. 2006 (Avian Pathology 35 (2): 77-85), Farsang et al. 2002 (Avian Pathology 31:

229-236) and Feng et al. 2014 (Virus Genes 49: 292-303) describe how to isolate and differentiate different IBV strains.

IBV strains are typically differentiated by the coding sequence of the S1 subunit of the spike protein (Valastro et al. 2016. Infect Genet Evol. 39:349-364) but can also be differentiated by their complete nucleotide sequence or the sequences of specific proteins such as the spike protein, nucleocapsid protein, envelope (E) protein or membrane (M) glycoprotein. Because the spike protein determines host tropism and antigenicity of IBV, the IBV genotypes are classified by the coding sequence of the subunit 1 of the spike proteins. Alternatively, IBV strains can be differentiated by their serotype. Serotype classification involves serological assays of the virus involving serotype-specific antibodies.

In another specific aspect of the IBV spike protein or fragment thereof according to the present invention the spike protein or fragment thereof is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy02), JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV spike protein or fragment thereof according to the present invention the spike protein or fragment thereof is not from a Beaudette strain.

In another specific aspect of the IBV spike protein or fragment thereof according to the present invention the Spike protein or fragment thereof is from an IBV selected from a list of genotypes or serotypes or strains consisting of: Massachusetts (not Beaudette), 4/91, QX, Q1, Italy 02, Arkansas, Connecticut, Georgia, LDT3, PL84084, Variant 2 and Brazil.

The wording "not Beaudette" is used equivalent to excluding Beaudette. Thus, the wording "Massachusetts (not Beaudette)" means that spike proteins or fragments thereof from Massachusetts strains such as M41, H52 and H120 are comprised, but spike proteins or fragments thereof from Beaudette strains are excluded.

In another specific aspect of the IBV spike protein or fragment thereof according to the present invention the Spike protein or fragment thereof is from an IBV selected from a list of genotypes or serotypes consisting of: Massachusetts (not Beaudette), 4/91, QX, Q1, Arkansas, Variant 2 and Brazil.

In another specific aspect of the IBV spike protein or fragment thereof according to the present invention the Spike protein or fragment thereof is from an IBV selected from a list of genotypes or serotypes consisting of Massachusetts (not Beaudette) and 4/91.

In another specific aspect of the IBV spike protein or fragment thereof according to the present invention the Massachusetts strain is selected from a list consisting of: H120, H52, Spain/98/308, IBMA5-1, SD/97/01, Spain/96/334 and M41-M21883.

In another specific aspect of the IBV spike protein or fragment thereof according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91attenuated and IB4-91.

In another specific aspect of the IBV spike protein or fragment thereof according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, SP2013-01470, SP2013-014171, SP2013-01478 and GB341/96.

In another specific aspect of the IBV spike protein or fragment thereof according to the present invention the Q1 strain is selected from a list consisting of: CK/CH/LDL/98I, CK/CH/LSD/08-10, J2, Q1, AR08ER22, AR08BA21, 12.185, 12.124, 12.216 and Chile-295-10.

In another specific aspect of the IBV spike protein or fragment thereof according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV spike protein or fragment thereof according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV spike protein or fragment thereof according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

In another specific aspect of the IBV spike protein or fragment thereof according to the present invention the Brazil strain is selected from a list consisting of: BR-1, BR-2, 23/2013, and IBV/Brasil/351/1984.

In another specific aspect of the IBV spike protein or fragment thereof according to the present invention the Spike protein or fragment thereof is from an IBV of Massachusetts (not Beaudette), QX or 4/91 genotype or serotype.

In another specific aspect of the IBV spike protein or fragment thereof according to the present invention the Spike protein or fragment thereof is from an IBV of Massachusetts (not Beaudette) genotype or serotype.

In another specific aspect of the IBV spike protein or fragment thereof according to the present invention the Spike protein or fragment thereof is from an IBV of QX genotype or serotype.

In another specific aspect of the IBV spike protein or fragment thereof according to the present invention the Spike protein or fragment thereof is from an IBV of 4/91 genotype or serotype.

In another specific aspect of the IBV spike protein or fragment thereof according to the present invention the IBV strain is H52, H120, QX SP2013-01478 or CR88.

In another specific aspect of the IBV spike protein or fragment thereof according to the present invention the IBV spike protein or fragment thereof consists of or comprises an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

The term "identity" or "sequence identity" is known in the art and refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

The terms "identity", "sequence identity" and "percent identity" are used interchangeably herein. For the purpose of this invention, it is defined here that in order to determine the percent identity of two amino acid sequences or two nucleic acid sequences, the sequences are aligned for optimal comparison purposes (e.g., gaps can be introduced in the sequence of a first amino acid or nucleic acid for optimal alignment with a second amino or nucleic acid sequence). The amino acid or nucleotide residues at corresponding amino acid or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are of the same length.

A sequence comparison may be carried out over the entire lengths of the two sequences being compared or over fragments of the two sequences. Typically, the comparison will be carried out over the full length of the two sequences being compared. However, sequence identity may be carried out over a region of, for example, twenty, fifty, one hundred or more contiguous amino acid residues.

The skilled person will be aware of the fact that different computer programs are available to determine the homology between two sequences. For instance, a comparison of sequences and determination of percent identity between two sequences can be accomplished using a mathematical algorithm. In a preferred embodiment, the percent identity between two amino acid or nucleic acid sequences is determined using the Needleman and Wunsch (J. Mol. Biol. (48): 444-453 (1970)) algorithm which has been incorporated into the GAP program in the Accelrys GCG software package (available at www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6. The skilled person will appreciate that all these different parameters will yield slightly different results but that the overall percentage identity of two sequences is not significantly altered when using different algorithms The protein sequences or nucleic acid sequences of the present invention can further be used as a "query sequence" to perform a search against public databases to, for example, to identify other family members or related sequences. Such searches can be performed using the BLASTN and BLASTP programs (version 2.0) of Altschul, et al. (1990) J. Mol. Biol. 215:403-10. BLAST protein searches can be performed with the BLASTP program, score=50, wordlength=3 to obtain amino acid sequences homologous to protein molecules of the invention. To obtain gapped alignments for comparison purposes, Gapped BLAST can be utilized as described in Altschul et al. (1997) Nucleic Acids Res. 25(17): 3389-3402. When utilizing BLAST and Gapped BLAST programs, the default parameters of the respective programs (e.g., BLASTP and BLASTN) can be used. See the homepage of the National Center for Biotechnology Information at www.ncbi.nlm.nih.gov/.

As used herein, it is in particular understood that the term "identical to the sequence of SEQ ID NO: X" is equivalent to the term "identical to the sequence of SEQ ID NO: X over the length of SEQ ID NO: X" or to the term "identical to the sequence of SEQ ID NO: X over the whole length of SEQ ID NO: X", respectively. In this context, "X" is any integer selected from 1 to 84 so that "SEQ ID NO: X" represents any of the SEQ ID NOs mentioned herein.

In another specific aspect of the IBV spike protein or fragment thereof according to the present invention the IBV spike protein or fragment thereof consists of or comprises an amino acid sequence as shown in SEQ ID NO: 2 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 3 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 4 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 5 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 6 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 7 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof consists of or comprises an amino acid sequence as shown in SEQ ID NO: 8 or 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV spike protein or fragment thereof according to the present invention the IBV spike protein or fragment thereof is selected from a list of genotypes consisting of: GI-2 to 27, GII-1, GIII-1, GIV-1, GV-1, GVI-1.

Valastro et al 2016 (Infection, Genetics and Evolution 39; 349-364) describe a phylogeny-based classification system combined with a lineage nomenclature for the assignment of IBV strains. 6 genotypes (GI to GVI) are defined that together comprise 32 distinct viral lineages.

In another specific aspect of the IBV spike protein or fragment thereof according to the present invention the spike protein or fragment thereof is not from the GI-1 genotype. The GI-1 genotype relates to the Massachusetts genotype/serotype.

In another specific aspect of the avian coronavirus spike protein or fragment thereof according to the present invention said at least a part of the S1 subunit from an avian coronavirus with a restricted cell or tissue tropism is selected from the group consisting of: Infectious bronchitis virus (IBV); guinea fowl coronavirus (GfCoV) and turkey coronavirus (TCoV; turkey enteritis virus and bluecomb disease virus).

In another specific aspect of the avian coronavirus spike protein or fragment thereof according to the present invention said at least a part of the S1 subunit from an avian coronavirus with a restricted cell or tissue tropism is from IBV (infectious bronchitis virus).

In another specific aspect of the IBV spike protein or fragment thereof according to the present invention said at least a part of the S1 subunit is from an IBV selected from a list of genotypes or serotypes or strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy02, JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV spike protein or fragment thereof according to the present invention said at least a part of the S1 subunit is from an IBV selected from a list of genotypes or serotypes or strains consisting of Massachusetts (not Beaudette), 4/91, QX, Q1, Italy 02, Arkansas, Connecticut, Georgia, LDT3, PL84084, Variant 2 and Brazil.

In another specific aspect of the IBV spike protein or fragment thereof according to the present invention said at least a part of the S1 subunit is from an IBV selected from a list of genotypes or serotypes consisting of Massachusetts (not Beaudette), 4/91, QX, Q1, Arkansas, Variant 2 and Brazil.

In another specific aspect of the IBV spike protein or fragment thereof according to the present invention the Massachusetts strain is selected from a list consisting of: H120, H52, Spain/98/308, IBMA5-1, SD/97/01, Spain/96/334 and M41-M21883.

In another specific aspect of the IBV spike protein or fragment thereof according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91attenuated and IB4-91.

In another specific aspect of the IBV spike protein or fragment thereof according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV spike protein or fragment thereof according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV spike protein or fragment thereof according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV spike protein or fragment thereof according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV spike protein or fragment thereof according to the present invention the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

In another specific aspect of the IBV spike protein or fragment thereof according to the present invention the Brazil strain is selected from a list consisting of: BR-1, BR-2, 23/2013 and IBV/Brasil/351/1984.

In another specific aspect of the IBV spike protein or fragment thereof according to the present invention said at least a part of the S1 subunit is from an IBV selected from a list of genotypes or serotypes consisting of Massachusetts (not Beaudette), QX and 4/91.

In another specific aspect of the IBV spike protein or fragment thereof according to the present invention said at least a part of the S1 subunit is from an Massachusetts (not Beaudette) IBV genotype or serotype.

In another specific aspect of the IBV spike protein or fragment thereof according to the present invention said at least a part of the 51 subunit is from an QX IBV genotype or serotype.

In another specific aspect of the IBV spike protein or fragment thereof according to the present invention said at least a part of the 51 subunit is from an 4/91 IBV genotype or serotype.

In another specific aspect of the IBV spike protein or fragment thereof according to the present invention said at least a part of the 51 subunit is from an IBV strain H120, H52, QX SP2013-01478 or CR88.

In another specific aspect of the IBV spike protein or fragment thereof according to the present invention said at least a part of the 51 subunit is from an IBV strain H120 or H52.

In another specific aspect of the avian coronavirus spike protein or fragment thereof according to the present invention the at least a part of the 51 subunit is at least 1, 5, 10, 15, 20, 25, 50, 100, 150, 200, 250, 300, 350, 400 or 500 contiguous amino acids from a 51 subunit sequence of an avian coronavirus or IBV with a restricted cell or tissue tropism or a sequence having at least 90%, 95%, 96%, 97%, 98%, 99% sequence identity thereto.

In another specific aspect of the avian coronavirus or IBV spike protein or fragment thereof according to the present invention the at least a part of the 51 subunit is at least 1, 5, 10, 15, 20, 25, 50, 100, 150, 200, 250, 300, 350, 400 or 500 contiguous amino acids from a 51 subunit sequence of an avian coronavirus or IBV as described herein or a sequence having at least 90%, 95%, 96%, 97%, 98%, 99% sequence identity thereto.

In another specific aspect of the IBV spike protein or fragment thereof according to the present invention said at least a part of the 51 subunit from an IBV with a restricted cell or tissue tropism has at least 1, 5, 10, 15, 20, 25, 50, 100, 150, 200, 250, 300, 350, 400 or 500 contiguous amino acids of the amino acid sequence as shown in SEQ ID NO: 2, 3, 4, 5, 6, 7, 8, 77 or a sequence having at least 90%, 95%, 96%, 97%, 98%, 99% sequence identity thereto.

In another specific aspect of the avian coronavirus or IBV spike protein or fragment thereof according to the present invention the coronavirus or IBV with restricted cell or tissue tropism is restricted to infection and/or replication in emryonated chicken eggs and/or primary chicken kidney cells.

In another specific aspect of the avian coronavirus or IBV spike protein or fragment thereof according to the present invention the coronavirus or IBV with restricted cell or tissue tropism is not infecting and/or replicating in EB66 cells.

In another specific aspect of the avian coronavirus or IBV spike protein or fragment thereof according to the present invention the coronavirus or IBV with restricted cell or tissue tropism is not infecting and/or replicating in PBS-12SF and/or HEK 293T cells.

Fragment

In another specific aspect of the avian coronavirus or IBV spike protein or fragment thereof according to the present invention the fragment of the avian coronavirus or IBV spike protein has a length of at least 500, 750, 1000 or 1077 amino acids.

In another specific aspect of the avian coronavirus or IBV spike protein or fragment thereof according to the present invention the fragment of the avian coronavirus or IBV spike protein has a length of at least 1000 amino acids.

In another specific aspect of the avian coronavirus or IBV spike protein or fragment thereof according to the present invention the fragment of the avian coronavirus or IBV spike protein has a length of at least 500, 750, 1000 or 1075 amino acids from the N-Terminus.

The term "N-terminus" is well known to the person skilled in the art. The N-terminus is also termed amino-terminus, NH2-terminus, N-terminal end or amine-terminus. When the protein is translated from messenger RNA, it is created from N-terminus to C-terminus. Thus, the N-terminus is the start of an amino acid chain (protein or polypeptide) comprising said amine group (—NH2).

In another specific aspect of the avian coronavirus or IBV spike protein or fragment thereof according to the present invention the fragment of the avian coronavirus or IBV spike protein is the ectodomain of the spike protein.

The term "ectodomain" is well known to a person skilled in the art. The spike protein comprises different functional parts, the signal sequence, the ectodomain, the transmembrane domain and the endodomain (from N-terminus to C-terminus). Thus, after cleavage of the signal sequence, the N-terminus of the spike protein starts with the ectodomain The IBV spike ectodomains has a length of about 1075 amino acids and differs by a few amino acids in length dependent on the IBV strain.

In another specific aspect of the avian coronavirus or IBV spike protein according to the present invention the Cysteine at amino acid position 267 or the mutation at amino acid position 267 to Cysteine is genetically stable. Advantageously, the experimental data show that the Cysteine at amino acid position 267 or the mutation at amino acid position 267 to Cysteine is genetically stable and remains stable over time (over passage).

The term "genetically stable" means that the Cysteine at amino acid position 267 or the mutation at amino acid position 267 to Cysteine remains stable over time (over passage). Preferably, said Cysteine at amino acid position 267 or the mutation at amino acid position 267 to Cysteine is still present after at least 3 passages, more preferably after at least 6 passages, even more preferably after at least 9 passages, even more preferably after at least 12 passages, most preferred after 15 passages in cell culture or tissue culture of an IBV having said avian coronavirus or IBV spike protein according to the present invention.

Nucleotide Sequence and Plasmids

Further, the present invention provides a nucleotide sequence encoding the spike protein or fragment thereof as described herein.

Further, the present invention provides a plasmid comprising a nucleotide sequence as described herein.

The term "nucleic acid" or "nucleic acid sequence" or "nucleotide sequence" refers to polynucleotides including DNA molecules, RNA molecules, cDNA molecules or derivatives. The term encompasses single as well as double stranded polynucleotides. The nucleic acid of the present invention encompasses isolated polynucleotides (i.e. isolated from its natural context) and genetically modified forms. Moreover, comprised are also chemically modified polynucleotides including naturally occurring modified polynucleotides such as glycosylated or methylated polynucleotides or artificially modified ones such as biotinylated polynucleotides. Further, the terms "nucleic acid" and "polynucleotide" are interchangeable and refer to any nucleic acid. The terms "nucleic acid" and "polynucleotide" also specifically include nucleic acids composed of nucleotides with the nucleobases other than the five biologically occurring bases (adenine, guanine, thymine, cytosine and uracil).

The term "plasmid" refers to cytoplasmic DNA that replicates independently of the bacterial chromosome within a bacterial host cell. In a specific aspect of the present invention the term "plasmid" and/or "transfer plasmid" and/or "donor plasmid" refers to an element of recombinant DNA technology useful for construction of e.g. recombinant viruses or an expression cassette for insertion into a viral vector. In another specific aspect the term "plasmid" may be used to specify a plasmid useful for DNA vaccination purposes.

Cell

Further, the present invention provides a cell comprising a plasmid as described herein. The cell can be an eukaryotic or prokaryotic cell.

Viral Particle, Avian Coronavirus and IBV

Further, the present invention provides a viral particle comprising a spike protein or fragment thereof as described herein.

Further, the present invention provides an avian coronavirus comprising the spike protein or fragment thereof as described herein.

Further, the present invention provides an IBV (infectious bronchitis virus) comprising the spike protein as described herein.

In another specific aspect of the avian coronavirus or IBV according to the present invention the avian coronavirus or IBV is attenuated.

The term "attenuated" refers to a pathogen having a reduced virulence in comparison to the wildtype isolate. In the present invention, an attenuated IBV is one in which the virulence has been reduced so that it does not cause clinical signs of an IBV infection but is capable of inducing an immune response in the target animal, but may also mean that the clinical signs are reduced in incidence or severity in animals infected with the attenuated IBV in comparison with a "control group" of animals infected with non-attenuated IBV and not receiving the attenuated virus. In this context, the term "reduce/reduced" means a reduction of at least 10%, preferably 25%, even more preferably 50%, still more preferably 60%, even more preferably 70%, still more preferably 80%, still more preferably 90%, even more preferably 95% and most preferably of 100% as compared to the control group infected with non-attenuated IBV as defined above. Thus, an attenuated, IBV strain is one that is suitable for incorporation into an immunogenic composition comprising a modified live IBV.

In another specific aspect of the avian coronavirus or IBV according to the present invention the avian coronavirus or IBV is inactivated.

Any conventional inactivation method can be used for purposes of the present invention. Thus, inactivation can be performed by chemical and/or physical treatments which are known to the person skilled in the art. Preferred inactivation methods include the addition of cyclized binary ethylenimine (BEI) including the addition of a solution of 2-bromoethyleneamine hydrobromide (BEA), which has been cyclized to binary ethylenimine (BEI). Preferred further chemical inactivation agents comprise but are not limited to Triton X-100, Sodium deoxycholate, Cetyltrimethylammonium bromide, β-Propiolactone, Thimerosal, Phenol and Formaldehyde (Formalin). However, the inactivation may also comprise a neutralization step. Preferred neutralization agents include but are not limited to sodium thiosulfate, sodium bisulfite and the alike.

Preferred formalin inactivation conditions include formalin concentration between from about 0.02% (v/v)-2.0% (v/v), more preferably from about 0.1% (v/v)-1.0% (v/v), still more preferably from about 0.15% (v/v)-0.8% (v/v), even more preferably from about 0.16% (v/v)-0.6% (v/v), and most preferably about 0.2% (v/v)-0.4% (v/v). Incubation time depends on the resistance of the IBV. In general, the inaction process is performed until no growth of the IBV can be detected in a suitable cultivation system.

Preferably, the inactivated IBV of the present invention is formalin inactivated, preferably using the concentrations as described hereinabove.

The inactivated IBV of the invention may be incorporated into liposomes using known technology such as that described in Nature, 1974, 252, 252-254 or Journal of Immunology, 1978, 120, 1109-13. In another embodiment of the invention, the inactivated IBV of the invention may be conjugated to suitable biological compounds such as polysaccharides, peptides, proteins, or the like, or a combination thereof.

In another specific aspect of the avian coronavirus or IBV according to the present invention the avian coronavirus or IBV is genetically engineered.

The term "genetically engineered" refers to an avian coronavirus or IBV which has been mutated by using "reverse genetics" approaches. Preferably, the avian coronavirus or IBV according to the present invention has been genetically engineered. The reverse genetics technique involves the preparation of synthetic recombinant viral RNAs. However, "reverse genetics" techniques are well known to the person skilled in the art.

In another specific aspect of the avian coronavirus or IBV according to the present invention the avian coronavirus or IBV is a recombinant.

The term "recombinant" as used herein relates to a RNA genome (or RNA sequence, cDNA sequence or protein) having any modifications that do not naturally occur to the corresponding RNA genome (or RNA sequence, cDNA sequence or protein). For instance, a RNA genome (or RNA sequence, cDNA sequence or protein) is considered "recombinant" if it contains an insertion, deletion, inversion, relocation or a point mutation introduced artificially, e.g., by human intervention. Therefore, the RNA genomic sequence (or RNA sequence, cDNA sequence or protein) is not associated with all or a portion of the sequences (or RNA sequence, cDNA sequence or protein) with which it is associated in nature. The term "recombinant" as used with respect to a virus, means a virus produced by artificial manipulation of the viral genome. The term "recombinant virus" encompasses genetically modified viruses.

In another specific aspect of the avian coronavirus or IBV according to the present invention the avian coronavirus or IBV is chimeric.

The term "chimeric" refers to an avian coronavirus or IBV comprising one or more nucleotide sequences from another coronavirus or IBV. Preferably, the term refers to an IBV virus comprising one or more nucleotide sequences from another IBV strain.

In another specific aspect of the IBV according to the present invention the IBV is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (M41, H52, H120, Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

In another specific aspect of the IBV according to the present invention the IBV is selected from a list of genotypes or serotypes or strains consisting of: Massachusetts, 4/91, QX, Q1, Italy 02, Arkansas, Connecticut, Georgia, LDT3, PL84084, Variant 2 and Brazil.

In another specific aspect of the IBV according to the present invention the IBV is selected from a list of genotypes or serotypes consisting of: Massachusetts, 4/91, QX, Q1, Arkansas, Variant 2 and Brazil.

In another specific aspect of the IBV according to the present invention the Massachusetts strain is selected from a list consisting of: H120, H52, Spain/98/308, IBMA5-1, SD/97/01, Beaudette, Spain/96/334 and M41-M21883.

In another specific aspect of the IBV according to the present invention the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91 attenuated and IB4-91.

In another specific aspect of the IBV according to the present invention the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

In another specific aspect of the IBV according to the present invention the Q1 strain is selected from a list consisting of: CK/CH/LDL/98I, CK/CH/LSD/08-10, J2, Q1, AR08ER22, AR08BA21 and Chile-295-10.

In another specific aspect of the IBV according to the present invention the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

In another specific aspect of the IBV according to the present invention the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

In another specific aspect of the IBV according to the present invention the Variant 2 strain is selected from a list consisting of: IS/1494/06, IBV/Ck/EG/CU/4/2014, gammaCoV/Ck/Poland/G052/2016, Eg/CLEVB-2/IB V/012, D1344/2/4/10_EG, TR8 and IB VAR2-06.

In another specific aspect of the IBV according to the present invention the Brazil strain is selected from a list consisting of: BR-1, BR-2, 23/2013 and IBV/Brasil/351/1984.

In another specific aspect of the IBV according to the present invention the spike protein or fragment thereof is from an IBV of Massachusetts or 4/91 genotype or serotype.

In another specific aspect of the IBV according to the present invention the spike protein or fragment thereof is from an IBV of Massachusetts genotype or serotype.

In another specific aspect of the IBV according to the present invention the spike protein or fragment thereof is from an IBV of 4/91 genotype or serotype.

In another specific aspect of the IBV according to the present invention the IBV strain is H120, H52 or CR88.

In another specific aspect of the IBV according to the present invention the IBV strain is H120 or H52.

In another specific aspect of the IBV according to the present invention the IBV has a IBV spike protein or fragment thereof consisting of or comprising an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

In another specific aspect of the IBV according to the present invention the IBV has an extended cell or tissue tropism.

In another specific aspect of the IBV according to the present invention the IBV is infecting and/or replicating in at least one cell line or cell as described herein. Preferably, the IBV is infecting and/or replicating in at least one cell line as described herein.

Further, the present invention provides a cell comprising:
the viral particle as described herein, or
the avian coronavirus or IBV as described herein.

In another specific aspect of the cell according to the present invention the cell is a cell line or cell selected from the list consisting of: primary chicken embryo cells, a chicken embryo fibroblast cell line, a duck embryonic stem cell line, a human embryonic kidney cell line, a baby hamster kidney cell line, an african green monkey kidney cell line, a rabbit kidney cell line, a canine kidney cell line, a chicken liver cell line, a bovine kidney cell line, a porcine kidney cell line and an insect cell line.

In another specific aspect of the cell according to the present invention the cell is a cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

In another specific aspect of the cell according to the present invention the cell is a cell line selected from the list consisting of: DF-1, EB66, PBS-12, PBS-12SF, BHK, HEK 293T, Vero, MA104 and RK13.

In another specific aspect of the cell according to the present invention the primary chicken embryo cell is a fibroblast or a cell derived from liver or lung tissue.

Further, the present invention provides an immunogenic composition comprising:
the spike protein as described herein, or
the viral particle as described herein, or
the avian coronavirus or IBV as described herein.

Thus, the present invention also provides an immunogenic composition comprising an avian coronavirus or IBV comprising an avian coronavirus or IBV spike protein or fragment thereof, wherein at least a part of the 51 subunit is from an avian coronavirus or IBV with a restricted cell or tissue tropism, and wherein at amino acid position 267 is a Cysteine. Further, the present invention also provides an immunogenic composition comprising an avian coronavirus or IBV comprising a recombinant avian coronavirus or IBV spike protein or fragment thereof comprising a mutation at amino acid position 267 to Cysteine. Further, the amino acid sequence of SEQ ID NO:1 is used for determining the position numbering in the spike protein. Preferably, the amino acid sequence of the spike protein is aligned to the amino acid sequence of SEQ ID NO:1

Further, the present invention provides a vaccine comprising:
the spike protein as described herein, or
the viral particle as described herein, or
the coronavirus or IBV as described herein.

Further, the present invention provides a modified live vaccine with an extended cell or tissue tropism comprising:
the spike protein as described herein, or
the viral particle as described herein, or
the coronavirus or IBV as described herein.

The term "immunogenic composition" refers to a composition that comprises at least one antigen, which elicits an immunological response in the host to which the immunogenic composition is administered. Such immunological response may be a cellular and/or antibody-mediated immune response to the immunogenic composition of the invention. Preferably, the immunogenic composition induces an immune response and, more preferably, confers protective immunity against one or more of the clinical signs of a IBV infection. The host is also described as "subject". Preferably, any of the hosts or subjects described or mentioned herein is an avian or poultry.

Usually, an "immunological response" includes but is not limited to one or more of the following effects: the production or activation of antibodies, B cells, helper T cells, suppressor T cells, and/or cytotoxic T cells and/or gamma-delta T cells, directed specifically to an antigen or antigens included in the immunogenic composition of the invention. Preferably, the host will display either a protective immunological response or a therapeutically response.

A "protective immunological response" or "protective immunity" will be demonstrated by either a reduction or lack of clinical signs normally displayed by an infected host, a quicker recovery time and/or a lowered duration of infectivity or lowered pathogen titer in the tissues or body fluids or excretions of the infected host.

In case where the host displays a protective immunological response such that resistance to new infection will be enhanced and/or the clinical severity of the disease reduced, the immunogenic composition is described as a "vaccine".

The term "modified live" and "attenuated" are used interchangeable herein.

In another specific aspect of the immunogenic composition or vaccine according to the present invention the immunogenic composition or vaccine comprises a pharmaceutically acceptable carrier.

The term "pharmaceutical-acceptable carrier" includes any and all solvents, dispersion media, coatings, stabilizing agents, diluents, preservatives, antibacterial and antifungal agents, isotonic agents, adsorption delaying agents, adjuvants, immune stimulants, and combinations thereof.

"Diluents" can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others.

In another specific aspect of the immunogenic composition or vaccine according to the present invention the pharmaceutically acceptable carrier is phosphate buffered saline.

Preferably, the immunogenic composition further comprises sucrose gelatin stabilizer.

Preferably, the pharmaceutically acceptable carrier is chitosan.

Chitosan is a natural deacetylated polysaccharide from chitin in crustaceans (e.g., shrimp, crab), insects, and other invertebrates. Recently, Rauw et al. 2009 (Vet Immunol Immunop 134:249-258) demonstrated that chitosan enhanced the cellular immune response of live Newcastle disease vaccine and promoted its protective effect. Further, Wang et al., 2012 (Arch Virol (2012) 157:1451-1461) have shown results revealing the potential of chitosan as an adjuvant for use in a live attenuated influenza vaccine.

Preferably, the immunogenic composition can further include one or more other immunomodulatory agents such as, e.g. interleukins, interferons, or other cytokines. The amounts and concentrations of adjuvants and additives useful in the context of the present invention can readily be determined by the skilled artisan.

In some aspects, the immunogenic composition of the present invention contains an adjuvant. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.), JohnWiley and Sons, NY, pp 51-94 (1995) and Todd et al., Vaccine 15:564-570 (1997). Exemplary adjuvants are the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, are the copolymers EMA (Monsanto), which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from E. coli (recombinant or otherwise), cholera toxin, IMS 1314 or muramyl dipeptide, or naturally occurring or recombinant cytokines or analogs thereof or stimulants of endogenous cytokine release, among many others.

It is expected that an adjuvant can be added in an amount of about 100 µg to about 10 mg per dose, preferably in an amount of about 100 µg to about 10 mg per dose, more preferably in an amount of about 500 µg to about 5 mg per dose, even more preferably in an amount of about 750 µg to about 2.5 mg per dose, and most preferably in an amount of about 1 mg per dose. Alternatively, the adjuvant may be at a concentration of about 0.01 to 50%, preferably at a concentration of about 2% to 30%, more preferably at a concentration of about 5% to 25%, still more preferably at a concentration of about 7% to 22%, and most preferably at a concentration of 10% to 20% by volume of the final product.

In another specific aspect of the immunogenic composition or vaccine according to the present invention the immunogenic composition or vaccine is effective in the treatment and/or prophylaxis of clinical signs caused by IBV in a subject of need. The terms "treatment and/or prophylaxis", "clinical signs" and "of need" have been defined elsewhere.

In another specific aspect of the immunogenic composition or vaccine according to the present invention said immunogenic composition or vaccine is formulated for a single-dose administration.

The volume for a single-dose has been defined elsewhere herein.

It has furthermore been shown that one dose of the immunogenic composition of the present invention is effective after the administration of such single dose of such immunogenic composition or vaccine.

In another specific aspect of the immunogenic composition or vaccine according to the present invention the immunogenic composition or vaccine is administered subcutaneously, intramuscularly, oral, in ovo, via spray, via drinking water or by eye drop.

In another specific aspect of the immunogenic composition or vaccine according to the present invention the immunogenic composition or vaccine comprises 1 to 10 $\log_{10}$ EID50 per dose of the IBV.

In another specific aspect of the immunogenic composition or vaccine according to the present invention the immunogenic composition or vaccine comprises 2 to 5 $\log_{10}$ EID50 per dose of the IBV.

In another specific aspect of the immunogenic composition or vaccine according to the present invention the immunogenic composition or vaccine comprises 2 to 4 $\log_{10}$ EID50 per dose of the IBV.

Method for Manufacture, Culturing and Modification

Further, the present invention provides a method for altering the cell or tissue tropism of an avian coronavirus comprising the use of the avian coronavirus spike protein or fragment thereof as described herein.

Further, the present invention provides a method for extending the cell or tissue tropism of an avian coronavirus comprising the use of the avian coronavirus spike protein or fragment thereof as described herein.

Further, the present invention provides a method for the production or manufacture of an avian coronavirus with an extended cell or tissue tropism comprising the use of the avian coronavirus spike protein or fragment thereof as described herein.

Further, the present invention provides a method for culturing an avian coronavirus in a cell or tissue culture comprising the use of the avian coronavirus spike protein or fragment thereof as described herein.

Further, the present invention provides a method for modifying an avian coronavirus comprising modifying the amino acid position 267 in the spike protein of said avian coronavirus.

Further, the present invention provides a method for mutating the amino acid position 267 in an avian coronavirus spike protein comprising:
a) providing an avian coronavirus spike nucleotide or protein sequence,
b) identifying position 267 in the spike protein by alignment with a reference sequence,
c) mutating the position 267 of the spike protein of step b) into a cysteine,
d) obtaining the mutated spike protein of step c).

Furthermore, the present invention provides a method for mutating the amino acid position 267 in an avian coronavirus spike protein of an avian coronavirus comprising:
a) providing an avian coronavirus,
b) identifying position 267 in the spike protein by alignment with a reference sequence,
c) mutating the position 267 of the spike protein of step b) into a cysteine,
d) obtaining the mutated avian coronavirus of step c).

The term "obtaining" comprises the harvest, isolation, purification and/or formulation (e.g. finishing, inactivation and/or blending) of said spike protein or fragment thereof. The term "harvest" refers to collecting or recovering said avian coronavirus or IBV with the modified spike protein from the transfected or infected cell or cell line. Any conventional method known in the art can be used, e.g. any separation method. Well known methods in the art comprise centrifugation or filtration, such as using a semi-permeable membrane having a certain pore size. The term "isolation" comprises an isolation step of said avian coronavirus or IBV with the modified spike protein. Methods for the isolation from the transfected or infected cell or cell line are known to a person skilled in the art. Those methods comprise physical and/or chemical methods, including but are not limited to freeze thaw cycles, treatment with ultrasound and the alike. Methods for the "purification" of said avian coronavirus or IBV with the modified spike protein from the isolate are known to a person skilled in the art, for example by those methods described in Protein purification methods—a practical approach (E. L. V. Harris and S. Angel, eds., IRL Press at Oxford University Press). Those methods include, but are not limited to, separation by centrifugation and/or filtration, precipitation, size exclusion (gel filtration) chromatography, affinity chromatography, metal chelate chromatography, ion-exchange chromatography covalent chromatography, hydrophobic interaction chromatography, and the alike. The vector can be obtained in a purified pure form, or free or substantially free of other cellular materials or culture medium etc. After said isolation and/or purification the antigen exhibits a purity of at least 80%, preferably 80%-90%, more preferably 90%-97%, most preferred more than 97% up to an absolute pure form without any contamination.

According to a further aspect, "obtaining" as used herein may also include further finishing steps as part of the final formulation process, like the addition of buffer, inactivation, neutralization steps and the alike.

In another specific aspect of the method according to the present invention the spike protein or fragment thereof has at amino acid position 267 a Cysteine.

In another specific aspect of the method according to the present invention the Cysteine at amino acid position 267 is introduced by a mutation.

In another specific aspect of the method according to the present invention the mutation is an amino acid substitution, deletion or insertion.

In another specific aspect of the method according to the present invention a Phenylalanine or Leucine is modified or mutated into a Cysteine at amino acid at position 267.

In another specific aspect of the method according to the present invention the avian coronavirus is an IBV as described herein.

Thus, the present invention provides a method for altering the cell or tissue tropism of an IBV comprising the use of the avian coronavirus spike protein or fragment thereof as described herein.

Thus, the present invention provides a method for extending the cell or tissue tropism of an IBV comprising the use of the IBV spike protein or fragment thereof as described herein.

Thus, the present invention provides a method for the production or manufacture of an IBV with an extended cell or tissue tropism comprising the use of the IBV spike protein or fragment thereof as described herein.

Thus, the present invention provides a method for culturing an IBV in a cell or tissue culture comprising the use of the IBV spike protein or fragment thereof as described herein.

Thus, the present invention provides a method for modifying an IBV comprising modifying the amino acid position 267 in the spike protein of said IBV.

Thus, the present invention provides a method for mutating the amino acid position 267 in an IBV spike protein comprising:
a) providing an IBV spike nucleotide or protein sequence,
b) identifying position 267 in the spike protein by alignment with a reference sequence,
c) mutating the position 267 of the spike protein of step b) into a cysteine,
d) obtaining the mutated spike protein of step c).

Thus, the present invention provides a method for mutating the amino acid position 267 in an IBV spike protein of an IBV comprising:
a) providing an IBV,
b) identifying position 267 in the spike protein by alignment with a reference sequence,
c) mutating the position 267 of the spike protein of step b) into a cysteine,
d) obtaining the mutated IBV of step c).

In another specific aspect of the method according to the present invention the coronavirus spike protein is an IBV (infectious bronchitis virus) spike protein as described herein.

In another specific aspect of the method according to the present invention the Cysteine at amino acid position 267 or said mutation at amino acid position 267 to Cysteine leads to an extended cell or tissue tropism.

In another specific aspect of the method according to the present invention the avian coronavirus or IBV is infecting and/or replicating in a cell line or cell as described herein.

In another specific aspect of the method according to the present invention the numbering of amino acid position 267 is done as described herein.

Kits

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration preferably for administration to subjects, especially poultry. Associated with such container(s) can be a notice in the form prescribed by a governmental agency regulating the manufacture, use or sale of pharmaceuticals or biological products, which notice reflects approval by the agency of manufacture, use or sale for administration.

The present invention provides a kit comprising the viral particle, avian coronavirus, IBV, the immunogenic composition or vaccine as described herein.

In one specific aspect of the kit according to the present invention the kit further comprises an instruction letter for the treatment and/or prophylaxis of diseases of avians or an instruction letter for the treatment and/or prophylaxis of diseases of poultry or an instruction letter for the treatment and/or prophylaxis of IB.

In one specific aspect of the kit according to the present invention the kit further comprises a dispenser capable of administering a vaccine to said animal

Method of Treatment

Further, the present invention provides a method for immunizing a subject comprising administering to such subject an immunogenic composition as described herein.

The term "immunizing" relates to an active immunization by the administration of an immunogenic composition to a subject to be immunized, thereby causing an immunological response against the antigen included in such immunogenic composition.

Preferably, immunization results in lessening of the incidence of the particular avian coronavirus or IBV infection in a flock or in the reduction in the severity of clinical signs caused by or associated with the particular avian coronavirus or IBV infection.

Further, the immunization of a subject in need with the immunogenic compositions as provided herewith, results in preventing infection of a subject by avian coronavirus or IBV infection. Even more preferably, immunization results in an effective, long-lasting, immunological-response against IBV infection. It will be understood that the said period of time will last more than 1 month, preferably more than 2 months, preferably more than 3 months, more preferably more than 4 months, more preferably more than 5 months, more preferably more than 6 months. It is to be understood that immunization may not be effective in all subjects immunized However, the term requires that a significant portion of subjects of a flock are effectively immunized Preferably, a flock of subjects is envisaged in this context which normally, i.e. without immunization, would develop clinical signs normally caused by or associated with an avian coronavirus or IBV infection. Whether the subjects of a flock are effectively immunized can be determined without further ado by the person skilled in the art. Preferably, the immunization shall be effective if clinical signs in at least 33%, at least 50%, at least 60%, at least 70%, at least 80%, at least 90%, still more preferably in at least 95% and most preferably in 100% of the subjects of a given flock are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not immunized or immunized with an immunogenic composition that was available prior to the present invention but subsequently infected by the particular avian coronavirus or IBV.

Further, the present invention provides a method of treating or preventing clinical signs caused by IBV in a subject of need, the method comprises administering to the subject a therapeutically effective amount of an immunogenic composition or vaccine as described herein.

As shown in the Examples, the immunogenic composition or vaccine as provided herein has been proven to be efficacious in treating or preventing clinical signs caused by IBV in a subject. Therefore, the experimental data show that the modification of the amino acid at amino acid position 267 into a Cystein does not have any impact on the efficacy of the vaccine.

The term "treating or preventing" refers to the lessening of the incidence of the particular IBV infection in a flock or the reduction in the severity of clinical signs caused by or associated with the particular IBV infection. Thus, the term "treating or preventing" also refers to the reduction of the number of subjects in a flock that become infected with the particular IBV (=lessening of the incidence of the particular IBV infection) or to the reduction of the severity of clinical signs normally associated with or caused by a IBV infection or the reduction of virus shedding after infection with the particular IBV or preventing or lessening egg drop in laying hens after infection with the particular IBV in a group of subjects which subjects have received an effective amount of the immunogenic composition as provided herein in comparison to a group of subjects which subjects have not received such immunogenic composition.

The "treating or preventing" generally involves the administration of an effective amount of the immunogenic composition of the present invention to a subject or flock of subjects in need of or that could benefit from such a treatment/prophylaxis. The term "treatment" refers to the administration of the effective amount of the immunogenic composition once the subject or at least some subjects of the flock is/are already infected with such IBV and wherein such subjects already show some clinical signs caused by or associated with such IBV infection. The term "prophylaxis" refers to the administration of a subject prior to any infection of such subject with IBV or at least where such subject or none of the subjects in a group of subjects do not show any clinical signs caused by or associated with the infection by such IBV. The terms "prophylaxis" and "preventing" are used interchangeable in this application.

The term "an effective amount" as used herein means, but is not limited to an amount of antigen, that elicits or is able to elicit an immune response in a subject. Such effective amount is able to lessen the incidence of the particular IBV infection in a flock or to reduce the severity of clinical signs of the particular IBV infection.

Preferably, clinical signs are lessened in incidence or severity by at least 10%, more preferably by at least 20%, still more preferably by at least 30%, even more preferably by at least 40%, still more preferably by at least 50%, even more preferably by at least 60%, still more preferably by at least 70%, even more preferably by at least 80%, still more preferably by at least 90%, still more preferably by at least 95% and most preferably by 100% in comparison to subjects that are either not treated or treated with an immunogenic composition that was available prior to the present invention but subsequently infected by the particular IBV.

The term "clinical signs" as used herein refers to signs of infection of a subject from IBV. The clinical signs of infection depend on the pathogen selected. Examples for such clinical signs include but are not limited to respiratory distress, nephritis, salphingitis, abnormal egg production, ruffled feathers, depression, reduced growth rates and reduced appetite. Signs of respiratory distress encompass respiratory signs including gasping, coughing, sneezing, tracheal rales, nasal and ocular discharge, tracheal lesions and ciliostasis in the trachea. Signs of nephritis encompass kidney lesions and watery diarrhea. Signs of abnormal egg production encompass egg drop, eggs of smaller size, inferior shell, reduced internal egg quality, eggs with thin albumen and ciliostasis in the oviduct. However, the clinical signs also include but are not limited to clinical signs that are directly observable from a live animal. Examples for clinical signs that are directly observable from a live animal include nasal and ocular discharge, coughing, gasping, sneezing, tracheal rales, ruffled feathers, conjunctivitis, weight loss, reduced growth rates, reduced appetite, dehydration, watery diarrhea, lameness, lethargy, wasting and unthriftiness and the like.

Preferably, the clinical signs lessened in incidence or severity in a treated subject compared to subjects that are either not treated or treated with an immunogenic composition that was available prior to the present invention but subsequently infected by the particular IBV refer to a reduction of ciliostasis, a reduction of rales, a reduction of egg drop, a reduction of kidney lesions, a reduction of watery diarrhea, a reduction in weight loss, a lower virus load, a reduced viral shedding, or combinations thereof.

The term "in need" or "of need", as used herein means that the administration/treatment is associated with the boosting or improvement in health or clinical signs or any other positive medicinal effect on health of the subjects which receive the immunogenic composition in accordance with the present invention.

Further, the present invention provides a method of reducing the ciliostasis in a subject of need, in comparison to a subject of a non-immunized control group of the same species, the method comprises administering to the subject a therapeutically effective amount of an immunogenic composition or vaccine as described herein.

As shown in the Examples, the immunogenic composition or vaccine as provided herein has been proven to be efficacious in reducing ciliostasis.

The term "ciliostasis" refers to a reduced movement of the cilia in the trachea. Thus, ciliostasis may be determined by examining the inner lining of the tracheal rings for the movement of the cilia. It is in the general knowledge of a person skilled in the art how to determine the movement of the cilia in the trachea.

Preferably, the movement of the cilia is not reduced from day 10 after challenge or infection, more preferably from day 5 after challenge or infection, more preferably from day 4 after challenge or infection, more preferably from day 3 after challenge or infection and most preferably from day 1 or 2 after challenge or infection with the IBV as compared to a subject of a non-immunized control group of the same species.

The term "reduction of ciliostasis" means, that the ciliostasis is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the reduction of the ciliostasis.

Further, the present invention provides the immunogenic composition or vaccine as described herein for use in a method for immunizing a subject, the method comprises administering to the subject a therapeutically effective amount of said immunogenic composition or vaccine.

Further, the present invention provides the immunogenic composition or vaccine as described herein for use in a method of treating or preventing clinical signs caused by IBV in a subject of need, the method comprises administering to the subject a therapeutically effective amount of said immunogenic composition or vaccine.

Further, the present invention provides the immunogenic composition or vaccine as described herein for use in a method of reducing the ciliostasis in a subject of need, in comparison to a subject of a non-immunized control group of the same species, the method comprises administering to the subject a therapeutically effective amount of said immunogenic composition or vaccine.

In one specific aspect of the method or use according to the present invention said subject is avian.

The term "avian" is well known to the person skilled in the art. The term "avian" encompasses all birds including poultry.

In one specific aspect of the method or use according to the present invention said subject is poultry.

The term "poultry" is well known to the person skilled in the art. The term "poultry" encompasses chickens, turkeys, quails, pheasants, guineafowl, geese, and ducks. Further, the term "chicken" includes broiler, laying hens, and reproductive stocks for both also referred as breeders.

In one specific aspect of the method or use according to the present invention said subject is selected from the list consisting of chicken, turkey, quail, or pheasant.

In one specific aspect of the method or use according to the present invention said subject is chicken.

In one specific aspect of the method or use according to the present invention the immunogenic composition or vaccine is administered once.

It is understood, that a single-dose is administered only once. As shown in the Examples the immunogenic composition as provided herein has been proven to be efficacious after the administration of a single dose to a subject of need.

The dose volume per poultry depends on the route of vaccination and the age of the poultry.

Typically, eye drop vaccines are administered in a volume of 1 to 100 µl per dose at any age. Preferably, the single-dose for eye drop vaccines has a total volume between about 5 µl and 70 µl and more preferably between about 20 µl and 50 µl with a single 20 µl, 25 µl, 30 µl, 35 µl, 40 µl, 45 µl or 50 µl dose being preferred. Most preferred, the single-dose for eye drop vaccines has a total volume between about 30 µl and 50 µl with a single 30 µl, 35 µl, 40 µl, 45 µl or 50 µl dose being preferred.

Spray vaccines may contain the dose in a volume of 25 to 1000 µl for day-old poultry. Preferably, the single-dose for spray vaccines has a total volume between about 50 µl and 5000 µl, more preferably between about 75 µl and 2000 µl, more preferably between about 100 µl and 1000 µl, even more preferably between about 200 µl and 900 µl, even more preferably between about 300 µl and 800 µl and even more preferably between about 400 µl and 700 µl with a single 400

μl, 425 μl, 450 μl, 475 μl, 500 μl, 525 μl, 550 μl, 575 μl, 600 μl, 625 μl, 650 μl, 675 μl or 700 μl dose being preferred. Most preferred the single-dose has a total volume of 400 μl, 450 μl 500 μl, 550 μl, 600 μl, 650 μl or 700 μl.

The vaccine for in ovo vaccination may contain the dose in a volume of 50 to 100 μl, preferably 50 μl. Preferably, the single-dose for in ovo vaccines has a total volume between about 10 μl and 250 μl, more preferably between about 15 μl and 200 μl, even more preferably between about 20 μl and 150 μl, even more preferably between about 30 μl and 100 μl, even more preferably between about 30 μl and 75 μl and with a single 30 μl, 35 μl, 40 μl, 45 μl, 50 μl, 55 μl, 60 μl, 65 μl, 70 μl or 75 μl dose being preferred. Most preferred the single-dose has a total volume of 40 μl, 45 μl, 50 μl, 55 μl or 60 μl.

The vaccine for intramuscular or subcutaneous vaccination or one dose of a drinking water vaccine may contain the dose in a volume of 30 μl to 1000 μl. Preferably, the single-dose has a total volume between about 30 μl and 1000 μl, more preferably between about 50 μl and 500 μl, more preferably between about 75 μl and 250 μl and even more preferably between about 100 μl and 200 μl with a single 100 μl, 110 μl, 120 μl, 125 μl, 130 μl, 135 μl, 140 μl, 145 μl, 150 μl, 160 μl, 170 μl, 175 μl, 180 μl, 190 μl, 155 μl, or 200 μl dose being the most preferred.

In one specific aspect of the method or use according to the present invention the immunogenic composition or vaccine is administered at two or more doses.

However, the immunogenic composition can be administered at two or more doses, with a first dose being administered prior to the administration of a second (booster) dose.

In a preferred aspect of the two-time administration regimen, both the first and second doses of the immunogenic composition are administered in the same amount. Preferably, each dose is in the preferred amounts specified above. In addition to the first and second dose regimen, an alternate embodiment comprises further subsequent doses. For example, a third, fourth, or fifth dose could be administered in these aspects. Preferably, subsequent third, fourth, and fifth dose regimens are administered in the same amount as the first dose, with the time frame between the doses being consistent with the timing between the first and second doses mentioned above.

Preferably, the first administration of the vaccine is performed within the first three weeks of age, more preferably within the first week of age and most preferred at one day-of-age by methods as described below. A second administration can be performed within the first 20 weeks of age, preferably within 16-18 weeks of age, more preferably between 6-12 weeks of age. Exemplary, the iniatial (first) vaccination is performed at 1-10 days of age and the second vaccination (booster) is performed with a live or inactivated vaccine at 6-12 or 16-18 weeks of age. More preferably, the iniatial (first) vaccination is performed at one day-of-age and the second vaccination (booster) is performed with a live or inactivated vaccine at 6-12 or 16-18 weeks of age.

In case in ovo vaccination is used, preferably the first administration is performed when embryos are between 15 to 19 days old, preferably at day 17, 18 or 19, most preferably at day 18 of age. A second administration can be performed within the first three weeks of age, preferably within the first 10 days of age.

In one specific aspect of the method or use according to the present invention said immunogenic composition or vaccine is administered subcutaneously, intramuscularly, oral, in ovo, via spray, via drinking water or by eye drop.

The immunogenic composition is, preferably, administered topically or systemically. Suitable routes of administration conventionally used are oral or parenteral administration, such as intranasal, intravenous, intradermal, transdermal, intramuscular, intraperitoneal, subcutaneous, as well as inhalation, in ovo, via spray, via drinking water or by eye drop. However, depending on the nature and mode of action of a compound, the immunogenic composition may be administered by other routes as well. For example, such other routes include intracutaneously, intravenously, intravascularly, intraarterially, intraperitnoeally, intrathecally, intratracheally, intracutaneously, intracardially, intralobally, intralobarly, intramedullarly, intrapulmonarily, intrarectally, and intravaginally. However, most preferred the immunogenic composition is administered subcutaneously, intramuscularly, oral, in ovo, via spray, via drinking water or by eye drop.

Live IBV vaccines are preferably administered individually by eye drop, intranasal, intramuscular or subcutaneous.

More preferably, mass application methods, including drinking water and aerosol spray vaccination, are used. Also preferred is the use of vaccines as embryo vaccines (so-called in ovo vaccines) as described further below.

For example, broilers may be vaccinated at one-day of age or at 1-3 weeks of age, particularly for broilers with high levels of MDA. Laying stock or reproduction stock may be vaccinated initially at 1-10 days of age and boosted with the vaccine at 7-12 or 16-18 weeks of age.

In Ovo Administration

As outlined above, the present invention also provides an IBV vaccine that can be safely administered via the in ovo route and at the same time is able to induce a protective immune response. The in ovo administration is well known to the person skilled in the art and the person skilled in the art can perform in ovo administration without further ado. The in ovo administration of the vaccine involves the administration of the vaccine to an avian embryo while contained in the egg (for a review on in ovo vaccination see: Ricks et al., Advances in Vet. Med. 495-515, 1999). The vaccine may be administered to any suitable compartment of the egg (e. g. allantois fluid, yolk sac, amnion, air cell or into the embryo) as described in the art (Sharma; Am. J. Vet. Res. 45 1619-1623, 1984). Preferably the vaccine is administered below the shell (aircell) membrane and chorioallantoic membrane.

Preferably, the vaccine is injected into embryonated eggs during late stages of the embryonation, generally during the final quarter of the incubation period, preferably 3-4 days prior to hatch. Preferably, the administration is performed when embryos are between 15 to 19 days old, preferably at day 17, 18 or 19, most preferably at day 18 of age. Subsequently, the vaccinated embryonated eggs are transferred to an incubator for hatch. The process of in ovo administration can be automated using a robotic injection process as described in the prior art.

Usually conventional vaccines for post-hatch vaccination of poultry cannot be used for in ovo vaccination, because late stage embryos are highly susceptible to infection with most vaccine viruses examined However, International patent application WO 01/64244 discloses that IBV vaccines can be used for in ovo administration provided it is applied at a very low doses. Further, Wakenell et al. 1986 (Am. J. Vet. Res., 47 933-938) discloses that passaging an IB vaccine virus in tissue culture rendered the virus apathogenic for embryos.

In one specific aspect of the method or use according to the present invention said immunogenic composition or vaccine is administered via eye drop.

Typically, the live vaccine for post-hatch administration comprises the attenuated IBV in a concentration of $10^1$ to $10^8$ $EID_{50}$ (50% Egg Infective Dose) per dose, preferably in a concentration of $10^2$ to $10^5$ $EID_{50}$ per dose and, more preferably, in a concentration of $10^2$ to $10^4$ $EID_{50}$ per unit dose and, even more preferably, in a concentration of $10^2$ to $10^3$ $EID_{50}$ per dose.

The live vaccine for in ovo administration typically comprises an amount of the attenuated IBV of $10^2$ to $10^7$ $EID_{50}$/embryo, preferably $10^2$ to $10^3$ $EID_{50}$/embryo in a volume of 50 to 100 µl, preferably 50 µl.

Preferably, the immunogenic composition of the present invention comprises the IBV of the present invention in amounts of about 1 to about 10 $\log_{10}$ EID (egg infective dose)$_{50}$/ml per dose, preferably about 2 to about 8 $\log_{10}$ $EID_{50}$ per dose, preferably in an amount of about 2 to about 7 $\log_{10}$ EID50 per dose, more preferably in an amount of about 2 to about 6 $\log_{10}$ $EID_{50}$ per dose, even more preferably in an amount of about 2 to about 5 $\log_{10}$ $EID_{50}$ per dose, even more preferably in an amount of about 2 to about 4 $\log_{10}$ $EID_{50}$ per dose, most preferably in an amount of about 2 to about 3 $\log_{10}$ $EID_{50}$ per dose. More preferably, the immunogenic composition of the present invention comprises the IBV of the present invention in amounts of about 1, 1.5, 2, 2.5, 3, 3.5, 4, 4.5, 5, 5.5, 6, 6.5, 7, 7.5 or $\log_{10}$ $EID_{50}$ per dose.

In one specific aspect of the method or use according to the present invention the immunogenic composition or vaccine comprises 1 to 10 $\log_{10}$ $EID_{50}$ per dose of the IBV.

In one specific aspect of the method or use according to the present invention the immunogenic composition or vaccine comprises 2 to 5 $\log_{10}$ $EID_{50}$ per dose of the IBV.

In one specific aspect of the method or use according to the present invention the immunogenic composition or vaccine comprises 2 to 4 $\log_{10}$ $EID_{50}$ per dose of the IBV.

In one specific aspect of the method or use according to the present invention the immunogenic composition or vaccine is administered to subjects within the first week of age, within the first three days of age, within the first two days of age, or within the first day of age.

Preferably, the subject to be immunized is 1, 2, 3, 4, 5, 6, 7, 8, 9, 10, 11, 12, 13, 14, 15, 16, 17, 18, 19, 20 or 21 days of age. More preferably, said subject to be immunized is 1, 2, 3, 4, 5, 6, 7, 8, 9, 10, 11, 12, 13 or 14 days of age. Most preferably, said subject to be immunized is 1, 2, 3, 4, 5, 6 or 7 days of age.

However, it has to be understood that after vaccination of the subject being a few days of age, it does need several days for the immune system of the poultry to build up immunity against an IBV infection. Therefore, preferably, the subjects are immunized within the first 24 h of age.

In one specific aspect of the method or use according to the present invention the immunogenic composition or vaccine is administered to subjects within the first day of age. As shown in the Examples the immunogenic composition as provided herein has been proven to be safe and efficacious when administered to 1-day old poultry.

In one specific aspect of the method or use according to the present invention said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

The terms "treatment and/or prophylaxis" have been defined elsewhere, wherein the terms "prophylaxis" and "preventing" or "prevention" are used interchangeable in this application. Further, the terms "shedding" has been defined elsewhere, too.

The term "reducing", "reduced", "reduction" or "lower" means, that the efficacy parameter (ciliostasis, rales, egg drop, kidney lesions, watery diarrhea, weight loss, virus load, viral shedding) is reduced by at least 10%, preferably by at least 20%, more preferably by at least 30%, even more preferably by at least 40%, even more preferably by at least 50%, even more preferably by at least 60%, even more preferably by at least 70%, even more preferably by at least 80%, even more preferably by at least 90%, even more preferably by at least 95% and most preferably by 100% as compared to a subject of a non-immunized control group of the same species. It is in the general knowledge of a person skilled in the art how to measure the improvement in the efficacy parameters.

The term "virus load" or "virus titer" is a measure of the severity of an active viral infection, and can be determined by methods known to the person skilled in the art. The term "viral titre" is a measure of infectious units per volume of a virus preparation. Viral titre is an endpoint in a biological procedure and is defined as the dilution at which a certain proportion of tests carried out in parallel show an effect (Reed and Muench, 1938). The determination can be based on the detection of viral proteins such as by antibody binding to the viral proteins and further detection or, alternatively, by detection of viral RNA by amplification methods such as RT-PCR. Monitoring of virion associated viral RNA in plasma by nucleic acid amplification methods is a widely used parameter to assess the status and progression of retroviral disease, and to evaluate the effectiveness of prophylactic and therapeutic interventions. Exemplary, the virus load or virus titer can be calculated by estimating the live amount of virus in an involved body fluid such as a number of RNA copies per milliliter of blood plasma.

The term "ciliostasis" is well known to the person skilled in that art. The surface of the trachea is covered with specialised epithelial cells, which are lined with numerous, motile, hair-like structures called cilia. The term "ciliostasis" encompasses the reduction or loss of cilia and/or loss or partial loss of ciliary activity. Ciliostasis can be determined without further ado by the person skilled in the art.

The term "rales" is well known to the person skilled in that art. However, the term "rales" encompasses tracheal rales and refers to sounds emanating from the bronchi. Rales can be determined without further ado by the person skilled in the art.

The term "egg drop" is well known to the person skilled in that art. The term "egg drop" encompasses a decreased egg production.

In one specific aspect of the method or use according to the present invention the treatment or prevention results in a prevention or reduction of ciliostasis as compared to subjects of a non-treated control group of the same species.

In one specific aspect of the method or use according to the present invention the treatment or prevention results in a prevention or reduction of kidney lesions as compared to subjects of a non-treated control group of the same species.

In one specific aspect of the method or use according to the present invention the treatment or prevention results in a prevention or reduction of egg drop as compared to subjects of a non-treated control group of the same species.

The present invention further provides the viral particle, avian coronavirus, IBV, immunogenic composition or vaccine as described herein for therapeutic use.

The present invention further provides the viral particle, avian coronavirus, IBV, immunogenic composition or vaccine as described herein for use as an immunogen or vaccine.

The present invention further provides the viral particle, avian coronavirus, IBV, immunogenic composition or vaccine as described herein for use as a medicament.

The present invention further provides the use of the viral particle, avian coronavirus, IBV, immunogenic composition or vaccine as described herein for the manufacture of a medicament.

The present invention further provides the use of the viral particle, avian coronavirus, IBV, immunogenic composition or vaccine as described herein for the treatment and/or prophylaxis of IBV infections in a subject.

CLAUSES

The following clauses are also described herein:
1. An avian coronavirus spike protein or fragment thereof, wherein at least a part of the 51 subunit is from an avian coronavirus with a restricted cell or tissue tropism, and wherein at amino acid position 267 is a Cysteine.
2. A recombinant avian coronavirus spike protein or fragment thereof comprising a mutation at amino acid position 267 to Cysteine.
3. An IBV spike protein or fragment thereof, wherein at least a part of the 51 subunit is from an IBV with a restricted cell or tissue tropism, and wherein at amino acid position 267 is a Cysteine.
4. A recombinant IBV spike protein or fragment thereof comprising a mutation at amino acid position 267 to Cysteine.
Mutation 267
5. The avian coronavirus or IBV spike protein or fragment thereof of clause 1 or 3, wherein the Cysteine at amino acid position 267 is introduced by a mutation.
6. The avian coronavirus or IBV spike protein or fragment thereof of clause 2, 4 or 5, wherein the mutation is an amino acid substitution, deletion or insertion.
7. The avian coronavirus or IBV spike protein or fragment thereof of any one of clauses 2 and 4 to 6, wherein a hydrophobic amino acid at amino acid position 267 is mutated into a Cysteine; or a Phenylalanine or Leucine at amino acid position 267 is mutated into a Cysteine.
Extended Cell or Tissue Tropism
8. The avian coronavirus or IBV spike protein or fragment thereof of any one of clauses 1 to 7, wherein the Cysteine at amino acid position 267 or said mutation at amino acid position 267 to Cysteine leads to an extended cell or tissue tropism of the avian coronavirus or IBV.
9. The avian coronavirus or IBV spike protein or fragment thereof of any one of clauses 1 to 8, wherein the avian coronavirus or IBV is infecting and/or replicating in at least one cell line or cell selected from the list consisting of: primary chicken embryo cells from lung or liver or primary chicken fibroblasts, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.
10. The avian coronavirus or IBV spike protein or fragment thereof of any one of clauses 1 to 9, wherein the avian coronavirus or IBV is infecting and/or replicating in at least one cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+ (*Spodoptera frugiperda*).
11. The avian coronavirus or IBV spike protein or fragment thereof of any one of clauses 1 to 10, wherein the avian coronavirus or IBV is infecting and/or replicating in at least one cell line selected from the list consisting of: DF-1, EB66, PBS-12, PBS-12SF, BHK, HEK 293T, Vero, MA104 and RK13.
Numbering of Amino Acid Position 267
12. The avian coronavirus or IBV spike protein or fragment thereof of any one of clauses 1 to 11, wherein the numbering of amino acid position 267 refers to the amino acid position 267 in the spike protein of an IBV H52, an IBV H120 or an M41.
13. The avian coronavirus or IBV spike protein or fragment thereof of any one of clauses 1 to 12, wherein the numbering of amino acid position 267 refers to the amino acid position 267 in the spike protein of an IBV H52.
14. The avian coronavirus or IBV spike protein or fragment thereof of any one of clauses 1 to 12, wherein the numbering of amino acid position 267 refers to the amino acid position 267 in the spike protein as exemplarily given in SEQ ID NO:1.
15. The avian coronavirus or IBV spike protein or fragment thereof of any one of clauses 1 to 12, wherein the amino acid sequence of SEQ ID NO:1 is used for determining the position numbering in the spike protein.
16. The avian coronavirus or IBV spike protein or fragment thereof of any one of clauses 1 to 12, wherein for determining the amino position 267 in a spike protein the amino acid sequence is aligned to the amino acid sequence of SEQ ID NO:1.
17. The avian coronavirus or IBV spike protein or fragment thereof of any one of clauses 1 to 16, wherein the amino acid position 267 is within the S1 subunit of the spike protein.
18. The avian coronavirus or IBV spike protein or fragment thereof of any one of clauses 1 to 17, wherein the spike protein has one or more of the following amino acids selected from the group consisting of:
  264 is an asparagine, and/or
  265 is a threonine, and/or
  269 is a leucine, and/or
  271 is an asparagine, and/or
  272 is a phenylalanine.
Spike
19. The avian coronavirus spike protein or fragment thereof of any one of clauses 1 and 2 and 5 to 18, wherein the avian coronavirus spike protein or fragment thereof is selected from the group consisting of: infectious bronchitis virus (IBV); guinea fowl coronavirus (GfCoV) and turkey coronavirus (TCoV; turkey enteritis virus and bluecomb disease virus).
20. The avian coronavirus spike protein or fragment thereof of any one of clauses 1 and 2 and 5 to 19, wherein the avian coronavirus is IBV (infectious bronchitis virus).
21. The IBV spike protein or fragment thereof of any one of clauses 3 to 20, wherein the spike protein is from an IBV with a genotype or serotype or strain selected from a list consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

22. The IBV spike protein or fragment thereof of any one of clauses 3 to 21, wherein the spike protein is not from a Beaudette strain.

23. The IBV spike protein or fragment thereof of any one of clauses 3 to 22, wherein the Spike protein or fragment thereof is from an IBV selected from a list of genotypes or serotypes or strains consisting of Massachusetts (not Beaudette), 4/91, QX, Q1, Italy 02, Arkansas, Connecticut, Georgia, LDT3, PL84084, Variant 2 and Brazil.

24. The IBV spike protein or fragment thereof of any one of clauses 3 to 23, wherein the Spike protein or fragment thereof is from an IBV selected from a list of genotypes or serotypes consisting of Massachusetts (not Beaudette), 4/91, QX, Q1, Arkansas, Variant 2 and Brazil.

25. The IBV spike protein or fragment thereof of any one of clauses 3 to 24, wherein the Spike protein or fragment thereof is from an IBV selected from a list of genotypes or serotypes consisting of Massachusetts (not Beaudette) and 4/91.

26. The IBV spike protein or fragment thereof of clause 24, wherein the Massachusetts strain is selected from a list consisting of: H120, H52, Spain/98/308, IBMA5-1, SD/97/01, Spain/96/334 and M41-M21883.

27. The IBV spike protein or fragment thereof of clause 24, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91attenuated and IB4-91.

28. The IBV spike protein or fragment thereof of clause 24, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03, SP2013-01470, SP2013-014171, SP2013-01478 and GB341/96.

29. The IBV spike protein or fragment thereof of clause 24, wherein the Q1 strain is selected from a list consisting of: CK/CH/LDL/98I, CK/CH/LSD/08-10, J2, Q1, AR08ER22, AR08BA21, 12.185, 12.124, 12.216 and Chile-295-10.

30. The IBV spike protein or fragment thereof of clause 24, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

31. The IBV spike protein or fragment thereof of clause 24, wherein the Italy 02 strain is selected from a list containing of: Spain/99/316, Italy-02, UK-L633-04, It-497-02, Spain/05/866, Spain/04/221, Spain/00/337, Spain/155/09 and Spain/03/08.

32. The IBV spike protein or fragment thereof of clause 24, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

33. The IBV spike protein or fragment thereof of clause 24, wherein the Brazil strain is selected from a list consisting of: BR-1, BR-2, 23/2013, and IBV/Brasil/351/1984.

34. The IBV spike protein or fragment thereof of any one of clauses 3 to 24, wherein the Spike protein or fragment thereof is from an IBV of Massachusetts (not Beaudette), 4/91 or QX genotype or serotype.

35. The IBV spike protein or fragment thereof of any one of clauses 3 to 24, wherein the IBV strain is H52, H120, QX SP2013-01478 or CR88.

36. The IBV spike protein or fragment thereof of any one of clauses 3 to 35, wherein the IBV spike protein or fragment thereof consists of or comprises an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

37. The IBV spike protein or fragment thereof of any one of clauses 3 to 36, wherein the IBV spike protein or fragment thereof is selected from a list of genotypes consisting of: GI-2 to 27, GII-1, GIII-1, GIV-1, GV-1, GVI-1.

38. The IBV spike protein or fragment thereof of any one of clauses 3 to 37, wherein the spike protein or fragment thereof is not from the GI-1 genotype.

39. The avian coronavirus spike protein or fragment thereof of any one of clauses 1 and 5 to 38, wherein said at least a part of the S1 subunit from an avian coronavirus with a restricted cell or tissue tropism is selected from the group consisting of: Infectious bronchitis virus (IBV); guinea fowl coronavirus (GfCoV) and turkey coronavirus (TCoV; turkey enteritis virus and bluecomb disease virus).

40. The avian coronavirus spike protein or fragment thereof of any one of clauses 1 and 5 to 38, wherein said at least a part of the S1 subunit from an avian coronavirus with a restricted cell or tissue tropism is from IBV (infectious bronchitis virus).

41. The IBV spike protein or fragment thereof of any one of clauses 3 and 5 to 40, wherein said at least a part of the S1 subunit is from an IBV selected from a list of genotypes or serotypes or strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (such as M41, H52, H120; excluding Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).

42. The IBV spike protein or fragment thereof of any one of clauses 3 and 5 to 41, wherein said at least a part of the 51 subunit is from an IBV selected from a list of genotypes or serotypes or strains consisting of Massachusetts (not Beaudette), 4/91, QX, Q1, Italy 02, Arkansas, Connecticut, Georgia, LDT3, PL84084, Variant 2 and Brazil.

43. The IBV spike protein or fragment thereof of any one of clauses 3 and 5 to 41, wherein said at least a part of the 51 subunit is from an IBV selected from a list of genotypes or serotypes consisting of Massachusetts, 4/91, QX, Q1, Arkansas, Variant 2 and Brazil.

44. The IBV spike protein or fragment thereof of clause 43, wherein the Massachusetts strain is selected from a list consisting of: H120, H52, Spain/98/308, IBMA5-1, SD/97/01, Spain/96/334 and M41-M21883.
45. The IBV spike protein or fragment thereof of clause 43, wherein the 4/91 strain is selected from a list consisting of: Spain/98/328, Spain/92/35, IR-3654-VM, FR-CR88061-88, 1-R-85131-85, UK-1233-95, UK/3/91, Spain/00/336, UK/7/91, 4/91-pathogenic, 4/91attenuated and IB4-91.
46. The IBV spike protein or fragment thereof of clause 43, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.
47. The IBV spike protein or fragment thereof of clause 43, wherein the Q1 strain is selected from a list consisting of: CK/CH/LDL/98I, CK/CH/LSD/08-10, J2, Q1, AR08ER22, AR08BA21 and Chile-295-10.
48. The IBV spike protein or fragment thereof of clause 43, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.
49. The IBV spike protein or fragment thereof of clause 43, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.
50. The IBV spike protein or fragment thereof of clause 43, wherein the Brazil strain is selected from a list consisting of: BR-1, BR-2, 23/2013 and IBV/Brasil/351/1984.
51. The IBV spike protein or fragment thereof of any one of clauses 3 and 5 to 43, wherein said at least a part of the S1 subunit is from an IBV selected from a list of genotypes or serotypes consisting of Massachusetts (not Beaudette), QX and 4/91.
52. The IBV spike protein or fragment thereof of any one of clauses 3 and 5 to 43, wherein said at least a part of the S1 subunit is from an IBV strain H120, H52, QX SP2013-01478 or CR88.
53. The avian coronavirus spike protein or fragment thereof of any one of clauses 1 and 3 and 5 to 52, wherein the at least a part of the S1 subunit is at least 1, 5, 10, 15, 20, 25, 50, 100, 150, 200, 250, 300, 350, 400 or 500 contiguous amino acids from a S1 subunit sequence of an avian coronavirus or IBV with a restricted cell or tissue tropism or a sequence having at least 90%, 95%, 96%, 97%, 98%, 99% sequence identity thereto.
54. The avian coronavirus or IBV spike protein or fragment thereof of any one of clauses 1 and 3 and 5 to 52, wherein the at least a part of the S1 subunit is at least 1, 5, 10, 15, 20, 25, 50, 100, 150, 200, 250, 300, 350, 400 or 500 contiguous amino acids from a S1 subunit sequence of an avian coronavirus or IBV of any one of clauses 36 to 50 or a sequence having at least 90%, 95%, 96%, 97%, 98%, 99% sequence identity thereto.
55. The IBV spike protein or fragment thereof of any one of clauses 3 and 5 to 52, wherein said at least a part of the S1 subunit from an IBV with a restricted cell or tissue tropism has at least 1, 5, 10, 15, 20, 25, 50, 100, 150, 200, 250, 300, 350, 400 or 500 contiguous amino acids of the amino acid sequence as shown in SEQ ID NO: 2, 3, 4, 5, 6, 7, 8, 77 or a sequence having at least 90%, 95%, 96%, 97%, 98%, 99% sequence identity thereto.
56. The avian coronavirus or IBV spike protein or fragment thereof of any one of clauses 1 and 3 and 5 to 55, wherein the avian coronavirus or IBV with restricted cell or tissue tropism is restricted to infection and/or replication in emryonated chicken eggs and/or primary chicken kidney cells.
57. The avian coronavirus or IBV spike protein or fragment thereof of any one of clauses 1 and 3 and 5 to 56, wherein the avian coronavirus or IBV with restricted cell or tissue tropism is not infecting and/or replicating in EB66 cells.
58. The avian coronavirus or IBV spike protein or fragment thereof of any one of clauses 1 and 3 and 5 to 56, wherein the avian coronavirus or IBV with restricted cell or tissue tropism is not infecting and/or replicating in PBS-12 and/or HEK 293T cells.

Fragment

59. The avian coronavirus or IBV spike protein or fragment thereof of any one of clauses 1 to 58, wherein the fragment of the avian coronavirus or IBV spike protein has a length of at least 500, 750, 1000 or 1077 amino acids.
60. The avian coronavirus or IBV spike protein or fragment thereof of any one of clauses 1 to 59, wherein the fragment of the avian coronavirus or IBV spike protein has a length of at least 1000 amino acids.
61. The avian coronavirus or IBV spike protein of any one of clauses 1 to 60, wherein the Cysteine at amino acid position 267 or the mutation at amino acid position 267 to Cysteine is genetically stable.
62. A nucleotide sequence encoding the spike protein or fragment thereof of any one of clauses 1 to 61.
63. A plasmid comprising a nucleotide sequence of clause 62.
64. A cell comprising a plasmid of clause 63.
65. A viral particle comprising a spike protein or fragment thereof of any one of clauses 1 to 61.
66. An avian coronavirus comprising the spike protein or fragment thereof of any one of clauses 1 to 61.
67. An IBV (infectious bronchitis virus) comprising the spike protein of any one of clauses 3 to 61.
68. The avian coronavirus or IBV of clauses 66 or 67, wherein the avian coronavirus or IBV is attenuated.
69. The avian coronavirus or IBV of any one of clauses 66 to 68, wherein the avian coronavirus or IBV is genetically engineered.
70. The avian coronavirus or IBV of any one of clauses 66 to 69, wherein the avian coronavirus or IBV is recombinant.
71. The avian coronavirus or IBV of any one of clauses 66 to 70, wherein the avian coronavirus or IBV is chimeric.
72. The IBV of any one of clauses 67 to 71, wherein the IBV is from an IBV with a genotype selected from a list of strains consisting of: Arkansas (such as Arkansas 99), Brazil (such as BR-1, BR-2, 23/2013, IBV/Brasil/351/1984), California (such as California 1734/04, California 99), Connecticut, Delaware (such as Delaware 98), Dutch (such as D207, D212, D274, D3128, D3896, D8880, D1466), Florida, Georgia (such as Georgia GA-07, GA-08, GA-12, GA-13), Gray, Holte, Iowa (such as Iowa 97 and Iowa 69), Italy 02, JMK, LDT3, Maine (such as Maine 209), Massachusetts (M41, H52, H120, Beaudette), Pennsylvania (such as Pennsylvania 1220/98, Pennsylvania Wolg/98), PL84084, Qu (such as Qu-mv), QX (such as GB341/96), Q1, SE 17, Variant 2 (such as IS/1494/06, IBV/Ck/EG/CU/4/2014, gammaCoV/Ck/Poland/G052/2016) and 4/91 (793B, CR88).
73. The IBV of any one of clauses 67 to 72, wherein the IBV is selected from a list of genotypes or serotypes consisting of Massachusetts, 4/91, QX, Q1, Italy 02, Arkansas, Connecticut, Georgia, LDT3, PL84084, Variant 2 and Brazil.

74. The IBV of any one of clauses 67 to 73, wherein the IBV is selected from a list of genotypes or serotypes consisting of Massachusetts, 4/91, QX, Q1, Arkansas, Variant 2 and Brazil.

75. The IBV of clause 74, wherein the Massachusetts strain is selected from a list consisting of: H120, H52, Spain/98/308, IBMA5-1, SD/97/01, Beaudette, Spain/96/334 and M41-M21883.

76. The IBV of clause 74, wherein the 4/91 strain is selected from a list consisting of: Spain/98/328, Spain/92/35, IR-3654-VM, FR-CR88061-88, FR-85131-85, UK-1233-95, UK/3/91, Spain/00/336, UK/7/91, 4/91-pathogenic, 4/91attenuated and IB4-91.

77. The IBV of clause 74, wherein the QX strain is selected from a list consisting of: FR-L1450T-05, FR-L1450L-05, NL-L1449T-04, NL-L1449K-04, IBV/Ck/SP/170/09, IBV/Ck/SP/79/08, IBV/Ck/SP/248/09, HBN, IBVQX, LX4, BJQ, CK/CH/LGD/03 and GB341/96.

78. The IBV of clause 74, wherein the Q1 strain is selected from a list consisting of: CK/CH/LDL/98I, CK/CH/LSD/08-10, J2, Q1, AR08ER22, AR08BA21 and Chile-295-10.

79. The IBV of clause 74, wherein the Italy 02 strain is selected from a list consisting of: Spain/99/316, Italy-02, UK-L633-04, It-497-02, Spain/05/866, Spain/04/221, Spain/00/337, Spain/155/09 and Spain/03/08.

80. The IBV of clause 74, wherein the Arkansas strain is selected from a list consisting of: Ark99, ArkGA, ArkDPI, AL/5364/00, ARKDPI11, AL/0803/01, AL/7149/00, ArkDPI101, AL/1221/01, AL/1793/01 and AL/4614/98.

81. The IBV of clause 74, wherein the Variant 2 strain is selected from a list consisting of: IS/1494/06, IBV/Ck/EG/CU/4/2014, gammaCoV/Ck/Poland/G052/2016, Eg/CLEVB-2/IBV/012, D1344/2/4/10_EG, TR8 and IB VAR2-06.

82. The IBV of clause 74, wherein the Brazil strain is selected from a list consisting of: BR-1, BR-2, 23/2013 and IBV/Brasil/351/1984.

83. The IBV of any one of clauses 67 to 74, wherein the Spike protein or fragment thereof is from an IBV of Massachusetts or 4/91 genotype or serotype.

84. The IBV of any one of clauses 67 to 74, wherein the IBV strain is H120, H52 or CR88.

85. The IBV of any one of clauses 67 to 84, wherein the IBV has an IBV Spike Protein or fragment thereof consisting of or comprising an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

86. The IBV of any one of clauses 67 to 85, wherein the IBV has an extended cell or tissue tropism.

87. The IBV of any one of clauses 67 to 86, wherein the IBV is infecting and/or replicating in at least one cell line or cell of any one of clauses 9 to 11.

88. A cell comprising:
the viral particle of clause 65, or
the avian coronavirus or IBV of any one of clauses 66 to 87.

89. The cell of clause 88, wherein the cell is a cell line or cell selected from the list consisting of: primary chicken embryo cells, a chicken embryo fibroblast cell line, a duck embryonic stem cell line, a human embryonic kidney cell line, a baby hamster kidney cell line, an African green monkey kidney cell line, a rabbit kidney cell line, a canine kidney cell line, a chicken liver cell line, a bovine kidney cell line, a porcine kidney cell line and an insect cell line.

90. The cell of clauses 88 or 89, wherein the cell is a cell line selected from the list consisting of: DF-1 (Douglas Foster), EB66 (duck embryonic stem cell line), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+(*Spodoptera frugiperda*).

91. The cell of any one of clauses 88 to 89, wherein the cell is a cell line selected from the list consisting of: DF-1, EB66, PBS-12, PBS-12SF, BHK, HEK 293T, Vero, MA104 and RK13.

92. The cell of clause 89, wherein the primary chicken embryo cell is a fibroblast or a cell derived from liver or lung tissue.

93. An immunogenic composition comprising:
the spike protein of any one of clauses 1 to 61, or
the viral particle of clause 65, or
the avian coronavirus or IBV of any one of clauses 66 to 87.

94. A vaccine comprising:
the spike protein of any one of clauses 1 to 61, or
the viral particle of clause 65, or
the coronavirus or IBV of any one of clauses 66 to 87.

95. A modified live vaccine with an extended cell or tissue tropism comprising:
the spike protein of any one of clauses 1 to 61, or
the viral particle of clause 65, or
the coronavirus or IBV of any one of clauses 66 to 87.

96. The immunogenic composition or vaccine of any one of clauses 93 to 95, wherein the immunogenic composition or vaccine comprises a pharmaceutically acceptable carrier.

97. The immunogenic composition or vaccine of clause 96, wherein the pharmaceutically acceptable carrier is phosphate buffered saline.

98. The immunogenic composition or vaccine of any one of clauses 93 to 97, wherein the immunogenic composition or vaccine is effective in the treatment and/or prophylaxis of clinical signs caused by IBV in a subject of need.

99. The immunogenic composition or vaccine of any one of clauses 93 to 98, wherein the immunogenic composition or vaccine comprises 1 to 10 $\log_{10}$ $EID_{50}$ of the IBV.

100. The immunogenic composition or vaccine of any one of clauses 93 to 99, wherein the immunogenic composition or vaccine comprises 2 to 5 $\log_{10}$ $EID_{50}$ of the IBV.

101. The immunogenic composition or vaccine of any one of clauses 93 to 100, wherein the immunogenic composition or vaccine comprises 2 to 4 $\log_{10}$ $EID_{50}$ of the IBV.

102. A method for altering the cell or tissue tropism of an avian coronavirus comprising the use of the avian coronavirus spike protein or fragment thereof of any one of clauses 1 to 61.

103. A method for extending the cell or tissue tropism of an avian coronavirus comprising the use of the avian coronavirus spike protein or fragment thereof of any one of clauses 1 to 61.

104. A method for the production or manufacture of an avian coronavirus with an extended cell or tissue tropism comprising the use of the avian coronavirus spike protein or fragment thereof of any one of clauses 1 to 61.

105. A method for culturing an avian coronavirus in a cell or tissue culture comprising the use of the avian coronavirus spike protein or fragment thereof of any one of clauses 1 to 61.

106. A method for modifying an avian coronavirus comprising modifying the amino acid position 267 in the spike protein of said avian coronavirus.

107. A method for mutating the amino acid position 267 in an avian coronavirus spike protein comprising:
   a) providing an avian coronavirus spike nucleotide or protein sequence,
   b) identifying position 267 in the spike protein by alignment with a reference sequence,
   c) mutating the position 267 of the spike protein of step b) into a cysteine,
   d) obtaining the mutated spike protein of step c).

108. The method of any one of clauses 102 to 106, wherein the spike protein or fragment thereof has at amino acid position 267 a Cysteine.

109. The method of any one of clause 106 to 108, wherein the Cysteine at amino acid position 267 is introduced by a mutation.

110. The method of clause 109, wherein the mutation is an amino acid substitution, deletion or insertion.

111. The method of any one of clause 106 to 111, wherein a Phenylalanine or Leucine is modified or mutated into a Cysteine at amino acid at position 267.

112. The method of any one of clauses 102 to 111, wherein the avian coronavirus is an IBV of any one of clauses 67 to 87.

113. The method of any one of clauses 102 to 112, wherein the coronavirus spike protein is an IBV (infectious bronchitis virus) spike protein of any one of clauses 3 to 61.

114. The method of any one of clauses 102 to 113, wherein the Cysteine at amino acid position 267 or said mutation at amino acid position 267 to Cysteine leads to an extended cell or tissue tropism.

115. The method of any one of clauses 102 to 114, wherein the avian coronavirus or IBV is infecting and/or replicating in at least one cell line or cell of any one of clauses 9 to 11.

116. The method of to any one of clause 106 to 115, wherein the numbering of amino acid position 267 is done according to any one of clauses 12 to 18.

Kit Clauses

117. A kit comprising the viral particle, avian coronavirus, IBV, the immunogenic composition or vaccine of any one of clauses 65 to 88 and 93 to 101.

118. The kit of clause 117, wherein the kit further comprises an instruction letter for the treatment and/or prophylaxis of diseases of avians or an instruction letter for the treatment and/or prophylaxis of diseases of poultry or an instruction letter for the treatment and/or prophylaxis of IB.

119. The kit of clauses 117 or 118, wherein the kit further comprises a dispenser capable of administering a vaccine to said animal.

Method of Treatment Clauses

120. A method for immunizing a subject comprising administering to such subject an immunogenic composition or vaccine of any one of clauses 93 to 101.

121. A method of treating or preventing clinical signs caused by IBV in a subject of need, the method comprises administering to the subject a therapeutically effective amount of an immunogenic composition or vaccine of any one of clauses 93 to 101.

122. A method of reducing the ciliostasis in a subject of need, in comparison to a subject of a non-immunized control group of the same species, the method comprises administering to the subject a therapeutically effective amount of an immunogenic composition or vaccine of any one of clauses 93 to 101.

123. The immunogenic composition or vaccine of any one of clauses 93 to 101 for use in a method for immunizing a subject, the method comprises administering to the subject a therapeutically effective amount of said immunogenic composition or vaccine.

124. The immunogenic composition or vaccine of any one of clauses 93 to 101 for use in a method of treating or preventing clinical signs caused by IBV in a subject of need, the method comprises administering to the subject a therapeutically effective amount of said immunogenic composition or vaccine.

125. The immunogenic composition or vaccine of any one of clauses 93 to 101 for use in a method of reducing the ciliostasis in a subject of need, in comparison to a subject of a non-immunized control group of the same species, the method comprises administering to the subject a therapeutically effective amount of said immunogenic composition or vaccine.

126. The method or use of any one of clauses 120 to 125, wherein said subject is avian.

127. The method or use of any one of clauses 120 to 126, wherein said subject is poultry.

128. The method or use of any one of clauses 120 to 127, wherein said subject is selected from the list consisting of chicken, turkey, quail, or pheasant.

129. The method or use of any one of clauses 120 to 128, wherein said subject is chicken.

130. The method or use of any one of clauses 120 to 129, wherein the immunogenic composition or vaccine is administered once.

131. The method or use of any one of clauses 120 to 129, wherein the immunogenic composition or vaccine is administered at two or more doses.

132. The method or use of any one of clauses 120 to 131, wherein said immunogenic composition or vaccine is administered subcutaneously, intramuscularly, oral, in ovo, via spray, via drinking water or by eye drop.

133. The method or use of any one of clauses 120 to 132, wherein said immunogenic composition or vaccine is administered via eye drop.

134. The method or use of any one of clauses 120 to 133, wherein the immunogenic composition or vaccine comprises 1 to 10 $\log_{10}$ $EID_{50}$ per dose of the IBV.

135. The method or use of any one of clauses 120 to 134, wherein the immunogenic composition or vaccine comprises 2 to 5 $\log_{10}$ $EID_{50}$ per dose of the IBV.

136. The method or use of any one of clauses 120 to 135, wherein the immunogenic composition or vaccine comprises 2 to 4 $\log_{10}$ $EID_{50}$ per dose of the IBV.

137. The method or use of any one of clauses 120 to 136, wherein the immunogenic composition or vaccine is administered to subjects within the first week of age, within the first three days of age, within the first two days of age, or within the first day of age.

138. The method or use of any one of clauses 120 to 137, wherein the immunogenic composition or vaccine is administered to subjects within the first day of age.

139. The method or use of any one of clauses 120 to 138, wherein said method results in an improvement in an efficacy parameter selected from the group consisting of: prevention or reduction of ciliostasis, prevention or reduction of rales, prevention or reduction of egg drop, prevention or reduction of kidney lesions, prevention or reduction of watery diarrhea, prevention or reduction in weight loss, a lower virus load, a reduced viral shedding or combinations thereof, in comparison to a subject of a non-treated control group of the same species.

140. The method or use of any one of clauses 120 to 139, wherein the treatment or prevention results in a prevention or reduction of ciliostasis as compared to subjects of a non-treated control group of the same species.

141. The method or use of any one of clauses 120 to 140, wherein the treatment or prevention results in a prevention or reduction of kidney lesions as compared to subjects of a non-treated control group of the same species.

142. The method or use of any one of clauses 120 to 141, wherein the treatment or prevention results in a prevention or reduction of egg drop as compared to subjects of a non-treated control group of the same species.

143. The viral particle, avian coronavirus, IBV, immunogenic composition or vaccine of any one of clauses 65 to 87 and 93 to 101 for therapeutic use.

144. The viral particle, avian coronavirus, IBV, immunogenic composition or vaccine of any one of clauses 65 to 87 and 93 to 101 for use as an immunogen or vaccine.

145. The viral particle, avian coronavirus, IBV, immunogenic composition or vaccine of any one of clauses 65 to 87 and 93 to 101 for use as a medicament.

146. Use of the viral particle, avian coronavirus, IBV, immunogenic composition or vaccine of any one of clauses 65 to 87 and 93 to 101 for the manufacture of a medicament.

147. Use of the viral particle, avian coronavirus, IBV, immunogenic composition or vaccine of any one of clauses 65 to 87 and 93 to 101 for the treatment and/or prophylaxis of IBV infections in a subject.

BRIEF DESCRIPTION OF THE DRAWINGS

FIG. 1. In ovo kinetics for H52 rIBV S F267C in comparison to H52 rIBV wild type virus assessed by detection of viral load via RT-qPCR. Data point represent the mean of 5 samples per time point. Error bars indicate the standard deviation.

FIG. 2. Passaging of H52 rIBV S F267C in Eb66® cells. RT-qPCR CT values are determined at the time point of infection (t=0) and harvest (t=72) of each passage. P1 to P5 are generated by infection with a 1/10 dilution of the virus stock of the previous passage. P6 and P7 are generated by inoculation with a 1/1000 dilution of the previous passage. The experiment is repeated with an MOI of 0.001 for the first passage and similar results are obtained.

FIG. 5 Summary of ciliostasis scoring for protection by H52 rIBV S F267C against M41 challenge. The sum of the 10 individual scores for the 10 rings of one animal is calculated and is represented by one dot in the graph. Maximum ciliostasis corresponds to a score of 40, while no ciliostasis is represented by a score of 0. Mean and significance are calculated using GraphPad Prism and an ordinary one-way ANOVA test (p<0,0001).

FIG. 6. Summary of RT-qPCR results of kidneys tissues 7 days after challenge for the efficacy study of H52 rIBV S F267C. Each individual bird is indicated by one dot.

FIG. 7. Replication of H52 rIBV S F267C in PBS-12SF cells determined via immunofluorescence analysis. One of three independent experiments is shown.

FIG. 8: Relication of H52 rIBV S F267C in PBS-12SF cells determined via nucleic acid extraction from the supernatant and subsequent RT-qPCR analysis. One of two independent experiments is shown.

FIG. 9. Replication of H52 rIBV S F267C in HEK 293T cells determined via immunofluorescence analysis. One of three independent experiments is shown.

FIG. 10. In ovo kinetics for CR88 rIBV S L269C in comparison to CR88 rIBV wild type virus assessed by detection of viral load via RT-qPCR. Data point represent the mean of 5 samples per time point. Error bars indicate the standard deviation.

FIG. 11. Passaging of CR88 rIBV S L269C in Eb66® cells. RT-qPCR CT values are determined at the time point of infection (t=0) and harvest (t=72) of the respective passage. CR88 rIBV wild type is included as negative control. For CR88 rIBV S L269C data for P2, P5 and P8 are shown. The CR88 rIBV included in the same passaging experiment has one passage less in the initial passage (P1) and the last passage (P7). Each passage is generated by infection with a 1/100 dilution of the previous passage.

FIG. 16. In ovo kinetics for H52 rIBV QX S L270C and CR88 rIBV QX S L270C compared to IBV QX, H52 rIBV and CR88 rIBV, assessed by detection of viral load via RT-qPCR. Data point represent the mean of 5 samples per time point. Error bars indicate the standard deviation.

FIG. 17. Passaging of CR88 rIBV QX S L270C in Eb66® cells. RT-qPCR CT values are determined at the time point of infection (t=0) and harvest (t=72) of the respective passage.

FIG. 18. Passaging of H52 rIBV QX S L270C in Eb66® cells. RT-qPCR CT values are determined at the time point of infection (t=0) and harvest (t=72) of the respective passage.

FIG. 19. Replication kinetics of H52 rIBV QX S L270C and CR88 rIBV QX S L270C in EB66® cells. Cells are infected with rIBV at an MOI of 0.001 based on $TCID_{50}$ titers from the third EB66®-propagated passage of the viruses. Nucleic acids are isolated at 0, 8, 24 and 48 hpi and analyzed via IBV-specific RT-qPCR. Each data point represents the mean ct value of three independent experiments, each performed in triplicates. Error bars indicate the standard error of the mean (SEM).

SEQUENCES OVERVIEW

Figure 3:
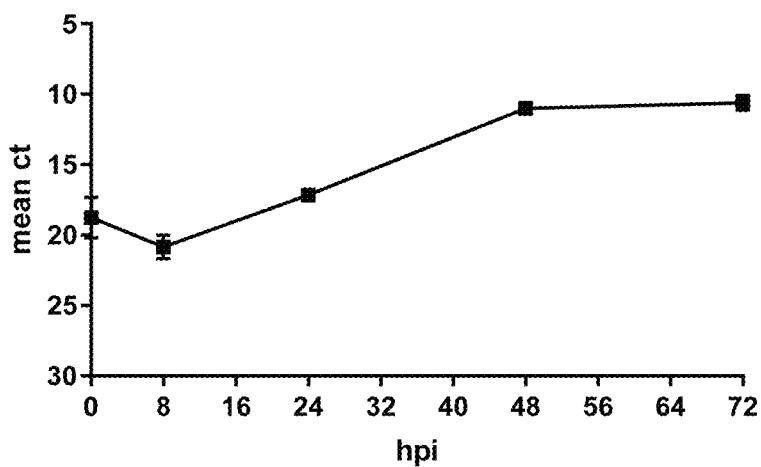
FIG. 3. Replication kinetics of H52 rIBV S F267C in EB66® cells. Cells are infected with rIBV at an MOI of 0.001 based on TCID50 titers from the third EB66®-propagated passage of the viruses. Nucleic acids are isolated at 0, 8, 24, 48 and 72 hpi and analyzed via IBV-specific RT-qPCR. Each data point represents the mean ct value of three independent experiments. Error bars indicate the standard error of the mean (SEM).

SEQ ID NO:1 IBV H52 spike protein
SEQ ID NO:2 IBV H52 spike protein with F267C mutation
SEQ ID NO:3 IBV CR88 spike with L269C mutation
SEQ ID NO:4 IBV QX spike protein with L270C mutation
SEQ ID NO:5 IBV Q1 spike protein with L271C mutation
SEQ ID NO:6 IBV Var 2 spike protein with L270C mutation
SEQ ID NO:7 IBV BR-I spike protein with L274C mutation
SEQ ID NO:8 IBV Ark spike protein with L274C mutation
SEQ ID NO:9 pUC57-s H52 rIBV donor plasmid
SEQ ID NO:10 pUC57-s H52 rIBV S F267C donor plasmid
SEQ ID NO:11 IBV CR88 spike sequence
SEQ ID NO:12 pUC57-s CR88 mIBV donor plasmid
SEQ ID NO:13 pGEM-T IBV CR88 spike plasmid
SEQ ID NO:14 pUC57-s CR88 rIBV S L269C donor plasmid
SEQ ID NO:15 pGEM-T IBV CR88 spike with L269C mutation
SEQ ID NO:16 to 64 primers
SEQ ID NO:65 IBV QX spike protein
SEQ ID NO:66 pGEM-T IBV QX S L270C plasmid
SEQ ID NO:67 pUC57-s CR88 rIBV donor plasmid
SEQ ID NO:68 pUC57-s CR88 rIBV QX S L270C donor plasmid
SEQ ID NO:69 pUC57-s H52 rIBV QX S L270C donor plasmid
SEQ ID NO:70 to 75 primers
SEQ ID NO:76 IBV ArkDPI spike protein
SEQ ID NO:77 IBV ArkDPI spike protein with L274C mutation
SEQ ID NO:78 pUC57-s IBV ArkDPI S L274C
SEQ ID NO:79 pUC57-s H52 rIBV ArkDPI S Ecto L274C donor plasmid
SEQ ID NO:80 to 84 primers

EXAMPLES

The following examples are set forth below to illustrate specific embodiments of the present invention. These examples are merely illustrative and are understood not to limit the scope or the underlying principles of the present invention.

Example 1

Generation of Recombinant IBV H52 in which the Amino Acid 267 of the Spike Protein is Mutated to a Cysteine For the generation of recombinant IBV the method of targeted RNA recombination as described by van Beurden et al. (Virol J. 2017; 14(1):109) is applied.

Donor Plasmid Construction

The pUC57-s IBV-5-1b-S-SIR-3T donor plasmid, hereafter referred to as pUC57-s H52 rIBV donor plasmid (SEQ ID NO:9), is used as template for the construction of the H52 rIBV donor plasmid with a H52 spike in which the amino acid 267 of the H52 spike (SEQ ID NO:1) 51 subunit is mutated from a phenylalanine to a cysteine (SEQ ID NO:2) which is called pUC57-s H52 rIBV S F267C (SEQ ID NO:10). Mutation of the wild type sequence is achieved by using the Q5® Site-Directed Mutagenesis Kit (NEB) with the primers PO1942 and PO1943 (table 1) and according to the kit protocol, with an annealing temperature of 58° C. and an elongation time of 5 minutes and 30 seconds. Positive clones are identified by EcoRV and XhoI restriction digest, flowed by Sanger sequencing with primers PO618 and PO633 (table 1). Afterwards, the integrity of the spike and donor region sequence is confirmed by sequencing with primers SEQ ID NO:19 to SEQ ID NO: 40 in table 1.

TABLE 1

Primers for SDM and sequencing

| SEQ ID NO: | Name | Sequence |
|---|---|---|
| 64 | M13-24F | ccagggttttcccagtcacg |
| 16 | M13-24R | cggataacaatttcacacagg |
| 17 | PO1942 | aacactattttcacgatagac |
| 18 | PO1943 | aatactacttgtacgttacacaatttc |
| 19 | PO618 | taaatggtgatcttgttt |
| 20 | PO632 | gcattcactgctgtacaa |
| 21 | PO633 | cgctcttagtaacataaac |
| 22 | PO636 | ctgaggtcaatgctttatc |
| 23 | PO706 | gacagagcacaagtttgatc |
| 24 | PO709 | acttcaagcatttgtacagg |
| 25 | PO710 | ggtcaacaatgtaattttgct |
| 26 | PO713 | gcagatgctaaaacagaaag |
| 27 | PO714 | tcacctgaacaatcttcagc |
| 28 | PO715 | ggtcaccagtatatttctgc |
| 29 | PO718 | aaagaagcaggatgatgaag |
| 30 | PO726 | aagagatgttggtaacacct |
| 31 | PO728 | ctaaaccggctggttttaat |
| 32 | PO729 | ccatagcttttgccactatt |
| 33 | PO731 | cgcttgtaaatagaaggtct |
| 34 | PO732 | acataccaaggccacttaat |
| 35 | PO733 | ggtcctgttccagtatagta |
| 36 | PO734 | cttgtcctgctttgttaaga |
| 37 | PO756 | gtggatcgtcttataactgg |
| 38 | PO759 | ctcgcattacaaaggctaag |
| 39 | PO766 | ccagttataggacacccatc |
| 40 | PO767 | gttggttcttctggaaatgt |

Targeted RNA Recombination and Rescue of Recombinant IBV

The H52 murinized (m)IBV helper virus and recombinant IBV are generated as described by van Beurden et al. (Virol J. 2017; 14(1):109). Briefly, for the generation of H52 rIBV S F267C, LR7 cells are infected with H52 mIBV and electroporated with in vitro transcript generated from the pUC57-s H52 SF267C donor plasmid (SEQ ID NO:10) and subsequently injected into 8 day old embryonated SPF chicken eggs (VALO BioMedia). After up to 8 days of incubation, the allantoic fluids of all eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers PO1323 and PO1324 (table 2) binding in H52 IBV lab and H52 IBV S spike are used to distinguish the recombinant IBV from mIBV. Positive samples are further analyzed to confirm the presence of the intended spike F267C mutation using the SuperScript™ III One-Step RT-PCR System with Platinum™ Taq DNA Polymerase with primers PO618 and PO633 (table 2) followed by QIAquick PCR purification and Sanger sequencing with the same primers. The positive allantoic fluid of the egg inoculated with the highest dilution of LR7 cells is used for an end-point dilution in 8-day old SPF eggs. Nucleic acids isolation and sample analysis is conducted as described above. The same procedure is applied for a second end-point dilution. Afterwards, one positive-tested allantoic fluid is used for propagation in 10-day old embryonated SPF chicken eggs. The allantoic fluid is diluted 1:1000 in 1×PBS and 100 µl are injected per egg, which are subsequently incubated at 37.5° C. and 60% humidity. Allantoic fluid is harvested 48 hours post inoculation, pooled, cleared from debris and stored at −80° C.

TABLE 2

PCR and sequencing primers used to identify rescued H52 rIBV and to confirm the targeted S F267C mutation.

| SEQ ID NO: | Name | Sequence |
|---|---|---|
| 41 | PO1323 | tcagcatggacgtgtggtta |
| 42 | PO1324 | ccccatgtaaatgccaacca |
| 19 | PO618 | taaatggtgatcttgttt |
| 21 | PO633 | cgctcttagtaacataaac |

In Vitro and in Ovo Characterization of Recombinant IBV
Determination of Embryo Infectious Dose 50% ($EID_{50}$)

An aliquot of the virus stock is thawed and 10-fold diluted in 1×PBS to determine the 50% embryo infectious dose ($EID_{50}$ by inoculation of 100 µl into the allantoic cavity of five 8-day old embryonated chicken eggs per dilution. Eggs are incubated at 36.5° C., 60% humidity until 7 days post inoculation. Eggs with dead embryos after 24 hours are excluded from the experiment. All other eggs with dead embryos at 7 days post inoculation are considered positive. All eggs with living embryos are canceled from the bottom at 7 days post inoculation to identify dwarfs, which are considered positive. The $EID_{50}$/ml is calculated with the formula of Reed and Muench (Am J Epidemiol, 1938; 27(3):493-497).

Tissue Culture Infectious Dose 50% ($TCID_{50}$)

Eb66® cell viability is analyzed with BioRad TC20 and trypan blue with the gate set to 6-13 µm. Per 96 well 2×10⁶ living Eb66® cells/ml in EX-CELL® EBx™ GRO-I Serum-Free Media+2.5 mM L-Glutamine are seeded 1 day prior to inoculation and incubated at 37° C. and 7.5% $CO_2$. A 10-fold serial dilution of the virus in Eb66® cell medium is performed and 100 µl per dilution (at least 4 replicates per dilution) are added to Eb66® cells after removing the culture medium. If allantoic fluid is used for infection it is passed though a 0.45 µm pore sized filter prior to dilution. Infected cells are incubated for 72 hours followed by immunofluorescence staining to identify positive wells. Medium is aspirated from all wells, which are subsequently washed with 1×PBS before the addition of 100 µl ethanol per well for cell fixation for 10 min at RT and subsequent air drying of the cells. The cells are incubated with 100 µl of primary chicken anti-IBV Mass serum (Boehringer Ingelheim), diluted 1:250 in 1×PBS, for 45 min at room temperature. After removal of the primary antibody each well is washed three times with 1×PBS. 100 µl of secondary Alexa Fluor 488 goat anti-chicken IgG antibody (ThermoFisher Scientific, 1:500 dilution in 1×PBS) are added and incubated for 45 min at room temperature in the dark. After removal of the secondary antibody, each well is washed three times with 1×PBS, leaving the final wash on the cells. Positive wells are identified by fluorescence microscopy and recorded to calculate the $TCID_{50}$/ml with the formula of Reed and Muench (Am J Epidemiol, 1938; 27(3):493-497).

In Ovo Replication Kinetics

Eight day-old embryonated chicken eggs are inoculated with $10^2$ $EID_{50}$ of rIBV and the respective controls. Eggs are canceled daily after 0, 8, 24, 34, 48 and 72 hours of incubation and embryo mortality is recorded. Five preselected eggs per sample and time point are removed and transferred to 4° C. for at least 2 hours. Subsequently, the allantoic fluid is harvested and stored at −80° C. For analysis, samples are thawed and diluted 1:10 in 1×PBS without Ca and Mg and nucleic acids are extracted with the QIAamp DNA Blood Mini kit (Qiagen) with addition of carrier RNA using the Hamilton Starlet pipet robot. Extracted nucleic acids are analyzed by RT-qPCR for the relative amount of IBV RNA with a protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the ABI™ 7900HT Fast Real-Time PCR System (Thermo Fisher Scientific). All nucleic acid samples are analyzed in triplicates using a 10-fold dilution series of IBV H52 as reference.

Figures 1, 2:
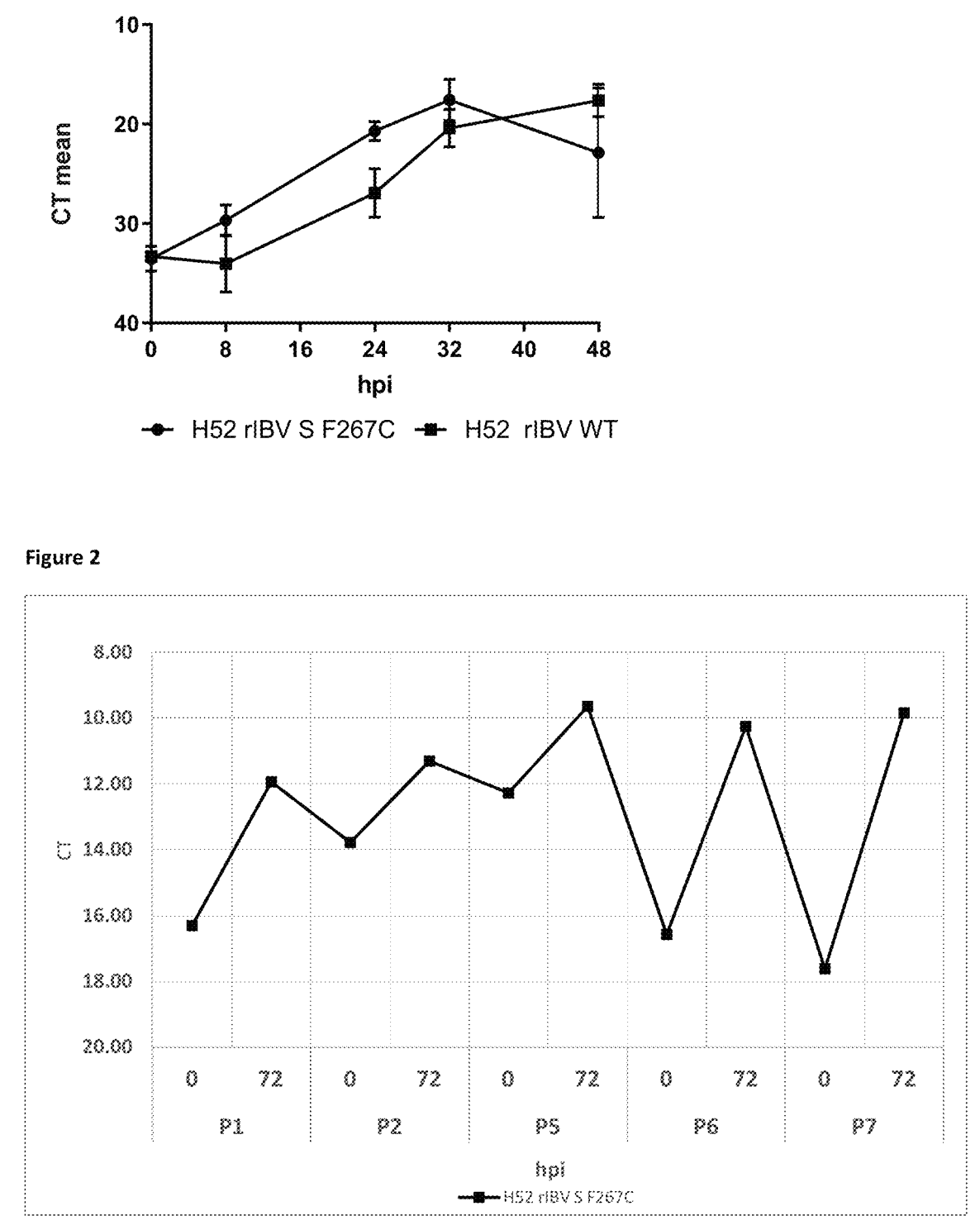

Similar in ovo replication kinetics are observed for H52 rIBV wild type and H52 rIBV S F267C (FIG. 1). This suggests no disadvantage by the mutation of Phenylalanine to Cysteine at the position 267 of the spike for in ovo replication efficiency of the mutated rIBV compared to the wild type rIBV.

Passaging of rIBV in Eb66® Cells

Eb66® cells are seeded at a density of 4×10⁵ cells/ml in EX-CELL® EBx™ GRO-I Serum-Free Media+2.5 mM L-Glutamine into T25 flasks with a total volume of 5 ml and are infected with rIBV and controls. The cultures are incubated for 72 hours at 37° C. and 7.5% $CO_2$ and shaking at 100 rpm. The culture is harvested and stored at −80° C. For passages 1, 2, 5, 6 and 7 virus replication is assessed via RT-qPCR. For this, 250 µl of the suspension are removed directly after inoculation (time point 0 h) and after harvest (time point 72 h) for nucleic acid isolation. Nucleic acids are isolated with the MagMAX™ Core Nucleic Acid Purification Kit (ThermoFisher) and the KingFisher™ Duo Prime Purification System (ThermoFisher). The RT-qPCR is performed as described above.

To analyze if H52 rIBV S F267C is able to replicate in cells, Eb66® cells were inoculated with a 1/10 dilution of the allantoic fluid stock. Propagation of the virus is detected by a decreased ct value after 72 hours in the first and following passages. Due to dilution of the virus for the next passage the ct value increases compared to the ct value measured at harvest of the inoculum before decreasing again during the 72 h culture due to virus replication. Replication becomes even more obvious in higher passages 6 and 7 for which the inoculation is conducted with a 1/1000 dilution of the previous passage (FIG. 2). The results clearly show replication of H52 rIBV F267C over 7 passages in Eb66® cells. Thus, it is apparent that the modification to a Cystein at Position 267 is genetically stable since the IBV still has the extended cell culture/tissue tropism after 7 passages.

In addition, the infectious titers for the allantoic fluid stock ($10^{6.33}$ $TCID_{50}$/ml, $10^{7.22}$ $EID_{50}$/ml) and Eb66® passages P1 ($10^{4.67}$ $TCID_{50}$/ml), P5 ($10^{5.33}$ $TCID_{50}$/ml) and P7 ($10^{6}$ $TCID_{50}$/ml, $10^{5.84}$ $EID_{50}$/ml) are determined. They confirm efficient replication of H52 rIBV S F267C during the Eb66® passaging process and sustained infectivity in SPF eggs. The F267C mutation therefore enables replication in cell lines without disturbing the ability to replicate in ovo.

Eb66® Cell Replication Kinetics

Figure 4:
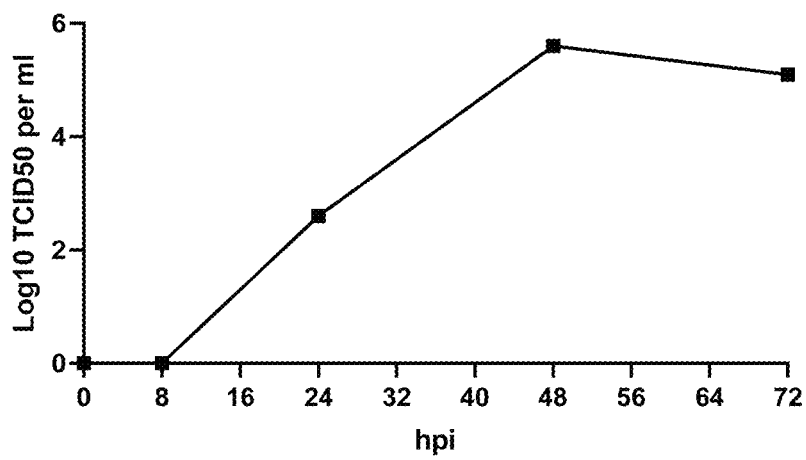
FIG. 4. Replication kinetics of H52 rIBV S F267C in EB66® cells. Samples of time points 0, 8, 24, 48 and 72 hpi are analyzed by TCID50 titration. Results of one experiment are shown.

Passage 3 harvested from Eb66® cells is used to perform replication kinetics in Eb66® cells. Eb66® cells are seeded and incubated as described for passaging and infected with an MOI of 0.001 based on the $TCID_{50}$ titer. Samples are taken directly after inoculation, as well as 8, 24, 48 and 72 hpi (hours post infection). Samples are analyzed for viral RNA content as described for the passaging experiment (FIG. 3). In addition, samples are analyzed for their infectivity via $TCID_{50}$ assay (FIG. 4). Efficient replication is detected with both methods and a plateau phase for replication is reached as early as 48 hours post infection. Conclusively, the replication cycle in Eb66® cells is equally efficient as in embryonated chicken eggs.

Determination of Vaccine Efficacy

Fertilized SPF eggs are incubated for 18 days in an egg setter at 99.7° F. and 50% humidity with 1 turn per hour. At day 18 of incubation the eggs are candled and fertile eggs are transferred to the hatcher and incubated at 99° F. and 70% humidity until hatch. Chicks without clinical signs or deformation are randomly distributed into respective treatment groups and transferred into separate isolators. Three chicks serve as strict negative control (SNC) group, five chicks are enrolled in the challenge control (CC) group and at least 10 in groups which are vaccinated with the Eb66®-adapted recombinant IBV and are subsequently challenged. Animals are kept under housing conditions in compliance to local and national requirements for animal welfare recommendations. The light regime is adjusted to 16 hours light per day. Feed and water are provided ad libitum. After transfer to the isolator, chicks are vaccinated (1-day old) with $10^3$ $EID_{50}$ per chicken via eye drop (total volume 50 µl, 25 µl per eye) while the SNC and CC groups remain untreated. At 21 days post vaccination chickens of the CC and vaccinated groups are challenged with $10^3$ to $10^4$ $EID_{50}$ per chicken of the homologous challenge strain via eye drop (total volume 50 µl, 25 µl per eye). At 7 days post challenge all chickens are euthanized, kidneys are removed and stored in RNAlater Stabilization Solution (ThermoFisher) at 4° C. for IBV-specific RT-qPCR analysis. In addition, tracheas are removed and transferred into 50 ml tubes with warm cell culture medium. Afterwards, tracheas are cleaned from connective tissues and flushed with cell culture medium. The tracheas are cut into tracheal rings using the McIlwain tissue chopper set to 0.6-0.8 mm slice thickness. Per trachea three rings of the upper part, four rings of the middle part and three rings of the lower part are analyzed for ciliar beating by light microscopy and scored for ciliostasis (see table 3). A ring is recorded as normal if more than 50% of the internal ring shows vigorous ciliar movement (Score 2 and lower). A ring is recorded as positive for ciliostasis if less than 50% of the cilia are beating (Score 3 and 4). An animal is considered protected if not fewer than 9 out of 10 rings show normal ciliar activity.

For IBV-specific RT-qPCR analysis kidney tissue pieces are warmed up to room temperature and transferred to separate 2 ml Precellys tubes, which are filled with medium and PBS, respectively. Kidneys are homogenized with the Precellys® tissue homogenizer (Bertin Instruments) for 1×20 sec at 6800 rpm. Choanal wabs are eluted in 2 ml 1×PBS. Nucleic acids are isolated from 200 µl eluate and tissue homogenate respectively using the MagMAX™ Core Nucleic Acid Purification Kit (ThermoFisher) and the KingFisher™ Duo Prime Purification System (ThermoFisher). RT-qPCR is performed as described for the in ovo kinetics above, except for using a StepOnePlus™ Real-Time PCR System (ThermoFisher).

TABLE 3

Scoring of ciliostasis in tracheal rings

| Ciliar activity [%] | Ciliostasis score |
| --- | --- |
| 100 | 0 |
| 75-99 | 1 |
| 50-74 | 2 |
| 25-49 | 3 |
| 0-25 | 4 |

Figures 5, 6:
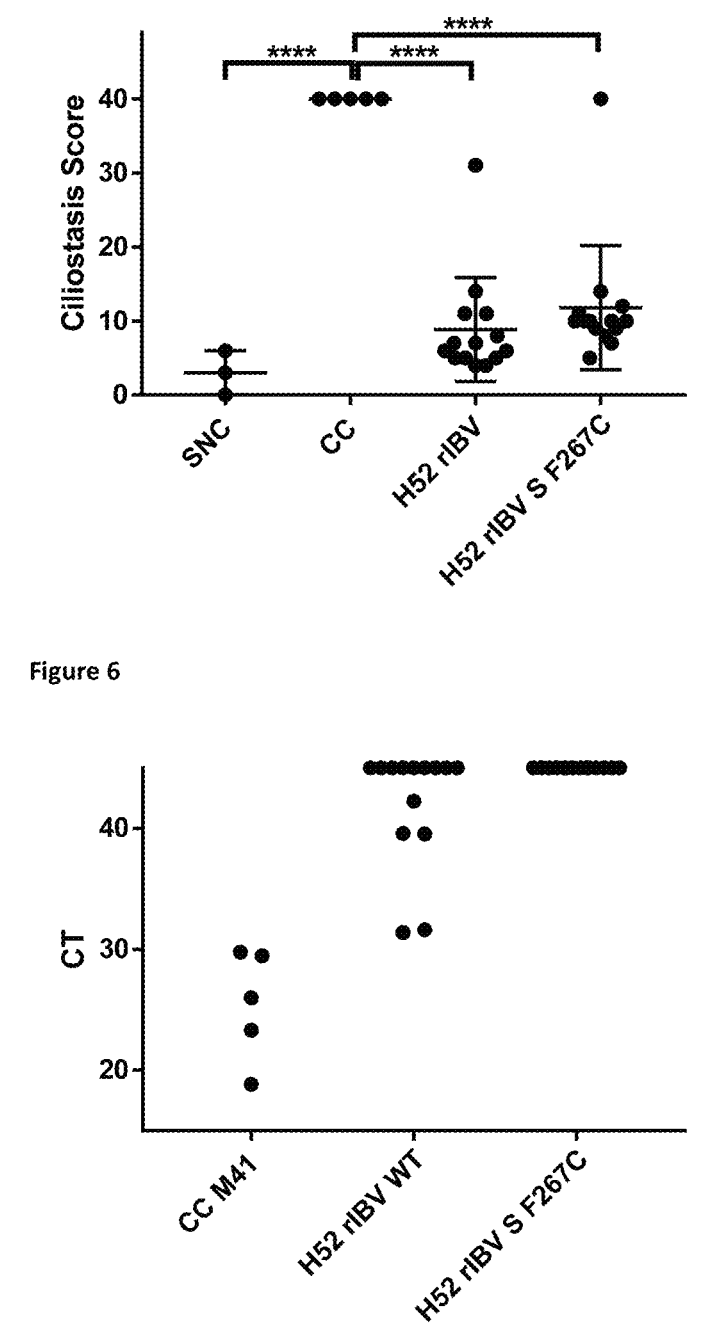

The objective of the study is to demonstrate that the cell culture adapted H52 rIBV S F267C passaged eight times in Eb66® cells is able to confer protection against challenge with virulent M41 strain. All chickens are observed daily for clinical signs and no clinical signs are recorded after vaccination or challenge. Back titrations for the vaccination with H52 rIBV and H52 rIBV S F267C at 1-day of age determine a titer of $10^{3.2}$ $EID_{50}$/animal and $10^{2.87}$ $EID_{50}$/animal (target $10^3$ $EID_{50}$/animal), respectively, and $10^3$ $EID_{50}$/animal (target $10^3$ $EID_{50}$/animal) for challenge with IBV M41 at 21 days post vaccination. Ciliostasis is scored as described in table 3 and results are depicted in FIG. 5.

The average ciliostasis value of the sum of the 10 individual scores for each animal and the protection rates are summarized in table 4. All animals of the strict negative control show normal ciliar movement (100% protection) while all animals of the challenge control group are positive for ciliostasis (0% protection). In contrast, 93% of the animals vaccinated with H52 rIBV are protected and equally well protected are the animals vaccinated with the Eb66®-passaged H52 rIBV S F267C.

TABLE 4

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0) For not affected animals, at least 9 of the 10 tracheal explants show normal ciliar activity.

| Vaccine | Challenge | #animals/ not affected | Mean Ciliostasis Score | Not affected [%] |
|---|---|---|---|---|
| — | — | 3/3 | 3 | 100 |
| — | M41 | 5/0 | 40 | 0 |
| H52 rIBV | M41 | 14/13 | 8.9 | 93 |
| H52 rIBV S F267C | M41 | 14/13 | 11.8 | 93 |

In addition, the viral load in the kidneys of animals vaccinated with H52 rIBV S F267C is as efficiently reduced as for H52 rIBV and compared to the M41 challenge control (FIG. 6). In summary, the H52 rIBV S F267C propagated in Eb66® cells protects as efficient against virulent M41 challenge as the H52 rIBV wild type. Further, the modification to a Cystein at Position 267 is genetically stable.

Infection of PBS-12SF Cells with rIBV

Figures 7, 8, 9:
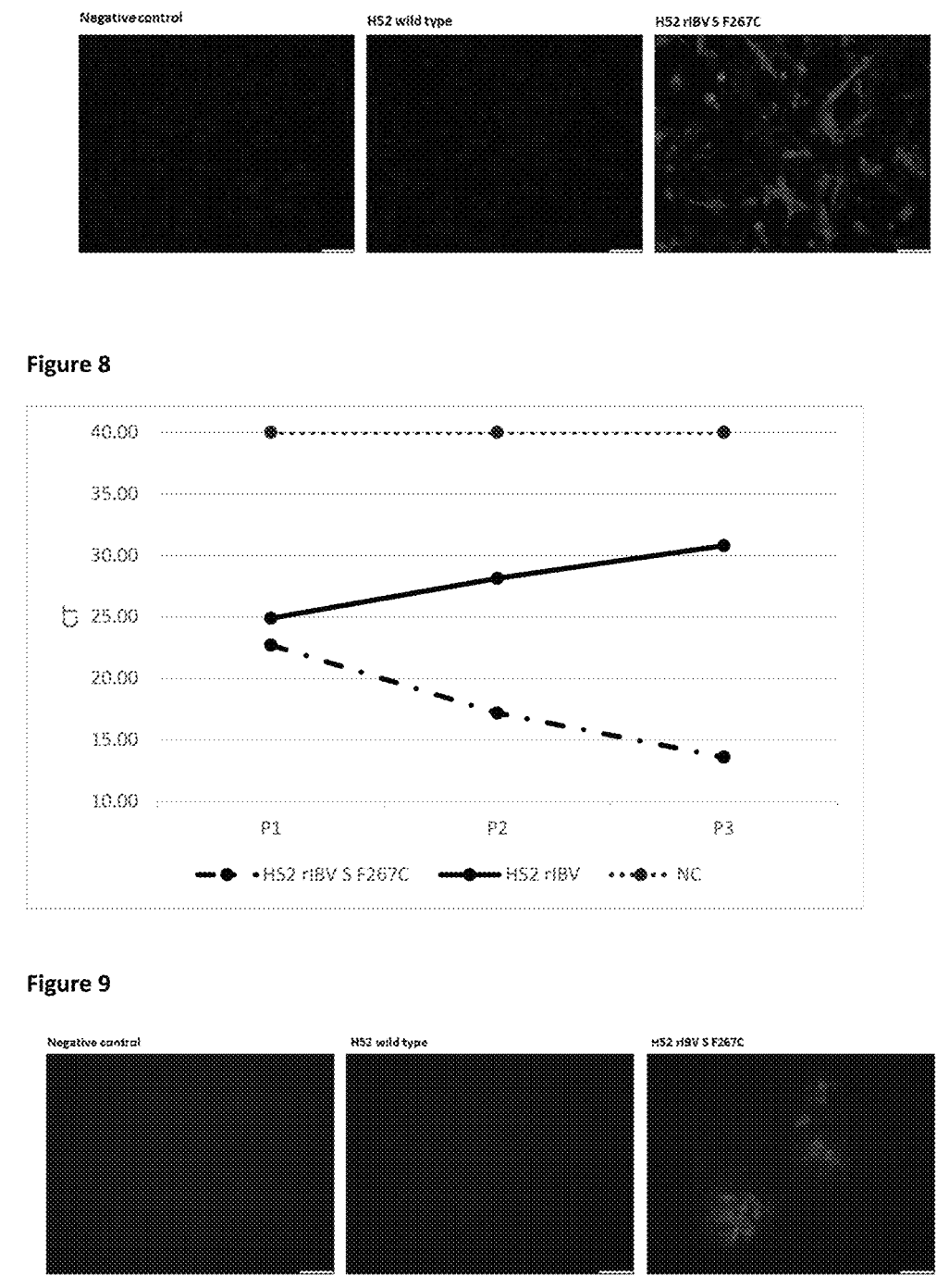

The ability to infect PBS-12SF cells is analyzed for the allantoic fluid stocks of H52 rIBV S F267C and H52 rIBV as negative control. PBS-12SF cells are seeded in OptiPRO SFM (ThermoFisher Scientific)+10% GlutaMAX (ThermoFisher Scientific) medium into 12-well plates to reach 80 to 90% confluence on the next day. The cells are incubated at 37° C. and 5% $CO_2$. Before infection the allantoic fluid virus stocks are passed through a 0.45 µm pore sized filter. PBS-12SF cells are infected with $10^{5.74}$ $EID_{50}$ of each virus per well for 4 hours at 37° C. and 5% $CO_2$ before the supernatant is taken off and fresh medium is added for further incubation. After 72 hours the supernatant is taken off and the cells are washed with 1×PBS and 50 µl TrypLE Select (ThermoFisher Scientific) are added to detach cells. Cells are resuspended in supernatant and transferred to a T25 flask with 80-90% confluent PBS-12SF cells (P2), which is incubated for 72 hours. Again, the supernatant and cells are collected and transferred to a T75 flask with 80-90% confluent PBS-12SF cells, which is incubated for 72 hours (P3). The supernatant is harvested. The cells are detached by trypsin treatment and seeded into 12 well plates at a ratio of 1 to 3 in fresh medium and incubated until the next day. Medium is aspirated, cells are washed with 1×PBS, fixed with ice-cold 100% ethanol and air dried. Subsequently cells are rehydrated with 1×PBS and afterwards the primary chicken anti-IBV Mass serum (Boehringer Ingelheim) is added at a dilution of 1 to 200 and incubated for 45 minutes at room temperature. After removal of the antibody, cells are washed and the secondary Alexa Fluor 488 goat anti-chicken IgG antibody (ThermoFisher Scientific, 1:500 dilution in 1×PBS) is added for 45 minutes at room temperature in the dark. Finally, the cells are washed three times with 1×PBS and analyzed by fluorescence microscopy (FIG. 7). Infected cells are detected for H52 rIBV S F267C, while cells infected with H52 rIBV wild type and the uninfected negative control remain negative as expected. Furthermore, 250 µl of supernatant were stored after each of the passages 1, 2 and 3 for nucleic acid extraction and RT-qPCR as described above. A continuous decrease in the ct value (corresponding to replication and propagation of the virus) can be observed for H52 rIBV S F267C over the passaging process while the ct value for H52 rIBV wild type increases as expected. (FIG. 8).

In summary, these data confirm that the single mutation of Phenylalanine to Cysteine at position 267 of the H52 spike renders the virus capable to replicate in PBS12-SF cells, while the H52 wild type virus lacks this ability.

Infection of HEK-293T Cells with rIBV

The ability to infect HEK 293T cells is analyzed for the allantoic fluid stocks of H52 rIBV S F267C and H52 rIBV as negative control. 293T cells are seeded in DMEM (Lonza)+10% FCS (SAFC)+L-Glutamine (Lonza)+1% P/S (Gibco) medium into 12-well plates to reach 80 to 90% confluence on the next day. The cells are incubated at 37° C. and 5% $CO_2$. Before infection the allantoic fluid virus stocks are passed through a 0.45 µm pore sized filter. HEK 293T cells are infected with roughly $10^6$ $EID_{50}$ of each virus per well. After 72 hours the supernatant is taken off and the cells are washed with 1×PBS and 50 µl TrypLE Select (ThermoFisher Scientific) are added to detach cells. Cells are resuspended in supernatant and transferred to a T25 flask with 80-90% confluent HEK 293T cells and 5 ml fresh medium (P2), which is incubated for 72 hours. Again, the supernatant and cells are collected and transferred to a T75 flask with 80-90% confluent HEK 293T cells and 10 ml fresh medium, which is incubated for 72 hours (P3). The supernatant is harvested. The cells are detached by trypsin treatment and seeded into 12 well plates at a ratio of 1 to 3 in fresh medium and incubated until the next day. Medium is aspirated, cells are washed with 1×PBS, fixed with ice-cold 100% ethanol and air dried. Subsequently cells are rehydrated with 1×PBS and afterwards the primary chicken anti-IBV Mass serum (Boehringer Ingelheim) is added at a dilution of 1 to 200 and incubated for 45 minutes at room temperature. After removal of the antibody, cells are washed and the secondary Alexa Fluor 488 goat anti-chicken IgG antibody (ThermoFisher Scientific, 1:500 dilution in 1×PBS) is added for 45 minutes at room temperature in the dark. Finally, the cells are washed three times with 1×PBS and analyzed by fluorescence microscopy (FIG. 9). Infected cells are detected for the positive control as well as H52 rIBV S F267C, while cells infected with H52 rIBV wild type and the uninfected negative control remain negative as expected.

In summary, these data confirm that the single mutation of Phenylalanine to Cysteine at position 267 of the H52 spike renders the virus capable to replicate in HEK 293T cells, while the H52 wild type virus lacks this ability.

Conclusion Example 1

The data show that the mutation to Cysteine at the position 267 of the spike sequence (reference sequence for the numbering is SEQ ID NO:1) in an IBV leads to an extended cell culture and tissue tropism. An H52 recombinant IBV having the F267C mutation in the spike protein can be efficiently cultured in different cell lines such as EB66, PBS-12SF and HEK 293T cells. It is assumed that said IBV can be cultured in other cell lines as well. Further, said mutation has no impact on in ovo replication of the virus and the replication kinetics in ovo and in vitro are similar. Finally, vaccine efficacy is sustained even after passaging in a cell line, laying the basis for successful IBV vaccine development without a need for in ovo culture but using cell lines instead.

Example 2

Generation of Recombinant IBV CR88 in which the Amino Acid 269 of the Spike Protein is Mutated to a Cysteine In order to determine if the change to a Cysteine at position 267 in the IBV spike can also be applied to other genotypes or serotypes, the spike amino acid sequence (SEQ ID NO:11) of the CR88 IBV strain was aligned to the H52 Spike amino acid sequence (SEQ ID NO:1) to determine the position equivalent to amino acid position 267 of H52 spike for IBV CR88 spike, which was determined as the Leucine at position 269 of the CR88 spike.

Construction of an IBV CR88 Murinized Donor Plasmid

To generate the CR88 murinized (m)IBV donor plasmid the donor sequence is synthesized by a commercial supplier: 497 bases of the 5' UTR of the CR88 genome are fused to the 3' part of the lab region (752 bases) and the first 72 bases coding for the CR88 IBV spike, followed by 3753 bases of the MHV spike ectodomain, continuing with the terminal 210 bases of the CR88 IBV spike and the following sequence until the 3' end of the genome. In addition, a SacI restriction site and the sequence of the T7 promoter is added to the 5' end of the donor region, as well as a 100x polyA sequence, followed by a Not I restriction site for linearization at the 3' end, respectively. A silent A to C mutation at position 5634 of the assembled sequence is introduced to generate an XhoI restriction site. The synthesized sequence is inserted into pUC57-simple to yield the pUC57-s CR88 mIBV donor plasmid (SEQ ID NO:12).

Rescue of CR88 mIBV

CR88 mIBV is rescued in analogy to H52 mIBV (van Beurden et al. Virol J. 2017; 14(1):109) with some alterations: The virus allantoic fluid stock is concentrated via ultracentrifugation before isolation of the viral RNA for electroporation. 18 ml of viral allantoic fluid are centrifuged at 50,000×g for 2 hours through a 2 ml 20% Sucrose cushion in TNE (Tris, NaCl, EDTA) buffer. The supernatant is discarded and the pellet resuspended in 150 µl TNE buffer followed by RNA isolation with QIAamp viral RNA mini kit (Qiagen). Further, chicken embryo fibroblasts (CEFs) instead of BHK cells are used for electroporation (2 pulses 250V/300 µF, 10 sec break) and 1.25% DMSO is added to the electroporation mixture.

Donor Plasmid Construction

The CR88 spike nucleic acid sequence with flanking sequences is synthesized by a commercial supplier and cloned into pGEM-T (SEQ ID NO:13). It is used as a template for site directed mutagenesis to change the leucine at amino acid position 269 of the IBV CR88 spike (SEQ ID NO:11) into a cysteine (SEQ ID NO:3). For this, the QuikChangeMulti Site-Directed Mutagenesis Kit (Agilent Technologies) according to the manufacturer's protocol and the primer PO1886 (table 5) designed by the corresponding online tool are used. Positive clones are identified by restriction digest and analyzed for the presence of the desired mutation by Sanger sequencing with primer PO618 and PO1410 (table 5). For the generation of the pUC57-s CR88 rIBV S L269C donor plasmid (SEQ ID NO:14), the pGEM-T CR88 S L269C plasmid containing the mutated CR88 spike sequence (SEQ ID NO:15) is digested with PacI, XhoI and PvuI. The band corresponding to the spike is cut from the gel and purified with the QIAquick gel extraction kit (Qiagen). Further, the CR88 mIBV donor plasmid (SEQ ID NO:12) is digested with PacI, XhoI and KpnI to obtain the donor plasmid backbone. The band with the highest molecular weight is cut from the gel and purified via QIAquick Gel Extraction Kit (Qiagen). The purified spike insert and CR88 donor plasmid backbone are ligated using T4 DNA ligase (ThermoFisher Scientific) at 16° C. over night. The ligation mixture is transformed into NEB 5-α competent E. coli (NEB) by heat shock. After GeneJET Plasmid Miniprep Kit (ThermoFisher Scientific), positive clones are identified by restriction digest and characterized for the targeted mutation by Sanger sequencing with primers PO618, PO1014 (table 5).

Targeted RNA Recombination and Rescue of Recombinant IBV

For rescue of CR88 rIBV S L269C, LR7 cells are infected with CR88 mIBV and electroporated with in vitro transcript generated from the NotI linearized pUC57-s CR88 S L269C donor plasmid, and subsequently injected into 8-day old embryonated SPF chicken eggs (VALO BioMedia). After up to 8 days of incubation, the allantoic fluids of all eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers PO1728 and PO1729 (Table 5) binding in CR88 IBV lab and CR88 IBV S spike are used to distinguish the recombinant IBV from mIBV. The positive allantoic fluid of the egg inoculated with the highest dilution of LR7 cells is used for an end-point dilution in 8-day old embryonated SPF eggs. Nucleic acid isolation is conducted as described above. Samples are analyzed via RT-qPCR conducted according to the protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the StepOnePlus or the ABI7900 HT Fast Real-Time PCR Systems (ThermoFisher Scientific). Afterwards, one positive-tested allantoic fluid of a high dilution is used for propagation in 8-day old embryonated SPF chicken eggs. The allantoic fluid is diluted 1:100 in 1×PBS and 100 µl is injected per egg which are subsequently incubated at 37.5° C. and 60% humidity. Allantoic fluid is harvested at 48 hours post inoculation, cleared from debris and stored at −80° C.

TABLE 5

SDM primer to obtain the CR88 S L269C mutation and sequencing primers for confirmation of the targeted mutation and confirmation of CR88 rIBV rescue.

| SEQ ID NO: | Name | Sequence |
|---|---|---|
| 43 | PO1886 | gtatatcgagaaagtagcac taacactacttgtaagttaa ctaatttcagttttactaatg |
| 19 | PO618 | taaatggtgatcttgttt |
| 44 | PO1410 | tttgtatacgagagccatca |
| 45 | PO1728 | tcagcgtggacatgtggtta |
| 46 | PO1729 | ccccatataggtgccaacct |

In Vitro and in Ovo Characterization of Recombinant IBV

The Embryo infectious dose 50% ($EID_{50}$) and the tissue culture infectious dose 50% ($TCID_{50}$) for CR88 rIBV S L269C are determined as described for H52 rIBV S F267C.

Further, the in ovo and in vitro replication kinetics and the passaging was conducted as described for H52 rIBV S F267C.

Figures 10, 11:
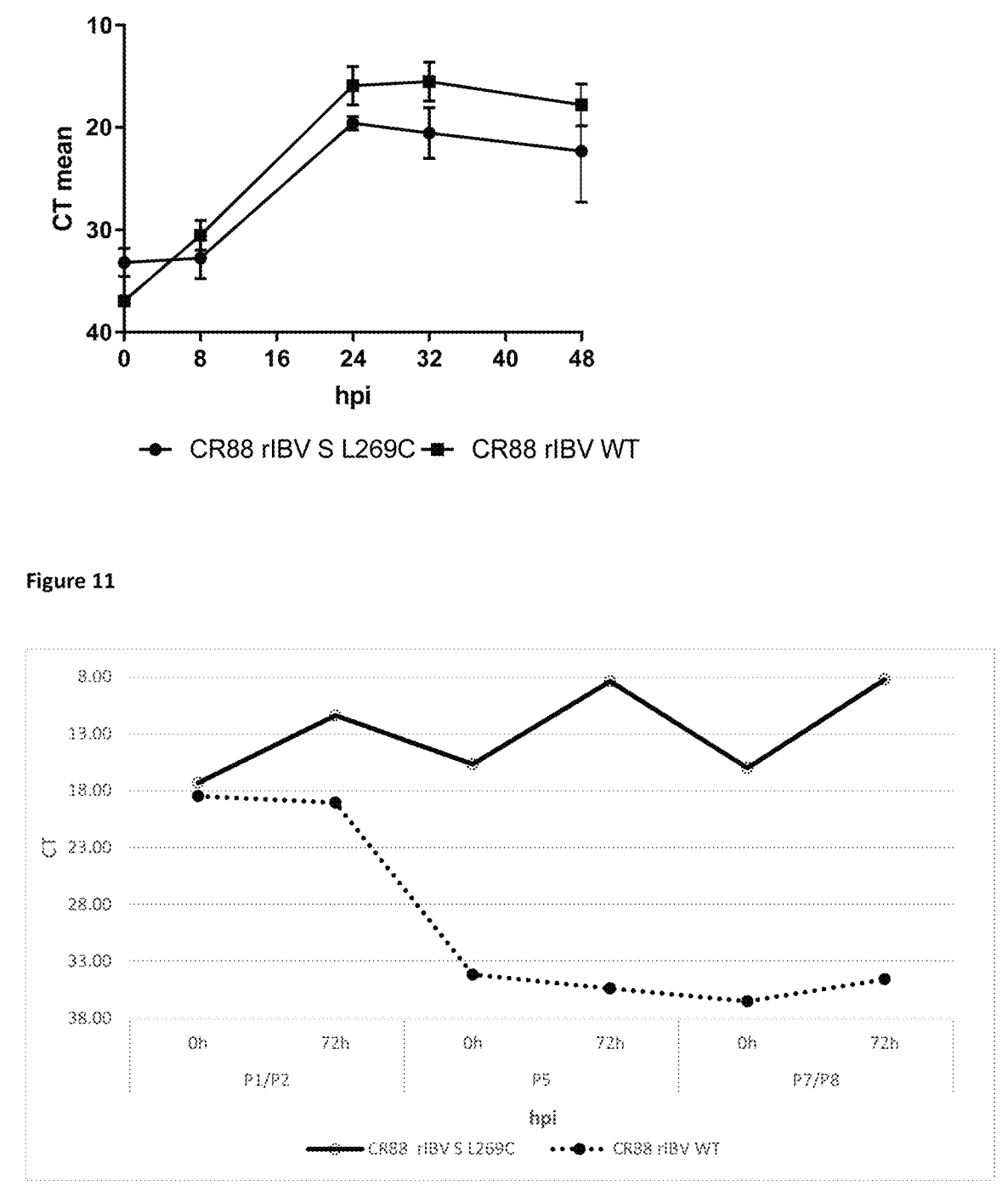

Similar in ovo replication kinetics are observed for CR88 rIBV wild type and CR88 rIBV S L269C (FIG. 10). This suggests no disadvantage of the Cysteine mutation in the spike of CR88 rIBV S L269C for the in ovo replication efficiency of the mutated rIBV compared to the wild type rIBV CR88 as it was shown for H52 rIBV S F267C and H52 rIBV wild type.

Figure 12:
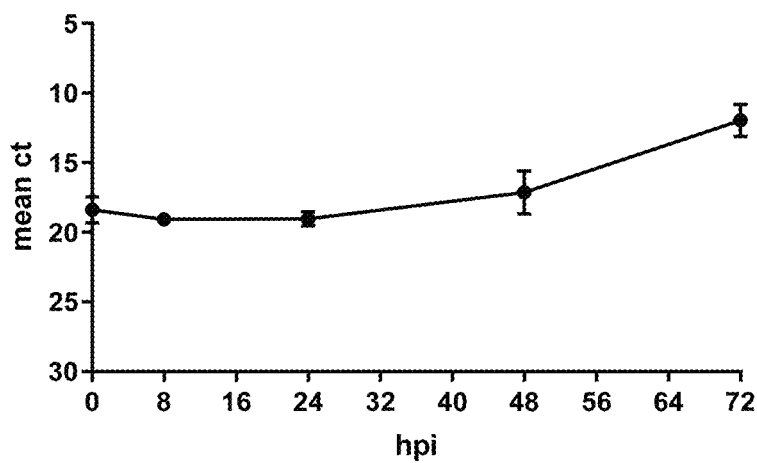
FIG. 12. Replication kinetics of CR88 rIBV S L269C in EB66® cells. Cells are infected with rIBV at an MOI of 0.001 based on $TCID_{50}$ titers from the third EB66®-propagated passage of the viruses. Nucleic acids are isolated at 0, 8, 24, 48 and 72 hpi and analyzed via IBV-specific RT-qPCR. Each data point represents the mean ct value of three independent experiments. Error bars indicate the standard error of the mean (SEM).
Figure 13:
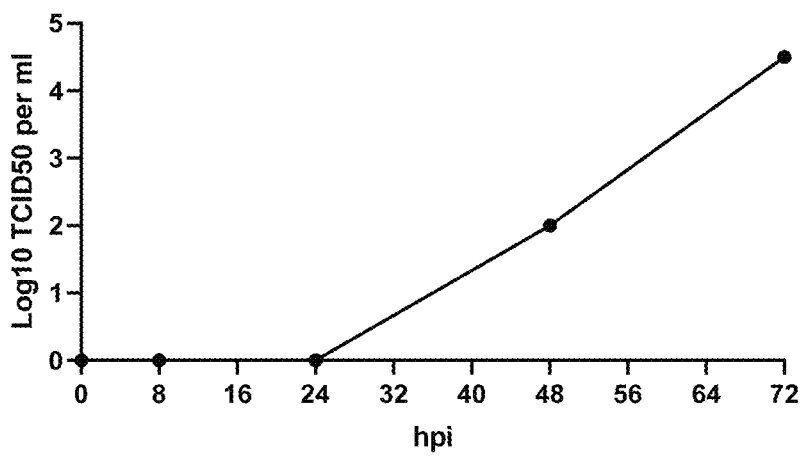
FIG. 13. Replication kinetics of CR88 rIBV S L269C in EB66® cells. Samples of time points 0, 8, 24, 48 and 72 hpi are analyzed by TCID50 titration. Results of one experiment are shown.

To analyze if CR88 rIBV S L269C is able to replicate in cells, Eb66® cells are inoculated with a 1/100 dilution of the allantoic fluid stock. Propagation of the virus is detected by a decreased ct value after 72 hours in the first and following passages. Due to dilution of the virus for the next passage the ct value increases compared to the ct value measured at harvest of the inoculum before decreasing again during the 72 h culture due to virus replication. Replication of CR88 rIBV S L269C is clearly visible over the passaging process by a decreasing ct value for the 72h time point compared to the 0 h time point directly after infection. In contrast, the ct values of the CR88 rIBV wild type negative control confirm no replication for this virus in any of the analyzed passages and dilution of the initial inoculum during the passaging process (FIG. 11). The results clearly show replication of CR88 rIBV L269C over 7 passages in Eb66® cells while wild type virus is not able to replicate, highlighting that the L269C mutation in the spike is crucial for the extended cell or tissue tropism. Efficient replication for CR88 rIBV S L269C is also detected via RT-qPCR (FIG. 12) and $TCID_{50}$ determination (FIG. 13) in a replication kinetic experiment in Eb66® cells.

In addition, the infectious titers for the allantoic fluid stock ($10^3$ $TCID_{50}$/ml, $10^8$ $EID_{50}$/ml) and Eb66® passages P1 ($10^{3.5}$ $TCID_{50}$/ml, $10^{5.84}$ $EID_{50}$/ml), P5 ($10^{5.3}$ $TCID_{50}$/ml) and P8 ($10^6$ $TCID_{50}$/ml, $10^6$ $EID_{50}$/ml) are determined. They confirm efficient replication of CR88 rIBV S L269C during the Eb66® passaging process and sustained infectivity in SPF eggs. The L269C mutation therefore enables replication in cell lines without disturbing the ability to replicate in ovo.

Determination of Vaccine Efficacy

Figure 14:
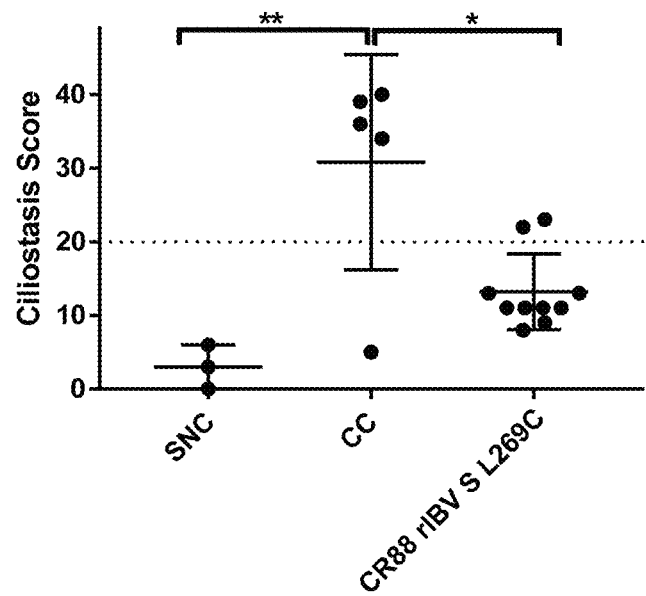
FIG. 14 Summary of ciliostasis scoring for protection by CR88 rIBV S L269C against 793B challenge. The sum of the 10 individual scores for the 10 rings of one animal is calculated and is represented by one dot in the graph. Maximum ciliostasis corresponds to a score of 40, while no ciliostasis is represented by a score of 0. Mean and significance are calculated using GraphPad Prism and an ordinary one-way ANOVA test (*p<0.02, **p<0.007).

Testing for the efficacy of CR88 rIBV S L269C against challenge with IBV 793B was conducted as described for H52 rIBV S F269C above. The objective of the study is to demonstrate that the cell culture adapted CR88 rIBV S L269C passaged one time in Eb66® cells is able to confer protection against a virulent 793B strain. All chickens are observed daily for clinical signs. No clinical signs are recorded after vaccination or challenge. Back titrations for the vaccination with CR88 rIBV S L269C at 1-day of age determine a titer of $10^{3.6}$ $EID_{50}$/animal (target $10^3$ $EID_{50}$/animal), respectively, and $10^{4.1}$ $EID_{50}$/animal (target $10^4$ $EID_{50}$/animal) for challenge with IBV 793B at 21 days post vaccination. Ciliostasis is scored as described in table 3 and results are depicted in FIG. 14 and summarized in table 6. All animals of the strict negative control show normal ciliar movement while 4 of the 5 animals of the challenge control group are positive for ciliostasis. In contrast, 80% of the animals vaccinated with CR88 rIBV S L269C are protected.

TABLE 6

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score 0). For not affected animals, at least 9 of the 10 tracheal explants show normal ciliar activity.

| Vaccine | Challenge | #animals/ not affected | Mean Ciliostasis Score | Not affected [%] |
|---|---|---|---|---|
| — | — | 3/3 | 3 | 100 |
| — | 793B | 5/1 | 30.8 | 20 |
| CR88 rIBV S L269C | 793B | 10/8 | 13.2 | 80 |

Figure 15:
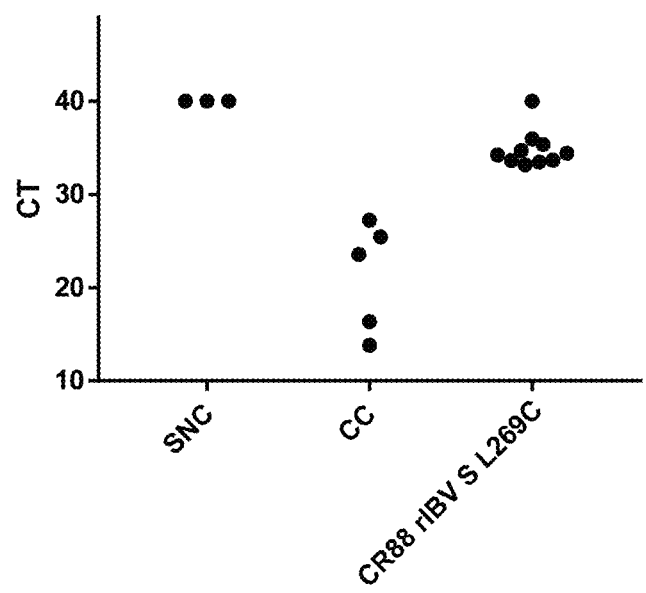
FIG. 15. Summary of RT-qPCR results of kidneys tissues 7 days after challenge for the efficacy study of CR88 rIBV S L269C. Each individual bird is indicated by one dot.

In addition, the viral RNA load is significantly reduced in kidneys of animals vaccinated with CR88 rIBV S L269C compared to the challenge control (FIG. 15). In summary, the CR88 rIBV S L269C propagated in Eb66® cells efficiently protects against virulent 793B challenge. The spike mutation L269C adapts the virus to propagation in cells while the in vivo efficacy is sustained.

Conclusion Example 2

The data show that the mutation to Cysteine at position 267 of the spike (reference sequence for the numbering is SEQ ID NO:1) corresponding to position 269 in CR88 spike leads to an extended cell or tissue tropism in a recombinant IBV CR88, too. Further, said mutation has no impact on in ovo replication of the virus. Finally, vaccine efficacy is sustained even after propagation in a cell line, laying the basis for successful IBV vaccine development without a need for in ovo culture but using cell lines instead.

Example 3

Generation of Chimeric Recombinant IBV CR88 or H52 in which the CR88 or H52 Spike Gene is Replaced by a QX Spike Gene in which the Amino Acid 270 of the Spike Protein is Mutated to a Cysteine In order to further elaborate if the change to a Cysteine at position 267 of the spike to achieve cell culture tropism can be transferred to additional IBV genotypes, the QX spike amino acid (SEQ ID NO:65) sequence was aligned to the H52 spike amino acid sequence (SEQ ID NO:1) to determine the position equivalent to amino acid position 267 of H52 spike for IBV QX spike, which was determined as the Leucine at position 270 of the QX spike.

In order to analyze the potential of a QX spike with a mutation at amino acid position 270 to Cysteine to infect cells, a recombinant IBV CR88 and a recombinant IBV H52 are generated in which the sequence encoding the CR88 spike or H52 spike respectively is replaced by the sequence encoding a QX spike with a Cysteine at position 270 of the spike protein (SEQ ID NO:4). For this the steps for the construction and rescue of an H52 mIBV and CR88 mIBV are conducted as described in example 1 and 2.

Cloning and Mutation of the QX Spike Gene

The QX spike sequence is amplified from IBV QX viral RNA via one step RT-PCR (SuperScript® III One-Step RT-PCR, Platinum® Taq) using the primers PO1367 and PO1347 (table 7) and cloned using the pGEM-T vector System (Promega). It serves as template for site directed mutagenesis using the primers PO2163 and PO2164 (table 7) designed with the NEBaseChanger to generate the a plasmid pGEM-T IBV QX S L270C (SEQ ID NO:66). To identify clones with plasmids carrying the desired mutation Sanger sequencing with the primers PO1398 and PO633 located in the region flanking the mutation is performed after a positive restriction digest (table 7).

TABLE 7

Primers for cloning and site-directed mutagenesis of the QX spike sequence

| SEQ ID NO | Name | Sequence |
| --- | --- | --- |
| 47 | PO1367 | cgcggatccgccaccatgtt ggtgaagtcactg |
| 48 | PO1347 | gcggcggccgcttaaacaga ctlittaggtctg |
| 49 | PO2163 | taatactacttgtgcgttaa ctaattttacttttagtaatg |
| 50 | PO2164 | acactactttcacgatag |
| 51 | PO1398 | aatttaaacagttagcgtatc |
| 21 | PO633 | cgctcttagtaacataaac |

Donor Plasmid Construction

The pUC57-s H52 rIBV QX S L270C donor plasmid (SEQ ID NO:69) is constructed using the NEBuilder® HiFi DNA Assembly Cloning Kit (NEB) and online tool for primer design. For this, the pUC57-s H52 rIBV donor plasmid (SEQ ID NO:9) is digested using the restriction sites EcoRV, PmlI and BlpI close to the H52 spike coding sequence to linearize the plasmid and remove the H52 spike and flanking sequences. The QIAquick gel extraction kit (Qiagen) is used to purify the band corresponding to the pUC57-s IBV H52 backbone without the H52 spike coding sequence. The QX S L270C nucleic acid coding sequence and the flanking 5' and 3' IBV H52 sequences are amplified in three separate PCR reactions with Q5® High-Fidelity DNA Polymerase (NEB; see table 8 for primers). The PCR products are purified by QIAquick gel extraction (Qiagen) and are used for Gibson assembly with the NEBuilder® HiFi DNA Assembly Cloning Kit (NEB) according to the kit protocol to generate the pUC57-s H52 rIBV QX S L270C (SEQ ID NO:69) donor plasmid.

The pUC57-s CR88 rIBV QX S L270C donor plasmid (SEQ ID NO:68) is constructed using the NEBuilder® HiFi DNA Assembly Cloning Kit (NEB) and online tool for primer design. Two PCR fragments are generated: One for the CR88 backbone using pUC57-s CR88 rIBV (SEQ ID NO:67) as template and one for the mutated QX spike L270C using pGEM-T IBV CR88 S L270C (SEQ ID NO:66) as template for Q5 PCR with the primers in table 8. The PCR products are gel purified with the QIAquick gel extraction kit (Qiagen) before they were used for Gibson assembly according to the kit protocol to generate the pUC57-s CR88 rIBV QX S L270C donor plasmid (SEQ ID NO:68).

TABLE 8

Primers designed with the NEBuilder online tool for Gibson assembly of pUC57-s CR88 rIBV QX L270C donor plasmid (PCR 1, 2) and the pUC57-s H52 rIBV QX L270C (PCR 3, 4, 5)

| PCR | SEQ ID NO | Primer name | product | Sequence |
| --- | --- | --- | --- | --- |
| 1 | 52 | PO2207 | QX spike | aagtgtggtaagttactggtaaga gatgttggtgaagtcactg |
|   | 53 | PO2208 |  | agaaaagatgtgggacttttaatc attaaacagacttttaggtctg |
| 2 | 54 | PO2209 | CR88 backbone | tgattaaaagtcccacatcttttc taatattattaattcttctttgg |
|   | 55 | PO2210 |  | ctcttaccagtaacttaccacact taattaaattaaagactaagtc |
| 3 | 70 | PO1783 | H52 5' flank | cagagcacaagtttgatcttgtga tATCTGATATGTATACAGACAATG ATTC |
|   | 71 | PO2062 |  | acttcaccaacatCTCTTACCAGT AACTTACC |
| 4 | 72 | PO2063 | QX S L270C | ttactggtaagagATGTTGGTGAA GTCACTG |
|   | 73 | PO2064 |  | ggactttggatcaTTAAACAGACT TTTTAGGTCTG |
| 5 | 74 | PO2065 | H52 3' flank | aaagtctgtttaaTGATCCAAAGT CCCACTAG |
|   | 75 | PO1788 |  | cttaactcctggaattactaacca cGTGTACCAAAATAAACAACAAGC |

Successful assembly of the pUC57-s CR88 rIBV QX S L270C and the pUC57-s H52 rIBV QX S L270C is identified by plasmid restriction digest with NheI and NotI or EcoRV, BlpI and PmlI respectively and characterized by sequencing with the primers in table 9.

TABLE 9 primers for sequencing of the pUC57-s CR88 rIBV QX S L270C and pUC57-s H52 rIBV QX S L270C donor plasmids.

| SEQ ID NO | Primer name | Sequence |
| --- | --- | --- |
| 56 | PO1565 | caggattgtgcatggtggac |
| 51 | PO1398 | aatttaacagttagcgtatc |
| 57 | PO2090 | gaagtgaayacaagatcaccattt |
| 58 | PO1420 | tgactgattctgctgctaaa |
| 44 | PO1410 | tttgtatacgagagccatca |
| 59 | PO1421 | tcttgaaaccccccaagtag |
| 60 | PO1425 | tatattcagcatcagttggc |
| 61 | PO1422 | ggattttgtggtagtggaag |
| 62 | PO1575 | ccactattgcagtaacattaaca |
| 63 | PO1567 | ctagactgtaagttactattg |

Targeted RNA Recombination and Rescue of Recombinant IBV

For rescue of CR88 rIBV QX S L270C and H52 rIBV QX S L270C, LR7 cells are infected with CR88 mIBV or H52 mIBV respectively and electroporated with in vitro transcript generated from the NotI or MssI linearized pUC57-s CR88 rIBV QX S L270C or pUC57-s H52 rIBV QX S L270C donor plasmid respectively, and subsequently injected into 8-day old embryonated SPF chicken eggs (VALO BioMedia). After up to 8 days of incubation, the allantoic fluids of some eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers PO1398 and PO633 (Table 7) binding in the QX spike sequence are used to identify the rescue of recombinant virus. The positive (defined by embryonic death or by a positive RT-PCR result) allantoic fluid of the egg inoculated with the highest dilution of LR7 cells is used for an end-point dilution in 8-day old embryonated SPF eggs. Nucleic acid isolation is conducted as described above. Samples are analyzed via RT-qPCR conducted according to the protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the StepOnePlus or the ABI7900 HT Fast Real-Time PCR Systems (ThermoFisher Scientific). Afterwards, one positive-tested allantoic fluid of a preferably high dilution is used for propagation in 8-day old embryonated SPF chicken eggs. The allantoic fluid is diluted 1:100 in 1×PBS and 100 µl is injected per egg, which are subsequently incubated at 37.5° C. and 60% humidity. Allantoic fluid is harvested at 48 hours post inoculation, cleared from debris and stored at −80° C.

In Vitro and in Ovo Characterization of Recombinant IBV

The Embryo infectious dose 50% (EID50) and the tissue culture infectious dose 50% (TCID50) for CR88 rIBV QX S L270C and H52 rIBV QX S L270C is determined as described for H52 rIBV S F267C. Further, the in ovo and in vitro replication kinetics and the passaging was conducted as described for H52 rIBV S F267C.

Figures 16, 17:
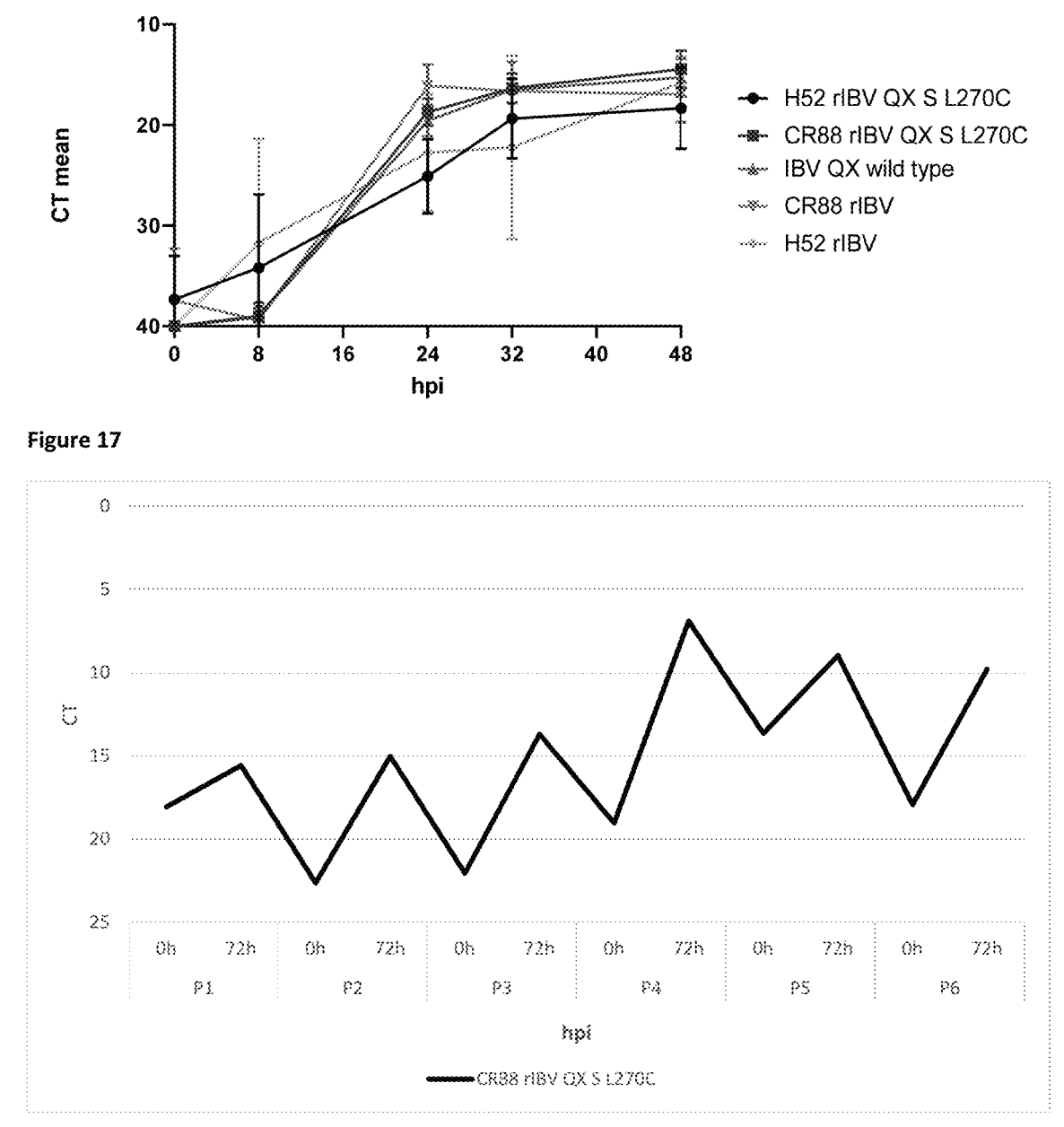

Similar peak ct values after 48 hours with slightly different in ovo replication kinetics are observed for CR88 rIBV QX S L270C and H52 rIBV QX S L270C (FIG. 16). While CR88 rIBV QC L270C replicates very similar to CR88 rIBV and IBV QX wild type, H52 rIBV QX s L270C replicates more similar to H52 rIBV. This suggests no disadvantage of the Cysteine mutation in the spike of CR88 rIBV QX S L270C and H52 rIBV QX S L270C for the in ovo replication efficiency of the mutated rIBV compared to other rIBV or wild type IBV.

Figures 18, 19:
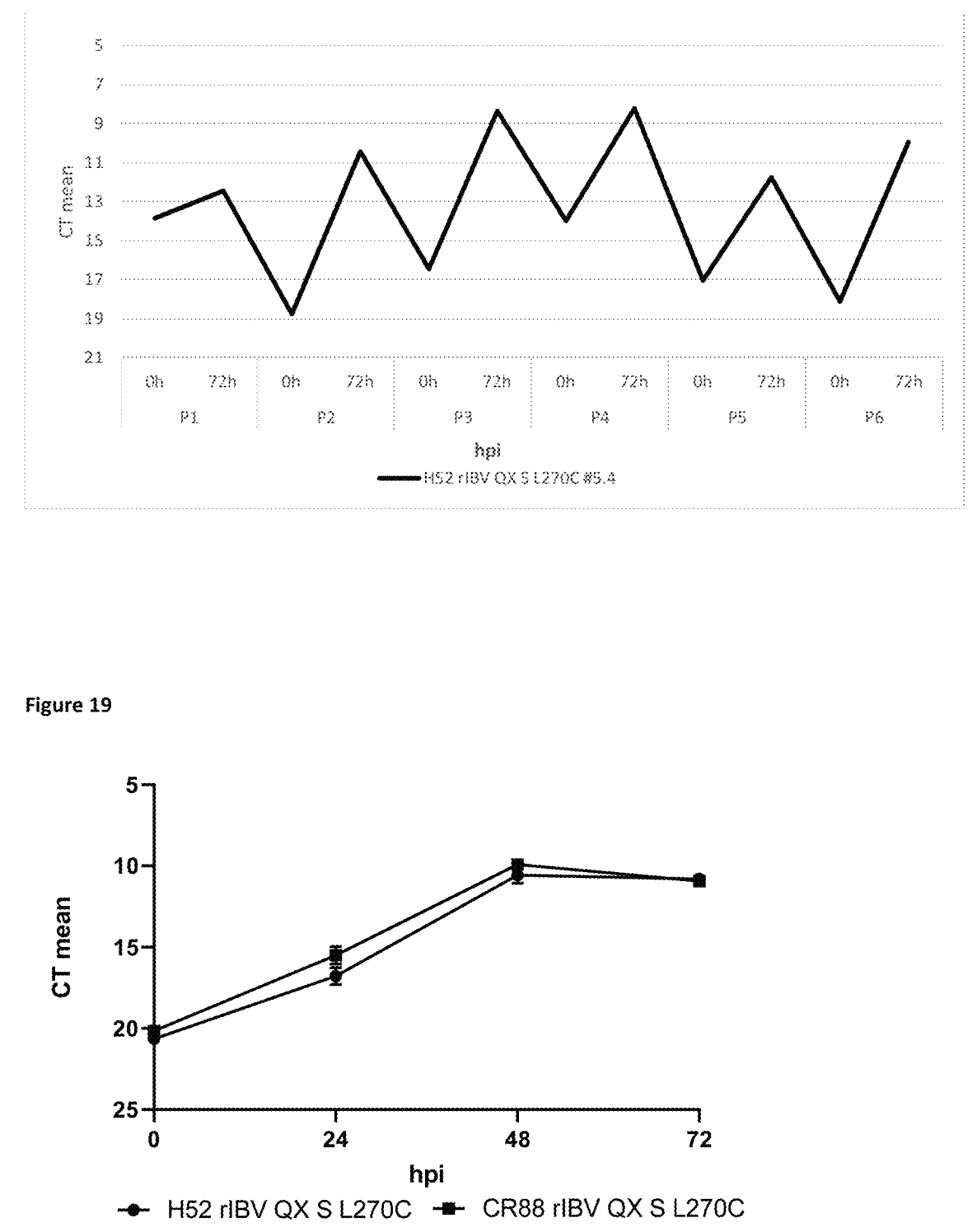

To analyze if CR88 rIBV QX S L270C and H52 rIBV QX S L270C are able to replicate in cells, EB66® cells are inoculated with a 1/100 dilution of the allantoic fluid stock. Propagation of the viruses is analyzed by isolation of viral RNA and subsequent RT-qPCR analysis. Replication of CR88 rIBV QX S L270C and H52 rIBV QX S L270C is clearly visible over the passaging process by a decreasing mean ct value for the 72h time point compared to the 0 h time point directly after infection (FIGS. 17 and 18). Due to dilution of the virus for the next passage the ct value increases compared to the ct value measured at harvest of the inoculum before decreasing again during the 72 h culture due to virus replication. Efficient replication for of CR88 rIBV QX S L270C and H52 rIBV QX S L270C is also detected via RT-qPCR (FIG. 19) in a replication kinetic experiment in Eb66® cells. Both viruses display similar replication patterns with peak CT values after 48 hours.

In addition, the infectious titers for the allantoic fluid stock of CR88 rIBV QX S L270C ($10^8$ $EID_{50}$/ml) and Eb66® passages P2 ($10^6$ $TCID_{50}$/ml, $10^{8.17}$ $EID_{50}$/ml), P6 ($10^6$ $TCID_{50}$/ml, $10^{7.83}$ $EID_{50}$/ml) and P9 ($10^6$ $TCID_{50}$/ml, $10^{8.5}$ $EID_{50}$/ml) are determined. Further, the infectious titers for the allantoic fluid stock of H52 rIBV QX S L270C ($10^8$ $EID_{50}$/ml) and Eb66® passages P3 ($10^{4.5}$ $TCID_{50}$/ml, $10^{8.13}$ $EID_{50}$/ml) and P6 ($10^{5.5}$ $TCID_{50}$/ml, $10^{8.13}$ $EID_{50}$/ml) are determined. They confirm efficient replication of CR88 rIBV QX S L270C during the Eb66® passaging process and sustained infectivity in SPF eggs. The L270C mutation therefore enables replication in cell lines without disturbing the ability to replicate in ovo.

Determination of Vaccine Efficacy

Figure 20:
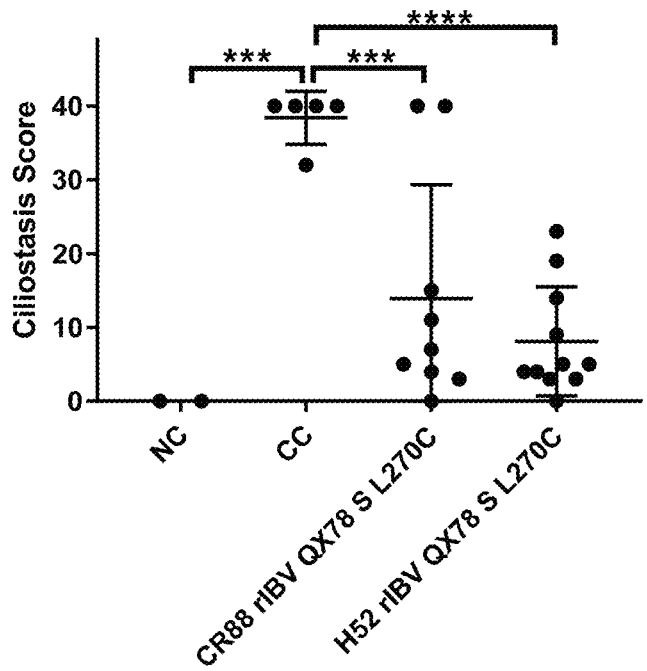
FIG. 20. Summary of ciliostasis scoring for protection by CR88 rIBV QX S L270C and H52 rIBV QX S L270C against D388 QX challenge. The sum of the 10 individual scores for the 10 rings of one animal is calculated and is represented by one dot in the graph. Maximum ciliostasis corresponds to a score of 40, while no ciliostasis is represented by a score of 0. Mean and significance are calculated using GraphPad Prism and an ordinary one-way ANOVA test (*p<0.001, **p<0.0001).

Testing for the efficacy of CR88 rIBV QX S L270C and H52 rIBV QX S L270C against challenge with IBV D388 QX was conducted as described for H52 rIBV S F269C above. The objective of the study is to demonstrate that the cell culture adapted CR88 rIBV QX S L270C and H52 rIBV QX S L270C passaged six times in EB66® cells is able to confer protection against a virulent D388 QX strain. All chickens are observed daily for clinical signs. No clinical signs are recorded after vaccination or challenge. Back titrations for the vaccination with CR88 rIBV QX S L270C and H52 rIBV QX S L270C at 1-day of age determine a titer of $10^{4.2}$ $EID_{50}$/animal and $10^{3.3}$ $EID_{50}$/animal (target $10^3$ $EID_{50}$/animal), respectively, and $10^{3.5}$ $EID_{50}$/animal (target $10^3$ $EID_{50}$/animal) for challenge with IBV D388 QX at 21 days post vaccination. Ciliostasis is scored as described in table 3 and results are depicted in FIG. 20 and summarized in table 10. All animals of the strict negative control show normal ciliar movement while all animals of the challenge control group are positive for ciliostasis. In contrast, 78% and 91% animals vaccinated with CR88 rIBV QX S L270C or H52 rIBV QX S L270C are protected.

TABLE 10

Summary of ciliostasis scoring for protection at 28 days post vaccination and 7 days post challenge. The mean ciliostasis score per group is calculated by adding up the sum score of the individual chickens per group and dividing the group sum by the number of animals (highest possible score 40, lowest possible score. 0). For not affected animals, at least 9 of the 10 tracheal explants show normal ciliar activity.

| Vaccine | Challenge | #animals/ not affected | Mean Ciliostasis Score | Not affected [%] |
|---|---|---|---|---|
| — | — | 3/2* | 0 | 100 |
| — | D388 QX | 5/0 | 38.4 | 0 |
| CR88 rIBV QXS L270C | D388 QX | 9/7 | 13.9 | 78 |
| H52 rIBV QXS L270C | D388 QX | 11/10 | 8.1 | 91 |

*one animal of the strict negative control died, death was not associated to IBV clinical signs or lesions.

Figure 21:
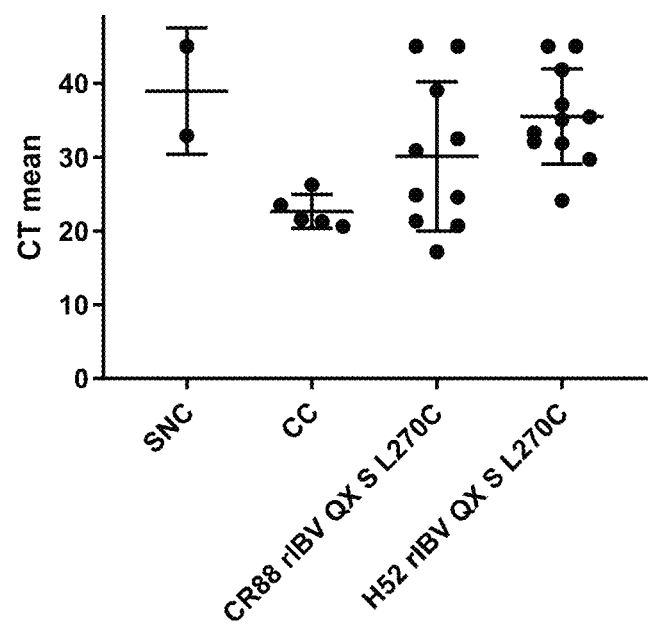
FIG. 21. Summary of RT-qPCR results of kidneys tissues 7 days after challenge for the efficacy study of CR88 rIBV QX S L270C and H52 rIBV QX S L270C. Each individual bird is indicated by one dot.

In addition, the viral RNA load is significantly reduced in kidneys of animals vaccinated with CR88 rIBV QX S L270C or H52 rIBV QX L270C compared to the challenge control animals (FIG. 21). In summary, CR88 rIBV QX S L270C and H52 rIBV QX S L270C propagated in EB66® cells efficiently protects against virulent D388 QX challenge. The spike mutation L270C adapts the virus to propagation in cells while the in vivo efficacy is sustained.

Conclusion Example 3

The data show that the mutation to Cysteine at position 267 of the spike (reference sequence for the numbering is SEQ ID NO:1) corresponding to position 270 in IBV QX spike leads to an extended cell or tissue tropism, too. In addition, the tissue culture tropism of a spike with the Cysteine mutation is not restricted to the homologous genetic background, as the QX L270C spike is inserted into the CR88 and H52 genetic backbone and the CR88 rIBV QX S L270C and H52 rIBV QX S L270C efficiently replicate in cells and efficiently protect against virulent IBV D388 QX challenge.

Example 4

Generation of Chimeric Recombinant IBV H52 in which the H52 Spike Ectodomain Coding Sequence is Replaced by an ARKDPI Spike Ectodomain Coding Sequence in which the Amino Acid 274 of the Spike Protein is Mutated to a Cysteine In order to further elaborate if the change to a Cysteine at position 267 of the spike to achieve cell culture tropism can be transferred to additional IBV genotypes, the ArkDPI spike amino acid (SEQ ID NO:76) sequence was aligned to the H52 spike amino acid sequence (SEQ ID NO:1) to determine the position equivalent to amino acid position 267 of H52 spike for IBV ArkDPI spike, which was determined as the Leucine at position 274 of the ArkDPI spike.

In order to analyze the potential of a ArkDPI spike with a mutation at amino acid position 274 to Cysteine to infect cells, a recombinant IBV H52 is generated in which the sequence encoding the H52 spike is replaced by the sequence encoding an ArkDPI spike with a Cysteine at position 274 of the ArkDPI spike protein (SEQ ID NO:77). For this the steps for the construction and rescue of an H52 mIBV are conducted as described in example 1.

Donor Plasmid Construction

The pUC57-s ArkDPI spike L274C plasmid (SEQ ID NO:78) is synthesized by a commercial supplier. The pUC57-s H52 rIBV ArkDPI S Ecto L274C donor plasmid (SEQ ID NO:79) is constructed using the NEBuilder® HiFi DNA Assembly Cloning Kit (NEB) and online tool for primer design. For this, the pUC57-s H52 rIBV donor plasmid (SEQ ID NO:9) is digested using the restriction sites EcoRV, PmlI and BlpI close to the H52 spike coding sequence to linearize the plasmid and remove the H52 spike and flanking sequences. The QIAquick gel extraction kit (Qiagen) is used to purify the band corresponding to the pUC57-s IBV H52 backbone without the H52 spike coding sequence. The ArkDPI S Ecto L274C nucleic acid coding sequence and the flanking 5' and 3' IBV H52 sequences are amplified in three separate PCR reactions with Q5® High-Fidelity DNA Polymerase (NEB; see table 11 for primers). The PCR products are purified by QIAquick gel extraction (Qiagen) and are used for Gibson assembly with the NEBuilder® HiFi DNA Assembly Cloning Kit (NEB) according to the kit protocol to generate the pUC57-s H52 rIBV ArkDPI S Ecto L274C (SEQ ID NO:79) donor plasmid.

TABLE 11

Primers designed with the NEBuilder online tool for Gibson assembly of the pUC57-s H52 rIBV ArkDPI S Ecto L274C.

| PCR | SEQ ID NO | Primer name | product | Sequence |
|---|---|---|---|---|
| 1 | 70 | PO1783 | H52 5' flank | cagagcacaagtttgatcttgtg atatctgatatgtatacagacaa tgattc |

TABLE 11-continued

Primers designed with the NEBuilder online tool for Gibson assembly of the pUC57-s H52 rIBV ArkDPI S Ecto L274C.

| PCR | SEQ ID NO | Primer name | product | Sequence |
|---|---|---|---|---|
|  | 80 | PO2424 |  | catataaattagcactacatagt gcacac |
| 2 | 81 | PO2425 | ArkDPI S Ecto | atgtagtgctaatttatatgaca acgaatcttttg |
|  | 82 | PO2426 |  | acacataccaaggccacttaata taagttttg |
| 3 | 83 | PO2427 | H52 3' flank | taagtggccttggtatgtgtggc |
|  | 75 | PO1788 |  | tagcccttaactcctggaattac taaccacgtgtaccaaaataaac aacaagc |

Successful assembly of the pUC57-s H52 rIBV ArkDPI S Ecto L274C is identified by plasmid restriction digest with BlpI and XhoI.

Targeted RNA Recombination and Rescue of Recombinant IBV

For rescue of H52 rIBV ArkDPI S Ecto L274C, LR7 cells are infected with H52 mIBV respectively and electroporated with in vitro transcript generated from the MssI linearized pUC57-s H52 rIBV ArkDPI S Ecto L274C donor plasmid, and subsequently injected into 8-day old embryonated SPF chicken eggs (VALO BioMedia). After up to 8 days of incubation, the allantoic fluids of some eggs are analyzed separately for the rescue of recombinant IBV after RNA isolation with the MagMAX™ Core Nucleic Acid Purification Kit (ThermoFisher) and the KingFisher™ Duo Prime Purification System (ThermoFisher) and by using SuperScript™ III One-Step RT-PCR System with Platinum™ Taq DNA Polymerase (ThermoFisher). Primers PO1317 and PO633 (Table 12) binding in the ArkDPI spike sequence are used to identify the rescue of recombinant virus. The positive (defined by embryonic death or by a positive RT-PCR result) allantoic fluid of the egg inoculated with the highest dilution of LR7 cells is used for an end-point dilution in 8-day old embryonated SPF eggs. Nucleic acid isolation is conducted as described above. Samples are analyzed via RT-qPCR conducted according to the protocol adapted from Callison et al. (J Virol Methods. 2006; 138(1-2):60-5). Briefly, the same primers and probe are used and the thermoprofile is adapted for the use of TaqMan® Fast Virus 1-Step Master Mix (ThermoFisher) and the StepOnePlus or the ABI7900 HT Fast Real-Time PCR Systems (ThermoFisher Scientific). Afterwards, one positive-tested allantoic fluid preferably of a high dilution is used for propagation in 8-day old embryonated SPF chicken eggs. The allantoic fluid is diluted 1:100 in 1×PBS and 100 µl is injected per egg, which are subsequently incubated at 37.5° C. and 60% humidity. Allantoic fluid is harvested at 48 hours post inoculation, cleared from debris and stored at −80° C.

TABLE 12

Primers for detection of H52 rIBV ArkDPI S Ecto L274C.

| SEQ ID NO | Primer name | Sequence |
|---|---|---|
| 84 | PO1317 | taatactggyaatttttcaga |
| 21 | PO633 | cgctcttagtaacataaac |

In Vitro Characterization of Recombinant IBV

The Embryo infectious dose 50% (EID50) and the tissue culture infectious dose 50% (TCID50) for H52 rIBV ArkDPI S Ecto L274C is determined as described for H52 rIBV S F267C. Further, the in vitro replication kinetics and the passaging was conducted as described for H52 rIBV S F267C.

To analyze if H52 rIBV ArkDPI S Ecto L274C is able to replicate in cells, EB66® cells are inoculated with a 1/10 dilution of the allantoic fluid stock for the first passage and with a 1/10 or 1/100 dilution for the subsequent passages. Propagation of the viruses is analyzed by isolation of viral RNA and subsequent RT-qPCR analysis. Replication of H52 rIBV ArkDPI S Ecto L274C is clearly visible after three passages by a decreasing mean ct value for the 72h time point (11.59) compared to the 0 h time point (21.09) directly after infection.

Conclusion Example 4

The data show that the mutation to Cysteine at position 267 of the spike (reference sequence for the numbering is SEQ ID NO:1) corresponding to position 274 in IBV ArkDPI spike leads to an extended cell or tissue tropism, too. In addition, the tissue culture tropism of a spike with the Cysteine mutation is not restricted to the homologous genetic background, as the ArkDPI L274C spike ectodomain is inserted into the H52 genetic backbone and the H52 rIBV ArkDPI S Ecto L274C efficiently replicates in cells.

The invention claimed is:

1. An avian coronavirus spike protein or fragment thereof, wherein at least a part of the S1 subunit is from an avian coronavirus with a restricted cell or tissue tropism, and wherein at amino acid position 267 is a Cysteine, wherein the amino acid sequence of SEQ ID NO:1 is used for determining the position numbering in the spike protein and the Cysteine at amino acid position 267 leads to an extended cell or tissue tropism of the avian coronavirus.

2. A recombinant avian coronavirus spike protein or fragment thereof comprising a mutation at amino acid position 267 to Cysteine, wherein the amino acid sequence of SEQ ID NO:1 is used for determining the position numbering in the spike protein and the mutation at amino acid position 267 to Cysteine leads to an extended cell or tissue tropism of the avian coronavirus.

3. The avian coronavirus spike protein or fragment thereof of claim 1, wherein the avian coronavirus is IBV (infectious bronchitis virus).

4. The avian coronavirus spike protein or fragment thereof of claim 1, wherein the Cysteine at amino acid position 267 is introduced by a mutation.

5. The avian coronavirus spike protein or fragment thereof of any one of claims 1, wherein the avian coronavirus is infecting and/or replicating in at least one cell line selected from the list consisting of: DF-1 (Douglas Foster), PBS-12, PBS-12SF (PBS-12 serum free), BHK21 (baby hamster kidney), HEK 293T (human embryonic kidney), Vero (Verda Reno), MA104, RK13 (rabbit kidney), LMH (leghorn male hepatoma), MDCK (Madin-Darby canine kidney), MDBK (Madin-Darby bovine kidney), PK15 (porcine kidney), PK2A (porcine kidney), SF9, SF21 and SF+ (*Spodoptera frugiperda*).

6. The avian coronavirus spike protein or fragment thereof of any one of claim 1, wherein the amino acid position 267 is within the S1 subunit of the spike protein.

7. The avian coronavirus spike protein or fragment thereof of any one of claim 1, wherein the spike protein is not from an IBV Beaudette strain.

8. The IBV spike protein or fragment thereof of any one of claim 3, wherein the spike protein is from an IBV with a genotype or serotype or a strain selected from a list consisting of: Arkansas, Brazil, California, Connecticut, Delaware, Dutch, Florida, Georgia, Gray, Holte, Iowa, Italy-02, JMK, LDT3, Maine, H52, H120, M41, Pennsylvania, PL84084, Qu, QX, Q1, SE 17, Variant 2 and 4/91.

9. The IBV spike protein or fragment thereof of any one of claim 3, wherein the IBV spike protein or fragment thereof is selected from a list of genotypes consisting of: GI-2 to 27, GII-1, GIII-1, GIV-1, GV-1, GVI-1.

10. The IBV spike protein or fragment thereof of any one of claim 3, wherein the IBV spike protein or fragment thereof consists of or comprises an amino acid sequence as shown in SEQ ID NO: 2, 3, 4, 5, 6, 7, 8, 77 or a sequence having at least 80%, 85%, 90%, 93%, 95%, 96%, 97%, 98%, 99%, 99.5%, 99.6%, 99.7%, 99.8%, 99.9%, 99.95%, 99.98% or 99.99% sequence identity thereto.

11. The IBV spike protein or fragment thereof of any one of claim 3, wherein said at least a part of the S1 subunit is from an IBV selected from a list of genotypes or serotypes or strains consisting of: Arkansas, Brazil, California, Connecticut, Delaware, Dutch, Florida, Georgia, Gray, Holte, Iowa, Italy-02, JMK, LDT3, Maine, H52, H120, M41, Pennsylvania, Pennsylvania, PL84084, Qu, QX, Q1, SE 17, Variant 2 and 4/91.

12. The avian coronavirus spike protein or fragment thereof of any one of claim 1, wherein the avian coronavirus or IBV with restricted cell or tissue tropism is restricted to infection and/or replication in embryonated chicken eggs and/or in primary chicken kidney cells.

13. A nucleotide sequence encoding the spike protein or fragment thereof of any one of claim 1.

14. A plasmid comprising a nucleotide sequence of claim 13.

15. A cell comprising a plasmid of claim 14.

16. A viral particle comprising a spike protein or fragment thereof of any one of claim 1.

17. An avian coronavirus comprising the spike protein or fragment thereof of claim 1.

18. The avian coronavirus or IBV of claim 17, wherein the avian coronavirus or IBV is attenuated.

19. A cell comprising the viral particle of claim 16.

20. An immunogenic composition comprising the spike protein of claim 1.

21. A method for the production or manufacture of an avian coronavirus with an extended cell or tissue tropism comprising the use of the avian coronavirus spike protein or fragment thereof of any one of claim 1.

22. A method for culturing an avian coronavirus in a cell or tissue culture comprising the use of the avian coronavirus spike protein or fragment thereof of claim 1.

23. The method of claim 21 or 22, wherein the coronavirus spike protein is an IBV (infectious bronchitis virus) spike protein.

24. A method for immunizing a subject comprising administering to such subject an immunogenic composition of claim 20.

25. A method of treating or preventing clinical signs caused by IBV in a subject of need, the method comprises administering to the subject a therapeutically effective amount of an immunogenic composition of claim 20.

26. A method of reducing the ciliostasis in a subject of need, in comparison to a subject of a non-immunized control group of the same species, the method comprises administering to the subject a therapeutically effective amount of an immunogenic composition of claim 20.

27. The avian coronavirus spike protein or fragment thereof of claim 3, wherein the IBV with restricted cell or tissue tropism is restricted to infection and/or replication in embryonated chicken eggs and/or in primary chicken kidney cells.

28. An IBV (infectious bronchitis virus) comprising the spike protein of claim 3.

29. A cell comprising the avian coronavirus of claim 17.

30. A cell comprising the IBV of claim 28.

31. An immunogenic composition comprising the viral particle of claim 16.

32. An immunogenic composition comprising the IBV of claim 28.

33. The avian coronavirus spike protein or fragment thereof of claim 2, wherein the avian coronavirus is IBV (infectious bronchitis virus).

* * * * *